US008629251B2

(12) United States Patent
Benning et al.

(10) Patent No.: US 8,629,251 B2
(45) Date of Patent: Jan. 14, 2014

(54) **SPECIFIC DETECTION AND QUANTIFICATION OF PHOSPHATIDIC ACID USING AN *ARABIDOPSIS* TRIGALACTOSYLDIACYLGLYCEROL-4 (TGD4) PROTEIN**

(75) Inventors: Christoph Benning, East Lansing, MI (US); Zhen Wang, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 11 days.

(21) Appl. No.: 13/350,287

(22) Filed: Jan. 13, 2012

(65) Prior Publication Data

US 2012/0237949 A1 Sep. 20, 2012

Related U.S. Application Data

(63) Continuation-in-part of application No. 12/506,633, filed on Jul. 21, 2009, now Pat. No. 8,110,656.

(60) Provisional application No. 61/149,835, filed on Feb. 4, 2009, provisional application No. 61/085,187, filed on Jul. 31, 2008, provisional application No. 61/082,656, filed on Jul. 22, 2008.

(51) Int. Cl.
*G01N 33/566* (2006.01)
*C07K 14/00* (2006.01)
*G01N 21/64* (2006.01)

(52) U.S. Cl.
USPC ........... 530/395; 436/501; 435/7.8; 435/7.92; 435/801

(58) Field of Classification Search
None
See application file for complete search history.

(56) References Cited

U.S. PATENT DOCUMENTS 8,110,656 B2 2/2012 Benning et al.

FOREIGN PATENT DOCUMENTS

WO WO 03/074653 * 9/2003

OTHER PUBLICATIONS

"U.S. Appl. No. 12/506,633, 312 Amendment filed Oct. 26, 2011", 3 pgs.

"U.S. Appl. No. 12/506,633, Response filed Jun. 24, 2011 to Restriction Requirement mailed Apr. 27, 2011", 19 pgs.

"A printout from the GenBank database for *Arabidopsis* Gene At3g20320", (2010), 2 pgs.

Awai, K., et al., "A phosphatidic acid-binding protein of the chloroplast inner envelope membrane involved in lipid trafficking", *Proc. Natl. Acad. Sci. USA*, 103(28). (2006), 10817-10822.

Testerink, C., et al., "Phosphatidic acid: a multifunctional stress signaling lipid in plants", *Trends in Plant Science*, 10(8), (2005), 368-375.

"U.S. Appl. No. 12/506,633, 312, Amendment filed Oct. 26, 2011", 3 pgs.

"U.S. Appl. No. 12/506,633, Examiner Interview Summary mailed Jun. 22, 2011", 3 pgs.

"U.S. Appl. No. 12/506,633, Non Final Office Action mailed Dec. 6, 2010", 13 pgs.

"U.S. Appl. No. 12/506,633, Notice of Allowance mailed Sep. 9, 2011", 11 pgs.

"U.S. Appl. No. 12/506,633, Notice of Allowance mailed Oct. 17, 2011", 8 pgs.

"U.S. Appl. No. 12/506,633, PTO Response to 312 Amendment mailed Nov. 7, 2011", 2 pgs.

"U.S. Appl. No. 12/506,633, PTO Response to 312 Amendment mailed Nov. 16, 2011", 3 pgs.

"U.S. Appl. No. 12/506,633, Response filed Mar. 7, 2011 to Non Final Office Action mailed Dec. 6, 2010", 13 pgs.

"U.S. Appl. No. 12/506,633, Response filed Jun. 24, 2011 to Restriction Requirement mailed Apr. 24, 2011", 19 pgs.

"U.S. Appl. No. 12/506,633, Restriction Requirement mailed Apr. 27, 2011", 13 pgs.

* cited by examiner

*Primary Examiner* — Shafiqul Haq
*Assistant Examiner* — Galina Yakovleva
(74) *Attorney, Agent, or Firm* — Schwegman, Lundberg & Woessner, P.A.

(57) ABSTRACT

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. Phosphatidic acid may be in or from cells and tissues isolated from plants, animals and humans. For example, a trigalactosyldiacylglycerol-2 (TGD2) protein may be fused with a fluorescent probe to monitor and measure phosphatidic acid in vitro as well as in vivo. In other embodiments, a trigalactosyldiacylglycerol-4 (TGD4) protein may be fused with a fluorescent probe to monitor and measure phosphatidic acid in vitro as well as in vivo. In additional embodiments, a fragment comprising either a truncated TGD2 or TGD4 phosphatidic acid binding region protein may be used to monitor or measure phosphatidic acid.

36 Claims, 30 Drawing Sheets

A.

A.

B.

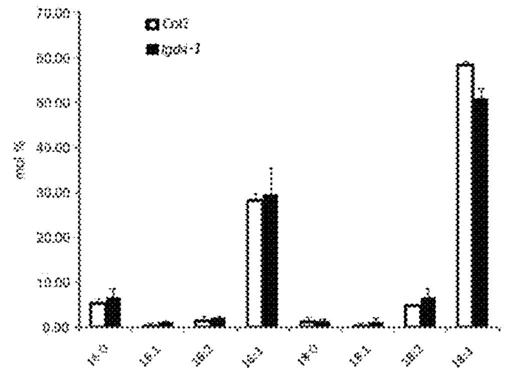

Figure 29

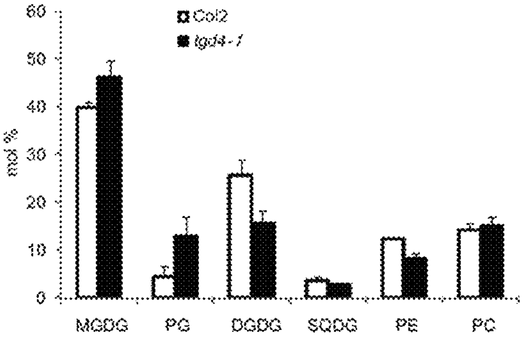

Figure 30

TGD4N-terminal (SEQ ID NO: 130) amino acids 1-286 (underlined region):
TGD4C-terminal (SEQ ID NO: 131) amino acids 309-479 (underlined region):

MNRMRWVGEGDIWDLDMSTPVTLEGTARAVPDDPLPLGLSRGTRLSRPKQVEFFHRFMASPLIPS
FSPIRPNTGDGGGGGFSLQRVLTLPFSNNWLVSLLGQFDVQRFVTEIDKTKAFGRGSSSTVASRL
NTIGKHLKDKSLYALGFCSEFLLSPDDTLLLSYDAYKGDLDKNPRAKAIFNHEFPLHNLTAEAVW
PGLFVDKHGEYWDVPLSMAIDLASLPAESGPSYHLCLHHNSGSPKKLHSDTMEVPPPSLLPGLSL
KSAVSYRTNMDLWRGTTPKLETCKPYDVFLSSPHVAVSGIIGSVMTAAFGENSIRSKFENDSEGV
GGFSLHFPSVNSGFMADALGRASLTAQYGNFQKFFFDLTRFHARLDFPHGLRFLTGATSVAQDLL
NSRQPSLEAFQKICPEVLVSLQQQIVGPFSFKVESGIEIDLRNGANPVTVDKTVFAIEYALQVLL
SAKAVVSYSPKQNEFMVELRFFET

TGD4 (SEQ ID NO: 132) amino acids 1-479 (hydrophobic region 23 amino acids (287D-309F) is underlined):

MNRMRWVGEGDIWDLDMSTPVTLEGTARAVPDDPLPLGLSRGTRLSRPKQVEFFHRFMASPLIPS
FSPIRPNTGDGGGGGFSLQRVLTLPFSNNWLVSLLGQFDVQRFVTEIDKTKAFGRGSSSTVASRL
NTIGKHLKDKSLYALGFCSEFLLSPDDTLLLSYDAYKGDLDKNPRAKAIFNHEFPLHNLTAEAVW
PGLFVDKHGEYWDVPLSMAIDLASLPAESGPSYHLCLHHNSGSPKKLHSDTMEVPPPSLLPGLSL
KSAVSYRTNMDLWRGTTPKLETCKPYDVFLSSPHVAVSGIIGSVMTAAFGENSIRSKFENDSEGV
GGFSLHFPSVNSGFMADALGRASLTAQYGNFQKFFFDLTRFHARLDFPHGLRFLTGATSVAQDLL
NSRQPSLEAFQKICPEVLVSLQQQIVGPFSFKVESGIEIDLRNGANPVTVDKTVFAIEYALQVLL
SAKAVVSYSPKQNEFMVELRFFET

ΔTGD4 (SEQ ID NO: 133) hydrophobic region of 23 amino acids (287D-309F) was removed:

MNRMRWVGEGDIWDLDMSTPVTLEGTARAVPDDPLPLGLSRGTRLSRPKQVEFFHRFMASPLIPS
FSPIRPNTGDGGGGGFSLQRVLTLPFSNNWLVSLLGQFDVQRFVTEIDKTKAFGRGSSSTVASRL
NTIGKHLKDKSLYALGFCSEFLLSPDDTLLLSYDAYKGDLDKNPRAKAIFNHEFPLHNLTAEAVW
PGLFVDKHGEYWDVPLSMAIDLASLPAESGPSYHLCLHHNSGSPKKLHSDTMEVPPPSLLPGLSL
KSAVSYRTNMDLWRGTTPKLETCKPYGENSIRSKFENDSEGVGGFSLHFPSVNSGFMADALGRAS
LTAQYGNFQKFFFDLTRFHARLDFPHGLRFLTGATSVAQDLLNSRQPSLEAFQKICPEVLVSLQQ
QIVGPFSFKVESGIEIDLRNGANPVTVDKTVFAIEYALQVLLSAKAVVSYSPKQNEFMVELRFFE
T

Figure 31A

SEQ ID NO: 134: starting with ATG and encoding amino acids 1 – 286 (underlined region)
SEQ ID NO: 135: starting with TTT and encoding amino acids 309-479 (underlined region):

```
   1 AGCTGGGTGT AGAAATCGAG CGACGGCGGC GGAGACGACG GAGATGAACA
  51 GAATGAGATG GGTCGGAGAG GGAGACATCT GGGACCTCGA TATGTCAACT
 101 CCGGTGACGC TCGAGGGCAC CGCACGAGCT GTTCCTGACG ATCCTCTTCC
 151 TCTAGGTCTC TCTAGAGGCA CTCGTCTATC TCGCCCTAAG CAAGTTGAGT
 201 TCTTCCACCG CTTCATGGCC TCACCTCTCA TCCCTTCCTT CTCCCCTATC
 251 CGTCCCAACA CCGGAGATGG AGGCGGTGGT GGATTCTCTC TTCAAAGAGT
 301 CCTCACTCTT CCTTTCTCCA ACAACTGGCT TGTGTCTCTT CTGGGCCAAT
 351 TCGATGTTCA GAGATTCGTA ACGGAGATAG ATAAGACTAA AGCTTTTGGT
 401 CGAGGGTCTT CGTCTACAGT AGCTTCTCGT TTAAACACAA TTGGCAAGCA
 451 TTTGAAGGAT AAATCTTTGT ACGCATTGGG TTTTTGTTCT GAGTTTTTGT
 501 TATCACCAGA TGATACTTTG CTTCTTAGCT ATGATGCTTA CAAAGGTGAT
 551 CTCGATAAGA ATCCTAGAGC TAAGGCTATC TTCAATCACG AGTTTCCGCT
 601 TCACAATCTG ACAGCAGAAG CGGTTTGGCC TGGACTTTTT GTGGATAAAC
 651 ATGGTGAATA TTGGGATGTG CCACTCTCAA TGGCTATTGA TCTAGCATCT
 701 CTTCCTGCTG AATCTGGTCC AAGTTACCAT TTATGTTTAC ACCATAACAG
 751 CGGATCACCC AAGAAGTTAC ATTCTGATAC TATGGAAGTG CCTCCACCGT
 801 CACTGCTTCC TGGTTTGTCT CTGAAATCTG CAGTCTCTTA TAGGACAAAC
 851 ATGGATCTCT GGAGGGGTAC CACTCCAAAG CTCGAAACTT GCAAGCCCTA
 901 TGATGTCTTC CTCAGTAGTC CTCATGTCGC AGTATCTGGG ATTATCGGCT
 951 CTGTGATGAC CGCAGCATTT GGTGAAAATT CAATCAGATC AAAATTTGAA
1001 AATGATTCTG AGGGTGTTGG AGGGTTCTCT CTTCATTTTC CATCTGTAAA
1051 TTCCGGATTC ATGGCTGATG CCTTAGGGCG GGCATCACTC ACAGCTCAAT
1101 ATGGAAACTT CCAGAAATTC TTCTTTGATC TCACCCGTTT CCATGCTAGA
1151 TTAGACTTTC CGCATGGTTT GAGGTTTCTT ACCGGTGCCA CTAGCGTCGC
1201 ACAAGATCTT TTAAATTCTC GGCAGCCTAG TTTAGAAGCA TTTCAGAAAA
1251 TCTGCCCTGA AGTATTAGTT TCTCTACAGC AACAGATTGT TGGACCGTTT
1301 AGTTTCAAAG TGGAGTCTGG AATTGAGATC GATCTGAGGA ACGGAGCTAA
1351 CCCTGTGACT GTAGATAAGA CAGTATTTGC TATTGAATAT GCTCTTCAAG
1401 TGCTTCTTTC TGCCAAGGCT GTTGTTTCGT ACTCCCCAAA ACAGAATGAG
1451 TTCATGGTTG AGCTTCGTTT CTTTGAGACA TAGTATCAGG ATTTTCCACT
1501 CAAAATGTCA AGCTTGATCC TGTGAAGATT GTAGTCTTGC AGAGAAGTAA
1551 ATACTAAATA GACAATGTTC TAATTGTTCA GTTTCTTATG TCAAACAGAA
1601 GAATGTTTCA ATAGAAGGGA AGTTTACATT TTGTTATAGT GTGATGTCTA
1651 CCAG//
```

*Ds*RED-ΔTGD4-His protein (SEQ ID NO: 138)

```
ATGAACAGAATGAGATGGGTCGGAGAGGGAGACATCTGGGACCTCGATATGTCAACT
CCGGTGACGC TCGAGGGCAC CGCACGAGCT GTTCCTGACG ATCCTCTTCC
TCTAGGTCTC TCTAGAGGCA CTCGTCTATC TCGCCCTAAG CAAGTTGAGT
TCTTCCACCG CTTCATGGCC TCACCTCTCA TCCCTTCCTT CTCCCCTATC
CGTCCCAACA CCGGAGATGG AGGCGGTGGT GGATTCTCTC TTCAAAGAGT
CCTCACTCTT CCTTTCTCCA ACAACTGGCT TGTGTCTCTT CTGGGCCAAT
TCGATGTTCA GAGATTCGTA ACGGAGATAG ATAAGACTAA AGCTTTTGGT
CGAGGGTCTT CGTCTACAGT AGCTTCTCGT TTAAACACAA TTGGCAAGCA
TTTGAAGGAT AAATCTTTGT ACGCATTGGG TTTTTGTTCT GAGTTTTTGT
      TATCACCAGA TGATACTTTG CTTCTTAGCT ATGATGCTTA CAAAGGTGAT
```

Figure 31B-1

```
CTCGATAAGA ATCCTAGAGC TAAGGCTATC TTCAATCACG AGTTTCCGCT
TCACAATCTG ACAGCAGAAG CGGTTTGGCC TGGACTTTTT GTGGATAAAC
ATGGTGAATA TTGGGATGTG CCACTCTCAA TGGCTATTGA TCTAGCATCT
CTTCCTGCTG AATCTGGTCC AAGTTACCAT TTATGTTTAC ACCATAACAG
CGGATCACCC AAGAAGTTAC ATTCTGATAC TATGGAAGTG CCTCCACCGT
CACTGCTTCC TGGTTTGTCT CTGAAATCTG CAGTCTCTTA TAGGACAAAC
ATGGATCTCT GGAGGGGTAC CACTCCAAAG CTCGAAACTT GCAAGCCCTA
TTTTGGTGAAAATT CAATCAGATC AAAATTTGAAAATGATTCTG AGGGTGTTGG AGGGTTCTCT CT
TCATTTTC CATCTGTAAATTCCGGATTC ATGGCTGATG CCTTAGGGCG GGCATCACTC ACAGCTCA
ATATGGAAACTT CCAGAAATTC TTCTTTGATC TCACCCGTTT CCATGCTAGA
TTAGACTTTC CGCATGGTTT GAGGTTTCTT ACCGGTGCCA CTAGCGTCGC
ACAAGATCTT TTAAATTCTC GGCAGCCTAG TTTAGAAGCA TTTCAGAAAA
TCTGCCCTGA AGTATTAGTT TCTCTACAGC AACAGATTGT TGGACCGTTT
AGTTTCAAAG TGGAGTCTGG AATTGAGATC GATCTGAGGA ACGGAGCTAA
CCCTGTGACT GTAGATAAGA CAGTATTTGC TATTGAATAT GCTCTTCAAG
TGCTTCTTTC TGCCAAGGCT GTTGTTTCGT ACTCCCCAAA ACAGAATGAG
TTCATGGTTG AGCTTCGTTT CTTTGAGACA T
```

AT3G06960.1 (SEQ ID NO: 136) (boxes mark the beginning and the end of the underlined coding sequence):

```
1 AGCTGGGTGT AGAAATCGAG CGACGGCGGC GGAGACGACG GAGATGAACA
51 GAATGAGATG GGTCGGAGAG GGAGACATCT GGGACCTCGA TATGTCAACT
101 CCGGTGACGC TCGAGGGCAC CGCACGAGCT GTTCCTGACG ATCCTCTTCC
151 TCTAGGTCTC TCTAGAGGCA CTCGTCTATC TCGCCCTAAG CAAGTTGAGT
201 TCTTCCACCG CTTCATGGCC TCACCTCTCA TCCCTTCCTT CTCCCCTATC
251 CGTCCCAACA CCGGAGATGG AGGCCGTGGT GGATTCTCTC TTCAAAGAGT
301 CCTCACTCTT CCTTTCTCCA ACAACTGGCT TGTGTCTCTT CTGGGCCAAT
351 TCGATGTTCA GAGATTCGTA ACGGAGATAG ATAAGACTAA AGCTTTTGGT
401 CGAGGGTCTT CGTCTACAGT AGCTTCTCGT TTAAACACAA TTGGCAAGCA
451 TTTGAAGGAT AAATCTTTGT ACGCATTGGG TTTTTGTTCT GAGTTTTTGT
501 TATCACCAGA TGATACTTTG CTTCTTAGCT ATGATGCTTA CAAAGGTGAT
551 CTCGATAAGA ATCCTAGAGC TAAGGCTATC TTCAATCACG AGTTTCCGCT
601 TCACAATCTG ACAGCAGAAG CGGTTTGGCC TGGACTTTTT GTGGATAAAC
651 ATGGTGAATA TTGGGATGTG CCACTCTCAA TGGCTATTGA TCTAGCATCT
701 CTTCCTGCTG AATCTGGTCC AAGTTACCAT TTATGTTTAC ACCATAACAG
751 CGGATCACCC AAGAAGTTAC ATTCTGATAC TATGGAAGTG CCTCCACCGT
801 CACTGCTTCC TGGTTTGTCT CTGAAATCTG CAGTCTCTTA TAGGACAAAC
851 ATGGATCTCT GGAGGGGTAC CACTCCAAAG CTCGAAACTT GCAAGCCCTA
901 TGATGTCTTC CTCAGTAGTC CTCATGTCGC AGTATCTGGG ATTATCGGCT
951 CTGTGATGAC CGCAGCATTT GGTGAAAATT CAATCAGATC AAAATTTGAA
1001 AATGATTCTG AGGGTGTTGG AGGGTTCTCT CTTCATTTTC CATCTGTAAA
1051 TTCCGGATTC ATGGCTGATG CCTTAGGGCG GGCATCACTC ACAGCTCAAT
1101 ATGGAAACTT CCAGAAATTC TTCTTTGATC TCACCCGTTT CCATGCTAGA
1151 TTAGACTTTC CGCATGGTTT GAGGTTTCTT ACCGGTGCCA CTAGCGTCGC
1201 ACAAGATCTT TTAAATTCTC GGCAGCCTAG TTTAGAAGCA TTTCAGAAAA
1251 TCTGCCCTGA AGTATTAGTT TCTCTACAGC AACAGATTGT TGGACCGTTT
1301 AGTTTCAAAG TGGAGTCTGG AATTGAGATC GATCTGAGGA ACGGAGCTAA
1351 CCCTGTGACT GTAGATAAGA CAGTATTTGC TATTGAATAT GCTCTTCAAG
1401 TGCTTCTTTC TGCCAAGGCT GTTGTTTCGT ACTCCCCAAA ACAGAATGAG
1451 TTCATGGTTG AGCTTCGTTT CTTTGAGACA TAGTATCAGG ATTTTCCACT
1501 CAAAATGTCA AGCTTGATCC TGTGAAGATT GTAGTCTTGC AGAGAAGTAA
1551 ATACTAAATA GACAATGTTC TAATTGTTCA GTTTCTTATG TCAAACAGAA
1601 GAATGTTTCA ATAGAAGGGA AGTTTACATT TTGTTATAGT GTGATGTCTA
1651 CCAG//
```

Figure 31B-2

**pLW01/*Ds*RED-His (underlining shows HIS tag) SEQ ID NO: 137:**

```
   1 CGGTAAAGCT CATCAGCGTG GTCGTGAAGC GATTCACAGA TGTCTGCCTG TTCATCCGCG
  61 TCCAGCTCGT TGAGTTTCTC CAGAAGCGTT AATGTCTGGC TTCTGATAAA GCGGGCCATG
 121 TTAAGGGCGG TTTTTTCCTG TTTGGTCACT GATGCCTCCG TGTAAGGGGG ATTTCTGTTC
 181 ATGGGGGTAA TGATACCGAT GAAACGAGAG AGGATGCTCA CGATACGGGT TACTGATGAT
 241 GAACATGCCC GGTTACTGGA ACGTTGTGAG GGTAAACAAC TGGCGGTATG GATGCGGCGG
 301 GACCAGAGAA AAATCACTCA GGGTCAATGC CAGCGCTTCG TTAATACAGA TGTAGGTGTT
 361 CCACAGGGTA GCCAGCAGCA TCCTGCGATG CAGATCCGGA ACATAATGGT GCAGGGCGCT
 421 GACTTCCGCG TTTCCAGACT TTACGAAACA CGGAAACCGA AGACCATTCA TGTTGTTGCT
 481 CAGGTCGCAG ACGTTTTGCA GCAGCAGTCG CTTCACGTTC GCTCGCGTAT CGGTGATTCA
 541 TTCTGCTAAC CAGTAAGGCA ACCCCGCCAG CCTAGCCGGG TCCTCAACGA CAGGAGCACG
 601 ATCATGCGCA CCCGTGGCCA GGACCCAACG CTGCCCGAGA TCTCGATCCC GCGAAATTAA
 661 TACGACTCAC TATAGGGAGA CCACAACGGT TTCCCTCTAG AAATAATTTT GTTTAACTTT
 721 AAGAAGGAGA TATACCATGG ACAACACCGA GGACGTCATC AAGGAGTTCA TGCAGTTCAA
 781 GGTGCGCATG GAGGGCTCCG TGAACGGCCA CTACTTCGAG ATCGAGGGCG AGGGCGAGGG
 841 CAAGCCCTAC GAGGGCACCC AGACCGCCAA GCTGCAGGTG ACCAAGGGCG GCCCCCTGCC
 901 CTTCGCCTGG GACATCCTGT CCCCCCAGTT CCAGTACGGC TCCAAGGCCT ACGTGAAGCA
 961 CCCCGCCGAC ATCCCCGACT ACATGAAGCT GTCCTTCCCC GAGGGCTTCA CCTGGGAGCG
1021 CTCCATGAAC TTCGAGGACG GCGGCGTGGT GGAGGTGCAG CAGGACTCCT CCCTGCAGGA
1081 CGGCACCTTC ATCTACAAGG TGAAGTTCAA GGGCGTGAAC TTCCCCGCCG ACGGCCCCGT
1141 AATGCAGAAG AAGACTGCCG GCTGGGAGCC CTCCACCGAG AAGCTGTACC CCCAGGACGG
1201 CGTGCTGAAG GGCGAGATCT CCCACGCCCT GAAGCTGAAG GACGGCGGCC ACTACACCTG
1261 CGACTTCAAG ACCGTGTACA AGGCCAAGAA GCCCGTGCAG CTGCCCGGCA ACCACTACGT
1321 GGACTCCAAG CTGGACATCA CCAACCACAA CGAGGACTAC ACCGTGGTGG AGCAGTACGA
1381 GCACGCCGAG GCCCGCCACT CCGGCTCCCA GGGATCCGAA TTCGAGCTCC GTCGACAAGC
1441 TTGCGGCCGC ACTCGAGCAC CACCACCACC ACCACTGAGA TCCGGCTGCT AACAAAGCCC
1501 GAAAGGAAGC TGAGTTGGCT GCTGCCACCG CTGAGCAATA ACTAGCATAA CCCCTTGGGG
1561 CCTCTAAACG GGTCTTGAGG GGTTTTTTGC TGAAAGGAGG AACTATATCC GGATTGGCGA
1621 ATGGGACGCG CCCTGTAGCG GCGCATTAAG CGCGGCGGGT GTGGTGGTTA CGCGCAGCGT
1681 GACCGCTACA CTTGCCAGCG CCCTAGCGCC CGCTCCTTTC GCTTTCTTCC CTTCCTTTCT
1741 CGCCACGTTC GCCGGCTTTC CCCGTCAAGC TCTAAATCGG GGGCTCCCTT TAGGGTTCCG
1801 ATTTAGTGCT TTACGGCACC TCGACCCCAA AAAACTTGAT TAGGGTGATG GTTCACGTAG
1861 TGGGCCATCG CCCTGATAGA CGGTTTTTCG CCCTTTGACG TTGGAGTCCA CGTTCTTTAA
1921 TAGTGGACTC TTGTTCCAAA CTGGAACAAC ACTCAACCCT ATCTCGGTCT ATTCTTTTGA
1981 TTTATAAGGG ATTTTGCCGA TTTCGGCCTA TTGGTTAAAA AATGAGCTGA TTTAACAAAA
2041 ATTTAACGCG AATTTTAACA AAATATTAAC GCTTACAATT TAGGTGGCAC TTTTCGGGGA
2101 AATGTGCGCG GAACCCCTAT TTGTTTATTT TTCTAAATAC ATTCAAATAT GTATCCGCTC
2161 ATGAGACAAT AACCCTGATA AATGCTTCAA TAATATTGAA AAAGGAAGAG TATGAGTATT
2221 CAACATTTCC GTGTCGCCCT TATTCCCTTT TTTGCGGCAT TTTGCCTTCC TGTTTTTGCT
2281 CACCCAGAAA CGCTGGTGAA AGTAAAAGAT GCTGAAGATC AGTTGGGTGC ACGAGTGGGT
2341 TACATCGAAC TGGATCTCAA CAGCGGTAAG ATCCTTGAGA GTTTTCGCCC CGAAGAACGT
2401 TTTCCAATGA TGAGCACTTT TAAAGTTCTG CTATGTGGCG CGGTATTATC CCGTATTGAC
2461 GCCGGGCAAG AGCAACTCGG TCGCCGCATA CACTATTCTC AGAATGACTT GGTTGAGTAC
2521 TCACCAGTCA CAGAAAAGCA TCTTACGGAT GGCATGACAG TAAGAGAATT ATGCAGTGCT
2581 GCCATAACCA TGAGTGATAA CACTGCGGCC AACTTACTTC TGACAACGAT CGGAGGACCG
2641 AAGGAGCTAA CCGCTTTTTT GCACAACATG GGGGATCATG TAACTCGCCT TGATCGTTGG
2701 GAACCGGAGC TGAATGAAGC CATACCAAAC GACGAGCGTG ACACCACGAT GCCTGTAGCA
2761 ATGGCAACAA CGTTGCGCAA ACTATTAACT GGCGAACTAC TTACTCTAGC TTCCCGGCAA
2821 CAATTAATAG ACTGGATGGA GGCGGATAAA GTTGCAGGAC CACTTCTGCG CTCGGCCCTT
2881 CCGGCTGGCT GGTTTATTGC TGATAAATCT GGAGCCGGTG AGCGTGGGTC TCGCGGTATC
2941 ATTGCAGCAC TGGGGCCAGA TGGTAAGCCC TCCCGTATCG TAGTTATCTA CACGACGGGG
3001 AGTCAGGCAA CTATGGATGA ACGAAATAGA CAGATCGCTG AGATAGGTGC CTCACTGATT
3061 AAGCATTGGT AACTGTCAGA CCAAGTTTAC TCATATATAC TTTAGATTGA TTTAAAACTT
3121 CATTTTTAAT TTAAAAGGAT CTAGGTGAAG ATCCTTTTTG ATAATCTCAT GACCAAAATC
3181 CCTTAACGTG AGTTTTCGTT CCACTGAGCG TCAGACCCCG TAGAAAAGAT CAAAGGATCT
3241 TCTTGAGATC CTTTTTTTCT GCGCGTAATC TGCTGCTTGC AAACAAAAAA ACCACCGCTA
3301 CCAGCGGTGG TTTGTTTGCC GGATCAAGAG CTACCAACTC TTTTTCCGAA GGTAACTGGC
3361 TTCAGCAGAG CGCAGATACC AAATACTGTC CTTCTAGTGT AGCCGTAGTT AGGCCACCAC
3421 TTCAAGAACT CTGTAGCACC GCCTACATAC CTCGCTCTGC TAATCCTGTT ACCAGTGGCT
3481 GCTGCCAGTG GCGATAAGTC GTGTCTTACC GGGTTGGACT CAAGACGATA GTTACCGGAT
3541 AAGGCGCAGC GGTCGGGCTG AACGGGGGGT TCGTGCACAC AGCCCAGCTT GGAGCGAACG
```

Figure 32C-1

```
3601 ACCTACACCG AACTGAGATA CCTACAGCGT GAGCTATGAG AAAGCGCCAC GCTTCCCGAA
3661 GGGAGAAAGG CGGACAGGTA TCCGGTAAGC GGCAGGGTCG GAACAGGAGA GCGCACGAGG
3721 GAGCTTCCAG GGGGAAACGC CTGGTATCTT TATAGTCCTG TCGGGTTTCG CCACCTCTGA
3781 CTTGAGCGTC GATTTTTGTG ATGCTCGTCA GGGGGGCGGA GCCTATGGAA AAACGCCAGC
3841 AACGCGGCCT TTTTACGGTT CCTGGCCTTT TGCTGGCCTT TTGCTCACAT GTTCTTTCCT
3901 GCGTTATCCC CTGATTCTGT GGATAACCGT ATTACCGCCT TTGAGTGAGC TGATACCGCT
3961 CGCCGCAGCC GAACGACCGA GCGCAGCGAG TCAGTGAGCG AGGAAGCGGA AGAGCGCCCA
4021 ATACGCAAAC CGCCTCTCCC CGCGCGTTGG CCGATTCATT AATGCAGCTG//
```

Figure 32C-2

SPECIFIC DETECTION AND QUANTIFICATION OF PHOSPHATIDIC ACID USING AN *ARABIDOPSIS* TRIGALACTOSYLDIACYLGLYCEROL-4 (TGD4) PROTEIN

The present application is a Continuation-In-Part of application Ser. No. 12/506,633, filed Jul. 21, 2009, now U.S. Pat. No. 8,110,656, that claims priority to the following provisional applications: Ser. No. 61/149,835, filed Feb. 4, 2009, Ser. No. 61/085,187 filed Jul. 31, 2008, and Ser. No. 61/082,656, filed Jul. 22, 2008, all of which are herein incorporated by reference in their entirety.

STATEMENT OF GOVERNMENT INTEREST

This invention was made with government support under NSF MCB 0741395 awarded by the National Science Foundation. The government has certain rights in the invention.

FIELD OF THE INVENTION

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. Phosphatidic acid may be in or from cells and tissues isolated from plants, animals and humans. For example, a trigalactosyldiacylglycerol-2 (TGD2) protein may be fused with a fluorescent probe to monitor and measure phosphatidic acid in vitro as well as in vivo. In other embodiments, a trigalactosyldiacylglycerol-4 (TGD4) protein may be fused with a fluorescent probe to monitor and measure phosphatidic acid in vitro as well as in vivo. In additional embodiments, a fragment comprising either a truncated TGD2 or TGD4 phosphatidic acid binding region protein may be used to monitor or measure phosphatidic acid.

BACKGROUND

The biogenesis of the photosynthetic thylakoid membranes inside plant chloroplasts requires enzymes at the plastid envelope and the endoplasmic reticulum (ER). Extensive lipid trafficking is required for thylakoid lipid biosynthesis. Trigalactosyldiacylglycerol (TGD) proteins are believed to be permease components of a bacterial-type ATP-Binding Cassette (ABC) transporter located in the chloroplast inner envelope membrane.

Trigalactosyldiacylglycerol proteins were suggested to have a phosphatidic acid-binding protein with a predicted mycobacterial-like cell entry domain such that they may be tethered to the inner chloroplast envelope membrane facing the outer envelope membrane. However, these specific phosphatidic acid binding sites had not been identified, purified and/or isolated.

This lack of knowledge has hampered the development of specific diagnostic and detection methods designed to detect and quantify phosphatidic acid in plants. What is needed in the art is a reliable, quantitatively sensitive, and routine laboratory assay to detect for the purposes of botanical diagnostics and as a laboratory research tool.

SUMMARY OF THE INVENTION

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. Phosphatidic acid may be in or from cells and tissues isolated from plants, animals and humans. For example, a trigalactosyldiacylglycerol-2 (TGD2) protein may be fused with a fluorescent probe to monitor and measure phosphatidic acid in vitro as well as in vivo. In other embodiments, a trigalactosyldiacylglycerol-4 (TGD4) protein may be fused with a fluorescent probe to monitor and measure phosphatidic acid in vitro as well as in vivo. In additional embodiments, a fragment comprising a truncated TGD2 or TGD4 phosphatidic acid binding region protein may be used to monitor or measure phosphatidic acid.

In one embodiment, the present invention contemplates a truncated trigalactosyldiacylglycerol 4 protein comprising a phosphatidic acid binding domain, wherein said protein is encoded by a nucleic acid sequence selected from the group consisting of SEQ ID NO: 134, SEQ ID NO: 135, SEQ ID NO: 138, and fragments thereof. In one embodiment, the nucleic acid sequence has a C-terminally attached label. In one embodiment, the C-terminally attached label is histidine. In one embodiment, the protein comprising a phosphatidic acid binding domain is selected from the group consisting of SEQ ID NO: 130, SEQ ID NO: 131, SEQ ID NO: 133, and fragments thereof. In one embodiment, the protein lacks a transit peptide domain. In one embodiment, the protein lacks a membrane associated domain. In one embodiment, the protein further comprising a fluorescent label.

In one embodiment, the present invention contemplates a method, comprising: a) providing: i) a trigalactosyldiacylglycerol 4 protein comprising a phosphatidic acid binding domain, wherein said protein is selected from the group consisting of SEQ ID NO: 130, SEQ ID NO: 131, SEQ ID NO: 132 and SEQ ID NO: 133, ii) a sample suspected of containing a lipid comprising a phosphatidic acid capable of binding to said trigalactosyldiacylglycerol 4 protein; and b) contacting said sample with said protein under conditions such that said phosphatidic acid binds to said trigalactosyldiacylglycerol 4 protein; and c) determining an amount of said phosphatidic acid binding to said trigalactosyldiacylglycerol 4 protein. In one embodiment, the phosphatidic acid is selected from the group consisting of a phosphatidic acid, a dipalmitoyl phosphatidic acid and distearoyl phosphatidic acid. In one embodiment, the trigalactosyldiacylglycerol 4 protein is a truncated protein. In one embodiment, the sample is immobilized on a membrane. In one embodiment, the sample comprises a liposome. In one embodiment, the liposome comprises a lipid selected from the group consisting of a dipalmitoyl phosphatidic acid and distearoyl phosphatidic acid. In one embodiment, the phosphatidic acid has a carbon chain length selected from the group consisting of 16 carbons and 18 carbons. In one embodiment, the sample comprises a plant sample. In one embodiment, the method further comprises identifying a plant disease with said phosphatidic acid-domain binding amount. In one embodiment, the method further comprises identifying a plant wound with said phosphatidic acid-domain binding amount. In one embodiment, the method further comprises identifying a plant stress with said phosphatidic acid-domain binding amount. In one embodiment, the plant stress is selected from the group consisting of biotic stress, abiotic stress, pathogen infection, drought, salinity, and cold. In one embodiment, the sample comprises a patient sample. In one embodiment, the method further comprises identifying a patient at risk for a disease with said amount of phosphatidic acid-domain binding. In one embodiment, the method further comprises identifying a patient disease with said amount of phosphatidic acid-domain binding. In one embodiment, the patient is a human patient. In one embodiment, the patient disease is polycystic kidney disease. In one embodiment, the sample is immobilized on a plastic plate. In one embodiment, the method further comprises an enzyme-linked immunosorbent assay capable of providing an optical density read out, wherein said determining an amount is measuring said optical density. In one embodiment, the method further comprises a test strip, wherein said determining an amount is observed on said test strip. In one embodiment, said determining an amount is determining an amount of phosphatidic acid-domain binding for use as a medical diagnostic. In one embodiment, the method further comprises a step before step b of treating the lipid under conditions that release a phosphatidic acid from said lipid.

In one embodiment, the present invention contemplates a kit, comprising: a) a first container comprising a trigalactosyldiacylglycerol 4 protein capable of binding to a phosphatidic acid, wherein said protein is encoded by a nucleic acid sequence selected from the group consisting of SEQ ID NO: 134, SEQ ID NO: 135, SEQ ID NO: 136, SEQ ID NO: 138, and fragments thereof, b) a second container comprising a plurality of buffers and a plurality of reagents, c) a set of instructions for determining the presence of a phosphatidic acid. In one embodiment, the protein is soluble. In one embodiment, the protein further comprises a label. In one embodiment, the kit further comprises choline chloride. In one embodiment, the phosphatidic acid is derived from a sample. In one embodiment, the instructions further comprise determining the amount of a phosphatidic acid. In one embodiment, the instructions further comprise a method for releasing a phosphatidic acid from a lipid comprising a phosphatidic acid. In one embodiment, the instructions further comprise a method for determining the presence of a lipid selected from the group consisting of a dipalmitoyl phosphatidic acid and distearoyl phosphatidic acid.

In one embodiment, the present invention contemplates a test strip comprising a phosphatidic acid binding protein 4 and a test sample. In one embodiment, the test sample comprises a phospholipid. In one embodiment, the phospholipid comprises phosphatidylinositol. In one embodiment, the phosphatidylinositol comprises phosphatidic acid. In one embodiment, the test strip further comprises a phosphatidic acid binding protein/phosphatidic acid complex. In one embodiment, the strip is Strip lot #JJ-032108-47. In one embodiment, the test strip is Strip lot #KB15011-47.

In one embodiment, the present invention contemplates a method comprising; a) providing; i) a test strip comprising a phosphatidic acid binding protein encoded by a nucleic acid sequence selected from the group consisting of SEQ ID NO: 134, SEQ ID NO: 135, SEQ ID NO: 137, and fragments thereof; ii) a test sample, wherein the sample comprises a phospholipid; and iii) a chlorine chloride solution; b) treating the phospholipid under conditions that release a phosphatidic acid; and c) placing the phosphatidic acid on the test strip under conditions such that the phosphatidic acid is captured by the phosphatidic acid binding protein, thereby forming a phosphatidic acid binding protein/phosphatidic acid complex, and d) detecting said phosphatidic acid binding protein/phosphatidic acid complex. In one embodiment, the phospholipid comprises phosphatidylinositol. In one embodiment, the test strip is Strip lot #JJ-032108-47. In one embodiment, the test strip is Strip lot #KB15011-47.

TGD2 proteins of *Arabidopsis* are proposed to be a substrate binding component of a lipid transfer complex in the inner chloroplast envelope membrane. Loss of function of this protein or other components of this complex may disrupt the endoplasmic reticulum (ER)-pathway of thylakoid lipid biosynthesis. In one embodiment, the present invention contemplates a minimal binding domain capable of specifically binding phosphatidic acid. Alternatively, the minimal binding domain may further comprise accessory binding domains that, in combination, create a complete TGD2 phosphatidic acid binding domain. Consequently, phosphatidic acid may be quantitatively detected from samples as described in the methods herein.

In one embodiment, the present invention contemplates a TGD2 protein comprising a phosphatidic acid binding domain, wherein said domain encompasses amino acid residues 201-225 (SEQ ID NO:12), wherein at least one of said residues is a proline. In one embodiment, the protein lacks a transit peptide domain and a transmembrane domain. In one embodiment, the domain further comprises at least one accessory binding domain. In one embodiment, the accessory binding domain comprises amino acid residues 251-300 (SEQ ID NO:103). In one embodiment, the accessory binding domain comprises amino acid residues 161-204 (SEQ ID NO:104). In one embodiment, the accessory binding domain comprises amino acid residues 291-340 (SEQ ID NO:105). In one embodiment, the domain comprises a phosphatidic acid binding motif. In one embodiment, an N-terminal β-strand and a C-terminal α-helix create the binding motif. In one embodiment, the binding motif comprises a $^{221}$Lysine. In one embodiment, the protein further comprises a label.

In one embodiment, the present invention contemplates a method, comprising: a) providing: i) a TGD2 protein comprising a phosphatidic acid binding domain, wherein said domain encompasses amino acid residues 201-225 (SEQ ID NO:12), wherein at least one of said residues is a proline; ii) a sample suspected of containing phosphatidic acid capable of binding to said domain; b) contacting said sample with said protein under conditions such that said phosphatidic acid binds to said domain; c) determining an amount of said phosphatidic acid-domain binding. In one embodiment, the sample comprises a plant sample. In one embodiment, the method further comprises identifying a plant disease with said phosphatidic acid-domain binding amount. In one embodiment, the method further comprises identifying a plant wound with said phosphatidic acid-domain binding amount. In one embodiment, the method further comprises identifying a plant stress with said phosphatidic acid-domain binding amount. In one embodiment, the plant stress is selected from the group consisting of biotic stress, abiotic stress, pathogen infection, drought, salinity, and cold.

In one embodiment, the present invention contemplates a kit, comprising: a) a first container comprising a TGD2 protein comprising a phosphatidic acid binding domain, wherein said domain encompasses amino acid residues 201-225 (SEQ ID NO:12), wherein at least one of said residues is a proline; b) a second container comprising a plurality of buffers and a plurality of reagents, wherein said protein is soluble; and c) a set of instructions for determining a phosphatidic acid. In one embodiment, the protein further comprises a label. In one embodiment, the phosphatidic acid is derived from a sample. In one embodiment, the protein further comprises at least one accessory binding protein. In one embodiment, the kit further comprises a test strip, capable of binding the TGD2 protein.

In one embodiment, the present invention contemplates a test strip comprising a phosphatidic acid binding protein and a test sample. In one embodiment, the test sample comprises a phospholipid. In one embodiment, the phospholipid comprises phosphatidylinositol. In one embodiment, the phosphatidylinositol comprises phosphatidic acid. In one embodiment, the test strip further comprises a phosphatidic acid binding protein/phosphatidic acid complex. In one embodiment, the test strip is Strip lot #JJ-032108-47. In one embodiment, the test strip is Strip lot #KB15011-47.

In one embodiment, the present invention contemplates a method comprising; a) providing i) a test strip comprising a phosphatidic acid binding protein; ii) a test sample, wherein the sample comprises a phospholipid; b) treating the phospholipid under conditions that release a phosphatidic acid; c) placing the phosphatidic acid on the test strip under conditions such that the phosphatidic acid is captured by the phosphatidic acid binding protein. In one embodiment, the method further comprises step (d) detecting said phosphatidic acid binding protein/phosphatidic acid complex. In one embodiment, the phospholipid comprises phosphatidylinositol. In one embodiment, the test strip is Strip lot #JJ-032108-47. In one embodiment, the test strip is Strip lot #KB15011-47.

DEFINITIONS

The term "trigalactosyldiacylglycerol" or "TGD" in relation to genes and proteins as used herein, refers to at least four genes, TGD1, TGD2, TGD3, and TGD4, which encode proteins, respectively, involved in ER-to-chloroplast lipid transfer in *Arabidopsis* (Awai et al., 2006, Lu et al., 2007, Xu et al., 2003, Xu et al., 2008, all of which are herein incorporated by reference).

The term "trigalactosyldiacylglycerol 1" or "TGD1" refers to genes and their encoded proteins containing multiple transmembrane domains and proposed to be a permease of a combined complex of TGD1, TGD 2 and TGD 3 proteins (Xu et al., 2003, all of which are herein incorporated by reference).

The term "trigalactosyldiacylglycerol 2" or "TGD2" refers to genes and their encoded proteins which have the capability to bind specifically to phosphatidic acid (PtdOH).

The term "trigalactosyldiacylglycerol 3" or "TGD3" refers to genes and encoded proteins which have ATPase activity found localized in the chloroplast stroma (Lu et al., 2007, herein incorporated by reference).

The term "trigalactosyldiacylglycerol 4" or "TGD4" refers to genes and their encoded proteins which have the capability to bind specifically to phosphatidic acid (PtdOH).

The term, "phosphatidic acid binding protein" as used herein, refers to any protein and/or enzyme that is capable of forming a complex with phosphatidic acid.

The term "phosphatidic acid binding domain" refers to a region of a protein capable of binding to a phosphatidic acid. The region may be shown by a linear amino acid sequence that contributes to binding or as an image showing a dimensional structure contributing to binding.

The term "binding" as used herein, refers to any interaction between an infection control composition and a surface. Such as surface is defined as a "binding surface". Binding may be reversible or irreversible. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

The term "truncated" in reference to a protein refers to a fragment of protein, i.e. at least one amino acid less than the full-length amino acid sequence.

The term "C-terminal" refers to an end of a peptide chain carrying the free alpha carboxyl group of the last amino acid.

The term "N-terminal" or "N-terminus" or "amino-terminus" or "NH2-terminus" or "N-terminal end" or "amine-terminus" or "amine-terminus" refers to a start of a protein or polypeptide sequence.

The term "membrane associated domain" refers to a fragment of a protein molecule that is attached to or associated with a cell membrane located in or surrounding a cell, i.e. extracellular or intracellular or integral.

The term "phosphatidic acid" as used herein, refers to any one of several acids $(RCOO)_2C_3H_5OPO_3H_2$ that are formed from phosphatides by partial hydrolysis and that yield on hydrolysis two fatty-acid molecules RCOOH and one molecule each of glycerol and phosphoric acid. A phosphatidic acid may be a dipalmitoyl phosphatidic acid, a distearoyl phosphatidic acid, etc.

The term "chlorine chloride" refers to a chloride salt of choline.

The term "patient", as used herein, is a human or animal and need not be hospitalized. For example, out-patients and persons in nursing homes are examples of "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "disease" refers to any deviation from or interruption of the normal structure or function of any body part, organ, or system that is manifested by a characteristic set of symptoms and signs and whose etiology, pathology, and prognosis may be known or unknown.

The term "enzyme-linked immunosorbent assay" or "ELISA" refers to a rapid immunochemical test and necessary reactants that involves an enzyme (a protein that catalyzes a biochemical reaction, i.e. a protein that binds to phosphatidic acid) and an antibody or antigen (immunologic molecules), i.e. TIC, TOC, etc., typically attached to a solid surface. As one example, a mixture of purified truncated TGD4 comprising a binding domain linked (coupled) to an enzyme (i.e. luciferase) or a detection molecule, i.e HIS, capable of binding to an enzyme, and the test sample (i.e. cell lysate, isolated membrane, etc) are added to the test system. If no phosphatidic acid is present in the test sample, then no phosphatidic acid with linked enzyme will specifically bind to the antibodies. The more phosphatidic acid which is present in the test sample, the more enzyme linked phosphatidic acid will bind. The substance the enzyme acts on is then added, and the amount of product measured by an optical density reading, such as a change in color of the solution which increases optical density over a sample treated in an identical manner which does not contain phosphatidic acid.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The terms "specific binding" or "specifically binding" when used in reference to the interaction of a lipid (i.e., for example, PA) and a protein or peptide (i.e., for example, TGD2 protein and/or a truncated TGD2 peptide) means that the interaction is dependent upon the presence of a particular structure (i.e., for example, a tertiary amino acid structure) on a protein; in other words a lipid is recognizing and binding to a specific protein structure rather than to proteins in general. For example, if a lipid is specific for tertiary structure "A", the presence of a protein containing tertiary structure A (or free, unlabelled A) in a reaction containing labeled "A", the lipid will reduce the amount of labeled A bound to the lipid.

A "variant" of a protein is defined as an amino acid sequence which differs by one or more amino acids from a polypeptide sequence or any ortholog and/or homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.). Included within this definition are alterations to the genomic DNA sequence which encodes TGD2 (i.e., for example, SEQ ID NO:1), the inability of a selected fragment of SEQ ID NO:1 to hybridize under high stringency conditions to a sample of genomic DNA (e.g., using allele-specific oligonucleotide probes), and improper or unexpected hybridization, such as hybridization to a locus other than a wild type chromosomal locus (e.g., using fluorescent in situ hybridization (FISH)).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring protein.

A "substitution" results from the replacement of one or more nucleotides or amino acids by different nucleotides or amino acids, respectively.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., Science 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: Molecular Cloning: A Laboratory Manual, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads), fluorescent dyes (e.g., fluorescein, texas red, rhodamine, green fluorescent protein, and the like), radiolabels (e.g., .sup.3H, sup.125I, .sup.35S, .sup.14C, or .sup.32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term, "test strip" as used herein, refers to any material capable of binding a protein, wherein the protein may capture a ligand without releasing from the material. For example, a test strip may comprises a glass slide coated with a polymer matrix, a silica material, absorbent fiber (i.e., for example, cloth or paper).

The term "test sample" or "sample" as used herein, refers to any material comprising phosphatidic acid that may be placed on a test strip, or may be treated for placement on a test strip such that the phosphatidic acid may be detected.

The term "complex" as used herein, refers to any stable interaction between two compounds such that a close association is formed. The complex may be stabilized by atomic interactions including, but not limited to, covalent bonding, non-covalent bonding, electrostatic interactions, hydrophobic interactions, or Van der Waals forces.

The term "capture" as used herein, refers to any compound having a stereospecific affinity for a second compound. For example, an antibody may capture a ligand wherein the antibody has been raised by an antigen to the ligand. Alternatively, a protein or enzyme may have a tertiary structure such that a ligand finds multiple points of interaction such that a stable complex is formed.

BRIEF DESCRIPTION OF DRAWINGS

FIG. 1 illustrates various exemplary embodiments and relationships of TGD2 amino acid sequences. Gene bank accession numbers for disclosed sequences: *Arabidopsis thaliana*, NP_566659.1 (SEQ ID NO: 5); *Vitis vinifera*, CAN71395.1 (SEQ ID NO: 6); *Oryza sativa*, EAY77419.1 (SEQ ID NO: 7; *Physcomitrella patens*, XP_001778862.1 (SEQ ID NO: 8); *Ostreococcus tauri*, CAL53419.1 (SEQ ID NO: 9); *Chlamydomonas reinhardtii*, XP_001699315.1 (SEQ ID NO: 10); *Prochlorococcus marinus* str. NATL2A, YP_292846.1 (SEQ ID NO:115); *Prochlorococcus marinus* str. MIT 9301, YP_001090537.1 (SEQ ID NO:116); *Synechococcus* sp. WH 5701, ZP_01083418.1 (SEQ ID NO:117); *Synechococcus* sp. CC9902, YP_376253.1 (SEQ ID NO:118); *Synechococcus* sp. JA-2-3B' a(2-13), YP_477327.1 (SEQ ID NO:119); *Anabaena variabilis*, YP_323182.1; *Nodularia spumigena*, ZP_01630545.1 (SEQ ID NO:120); *Crocosphaera watsonii*, ZP_00516249.1 (SEQ ID NO:121); *Cyanothece* sp. PCC 8801 (SEQ ID NO:122), ZP_02940544.1 (SEQ ID NO:123); *Microcystis aeruginosa*, CA090615.1 (SEQ ID NO:124); *Acaryochloris marina*, YP_001516641.1 (SEQ ID NO:125); *Thermosynechococcus elongatus*, NP_683197.1 (SEQ ID NO:126).

FIG. 2 presents exemplary data showing binding of DsRed-TGD2C WT fusion protein to PA as a function of weight percent of PA in PA/PC mixture.

FIG. 3 presents one exemplary embodiment of a phosphatidic acid (PA) binding domain on TGD2C by deletion and truncation mutagenesis.

FIG. 4 presents exemplary data showing the binding of a TGD2 minimal domain to PA.

FIG. 5A: PA binding for DsRed-TGD2C WT (DR-WT).

FIG. 5B: PA binding for DsRed-TGD2C minimal domain (DR-25).

FIG. 5C: Quantification of relative binding of PA for DR-WT and R-25.

FIG. 5D: PA binding for DsRed-TGD2C minimal domain (DR-25).

FIG. 5E: PA binding for DsRed-TGD2C with deletion of minimal domain (DR-Δ25).

FIG. 5F: Quantification of relative binding of PA for DR-25 and DR-Δ25.

FIG. 6A: A schematic of TGD2 domains indicating a predicted transit peptide domain (TP), a transmembrane domain (TMD), a conservative mammalian cell entry (MCE) domain, and a PA binding minimal domain (MBD).

FIG. 6B: Deletion and truncation mutants were generated on TGD2C and C-terminally fused to the DsRed open reading frame. Liposome-association assays were performed to assess binding of various mutants to PA liposomes (chromatographic plate, bottom).

FIG. 7A: schematically illustrates a TGD2 protein that is N-terminally truncated lacking a TMD and is C-terminally fused to the *Discosoma* sp. red fluorescent protein (DsRed, DR) open reading frame.

FIG. 7B: presents exemplary data from the expressed fusion protein using a protein-lipid overlay assay with a commercially available phospholipid-containing membrane strip. LPA, lysophosphatidic acid; LPC, lysophosphatidylcholine; Ptdlns, phosphatidylinositol; Ptdlns(3)P, phosphatidylinositol 3-phosphate; Ptdlns(4)P, phosphatidylinositol 4-phosphate; Ptdlns(5)P, phosphatidylinositol 5-phosphate; PE, phosphatidylethanolamine; PC, phosphatidylcholine; S1P, sphingosine 1-phosphate; Ptdlns(3,4)P2, phosphatidylinositol 3,4-bisphosphate; Ptdlns(3,5)P2, phosphatidylinositol 3,5-bisphosphate; Ptdlns(4,5)P2, phosphatidylinositol 4,5-bisphosphate; Ptdlns(3,4,5)P3, phosphatidylinositol 3,4,5-bisphosphate; PA, phosphatidic acid; PS, phosphatidylserine TGD2.

FIG. 8A: Membrane binding assay with commercial phospholipid-containing membrane.

FIG. 8B: Membrane binding assay with a plant lipid-containing membrane.

FIG. 8C: Liposome binding assay. Liposomes consisted of phosphatidylcholine (PC, first lane) or PC (60% wt/wt, second through fourth lanes) mixed with different molecular species of PA (40% wt/wt). PA molecular species tested were dioleoyl-PA (18:1), sn1-oleoyl, sn2-palmitoyl PA (18:1/16:0), and dipalmitoyl-PA (16:0). DGDG, prokaryotic digalactosyldiacylglycerol; DGDGe, eukaryotic digalactosyldiacylglycerol; L-PA, lysophosphatidic acid; L-PC, lysophosphatidylcholine; MGDG, prokaryotic monogalactosyldiacylglycerol; MGDGe, eukaryotic monogalactosyldiacylglycerol; PC, phosphatidylcholine; PE, phosphatidylethanolamine; PG, phosphatidylglycerol; PI, phosphatidylinositol; PIP(3), phosphatidylinositol 3-phosphate; PIP(4), phosphatidylinositol 4-phosphate; PIP(5), phosphatidylinositol 5-phosphate; PIP2(3,4), phosphatidylinositol 3,4-bisphosphate; PIP2(3,5), phosphatidylinositol 3,5-bisphosphate; PIP2(4,5), phosphatidylinositol 4,5-bisphosphate; PIP3(3,4,5), phosphatidylinositol 3,4,5-bisphosphate; PS, phosphatidylserine; S1P, sphingosine 1-phosphate; SQDG, sulfoquinovosyldiacylglycerol; TGDG, trigalactosyldiacylglycerol.

FIG. 10A: Thin-layer chromatogram of polar lipids. Lipids were visualized by α-naphthol staining.

FIG. 10B: Thin-layer chromatogram of neutral lipids. Lipids were visualized by exposure to iodine vapor.

FIG. 10C: Polar lipid composition (relative mol %) determined by quantification of fatty acid methylesters derived from individual lipids.

FIG. 10D: Fatty acid composition of the two galactolipids MGDG and DGDG.

FIG. 11A: Map position of the tgd2-1 mutation on chromosome 3 and structure of the TGD2 gene (At3g20320). Markers used for mapping and the respective number of recombinations are indicated. The TGD2 gene is indicated by a black box and expanded on the lowest line. The coding region of At3g20320 is shown as a shaded box. The darker shading indicates the predicted TMD. A region encoding an MCE domain is shown hashed. Introns are indicated by a line. Noncoding regions of the gene deduced from the cDNA are shown as open boxes.

FIG. 11B: Growth of different plants on soil (8 weeks old) with a genotype as indicated below the panel. Mutants were homozygous at all indicated loci. Three plants from independent transformation events expressing the TGD2 cDNA are indicated by "(c)."

FIG. 11C: Genotyping at the DGD1 locus. Point mutation-specific dCAPS markers were used, and ethidium bromide stained DNA diagnostic DNA fragments are shown with their respective lengths in base pairs.

FIG. 11D: Genotyping at the TGD2 locus. Point mutation-specific dCAPS markers were used, and ethidium bromide stained DNA diagnostic DNA fragments are shown with their respective lengths in base pairs.

FIG. 11E: Lipid phenotype of the six different plant lines. A section of thin-layer chromatogram stained for glycolipids is shown. DGDG, digalactosyldiacylglycerol; TGDG, trigalactosyldiacylglycerol.

FIG. 12A: Semiquantitative RT-PCR of mRNA levels derived from the TGD2 wild-type gene (top), the TGD2 wild-type gene and the tgd2-1 transgene (middle), and the ubiquitin (UBQ10) control (bottom). Negative images of ethidium bromide-stained gels are shown.

FIG. 12B: Polar lipid phenotype of the indicated plants. A section of the thin-layer chromatogram stained for glycolipids is shown. DGDG, digalactosyldiacylglycerol; SQDG, sulfoquinovosyldiacylglycerol; TGDG, trigalactosyldiacylglycerol.

FIG. 13A: Localization of full-length TGD2 protein fused to GFP (TGD2-GFP). The insertion of the respective protein into the membrane is schematically shown on the left. GFP, green fluorescence specific for GFP; Chl, red fluorescence of chloroplasts; the overlay of the two images is shown on the right. Confocal images are shown. (Scale bars: 10 μm)

FIG. 13B: Topology of the TGD2 protein. The wild-type TGD2 protein, the tgd2-1 mutant protein, and the GFP fusion were transiently produced in tobacco leaves, and isolated chloroplasts were analyzed. The TGD2 and tgd2-1 proteins were detected by using a TGD2-specific antibody. The GFP fusion was detected by using a GFP-specific antibody. Samples were untreated with protease (−) or treated with thermolysin (+, Th) or with trypsin (+, Tr). Immunoblots are shown.

FIG. 15A: Primary structure of TGD2 indicating a predicted transit peptide (TP), transmembrane domain (TMD) and a conservative mammalian cell entry (MCE) domain.

FIGS. 15B & 15C: A series of deletion and truncation mutants were generated on TGD2C and C-terminally fused to dsRed protein the same manner as WT TGD2C. Black ball represents dsRed protein, black bars represent deletion fragment. Liposome-association assays were performed to assess binding of various mutants to PC, PA/PC or PA liposomes. PA-specific binding data were summarized on the right. +++++, ++++, +++, ++, +, indicate a qualitative assessment of PA-specific binding in decreasing intensity, and −indicate no binding.

FIG. 17 presents an exemplary TGD2 ortholog sequences and phylogenetic organization in plants and Cyanobacteria.

FIG. 18A: Of phospholipids tested, the DsRED-TGD4-His protein bound specifically to PtdOH in a lipid overlay assay. LPtdOH, lysophosphatidic acid; LPtdCho, lysophosphatidylcholine; PtdIns, phosphatidylinositol; PtdIns(3)P, phosphatidylinositol 3-phosphate; PtdIns(4)P, phosphatidylinositol 4-phosphate; PtdIns(5)P, phosphatidylinositol 5-phosphate; PtdEtn, phosphatidylethanolamine; PtdCho, phosphatidylcholine; S1P, sphingosine 1-phosphate; Ptdlns(3,4)P2, phosphatidylinositol 3,4-bisphosphate; PtdIns(3,5)P2, phosphatidylinositol 3,5-bisphosphate; PtdIns(4,5)P2, phosphatidylinositol 4,5-bisphosphate; PtdIns(3,4,5)P3, phosphatidylinositol 3,4,5-triphosphate; PtdOH, phosphatidic acid; PtdSer, phosphatidylserine.

FIG. 18B: Of plant lipids tested, DsRED-TGD4-His protein bound to PtdOH in the lipid overlay assay. DAG, diacylglycerol; TAG, triacylglycerol; MGDG, monogalactosyldiacylglycerol; DGDG, digalactosyldiacylglycerol; SQDG, sulfoquinovosyldiacylglycerol; PtdGro, phosphatidylglycerol.

FIG. 18C: Effect of PtdOH fatty acyl chain length on DsRED-TGD4-His binding affinity in the liposome association assay. Liposomes contained 40 mol % PtdOH and 60 mol % PtdCho. M, protein marker; L, loading control; N, no liposome control; Fatty acids are indicated with their number of carbons: number of double bonds.

FIG. 18D: Effect of PtdOH fatty acyl desaturation levels on the DsRED-TGD4-His binding affinity in the liposome association assay. Liposomes contained 40 mol % PtdOH and 60-mol % PtdCho. 4ME 16:0, diphytanoyl phosphatidic acid; NBD-PtdOH, fluorescent NBD group labeled phosphatidic acid.

FIG. 18E: Effect of pH on PtdOH binding to DsRED-TGD4-His. Liposomes contained 40 mol % PtdOH and 60-mol % PtdCho.

FIG. 19A: A primary structure of the TGD4 protein, DsRED-His, DsRED-TGD4-His and truncation mutants. HR, hydrophobic region (cross-hatched bar); solid bar, TGD4; open bar, DsRED-His; gray bar, His tag; dashed line, deletion. The numbers refer to amino acids.

FIG. 19B: PtdOH binding affinity of DsRED-TGD4-His derivatives in the liposome-binding assay. Liposomes were made up of dioleoyl-PtdOH and dioleoyl-PtdCho. The weight percentage of PtdOH in the liposome varied from 0 to 80%. M, protein marker; L, loading control; N, no liposome control.

FIG. 20A: PtdOH separated by two-dimensional TLC. Wild type (WT) and tgd4-3 plants were compared. Abbreviations of lipids shown: TGDG, trigalactosyl-diacylglycerol.

FIG. 20B: Quantification of PtdOH by gas-liquid chromatography. Values represent the molar ratio of PtdOH to total lipids. Error bars indicated the standard deviation of three biological repeats.

FIG. 20C: PtdOH fatty acid profile of wild type (WT) and tgd4-2 mutants. Fatty acid species are designated with numbers of carbon:double bonds. Error bars represent the standard deviation of three plants.

FIG. 21A: Purified polyclonal antibody raised against DsRED-ΔTGD4-His specifically detects TGD4 in wild type (WT) but not in the tgd4-1 point mutant line. Numbers on the left indicate the molecular weights of protein markers in kDa.

FIG. 21B: TGD4 was enriched in chloroplast preparations compared to total leaf extracts. TOC75, chloroplast outer envelope marker; BIP, ER marker; RuBisBo, loading control.

FIG. 21C: TGD4 did not co-fractionate with ER markers on a sucrose gradient. TIC110, chloroplast inner envelope marker. Chlorophyll content serves as a thylakoid marker.

FIG. 22A: Wild-type (WT) chloroplasts were treated with 0 to 4 mg/ml Thermolysin. TX-100, tritonX-100; TOC 159, outer envelope marker. RuBisCo, stroma marker. TGD4 and TOC159 were detected by respective antibodies while RuBisCo was visualized by Coomassie Brilliant Blue staining.

FIG. 22B: Wild-type (WT) chloroplasts were treated with 0 to 0.8 mg/ml Trypsin.

FIG. 22C: Wild-type (WT) chloroplasts were treated with hypotonic buffer (alone), 2 M NaCl, 0.1 M $Na_2CO_3$ or 0.1 M NaOH followed by centrifugation. Chl, chloroplast; S, supernatant; P, pellet.

FIG. 22D: A histogram of the likelyhood of the secondary structure of TGD4 predicted by PROF (PredictProtein). Numbers represent the amino acids. WA, water accessibility.

FIG. 23A: 5 μg DsRED-TGD4-His was incubated with various protein stabilizers at 4° C. for 2 hours followed by centrifugation at 13,000×g for 10 minutes. The pellet was analyzed by SDS-PAGE. TBS: Tris-buffered saline, Glycerol: 20% glycerol; PEG: 20% polyethylene; Pectin: 5% pectin; ChoCl: 1 M choline chloride; Glycine: 1 M glycine; Urea: 1 M urea; BSA: 0.5 mg/ml bovine serum albumin; PBS: phosphate-buffered saline.

FIG. 23B: 5 μg DsRED-TGD4-His was treated with either 2 M sodium chloride or choline chloride as described above. NaCl alone is not able to stabilize DsRED-TGD4-His.

FIG. 24A: lipids isolated from wild type plants; and

FIG. 24B: lipids isolated from tgd4-1 mutant plants.

FIG. 27A: stained with α-naphthol,

FIG. 27B: stained with iodine vapor and

FIG. 27C: Three repeats are shown in each staining method. Abbreviations are DGDG, digalactosyldiacylglycerol; MGDG, monogalactosyldiacylglycerol; PC, phosphatidylcholine; PE, phosphatidylethanolamine; PG, phosphatidylglycerol; PI, phosphatidylinositol; and SQDG, sulfoquinovosyldiacylglycerol.

FIG. 29 shows an exemplary fatty acid profile of MGDG in the wild type Co12 (white columns) and the tgd4-1 mutant (black columns). Fatty acids are presented as the number of carbons followed by the number of double bonds. Three repeats are averaged and standard deviations are shown.

FIG. 30 shows an exemplary polar lipid composition of the wild type Co12 (white columns) and the tgd4-1 mutant (black columns). Three repeats were averaged and standard deviations are shown by error bar.

FIG. 31 shows an exemplary trigalactosyldiacylglycerol 4 (TGD4) nucleic acid sequence and encoded TGD4 proteins for use in expressing trigalactosyldiacylglycerol sequences and fragments thereof.

FIG. 31A: N-terminal amino acids 1-286 (SEQ ID NO: 130), C-terminal amino acids 309-479 (SEQ ID NO: 131), full-length TGD4 amino acids 1-479 (SEQ ID NO: 132), N-terminal coding sequence starting with ATG and encoding amino acids 1-286 (SEQ ID NO: 134), ΔTGD4 (SEQ ID NO: 133) hydrophobic region of 23 amino acids (287D-309F) was removed:

FIG. 31B-1-31B-2: N-terminal coding sequence starting with ATG (SEQ ID NO: 134) amino acids 1-286 and C-terminal coding sequence starting with TTT (SEQ ID NO: 135) encoding amino acids 309-479 and ΔTGD4 coding sequence (SEQ ID NO: 138).

FIG. 31C-1-31C-2: full-length TGD4 (AT3G06960.1) (SEQ ID NO: 136) boxes mark the beginning and the end of the underlined coding sequence.

FIG. 32 shows an exemplary pLW01/DsRED-His sequence (SEQ ID NO: 137) for use in expressing trigalactosyldiacylglycerol sequences and framents thereof. Underlined region shows location of nucleic acids encoding the His (6×HIS) marker.

DETAILED DESCRIPTION OF THE INVENTION

Figure 1A:
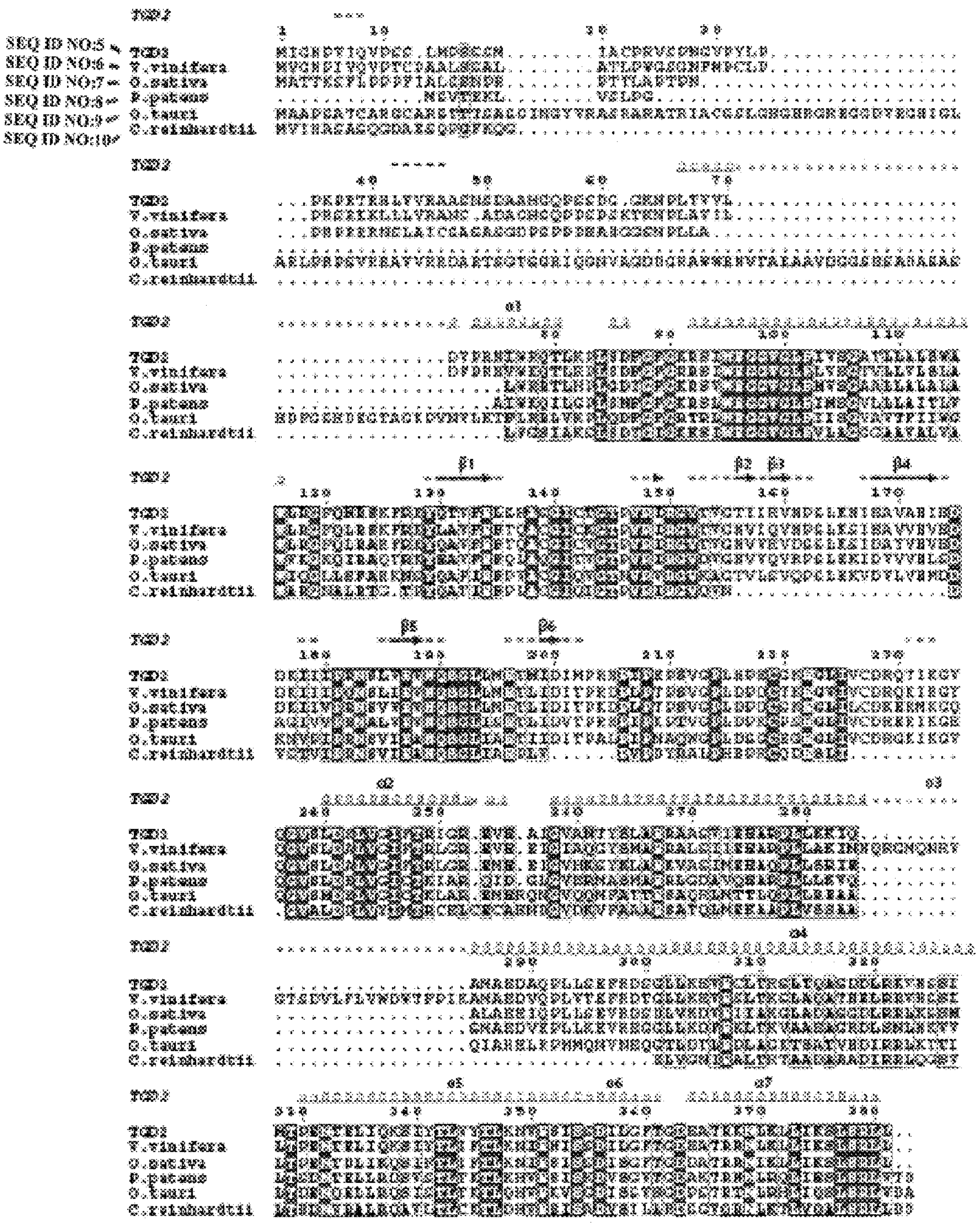
FIG. 1A: Alignments of the TGD2 sequence with various orthologs in plants and green algae. Predicted TGD2 secondary structure is shown on the top. Open boxes mark conserved residues, and black boxes indicate identical residues.

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. Phosphatidic acid may be in or from cells and tissues isolated from plants, animals and humans. For example, a trigalactosyldiacylglycerol-2 (TGD2) protein may be fused with a fluorescent probe to monitor and measure phosphatidic acid in vitro as well as in vivo. In other embodiments, a trigalactosyldiacylglycerol-4 (TGD4) protein may be fused with a fluorescent probe to monitor and measure phosphatidic acid in vitro as well as in vivo. In additional embodiments, a fragment comprising either a truncated TGD2 or TGD4 phosphatidic acid binding region protein may be used to monitor or measure phosphatidic acid.

Although phosphatidic acid is essential for animals, the amount in living cells is relatively low. Currently there are two methods typically used for detecting and quantifying phosphatidic acid in biological samples. 1. Two-Dimensional thin layer Chromatography coupled with Gas-Liquid Chromatography and 2. Tandem Mass Spectrometry. Both methods are time consuming or require expensive instrumentation. Further, the presence of different fatty acid chain lengths usually complicates the results using these methods. The inventors believe the compositions and methods of the present inventions overcome these limitations for accurately detecting phosphatidic acids. Further, compositions and methods of the present inventions are contemplated for use in identifying phosphatidic acids having particular carbon chain lengths.

The TGD4 protein and TGD4 truncated proteins discussed herein were able to detect phosphatidic acid specifically and unambiguously on a nano mole scale. No special equipment was needed beyond that available in routine clinical lab facilities. The method is contemplated for adaptation to high-throughput approaches. In one embodiment, a TGD4-HIS (histidine tag) expression construct of nucleic acid sequences was made as part of a pLW01/DsRED TGD4-HIS plasmid. The plasmid was used to transform an *E. coli* strain BL21 (DE3) for expression of DsRED-TGD4-HIS fusion protein. These recombinant proteins were purified on Ni-NTA columns. Target lipids were prepared as lipid extracts from test subjects including plants and animals. Lipid extract samples prepared from test subjects were then spotted onto nitrocellulose membranes. The purified TGD4 HIS tagged protein was then incubated on the spotted membrane under conditions that allowed TGD4 binding. Membranes were rinsed to remove unbound protein then incubated in an anti-HIS antibody followed by methods for visualization of bound antibody marking TGD4 bound to test lipids on the membrane. The results were quantified by ImageJ software. In other embodiments a plastic plate was used for liposome assays instead of a nitrocellulose membrane for an ELIZA type assay as one example of a high-throughput method. In conclusion, the invention presented herein is faster, accurate, sensitive, low-cost and capable for adaptation to high-throughput studies; see examples of methods in FIGS. 25 and 26.

In other embodiments, TGD2 may also be used in these types of methods in place of TGD4. TGD2 proteins of *Arabidopsis* are proposed to be a substrate binding component of a lipid transfer complex in the inner chloroplast envelope membrane. Loss of function of this protein or other components of this complex may disrupt the endoplasmic reticulum (ER)-pathway of thylakoid lipid biosynthesis. In one embodiment, the present invention contemplates a minimal binding domain capable of specifically binding phosphatidic acid. Alternatively, the minimal binding domain may further comprise accessory binding domains that, in combination, create a complete TGD2 phosphatidic acid binding domain. Consequently, phosphatidic acid may be quantitatively detected from samples as described in the methods herein.

The TGD2 protein of *Arabidopsis* is proposed to be the substrate binding component of a lipid transfer complex in the inner chloroplast envelope membrane. Loss of function of this protein or other components of this complex may disrupt the endoplasmic reticulum (ER)-pathway of thylakoid lipid biosynthesis.

In one embodiment, the present invention contemplates a method comprising fusing an open reading frame encoding the TGD2C truncated protein wherein the transit peptide and transmembrane domain are removed. In one embodiment, the protein is attached to the C-terminal of the *Discosoma* sp. red (DsRed) fluorescent protein open reading frame. In one embodiment, the fusion protein is in operable combination with a T7 promoter.

In one embodiment, the present invention contemplates a method comprising expressing a labeled TGD2C truncated fusion protein. In one embodiment, the label is a fluorescent label. In one embodiment, the fluorescent label comprises a *Discosoma* sp. red fluorescent protein (DsRed). Although it is not necessary to understand the mechanism of an invention, it is believed that the DsRed-TGD2C fusion protein specifically binds phosphatidic acid (PA). The data presented herein, demonstrates that the binding of DsRed-TGD2C to PA displays positive cooperativity with a Hill number of 5.8 and the apparent $K_d$ of 39.81 mol % PA (wt/wt). Further data presented herein, utilized deletion and truncation mutagenesis to identify a 25 amino acid TGD2C segment as a specific PA minimal binding domain.

The task of studying lipid-protein interactions is difficult due to the hydrophobicity property of the interacting molecules. Moreover, there are few reliable quantitative techniques available to assess specific binding kinetics and each method has its own limitations. Therefore, the present invention overcame these limitations by utilizing: (1) a protein-lipid overlay assay for rapid detection and qualitative assessment of binding; and (2) a liposome-association assay combined with densitometry quantification to evaluate relative binding between proteins. Together, these methods allow us to identify a specific binding domain and evaluate it semi-quantitatively.

I. Plant Lipid Biosynthesis.

As plant leaves expand, the demand on the lipid biosynthetic machinery is high because leaf cells contain one of the most extensive membrane systems found in Nature, for example, a chloroplast photosynthetic thylakoid membrane. Chloroplast thylakoid lipids include, but are not limited to, nonphosphorous galactolipids.

Galactolipid biosynthesis involves the formation of phosphatidic acid (PA) in the plastid and at the endoplasmic reticulum (ER) in many plants, including *Arabidopsis*. Browse et al., (1991) Annu. Rev. Plant Physiol. Plant Mol. Biol. 42:467-506; and Roughan et al., (1982) Annu. Rev. Plant Physiol. 33:97-132. Fatty acids derived from de novo synthesis in the plastid are assembled into PA in the plastid or at the ER. In *Arabidopsis*, diacylglycerols derived from the plastid pathway or the ER pathway are present in galactolipids in approximately equal proportion. Browse et al., (1986) Biochem. J. 235:25-31. The *Arabidopsis* lipid galactosyltransferases MGD1 and DGD1, which successively galactosylate diacylglycerol, are associated with the inner and the outer chloroplast envelope membranes, respectively. Benning et al., (2005) J. Biol. Chem. 280:2397-2400. The topology of the galactolipid biosynthetic machinery and the involvement of the ER pathway require extensive subcellular lipid trafficking, most of which is mechanistically not understood.

The inventors used a screening assay and discovered genes, i.e. TGD1, 2, and 3, involved with lipid synthesis in the chloroplasts. The respective tgd mutants accumulated abnormal oligogalactolipids, most prominently trigalactosyldiacylglycerol (TGDG), and lacked thylakoid lipids derived from the eukaryotic pathway. The accumulation of oligogalactolipids in these mutants were found to result from the activation of a processive galactosyltransferase, contemplated as a SENSITIVE TO FREEZING 2 (SFR2) protein. TGD1, 2, and 3 proteins resembled the components of a bacterial-type ATP Binding Cassette (ABC) transporter complex likely associated with the inner envelope membrane of the chloroplast. TGD1 contained multiple transmembrane domains and was proposed as a permease of the complex (Xu et al., 2003, herein incorporated by reference). TGD2 was similar to a substrate binding protein and bound specifically to phosphatidic acid (PtdOH) (Awai et al., 2006, herein incorporated by reference). TGD3 protein was discovered to function as an ATPase localized in the chloroplast stroma (Lu et al., 2007, herein incorporated by reference). TGD proteins were subsequently discovered involved in ER-to-chloroplast lipid transfer in *Arabidopsis* (Awai et al., 2006, Lu et al., 2007, Xu et al., 2003, Xu et al., 2008, all of which are herein incorporated by reference).

To date, two mutants of *Arabidopsis* have been described that affect lipid trafficking from the ER to the plastid. The actl (atsl) mutant is deficient in the plastidic glycerol 3-phosphate acyltransferase, and most of the galactolipids in this mutant are derived from the ER pathway. Kunst et al., (1988) Proc. Natl. Acad. Sci. USA 85:4143-4147. In contrast, galactolipids in the tgd1 mutant are primarily derived from the plastid pathway. Xu et al., (2003) EMBO J. 22:2370-2379. This mutant presents a complex lipid phenotype comprising: i) the accumulation of oligogalactolipids (i.e., for example, trigalactosyldiacylglycerol) and triacylglycerols in the leaves; ii) a 5-fold increase in PA content; and iii) an increase of 16-carbon fatty acids in the galactolipids. Xu et al., (2005) Plant Cell 17:3094-3110.

Such observations are believed indicative of a change in molecular species toward those formed de novo in the plastid. Xu et al., (2003) *EMBO J.* 22:2370-2379; and Xu et al., (2005) *Plant Cell* 17:3094-3110. These observations comprised pulse-chase labeling of leaves that were consistent with a disruption of the transfer of lipid molecular species from the ER to the plastid in the tgd1 mutant. Isolated tgd1 chloroplasts showed a decreased rate of conversion of labeled PA into galactolipids. The TGD1 protein resembles the permease component of bacterial ABC transporters and was shown to be an integral component of the inner chloroplast envelope membrane. Such data supports a proposed that TGD1 is a component of a PA transporter in the inner chloroplast envelope and may play a role in the biosynthesis of ER-derived molecular species of galactolipids. Stronger alleles of tgd1 led to increased embryo arrest and seed abortion, suggesting that the affected biological process is essential.

In one embodiment, the present invention contemplates a composition comprising a trigalactosyldiacylglycerol 2 (tgd2) mutant of *Arabidopsis*. In one embodiment, the composition comprises a TGD2 gene. In one embodiment, the composition comprises a TGD2 protein.

Pulse-chase labeling of leaves also indicates a disruption of the transfer of lipid molecular species from the ER to the plastid in the tgd1 mutant. For example, isolated tgd1 mutant chloroplasts show a decreased rate of conversion of labeled PA into galactolipids. The TGD1 protein resembles the permease component of bacterial ABC transporters and was shown to be an integral component of the inner chloroplast envelope membrane. Such observations lead to the proposal that TGD1 is a component of a PA transporter in the inner chloroplast envelope and that may be involved in biosynthesis of ER-derived molecular species of galactolipids. A second *Arabidopsis* TGD, trigalactosyldiacylglycerol 2 (tgd2), has been identified and characterized.

Protein importation into chloroplasts is believed to involve an interaction of protein complexes spanning the inner and outer chloroplast envelope membranes. Gutensohn et al., (2006) J. Plant Physiol. 163:333-347; and Jarvis et al., (2004) Curr. Biol. 14:R1064-R1077. Currently, knowledge about lipid importation into the plastid is extremely limited. Like protein importation into the plastid, ER-derived lipid importation during chloroplast biogenesis is extensive and presumably requires transporters mediating the transfer of lipids between and through the involved membranes.

As discussed above, TGD1 and TGD2 proteins may comprise components of a lipid transporter of the inner chloroplast envelope membrane. Although the analysis of the tgd1-1 mutant to date is far more extensive, it is apparent that the tgd2-1 mutation causes identical biochemical and physiological phenotypes: i) the accumulation of oligogalactolipids and triacylglycerols; ii) the increase of 16-carbon fatty acids in plastid lipids indicative of reduced presence of ER-derived molecular species; and iii) the increase in growth in the dgd1 background. Until the presently disclosed invention, a difference in phenotypes between TGD1 and TGD2 had not been identified, thereby suggesting that the products of the two genes are involved in the same biological process, thylakoid lipid biosynthesis from ER-derived precursors.

Currently available molecular analysis supported this interpretation because: i) TGD1 and TGD2 proteins are localized in the inner chloroplast envelope membrane; and ii) expression of green fluorescent protein (GFP) fusions for both proteins cause punctate fluorescence patterns in the periphery of plastids. Moreover, the *Arabidopsis* TGD1 and TGD2 proteins were reported as similar permeases and substrate-binding proteins of bacterial ABC transporters, respectively. Their corresponding bacterial orthologs are found in clusters, which is usually interpreted as meaning that the function of the gene products are in the same pathway or process. Overbeek et al., (2005) Nucleic Acids Res. 33:5691-5702.

Nonetheless, past research was unable to identify unambiguous evidence for any direct similarities in TGD1 and TGD2 function. Two findings suggest that TGD2 is active in a protein-lipid complex in *Arabidopsis* because: i) ectopic expression of the tgd2-1 mutant cDNA gives rise to the mutant phenotype, i.e., a dominant-negative mutation; and ii) the wild-type TGD2 protein is protected in isolated chloroplasts against trypsin whereas the TGD2 fusion protein is not. Both results can be interpreted as the association of the TGD2 protein with other proteins and/or specific lipid domains inaccessible to proteolytic activity.

Figure 8:
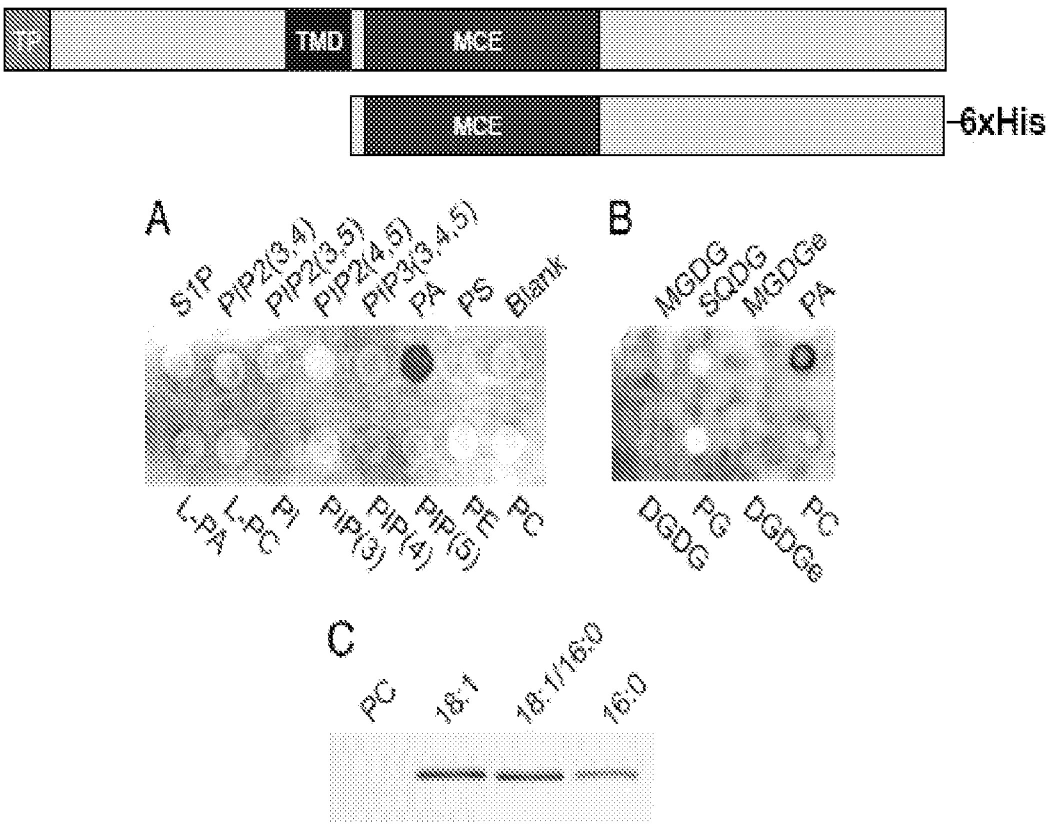
FIG. 8 presents exemplary data showing specific phosphidate binding to a recombinant TGD2C-His protein. Upper bars show the relative overlapping of a 6×His MCE binding fragment to a TGD2 protein. The 6×His TGD2 protein variant is N-terminally truncated lacking the TMD to exclude lipid binding to this region of the protein.
Figure 9:
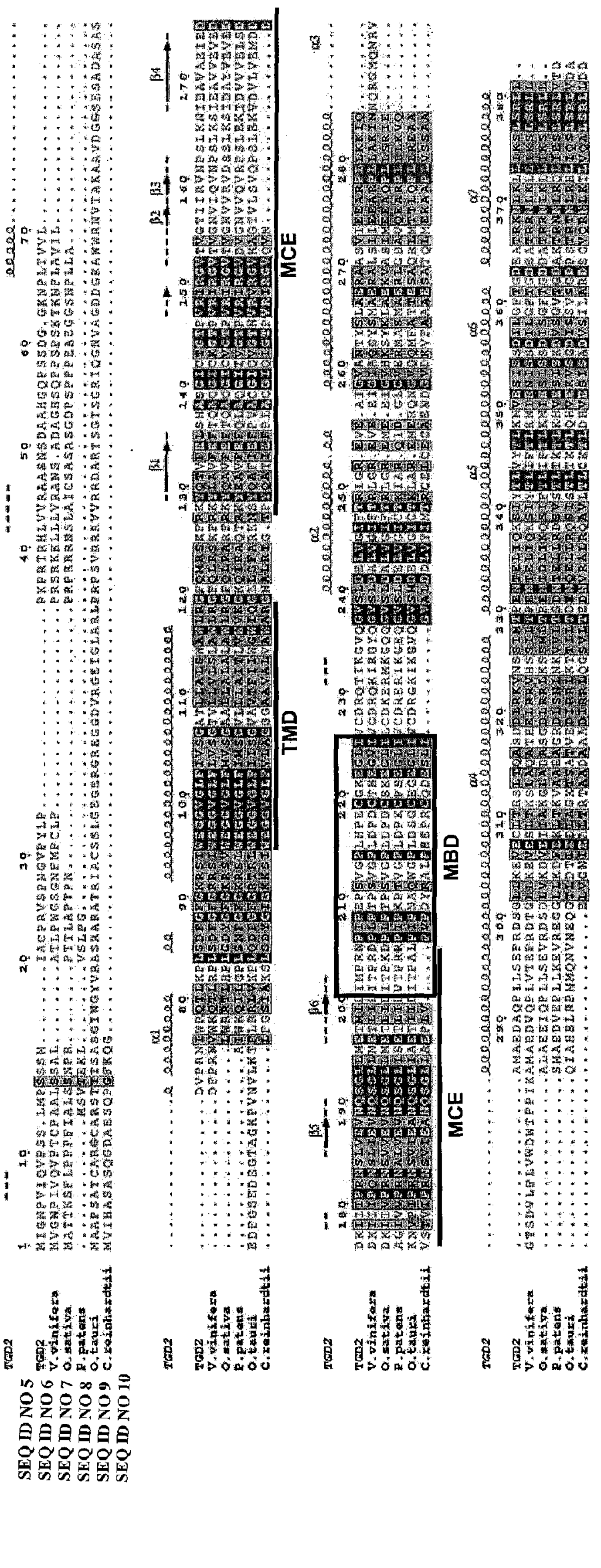
FIG. 9 demonstrates one exemplary embodiment of alignment comparisons showing that the TGD2 minimal PA binding domain is adjacent to the MCE domain.

Previous investigation of the tgd1-1 mutant indicated the accumulation of PA, and the reduced incorporation of PA into glycolipids of isolated plastids, led to the suggestion that the TGD1 protein is a component of a PA transporter. Xu et al., (2005) *Plant Cell* 17:3094-3110. Consistent with the proposed interaction of TGD1 and TGD2 in a PA-transporting complex, the recombinant TGD2 protein lacking the membrane-spanning domain was found to specifically bind PA. See, FIG. 8. An alternative interpretation would be that TGD2 binds PA as an effector molecule modulating the activity of TGD1. Further, TGD2 could remove a PA molecule from the outer envelope membrane and make it available to TGD1 for import into the plastid and conversion by the plastidic PA phosphatase. Because TGD2 appears to be tethered with its membrane-spanning domain to the inner envelope membrane, the PA binding domain might reach out to the inside of the outer envelope membrane either locally fusing the two membranes or extracting an ER-derived PA. Although, to date, there is no direct evidence for this hypothesis, one intriguing observation in support is derived from mycobacterial orthologs of TGD2 required for cell entry of the bacterium. Chitale et al., (2001) *Cell. Microbiol.* 3:247-254.

Recombinant bacterial orthologs can mediate the uptake of latex beads into mammalian cells, a process requiring an interaction of the protein on the bacterial surface with the mammalian cell membrane. The MCE domains present in the MCE proteins or bacterial substrate binding proteins associated with ABC transporters have been delineated based on sequence. The finding that TGD2 specifically binds PA, possibly through its MCE domain, might also be relevant to the possibilty that these bacterial proteins interact with membrane lipids.

II. Phosphatidic Acid and Plant Diseases.

Phosphatidic acid (PA) was recently identified as a putative signaling molecule in both plants and animals. Nonetheless, PA already appears to be equivalent to the classic second messengers $Ca^{2+}$ and/or cAMP. In plants, PA's formation may be triggered in response to various biotic and abiotic stress factors, including pathogen infection, drought, salinity, wounding and cold. In general, PA signal production is fast (i.e., for example, in minutes) and transient. Recently, reports indicated that PA formation in stress responses may be a result of phospholipases C and D activity. Moreover, some protein targets of PA have been identified. Testerink et al., "Phosphatidic acid: a multifunctional stress signaling lipid in plants" Trends Plant Sci. 2005 August; 10(8):368-375.

Phospholipid-derived molecules maybe involved as second messengers in plant defense signaling. Recent research has begun to reveal PA signals produced by the enzymes phospholipase C, phospholipase D and phospholipase A2 in relationship to their putative downstream targets. These include, but are not limited to, the activation of a MAP kinase cascade and triggering of an oxidative burst by phosphatidic acid; the regulation of ion channels and proton pumps by lysophospholipids and free fatty acids; and the conversion of free fatty acids into bioactive octadecanoids such as jasmonic acid. Laxalt et al., "Phospholipid signalling in plant defence" Curr Opin Plant Biol. 2002 August; 5(4):332-338.

PA may also be a positive regulator of RPM1- or RPS2-mediated disease resistance signalling, and that an observed biphasic PA production may be a conserved feature of signalling induced by the coiled-coil nucleotide binding domain leucine-rich repeat class of resistance proteins. Bacterial pathogens are believed to deliver type III effector proteins into plant cells during an infection. On susceptible host plants, type III effectors contribute to virulence, but on resistant hosts they betray the pathogen to the plant's immune system and are functionally termed avirulence (Avr) proteins. Recognition induces a complex suite of cellular and molecular events comprising the plant's inducible defence response. As recognition of type III effector proteins occurs inside host cells, defence responses can be elicited by in planta expression of bacterial type III effectors. Andersson et al., "Phospholipase-dependent signalling during the AvrRpm1- and AvrRpt2-induced disease resistance responses in *Arabidopsis thaliana*" Plant J. 2006 September; 47(6):947-59.

Recognition of either of two type III effectors, AvrRpm1 or AvrRpt2 from *Pseudomonas syringae*, induced a biphasic accumulation of phosphatidic acid (PA). The first wave of PA accumulation correlated with disappearance of monophosphatidylinosotol (PIP) and is thus tentatively attributed to activation of a PIP specific phospholipase C (PLC) in concert with diacylglycerol kinase (DAGK) activity. Subsequent activation of phospholipase D (PLD) produced large amounts of PA from structural phospholipids. This later wave of PA accumulation was several orders of magnitude higher than the PLC-dependent first wave. Inhibition of phospholipases blocked the response, and feeding PA directly to leaf tissue caused cell death and defence-gene activation. Inhibitor studies ordered these events relative to other known signalling events during the plant defense response. Influx of extracellular $Ca^{2+}$ occurred downstream of PIP-degradation, but upstream of PLD activation. Production of reactive oxygen species occurred downstream of the phospholipases.

The involvement of phospholipase C/diacylglycerol kinase (PLC/DGK)-mediated signalling in oxidative burst and hypersensitive cell death was studied in rice suspension-cultured cells treated with benzothiadiazole (BTH) and infected by *Xanthomonas oryza* pv. *oryza* (Xoo), believed to be a causative factor of rice leaf blight disease. Treatment of rice suspension cells with BTH resulted in a significant oxidative burst, as indicated by accumulation of superoxide anion and $H_2O_2$, and hypersensitive cell death, as determined by Evans blue staining. A peak in oxidative burst was detected 3-4 h after BTH treatment and hypersensitive cell death was observed 8 h after treatment. In addition, significant oxidative burst and hypersensitive cell death were detected in BTH-treated suspension cells, but not in untreated control cells, after Xoo infection. Scavengers and antioxidants of active oxygen species, e.g., superoxide dismutase, catalase, N-acetylcysteine, and flavone, reduced significantly the BTH-induced oxidative burst and hypersensitive cell death, indicating that oxidative burst is required for BTH-induced hypersensitive cell death. Expression of the PLC/DGK pathway genes, a diacylglycerol kinase gene, OsDAGK1, and a phosphoinositide-specific phospholipase C gene, OsPI-PLC1, and a defense-related EREBP transcriptional factor gene, OsBIERF3, was activated in rice cells after BTH treatment and in the BTH-treated cells after Xoo infection. Treatment of rice cells with phosphatidic acid, a phospholipid signalling molecule, resulted in the production of oxidative burst and hypersensitive cell death. However, neomycin, a PLC inhibitor, inhibited partially but not completely the production of oxidative burst, hypersensitive cell death, and expression of OsBIERF3 and OsDAGK1 induced by BTH in rice cells. These results suggest that PLC/DGK-mediated signalling plays an important role in BTH-induced oxidative burst, hypersensitive response, and activation of defense response in rice. Chen et al., "Phospholipase C/diacylglycerol kinase-mediated signalling is required for benzothiadiazole-induced oxidative burst and hypersensitive cell death in rice suspension-cultured cells" Protoplasma. 2007; 230(1-2):13-21.

Phospholipase D (PLD) has been implicated in multiple plant stress responses. Its gene transcription and activity increase upon exposure to various stresses, and manipulation of PLD protein levels leads to altered stress tolerance. The plant PLD family is relatively large and heterogeneous, and different PLD isoforms are involved in separate stress responses. PLD and its product, phosphatidic acid, exert their effects by functioning in signal transduction cascades and by influencing the biophysical state of lipid membranes. Bargmann et al., "The role of phospholipase D in plant stress responses" Curr Opin Plant Biol. 2006 October; 9(5):515-22.

Metabolomic approaches were used to elucidate some key metabolite changes occurring during interactions of *Magnaporthe grisea*, a causative factor of rice blast disease, with an alternate host, *Brachypodium distachyon*. Fourier-transform infrared (FT-IR) spectroscopy provided a high-throughput metabolic fingerprint of *M. grisea* interacting with the *B. distachyon* accessions ABR1 (susceptible) and ABR5 (resistant). Principal component-discriminant function analysis (PC-DFA) allowed the differentiation between developing disease symptoms and host resistance. Examination of PC-DFA loading plots indicated that fatty acids were one chemical group that discriminated between responses by ABR1 and ABR5 to *M. grisea*. To identify these, non-polar extracts of *M. grisea*-challenged *B. distachyon* were directly infused into an electrospray ionization mass spectrometer (ESI-MS). PC-DFA indicated that *M. grisea*-challenged ABR1 and ABR5 were differentially clustered away from healthy material. Subtraction spectra and PC-DFA loadings plots revealed discriminatory analytes (m/z) between each interaction and seven metabolites were subsequently identified as phospholipids (PLs) by ESI-MS-MS. Phosphatidyl glycerol (PG) PLs were suppressed during both resistant and susceptible responses. By contrast, different phosphatidic acid PLs either increased or were reduced during resistance or during disease development. This suggests considerable and differential PL processing of membrane lipids during each interaction which may be associated with the elaboration/suppression of defence mechanisms or developing disease symptoms. Allwood et al., "Metabolomic approaches reveal that phosphatidic and phosphatidyl glycerol phospholipids are major discriminatory non-polar metabolites in responses by Brachypodium distachyon to challenge by *Magnaporthe grisea*" Plant J. 2006 May; 46(3):351-68.

Multiple forms of phospholipase D (PLD) were activated in response to wounding, and the expressions of PLDα, PLDβ, and PLDγ differed in wounded *Arabidopsis* leaves. Antisense abrogation of PLDα decreased post-wounding phosphatidic acid induction, jasmonic acid (JA), and a JA-regulated gene for vegetative storage protein. Examination of the genes involved in the initial steps of oxylipin synthesis revealed that abrogation of the PLDα attenuated the wound-induced expression of lipoxygenase 2 (LOX2) but had no effect on allene oxide synthase (AOS) or hydroperoxide lyase in wounded leaves. The systemic induction of LOX2, AOS, and vegetative storage protein was lower in the PLDα-suppressed plants than in wild-type plants, with AOS exhibiting a distinct pattern. These results indicate that activation of PLD mediates wound induction of JA and that LOX2 is probably a downstream target through which PLD promotes the production of JA. Wang et al., "Involvement of phospholipase D in wound-induced accumulation of jasmonic acid in *arabidopsis*" Plant Cell. 2000 November; 12(11):2237-2246.

III. Phosphatidic Acid as a Signaling Lipid.

Over the years, several signaling lipids have been identified in plants (1, 2). Among those are various important sphingolipids, glycerol lipids and fatty acid metabolites (3-6). Phosphatidic acid (PA), was found to be one representative signaling lipid. PA may represent a lipid second messenger that transiently accumulates in plants within minutes after a pathogen attack and/or a variety of stress conditions (i.e., for example, osmotic and temperature stress) (7-9). PA may be generated via two distinct pathways: i) by phosphalipase D (PLD), which is believed to hydrolyze structural phospholipids to generate PA; or ii) by sequential action of phospholipase C (PLC) and diacylglycerol (DAG) kinase (DGK), wherein PLC can hydrolyze phsophatidylinositol-4,5-bisphosphate [PtdIns(4,5)P2, PIP2] into inositol-1,4,5-trisphosphate [Ins(1,4,5)P3] and DAG, which may be immediately converted to PA by DGK (10).

A. Phosphatidic Acid Targets.

Despite ongoing efforts, the identification of PA targets has remained elusive. A few cellular targets of PA have been described but no clear lipid binding motif has been found. Although it is not necessary to understand the mechanism of an invention, it is believed that predicting biochemical interactions with PA may be difficult because since the putative targets may not share sequence similarity. For example, in mammalian cells, protein kinases Raf-1 (11; 12), protein phosphatases SHP-1(13) and PP1(14), and protein kinase Cc (15) have been reported as PA targets. In yeast, the SNARE protein Spo20p (16) and the inositol-regulated transcriptional repressor Opi1p (17) are putative PA targets.

Similarly, a limited number of PA targets have so far been identified in plants, for example, ABI1 (ABA insensitive 1) (18) and PDK1 (phosphoinositide-dependent kinase 1) (19). In one embodiment, the present invention contemplates that PA may be a positive regulator of the ABA signaling pathway. Although it is not necessary to understand the mechanism of an invention, it is believed that ABI1 may be a protein phosphatase 2C that negatively regulates ABA signaling, whereupon the ABA response, PA becomes induced and binds to ABI1, thereby reducing its phosphatase activity and resulting in translocation to the plasma membrane. Alternatively, *Arabidopsis* PDK1 is believed to be a protein kinase that binds both PA and phosphoinositides, whose activation is limited to PA and not by polyphosphoinositides (19, 20). Additional PA targets were isolated using a PA-affinity matrix, consisting of a PA analogue covalently linked to Affi-Gel 10, which is incubated with suspension-cultured tomato or *Arabidopsis* cell lysates (21). Mass spectrometry has shown that phosphoenolpyruvate carboxylase (PEPC) preferentially binds to PA over other phospholipids (21).

B. TGD2 as a PA Carrier.

PA is also believed to act as a substrate that may be directly transported across the membranes by phospholipids and thus play a role in membrane biogenesis. For instance, it is believed that TGD2 comprises a PA target involved in lipid trafficking between the ER and chloroplast. One study has suggested that TGD2C (i.e., the C-terminal 6×-His tag-fused protein of TGD2 having both the N-terminal transit peptide and transmembrane domain removed) interacts selectively with PA (22). Further, an *Arabidopsis* TGD2 protein is proposed to be the substrate-binding component of a lipid transfer complex in the inner chloroplast envelope membrane. Supporting this mechanism is the observation that the lipid transfer complex also comprises TGD1, a permease, wherein loss of function of TGD1 results in accumulation of PA in *Arabidopsis* plants (23, 24). Loss of function of other lipid transfer complex components also disrupt the endoplasmic reticulum (ER)-pathway of thylakoid lipid biosynthesis. Thus, TGD proteins, in general, play an active role in PA transport between the ER and the chloroplast, and possibly thylakoid lipid biosynthesis pathway as well.

In some embodiments, the present invention overcomes the known problems in the art in identifying PA-binding domains of TGD2 proteins because they do not share sequence homology to any other known PA-binding domains including, but not limited to, PX (25), pleckstrin homology (20) and some C2 domains (26). In one embodiment, the present invention contemplates a method for characterizing PA-binding domains in TGD2. In one embodiment, the TGD2 PA-binding domain is characterized using a protein-lipid overlay. In one embodiment, the TGD2 PA-binding domain is characterized using a liposome-association assay. In one embodiment, the TGD2 PA-binding domain is characterized using a mutagenesis.

1. TGD2 Orthologs.

In one embodiment, a TGD2 gene encodes a 381 amino acid protein with a calculated molecular mass of 41.6 kDa (i.e., for example, Accession Number At3g20320; SEQ ID NO: 1). TGD2 proteins may contain a conserved mycobacterial cell entry domain (MCE, amino acids 127-204; SEQ ID NO: 2) expressed as a surface protein of some pathogenic mycobacteria. Mycobacterial cell entry proteins are believed to be virulence factors proposed to facilitate the bacterial entry into mammalian host cells (32).

In one embodiment, the present invention contemplates an MCE domain comprising a TGD2 PA-binding site and/or complex. For example, a TGD2 transmembrane domain (amino acids 96-118; SEQ ID NO: 3) and a TGD2 chloroplast targeting peptide (amino acids 1-45; SEQ ID NO: 4) were predicted, see, FIG. 3A. Orthologs to these sequences were found in plants, green algae and Cyanobacteria (29); see, FIG. 1B. Further, a multiple sequence alignment of TGD2 to these orthologs demonstrates their relatedness, see, FIG. 1A.

2. PA Binding to a dsRed-TGD2C Wild Type Fusion Protein.

TGD2C-His has been hypothesized to specifically bind to PA, possibly through its predicted mammalian cell entry (MCE) domain (22). The inventors discovered that a DsRed fusion protein system provided a fusion protein having improved solubility in order to perform quantitative binding assays to validate this hypothesis.

Figure 15:
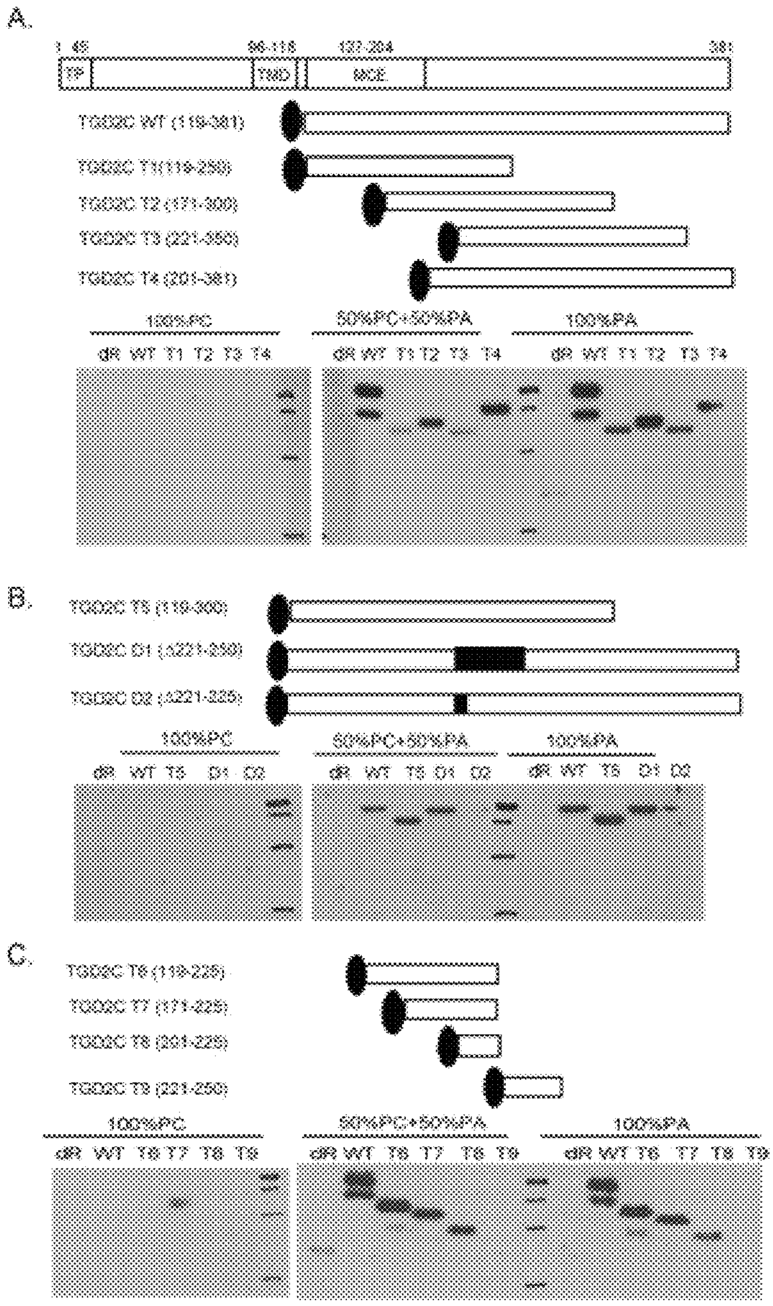
FIG. 15 presents exemplary data identifying a PA-binding minimal domain on TGD2C by deletion and truncation mutagenesis. Identification of a PA binding minimal domain on TGD2C by deletion and truncation mutagenesis.
Figure 16:
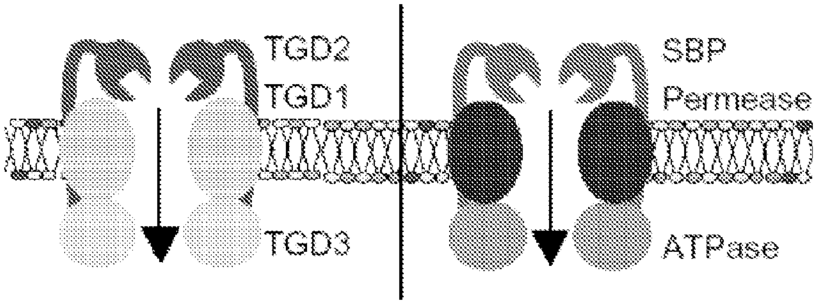
FIG. 16 presents an exemplary illustration showing the similarity between TGD proteins and bacterial ABC transporters.

For example, a commercial membrane strip pre-spotted with different phospholipids was used in a protein-lipid overlay assay with a DsRed-TGD2C WT fusion protein performed in accordance with Example II. The results suggested that, like TGD2C-His, a DsRed-TGD2C WT protein also shows specificity for PA over other lipids, see, FIG. 15, right. To verify that the binding was not due to non-specific PA interactions with DsRed, DsRed protein itself was also assayed for binding. No binding to any lipid for DsRed control was detected, indicating the specificity of this PA binding due to TGD2C protein moiety, see, FIG. 15, left.

Figure 2A:
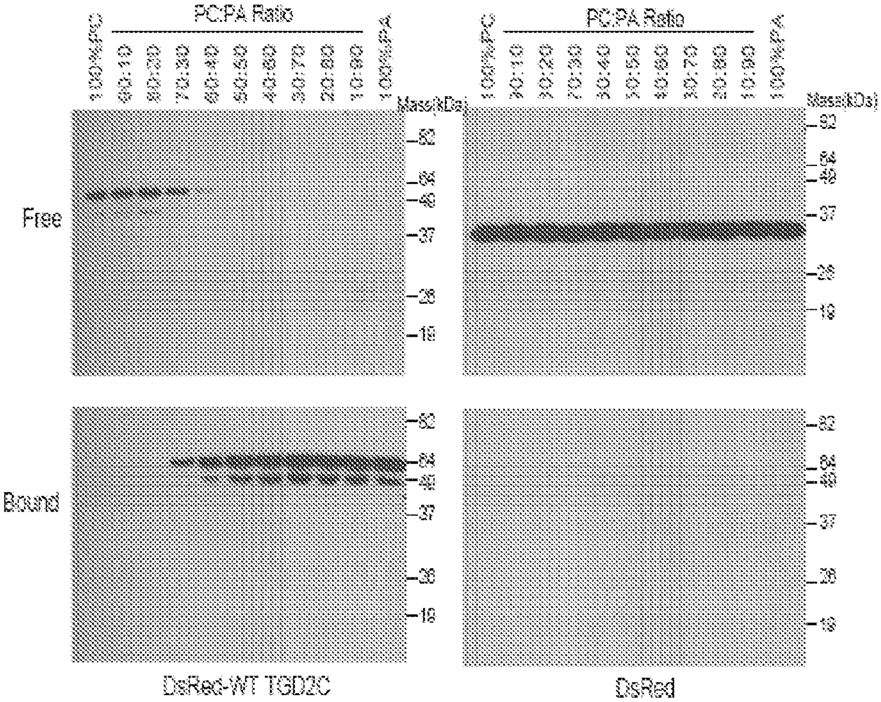
FIG. 2A: Analysis by liposome-association assay. A mixture of dioleoyl-PA and dioleoyl-PC was used where the weight percent of PA was varied from 0-100% (wt/wt), maintaining the total lipid invariant at 250 μg. 1 μg protein was used. P, protein recovered in the absence of lipids.

This result was further supported by lipsome association assay in accordance with Example III. In this assay, purified recombinant proteins were incubated with liposomes for 30 min at 30° C. before centrifugation at 20,000 g for 10 min to pellet the liposomes. Proteins bound to the liposomes were found associated with the lipid pellet, whereas non-binding proteins remained in the supernatant. In an effort to determine the optimal concentration of PA required for high specificity binding, a PA/PC liposome mixture containing varying weight fractions of PA was prepared and incubated with DsRed-TGD2CWT or DsRed alone. The DsRed-TGD2CWT fusion proteins were found to bind PC/PA liposome mixtures, as most of the proteins remained in the pellet/bound fraction, see, FIG. 2A, left panel, bottom. On the contrary, DsRed alone is almost exclusively present in the supernatant as a free form, see, FIG. 2A, right panel, top.

Figure 2B:
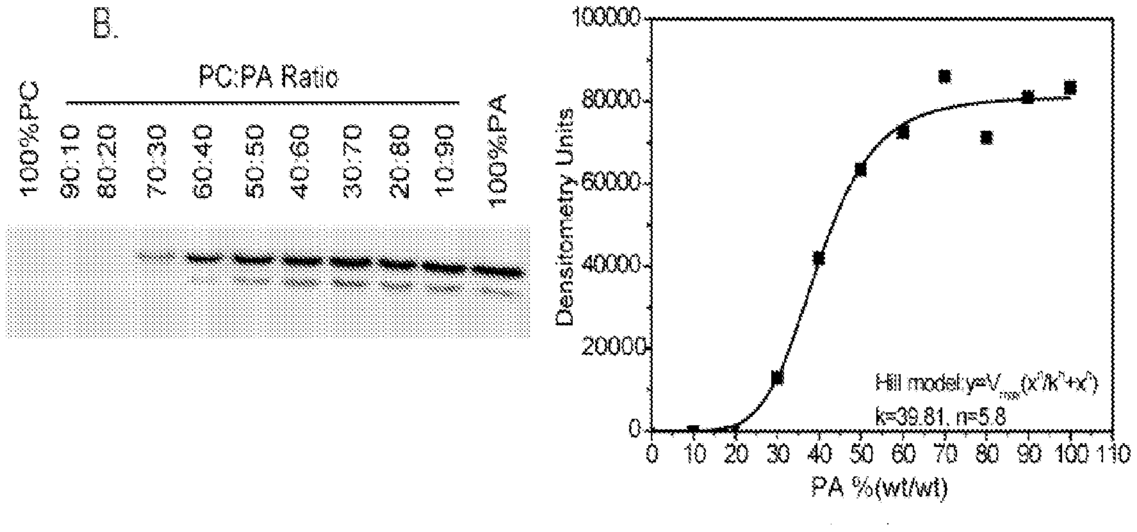
FIG. 2B: Association of DsRed-WT TGD2C to PA/PC liposomes as determined by scanning densitometry (left), and the values are plotted as a function of PA concentration in the liposomes (right). The data were fit to the modified Hill equation for receptor-ligand binding. A Hill number of 5.8 was obtained, suggestive of positive cooperativity.

At the tested protein concentration (1 μg total protein), a significant increase in binding occurred when the liposomes contained between approximately 30-40% PA. These blots were scanned, each individual band was quantified, and the resulted data was plotted and fit to the Hill equation for receptor-ligand binding, see, FIG. 2B. The data revealed that liposomes made with 100% PA bound the greatest amount of the protein. Moreover, from the Sigmoidal fit, the half maximal binding affinity ($K_d$) of DsRed-TGD2C WT for PA was estimated to be 39.8 mol % PA (wt/wt), which is comparable to the results obtained for RafC-PA association (20 mol % PA) (11). From the binding plot, a Hill number of 5.8 was obtained, suggestive of positive cooperativity, see, FIG. 2B. Again, this value is similar to that obtained for RafC-PA interaction (Hill number between 3.3 and 6.2) (11). The results may reflect that there is a cooperative sequestering of a domain of PA surrounding the C-terminal part of the TGD2 protein.

3. Identification of TGD2C PA Binding Regions.

It was reported that various reported PA-binding regions share no significant homology in primary structures (10). Consequently, attempting to identify any TGD2 PA binding domain was not intuitively obvious. In one embodiment, the present invention contemplates a method to identify TGD2 PA-binding regions by using a liposome-association assay. In one embodiment, the liposome association assay comprised incubating liposomes with purified mutant proteins. In one embodiment, the mutant proteins comprised amino acid sequences generated using a TGD2C nucleic acid template. In one embodiment, the TGD2C nucleic acid template generated deletion or truncation nucleic acid sequence mutants encoding a mutant TDG2C protein. In one embodiment, the nucleic acid sequence mutants were fused to a C-terminal end of a DsRed nucleic acid open reading frame. Although it is not necessary to understand the mechanism of an invention, it is believed that because the liposome association assay relies on a nonquantitative assessment of binding to identify regions of lipid interaction within the protein, maximizing the binding of TGD2 proteins was highly desired. The present data show that liposomes made with 100% PA bind the greatest amount of the TGD2 protein, see, FIG. 2. Hence, the binding reactions reported herein included liposomes comprised of 100% PA to achieve the highest lipid binding specificity. As a specificity control, liposomes comprised of 100% phosphatidylcholine (PC) and/or 50% PC+50% PA were included for comparison. Insolubility problems due to the deletion of large portions of the protein (i.e., for example, possibly exposing hydrophobic domain) were solved by using the DsRed protein as a solubilizing and stabling partner. As a result, all the generated mutant proteins disclosed herein were obtained at a satisfactory amount and purity. PA binding data for these representative TGD2 protein mutants are presented, see, FIG. 3.

Figure 3A:
FIG. 3A: A schematic of TGD2 domains indicating a predicted transit peptide domain (TP), a transmembrane domain (TMD) and a conservative mammalian cell entry (MCE) domain. Upper number represent linear order of amino acid residues.
Figure 3B:
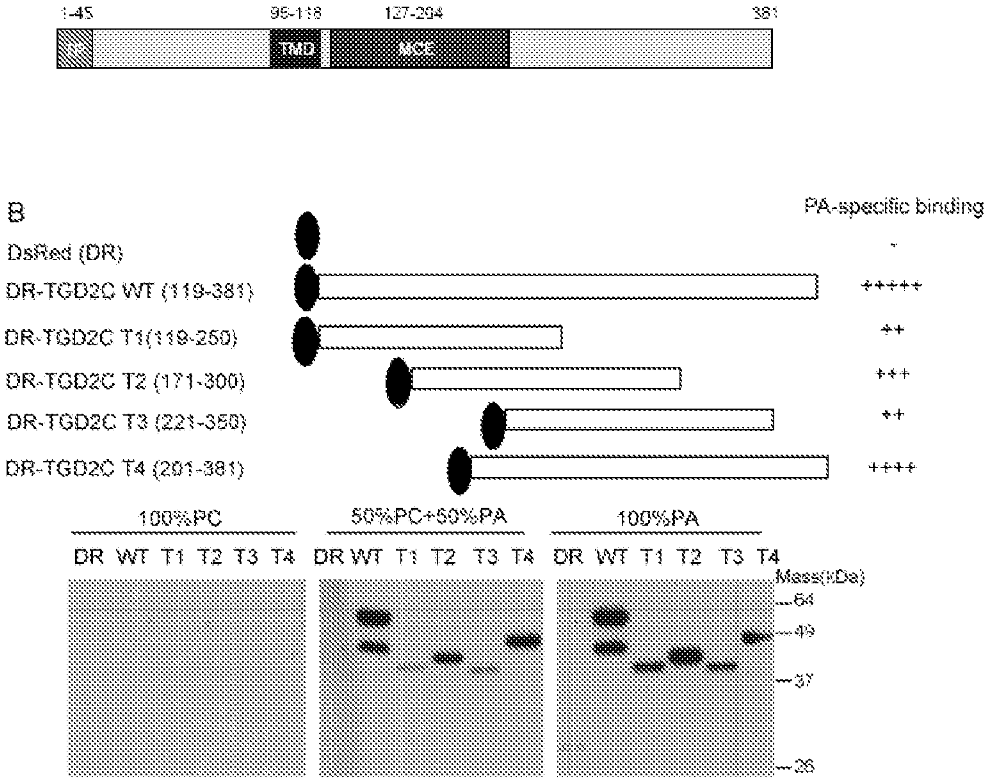
FIGS. 3B and 3C: Deletion and truncation mutants generated on TGD2C and C-terminally fused to the DsRed open reading frame the same manner as WT TGD2C. Black ball represents DsRed protein, grey bars represent deletion fragment. Liposome-association assays were performed to assess binding of various mutants to PC, PA/PC or PA liposomes. PA-specific binding data were summarized on the right. +++++, ++++, +++, ++, +, indicate a qualitative assessment of PA-specific binding in decreasing intensity, and –indicate no binding.
Figure 3C:
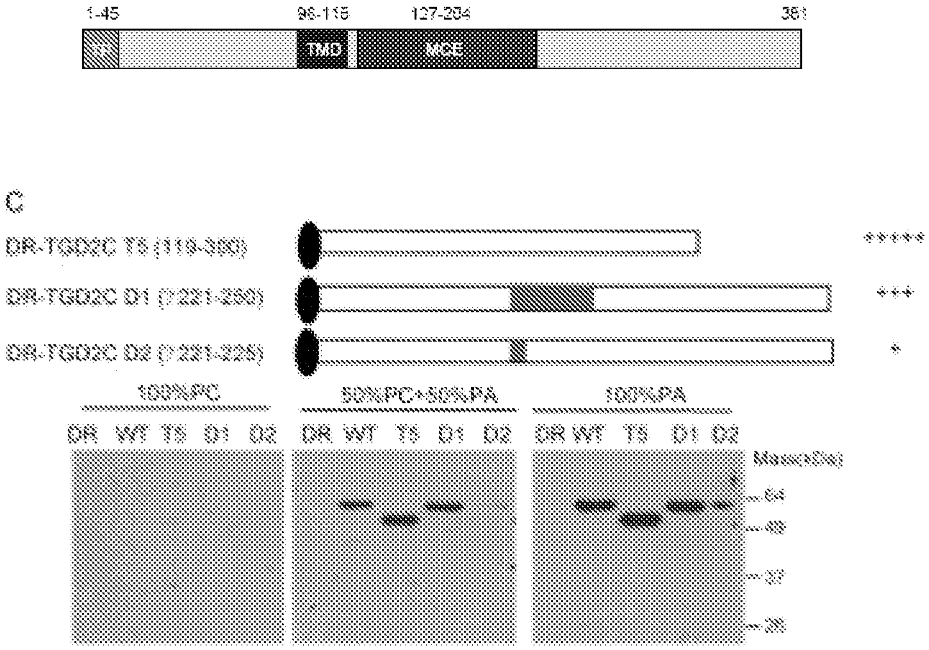

These data show binding characteristics of representative truncated TGD2 mutants ranging in length from between approximately 130 to 180 amino acids, see, FIG. 3A. DRWT (119-381) (SEQ ID NO:107) and four mutants displayed significant binding to PA, while having no interaction with the PC control lipid. DsRed itself does not display binding to either PC or PA, confirming the specificity of PA binding by TGD2, see, FIG. 3B. Although it is not necessary to understand the mechanism of an invention, it is believed that these data indicated that the PA-specific binding domain might reside in the TGD2 region comprising 221-250 amino acid residues (SEQ ID NO:40), since this region overlaps between the tested mutants.

Two internal deletion mutants within the 221-250 amino acid residues (SEQ ID NO:40) were then generated and tested for PA binding. Surprisingly, the deletion of the entire region of 221-250 amino acid residues (SEQ ID NO:40) did not seem to affect PA binding, while the deletion of a smaller 221-225 region (SEQ ID NO:108) decreased binding activity dramatically, see, FIG. 3C.

This data was completely counterintuitive and required considerable analysis before proceeding with further evaluation. Although it is not necessary to understand the mechanism of an invention, it is believed that protein folding effects may mediate this observation, wherein a deletion could potentially disrupt or reconstitute the protein structure and thus affect protein function depending on the realistic location of the function domain.

In one embodiment, the present invention contemplates a PA binding domain that is in or close to a TGD2 region comprising amino acid residues 221-250 (SEQ ID NO:40). Observations that a fifth mutant (i.e., comprising, amino acid residues 119-300 (SEQ ID NO:28)) also shows strong binding to PA provide corroborating data, see, FIG. 3C.

These initial deletion studies indicate that a region between residues 201 and 225 (SEQ ID NO:12) may be sufficient for PA specific binding, even when fused with DsRed. Furthermore, it was observed that this short fusion segment has much less overall binding, suggesting the presence of a minimal PA binding domain (infra).

4. Minimal TGD2 PA Binding Domain.

In one embodiment, the present invention contemplates a minimum TGD2 PA binding domain. In one embodiment, the binding domain was identified by fragmenting a TGD2 region comprising amino acid residues 119-250 (SEQ ID NO: 11). In one embodiment, the fragments were fused to DsRed, and assayed using liposome association.

Figure 4A:
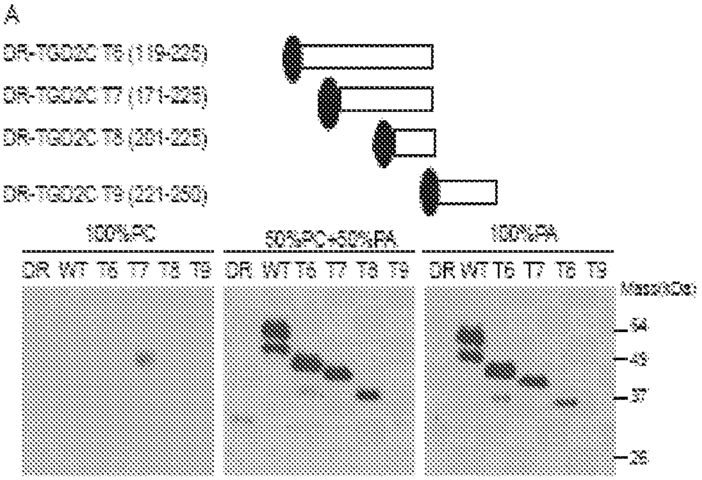
FIG. 4A: Truncation mutants generated to localize a PA binding domain. PA binding activities were assessed by liposome-association assay.
Figure 4B:
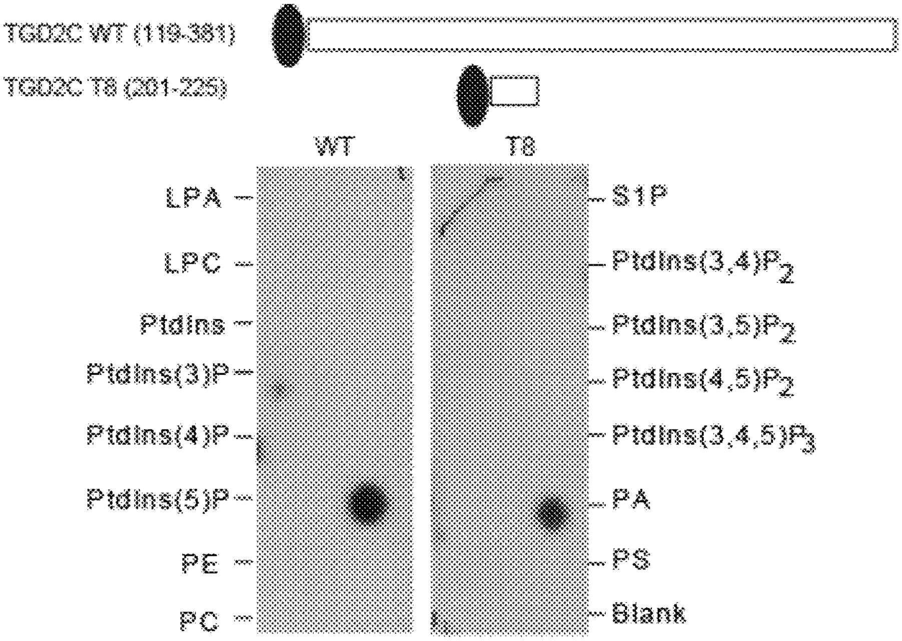
FIG. 4B: Verification of PA binding to a minimal domain (TGD2C T8 (201-225) (SEQ ID NO:12)) as compared to wild type (TGD2C WT (119-381) (SEQ ID NO:107)) by protein-lipid overlay assay conducted with commercial phospholipid-containing membrane strip. LPA, lysophosphatidic acid; LPC, lysophosphatidylcholine; Ptdlns, phosphatidylinositol; Ptdlns(3)P, phosphatidylinositol 3-phosphate; Ptdlns(4)P, phosphatidylinositol 4-phosphate; Ptdlns(5)P, phosphatidylinositol 5-phosphate; PE, phosphatidylethanolamine; PC, phosphatidylcholine; S1P, sphingosine 1-phosphate; Ptdlns(3,4)P2, phosphatidylinositol 3,4-bisphosphate; Ptdlns(3,5)P2, phosphatidylinositol 3,5-bisphosphate; Ptdlns(4,5)P2, phosphatidylinositol 4,5-bisphosphate; Ptdlns(3,4,5)P3, phosphatidylinositol 3,4,5-bisphosphate; PA, phosphatidic acid; PS, phosphatidylserine.

In brief, amino acids were removed from the N-terminal of TGD2C down to the middle of a TGD2C region comprising amino acid residues 221-250 (SEQ ID NO:40) (i.e., for example, amino acid residue 225), see, FIG. 4A. The data indicated that a 25 amino acid sequence (i.e., for example, amino acid residues 201-225; SEQ ID NO: 12) is sufficient to mediate specific binding to PA, see, FIG. 4A. A TGD2C region comprising amino acid residues 221-250 (SEQ ID NO:40) was also tested; however, no interaction to PA was detected. These data indicate that this TGD2C region may play a lesser role in PA binding, and partially explains why deletion of this region does not appreciably affect PA binding (supra). A protein-lipid overlay in accordance with Example II verified PA binding by the 25 amino acid sequence (SEQ ID NO: 12), see, FIG. 4B. Similar to DR-WT, this mutant itself binds PA on the membrane strip, with apparent lower affinity.

Figure 4C:
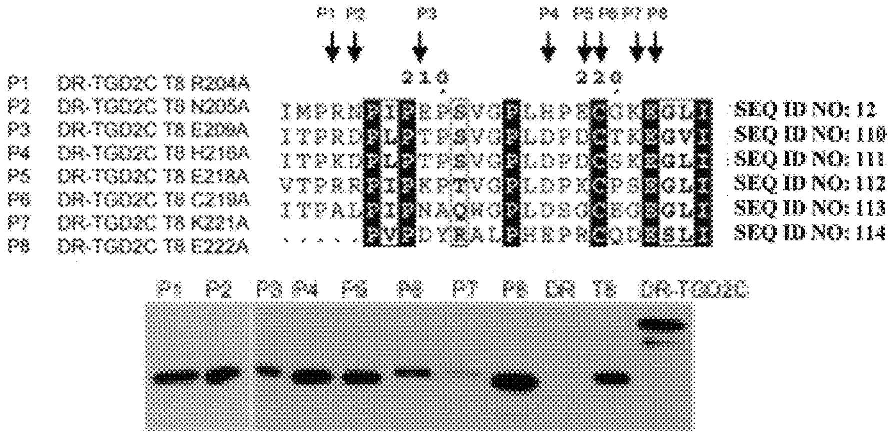
FIG. 4C: PA binding of point mutations on the minimal domain shown by liposome association assay with 100% PA liposomes. Point mutations are indicated by arrows.

Some reports have identified that TGD2 PA-binding regions involve basic amino acids and/or tryptophan residues (10). In particular, one recent study shows that electrostatic interactions of PA with basic amino acids (i.e., for example, lysine and/or arginine) combined with hydrogen bond interactions, may form a basis for specific binding of PA to PA targets (33). Based on sequence similarity of TGD2 to its closely related homologs in plants and green algae, several charged and/or conserved amino acids were picked as potential interesting residues in the 25-mer minimal domain for possibly mediating interactions with PA. An alanine screen was then performed to evaluate these residues within a minimal PA binding region of TGD2 (i.e., for example, SEQ ID NO:12). Point mutations were generated in the 25-mer minimal domain and fused with DsRed to test PA binding by liposome-association assay using 100% PA liposomes. The data demonstrate that, all point mutations have little or no effect on PA-liposome binding except K221A, see, FIG. 4C. This lysine-to-alanine mutation significantly reduced the amount of interaction with PA-liposomes. No detectable PC-liposome binding was observed for any of the constructs.

In one embodiment, the present invention contemplates a TGD2 PA binding domain comprising amino acid residues 201-225 (SEQ ID NO: 12). In one embodiment, the binding domain is adjacent to a MCE domain. Although it is not necessary to understand the mechanism of an invention, it is believed that mutation of $^{221}$Lys to $^{221}$Ala significantly diminishes PA binding. Further, upon generation of a point mutant (K221A) within a minimal domain, PA binding was diminished, thereby identifying $^{221}$Lys as an amino acid residue involved in PA binding. This discovery is consistent with previous hypotheses that basic amino acids and/or tryptophan might be involved in lipid PA binding (10; 33).

Figure 5:
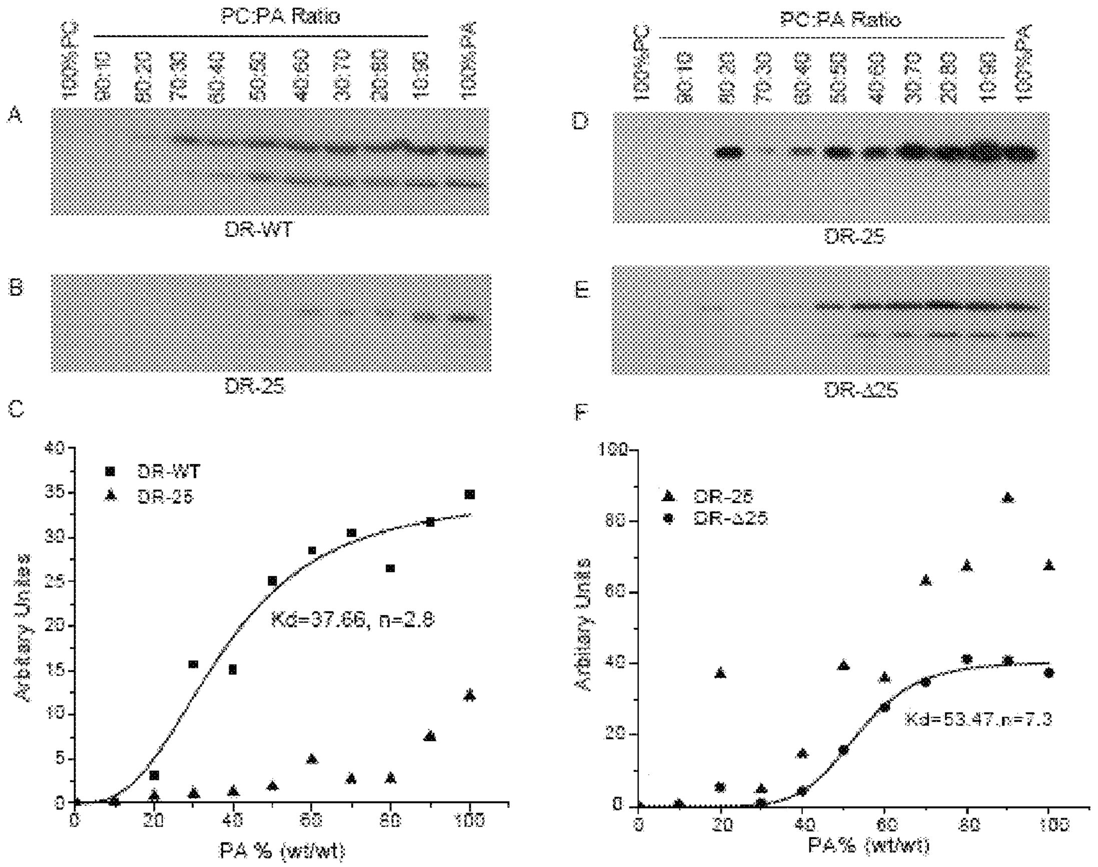
FIG. 5 presents exemplary data showing loss of positive cooperativity by a minimal binding domain.

Surprisingly, a PA binding TGD2 minimal domain is sufficient, but not necessary, to mediate interactions between TGD2 and PA liposomes. For example, a TGD2 fragment wherein a minimal domain was deleted still retains residual binding activity, albeit with significantly lower affinity. Moreover, a TGD2 protein having a minimal domain deletion still displays positive cooperativity to PA binding, see, FIGS. 5E and 5F. These data suggested the presence of accessory PA binding domains or segments that also play a role in cooperating PA binding by the minimal domain.

5. Accessory TGD2 PA Binding Components.

The above data showing that DR-WT protein displayed positive cooperativity upon PA binding suggested that a 25 amino acid sequence comprising a minimal PA binding domain may not be acting independently. Although it is not necessary to understand the mechanism of an invention, it is believed that the minimal binding domain may comprise accessory biochemical properties involved in PA binding. Liposome-association assay was performed with mixed PA/PC liposomes using DR-WT as a quantification control. The data show DR-25 binding to PA loses positive cooperativity, while DR-WT binding to PA still obeys the Hill equation, with a modified $K_d$ of 37.66 mol % and a Hill number of 2.8, see, FIGS. 5A-5C.

A 25-mer deletion mutant (designated as DR-Δ25) was generated that retained some residual PA binding activity. But moreover, the binding of this deletion mutant to PA also displayed positive cooperativity. An increased Kd of 53.47 mol % and a Hill number of 7.3 were identified from the fitting curve, see, FIGS. 5E and 5F. In contrast, the data show that DR-25 is not cooperative, see, FIGS. 5D and 5F. Apparently, a 25-mer minimal domain, alone, is sufficient to facilitate PA binding, but might also involve accessory components. In one embodiment, the present invention contemplates PA binding accessory components capable of modulating PA binding of TGD2 protein. This hypothesis is consistent with observations that some deletions of the TDG2 region comprising amino acid residues 221-250 (SEQ ID NO:40) do not affect PA binding, while some deletions of the TDG2 region comprising amino acid residues 221-225 (SEQ ID NO:108) significantly decrease PA binding activity. Although it is not necessary to understand the mechanism of an invention, it is believed that these observations also suggest that there are accessory PA binding components flanking the TGD2 region comprising amino acid residues 201-225 (SEQ ID NO:12), wherein different deletions differentially affect protein folding and, ultimately, functionality. This semi-quantitative analysis demonstrated that PA binding by a minimal domain lost positive cooperativity, which was also a property of wild type TGD2C protein.

Figure 6:
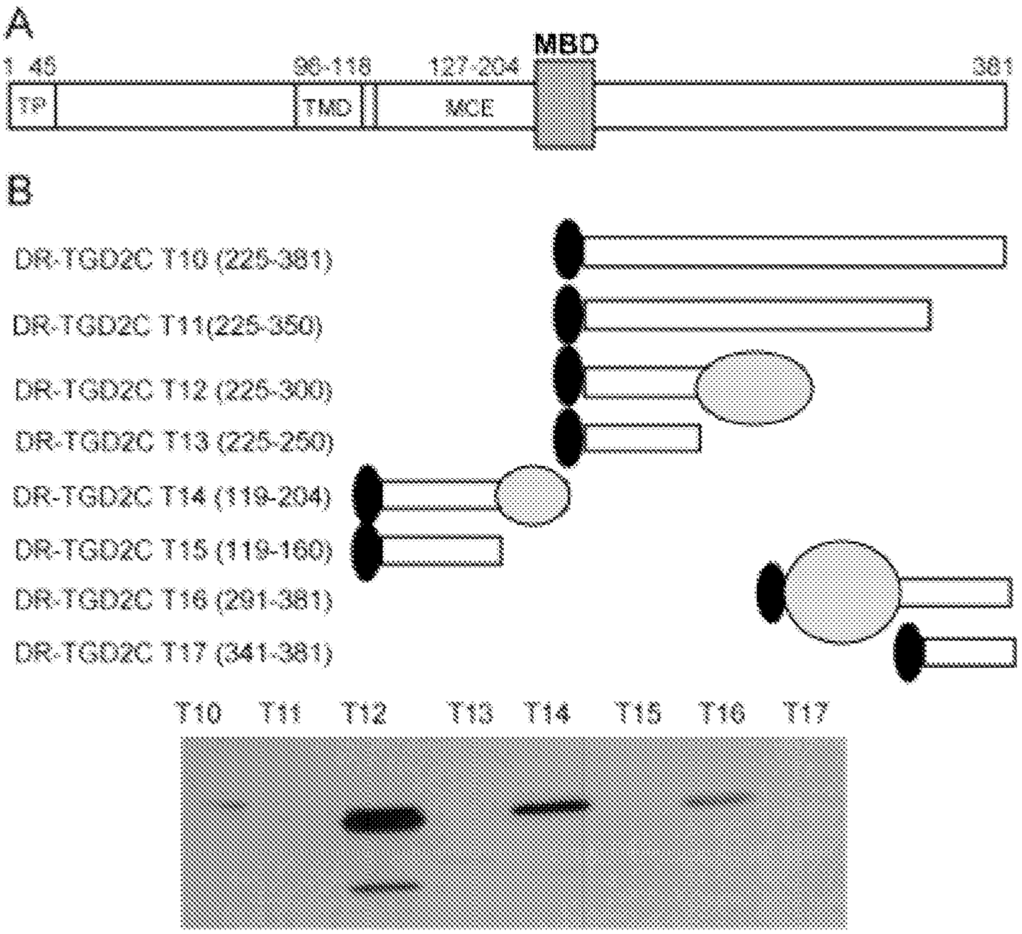
FIG. 6 illustrates additional embodiments of PA binding sites.

In one embodiment, the present invention contemplates a plurality of TGD2 accessory PA binding segments. For example, TGD2 mutants were generated with truncated sequences from either the C-terminus (i.e., for example, amino acid residue 381) or within the middle of TGD2 (i.e., for example, amino acid residue 204) and fused to a DsRed open reading frame, see, FIG. 6B. These mutated TGD2 proteins were tested for PA binding by using the liposome association assay using 100% PA liposomes. The data show that, at least four mutants were found to have various PA binding activity, see, FIG. 6B. In one embodiment, a TGD2 accessory PA binding site comprises amino acid residues 251-300 (SEQ ID NO:103). In one embodiment, a TGD2 accessory PA binding site comprises amino acid residues 161-204 (SEQ ID NO:104). In one embodiment, a TGD2 accessory PA binding site comprises amino acid residues 291-340 (SEQ ID NO:105).

6. A TDG2 PA Binding Motif.

In one embodiment, the present invention contemplates a TGD2 minimal PA binding region comprising a PA binding motif. In one embodiment, a PA binding motif further comprises at least three other regions in proximity with, or adjacent to, a TGD2 minimal PA binding domain. In one embodiment, the TGD2 minimal PA binding domain comprises amino acid residues 201-225 (SEQ ID NO:12), wherein at least one amino acid residue is a proline. In one embodiment, at least two amino acids are prolines. In one embodiment, at least three amino acids are prolines. In one embodiment, at least four amino acids are proline. In one embodiment, at least five amino acids are prolines. In one embodiment, at least six amino acids are prolines. Although it is not necessary to understand the mechanism of an invention, it is believed that proline residues within the TGD2 region comprising amino acid residues 201-225 (SEQ ID NO:12) may induce folding alongside an N-terminal β-strand and a C-terminal α-helix to form a PA binding site.

Figure 1B:
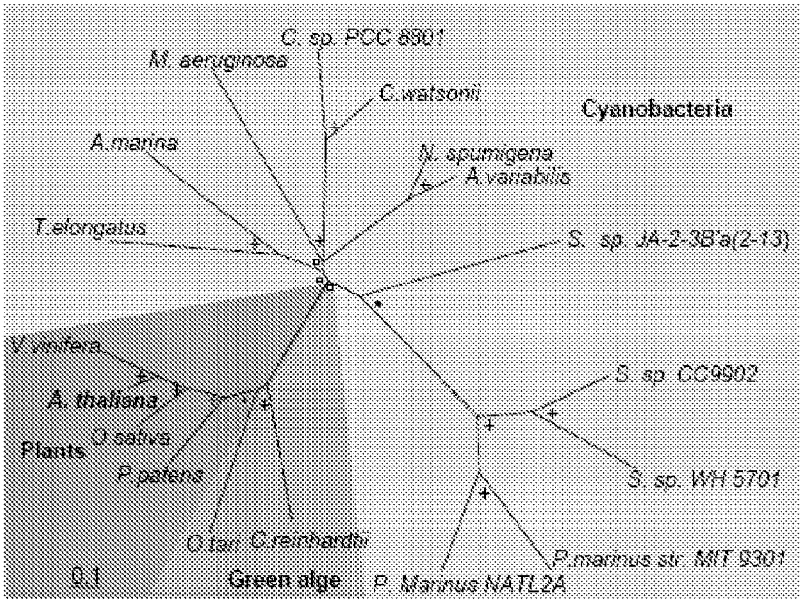
FIG. 1B: An 'unrooted tree' diagram showing the apparent relatedness of predicted TGD2 orthologs in plants, green algae and Cyanobacteria. Boot strapping values>950 are marked by +, those between 500 and 950 are marked with a solid circle, and those under 500 are marked by open square.

This proline-induced folding hypothesis is supported by a secondary structure prediction showing that residues 201-225 (SEQ ID NO:12) is a loop-strand fold lacks helical or β-strand structure, see, FIG. 1A. Therefore, a full PA binding domain on TGD2 likely comprises amino acid residues comprising a minimal PA binding domain (i.e., for example, TGD2 amino acid residues 201-225 (SEQ ID NO:12)) as well as amino acid residues present in both sides of a minimal PA binding domain (i.e., for example, amino acid residues 161-204 (SEQ ID NO:104) and/or amino acid residues 251-300 (SEQ ID NO:103)). Such a combination of a minimal PA binding domain with at least one accessory PA binding domain is believed to generate a complete PA binding domain having a complicated tertiary binding structure.

Because the TGD2 protein resembles substrate binding proteins of bacterial ABC transporters, and because the tgd2-1 phenotype was consistent with a defect in lipid transfer into the chloroplast, the TGD2 protein was tested for the specific binding of different lipids. To distinguish lipid binding to the TMD from lipid binding to a possible substrate site in the C-terminal domain, an N-terminally truncated version, TGD2-dTMD-His, was produced in *Escherichia* tag was used for purification and detection of TGD2-dTMD-His by an anti-His tag antibody. A commercial membrane with different phospholipids and membranes with plant-specific lipids were used. Of the lipids tested, including diacylglycerol, PA bound to TGD2-dTMD-His, see, FIG. 8A.

By employing an independent approach, the TGD2-dTMD-His protein bound phosphatidylcholine liposomes containing different molecular species of PA, see, FIG. 8B. Liposomes consisting of phosphatidylcholine alone did not bind. Binding was independent of the molecular species of PA at least at the semiquantitative immunoblot level. The results suggested that TGD2 contains a PA-specific binding domain in the C-terminal part of the protein.

7. Expression of TGD2 Fusion Proteins.

Proteins containing different fragments of *Arabidopsis* TGD2 were C-terminally fused to DsRed protein (i.e., for example, a *Discosoma* sp. reef coral protein) and expressed in *E. coli* BL-21 (DE3) strain using a DsRed-plw01-His vector in accordance with Example I. The quality of the expressed fusion protein was routinely monitored by SDS-PAGE followed by Coomassie Brilliant Blue staining. Typically, the purity of the DsRed-TGD2 fusion proteins was greater than 90%. A variety of DsRed-TGD2 mutated fusion proteins have been evaluated, see, Table 2.

TABLE 2

PCR primers used to create dsRed-TGD2 mutated fusion proteins.

| dsRed-TGD2 protein | mutation | 5' primer | 3' primer |
|---|---|---|---|
| TGD2C WT (SEQ ID NO: 13) (119-391) | WT | 5'-CCG GAG CTC GGT TTT CAA ATG CGG TC-3' (SEQ ID NO: 14) | 5'-CGG CTC GAG TAG TAG CCT GCT TAG GG-3' (SEQ ID NO: 15) |
| TGD2C TI (SEQ ID NO: 11) (119-250) | 119-250 | 5'-CCG GAG CTC GGT TTT CAA ATG CGG TC-3' (SEQ ID NO: 14) | 5'-GCG CTC GAG AAT ACG AGT GAA AAT TCC-3' (SEQ ID NO: 18) |
| TGD2C T2 (SEQ ID NO: 19) (171-300) | 171-300 | 5'-CCG GAG CTC GCT GAG ATA GAA GAT G-3' (SEQ ID NO: 20) | 5'-CGA CTC GAG GCT ATC ACG AAA CTC AG-3' (SEQ ID NO: 21) |
| TGD2C T3 (SEQ ID NO: 22) (221-350) | 221-350 | 5'-CAG GAG CTC AAG GAA GGT CTG ATC G-3' (SEQ ID NO: 23) | 5'-CGG CTC GAG GAC GTT CTT CAA AGT AT-3' (SEQ ID NO: 24) |
| TGD2C T4 (SEQ ID NO: 25) (201-381) | 201-381 | 5'-CCG GAG CTC ATT ATG CCT AGG AAT CCG-3' (SEQ ID NO: 26) | 5'-CGG CTC GAG TAG TAG CCT GCT TAG GG-3' (SEQ ID NO: 27) |
| TGD2C T5 (SEQ ID NO: 28) (119-300) | 119-300 | 5'-CCG GAG CTC GGT TTT CAA ATG CGG TC-3' (SEQ ID NO: 14) | 5'-CGA CTC GAG GCT ATC ACG AAA CTC AG-3' (SEQ ID NO: 21 |
| TGD2C T6 (SEQ ID NO: 31) (119-225) | 119-225 | 5'-CCG GAG CTC GGT TTT CAA ATG CGG TC-3' (SEQ ID NO: 14) | 5'-CGG CTC GAG GAT CAG ACC TTC CTT AC-3' (SEQ ID NO: 33) |
| TGD2C T7 (SEQ ID NO: 34 (171-225) | 171-225 | 5'-CCG GAG CTC GCT GAG ATA GAA GAT G-3' (SEQ ID NO: 35) | 5'-CGG CTC GAG GAT CAG ACC TTC CTT AC-3' (SEQ ID NO: 33) |
| TGD2C T8 (SEQ ID NO: 12 (201-225) | 201-225 | 5'-CCG GAG CTC ATT ATG CCT AGG AAT CCG-3' (SEQ ID NO: 26) | 5'-CGG CTC GAG GAT CAG ACC TTC CTT AC-3' (SEQ ID NO: 33) |
| TGD2C T9 (SEQ ID NO: 40) (221-250) | 221-250 | 5'-CAG GAG CTC AAG GAA GGT CTG ATC G-3' (SEQ ID NO: 23) | 5'-GCG CTC GAG AAT ACG AGT GAA AAT TCC-3' (SEQ ID NO: 18) |
| TGD2C D1 (SEQ ID NO: 43) (Δ221-250) | 221-250 deleted | 5'-CTG CAT CCT GAA TGT GGT GGA CGC GAA GTT GAG GCC-3' (SEQ ID NO: 44) | 5'-GGC CTC AAC TTC GCG TCC ACC ACA TTC AGG ATG CAG-3' (SEQ ID NO: 45) |

TABLE 2-continued

| PCR primers used to create dsRed-TGD2 mutated fusion proteins. | | | |
|---|---|---|---|
| dsRed-TGD2 protein | mutation | 5' primer | 3' primer |
| TGD2C D2 (SEQ ID NO: 46) (Δ221-225) | 221-225 deleted | 5'-CTG CAT CCT GAA TGT GGT GTT TGT GAT AGG CAG ACA-3' (SEQ ID NO: 47) | 5'-TGT CTG CCT ATC ACA AAC ACC ACA TTC AGG ATG CAG-3' (SEQ ID NO: 48) |

Results from one previous study indicated that the C-terminus of TGD2 protein lacking a transit peptide domain and transmembrane domain (TGD2C) could bind to PA when fused with 6×His tag (22). However, a major drawback of using this reported His-tag-fused-TGD2C protein is bad solubility, which brings significant technical difficulties when attempting mutagenesis and other in vitro studies. In fact, most reports in the lipid binding field use GST-fusion techniques to create a better solubilized protein. Further, GST-TGD2 fusion proteins also resulted in unsatisfactory results. While expression and purification of the GST-TGD2 fusion protein was possible, GST alone resulted in non-specific PA binding to the tested lipid substrates, leading to controversial conclusions.

Among several other expression systems tested, DsRed-fusion provided an optimized assay system and is described herein. The DsRed-monomer is an engineered mutant of the red fluorescent protein from *Discosoma* sp. reef coral, and has specific advantages of being extremely stable and highly soluble. These properties allow expression of soluble DsRed-TGD2 fusion proteins in order to monitor 'real time' fluorescence during recombinant protein production and purification.

Figure 7:
FIG. 7 presents exemplary data showing the binding of DsRed-TGD2C WT fusion protein to PA.
Figure 7:
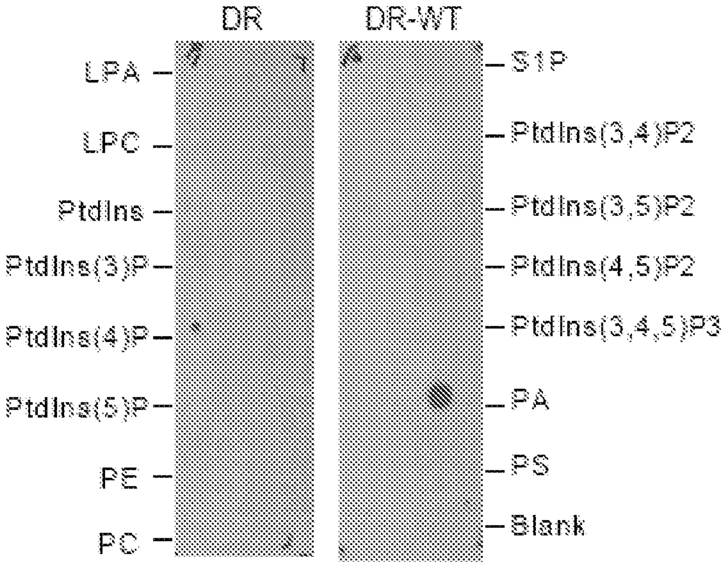

The data presented herein utilizes the same C-terminus of TGD2 protein as reported in the GST fusions, but were fused to DsRed instead. As discussed above, these DsRed-TGD2 fusion proteins demonstrated specific PA binding using protein-lipid overlay assay, see, FIG. 7. Furthermore, a minimal PA binding domain in TGD2 was identified that is sufficient to mediate the interaction between the protein and lipid. These data: i) demonstrate that TGD2 specifically binds PA and is a possible substrate for transportation by the proposed TGD123 complex; and (2) define a specific TGD2 PA binding domain that does not show any sequence or structure homology with known PA targets.

8. TGD2 Crystallography.

As discussed above, it is generally known that PA-binding regions reveal no significant homology in primary protein structure (i.e., linear amino acid sequence). (10). None of the previously reported PA targets were predicted by common amino acid sequences. Attempts to identify other PA binding proteins using a TGD2-minimal PA binding domain sequence (i.e., for example, amino acid residues 201-225 (SEQ ID NO:12)) yielded no results when searching a non-redundant protein database, see, FIG. 1A. Hence, homology modeling of TGD2 failed to find other possible PA binding sites in order to generate a working model. Therefore, further analysis will focus on crystallization PA with the full-length TGD2 in an effort to circumvent these difficulties.

IV. Isolation of a tgd2-1 Mutant.

The tgd2-1 mutant was initially identified during a suppressor screen in the dgd1 mutant background using a chemically induced mutant population. Xu et al., (2003) *EMBO J.* 22:2370-2379. The dgd1 mutant was reported to be deficient in DGD1, the protein believed responsible for the bulk of digalactolipid biosynthesis, Dormann et al., (1999) *Science* 284:2181-2184.

Presence of the tgd2-1 mutation in the dgd1 background partially alleviated the digalactolipid deficiency and caused the accumulation of a lipid co-chromatographing with trigalactosyldiacylglycerol diagnostic for all tgd mutants. Crossing the double-homozygous dgd1/tgd1-1 and dgd1/tgd2 mutants gave rise to uniform plants in the F1 generation with a homozygous dgd1-like phenotype, suggesting that tgd1-1 and tgd2-1 are not allelic. The tgd2-1/dgd1 homozygous double mutant was crossed to *Arabidopsis* wild-type, ecotype Columbia-2 (Col-2). The F1 plants showed a wild-type lipid phenotype confirming that the tgd2-1 mutant allele is recessive. After selfing and lipid analysis, F2 plants homozygous at the tgd2-1 locus were genotyped at the DGD1 locus by using a derived cut amplified polymorphic sequence (dCAPS) marker to test for loss of the dgd1 mutation. A homozygous tgd2-1 mutant line was back-crossed with wild type (Col-2) three times to reduce the chance of secondary mutations. Unless indicated otherwise, further analysis was done with this tgd2-1 mutant in the wild-type background.

Figure 10:
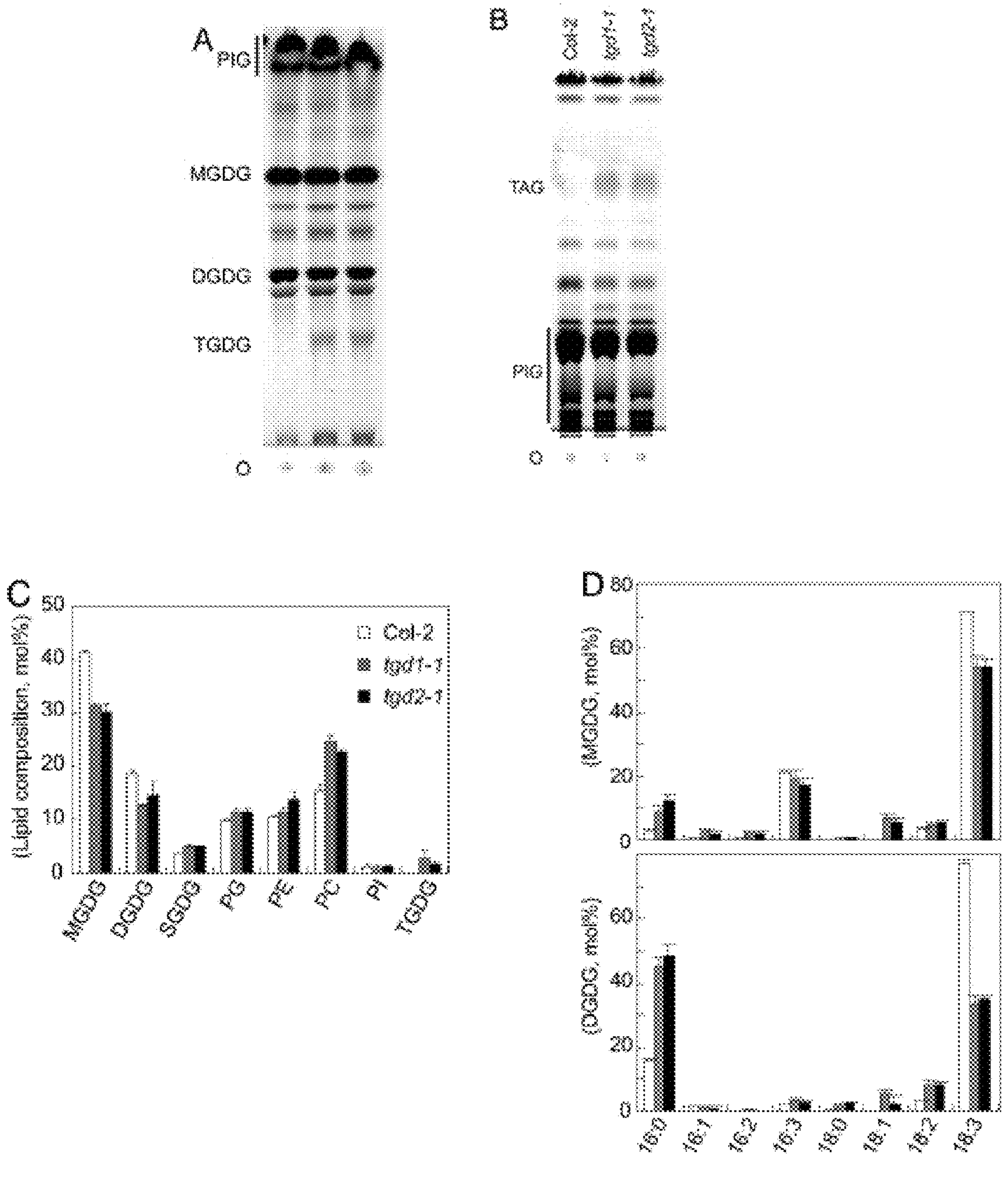
FIG. 10 presents exemplary data showing a lipid phenotype of the tgd2-1 mutant as compared with the tgd1-1 mutant and the Col-2 wild type. Fatty acids are indicated with number of carbons:number of double bonds. DGDG, digalactosyldiacylglycerol; MGDG, monogalactosyldiacylglycerol; O, origin; PC, phosphatidylcholine; PE, phosphatidylethanolamine; PG, phosphatidylglycerol; PI, phosphatidylinositol; PIG, pigments; SQDG, sulfoquinovosyldiacylglycerol; TAG, triacylglycerol; TGDG, trigalactosyldiacylglycerol.

Compared to the wild type, tgd2-1 plants were consistently smaller and slightly pale, as was observed for the tgd1-1 mutants, Xu et al., (2005) *Plant Cell* 17:3094-3110. Chlorophyll contents were reduced to a similar extent in the tgd1-1 and tgd2-1 mutants [chlorophyll (Chl) per gram of fresh weight (FW)±SD, n=4: wild type, 1,136±138 $\mu g_{Chl} \cdot g^{-1}$ FW; tgd1-1, 553±115 $\mu g_{Chl} \cdot g^{-1}$ FW; tgd2-1, 656±145 $\mu g_{Chl} \cdot g^{-1}$ FW]. Leaf lipid extracts of the wild type and the tgd1-1 and tgd2-1 mutants were compared by TLC. In the tgd2-1 sample a lipid staining positive for sugar and cochromatographing with authentic trigalactolipid of tgd1-1 is present, see, FIG. 10A. A lipid co-chromatographing with authentic triacylglycerol accumulating in tgd1-1 leaves was present in the tgd2-1 sample as well, see, FIG. 10B. Quantitative analysis of the polar lipids indicated similar changes in the two mutants with relative amounts of the monogalactolipid and digalactolipid reduced and relative amounts of phosphatidylcholine increased. See, FIG. 10C. In addition, trigalactolipid was present to a similar extent in both mutants (tgd1-1, 2.7±1.4 mol %; tgd2-1, 1.6±0.4 mol %; n=4; data are ±SD) but was not detectable in the wild type. Analyzing the fatty acid composition of the two galactolipids indicated a reduction of 18-carbon fatty acids and an increase in 16-carbon fatty acids to the same extent in both mutants, see, FIG. 10D. These overall fatty acid compositions for the tgd2-1 mutant imply a change in molecular species distribution in the two galactolipids consistent with a reduction of molecular species derived from the ER pathway. In addition, similar to the tgd1-1 mutant carrying a weak chemically-induced mutant allele, the tgd2-1 mutant produced a fraction (approximately 43%, 281 of 651 in a representative sample) of aborted seeds.

Figure 11:
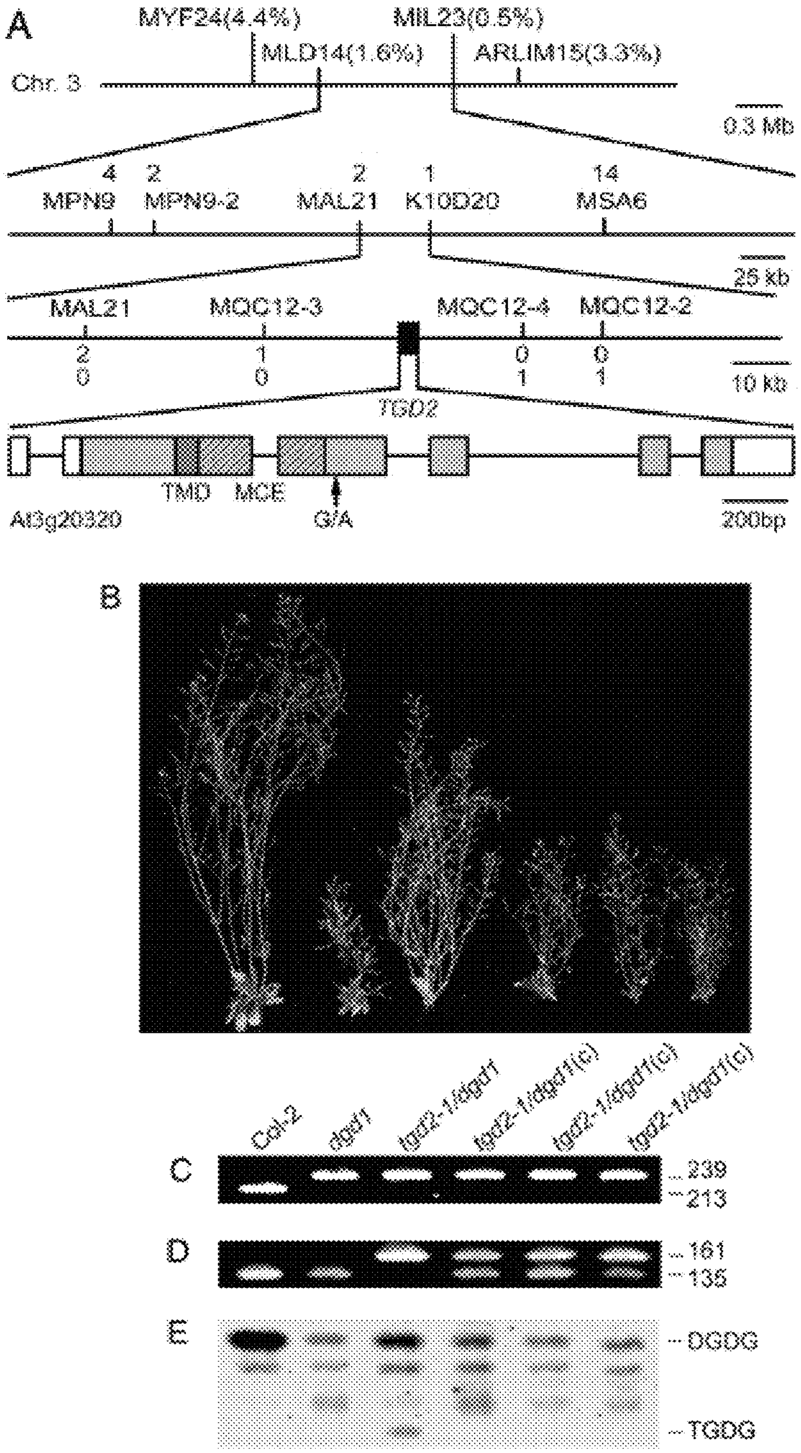
FIG. 11 presents exemplary data showing an identification of a TGD2 locus.

In a mapping population of 93 homozygous tgd2-1 F2 mutant plants (186 chromosomes) from a cross between the homozygous tgd2-1 mutant in the dgd1 (Col-2) background and a plant from the ecotype Landsberg erecta the tgd2-1 mutant locus was mapped close to cut amplified polymorphic sequence (CAPS) marker ARLIM15.1 (arabidopsis.org) at approximately 30 cM on chromosome 3, see, FIG. 11A. In an enlarged F2 mapping population from the same cross (3,506 chromosomes) the tgd2-1 mutant locus was mapped to an approximately 45-kb fragment flanked by CAPS marker MQC12-3 and dCAPS marker MQC12-4, see, FIG. 11A. This region falls onto the *Arabidopsis* bacterial artificial chromosome clone MQC12 (Gen-Bank accession no. AB024036 (SEQ ID NO:129)) and encompasses 14 predicted or confirmed genes (At3g20270-At3g20390). Notably, the translation product of At3g20320 (SEQ ID NO:1) was similar to the ttg2C protein (GenBank accession no. AAD17959 (SEQ ID NO:128); 25.0% identity over >100 aa) of *Pseudomonas putida*. This protein is predicted to be the substrate-binding protein of an ABC transporter, and its ORF is flanked by one encoding the ABC transporter permease ttg2B (GenBank accession no. AAD17958 (SEQ ID NO:127)). Most notably, the *Arabidopsis* TGD1 protein is similar to ttg2B (29.6% identity over >100 aa) of *P. putida*. The predicted bacterial ABC transporter encoded by the ttg2 operon in *P. putida* has been genetically implicated in toluene resistance, Kim et al., (1998) J. Bacteriol. 180:3692-3696. The At3g20320 cDNA sequence obtained by RT-PCR from the *Arabidopsis* tgd2-1 mutant contained a G-to-A mutation (See, FIG. 2A) corresponding to position 7,088,870 of the assembled chromosome 3 sequence (GenBank accession no. NC 003074) and leading to a glycine-to-arginine change in the amino acid sequence, see, FIG. 11A. This mutation was confirmed by designing a tgd2-1 allele-specific dCAPS marker that was later used for genotyping. See, FIG. 11D.

The TGD2 ORF of 1,146 bp encodes a protein of 41.6 kDa. In addition to the similarity to bacterial substrate binding proteins, the TGD2 protein contains a MCE domain (amino acids 99-216 (SEQ ID NO:109)), see, FIG. 11A, bottom. This domain is found in surface proteins of pathogenic mycobacteria. These proteins may comprise virulence factors proposed to facilitate the bacterial entry into mammalian host cells, Chitale et. al., (2001) *Cell. Microbiol.* 3:247-254. The mutation in tgd2-1 affects amino acid 234 just outside this MCE domain. A transmembranespanning domain (TMD) in TGD2 (amino acids 96-118 (SEQ ID NO:3)) was predicted by using SOSUI software, Hirokawa et al., (1998) *Bioinformatics* 14:378-379. A chloroplast targeting peptide of 45 N-terminal amino acids was predicted (score 0.545) by using CHLOROP with default settings. Emanuelsson et al., (1999) *Protein Sci.* 8:978-984.

V. TGD2 cDNA Expression.

The tgd2-1 mutation in the dgd1 mutant background led to increased growth compared with the homozygous dgd1 mutant. This phenotype was reversed by expression of the wild-type TGD2 cDNA under the control of the 35S-CMV (cauliflower mosaic virus) promoter in the tgd2-1/dgd1 homozygous double mutant, see, FIG. 11B. The genotypes were confirmed by using mutant allele-specific dCAPS markers, see, FIGS. 11C and 11D. In both transgenic lines two bands were present, a first band corresponding to a wild-type cDNA and a second band corresponding the a tgd2-1 genomic mutant locus, see, FIG. 11D. Reversion of the digalactolipid and the trigalactolipid phenotype of the tgd2-1/dgd1 double mutant to the homozygous dgd1 phenotype was observed as well, see, FIG. 11E. This complementation analysis confirmed the identity of the TGD2 gene as At3g20320.

The similarity of tgd1-1 and tgd2-1 mutant phenotypes and the organization of predicted bacterial orthologs of these two *Arabidopsis* genes in operons suggested that TGD1 and TGD2 act together in the same cellular process possibly as part of a larger lipid transfer complex. Expression of the tgd2-1 mutant cDNA under the control of the 35S-CMV promoter in the wild type led to the accumulation of a lipid cochromatographing with the trigalactolipid accumulating in the tgd1-1 and tgd2-1 mutants, see, FIG. 12B.

Figure 12:
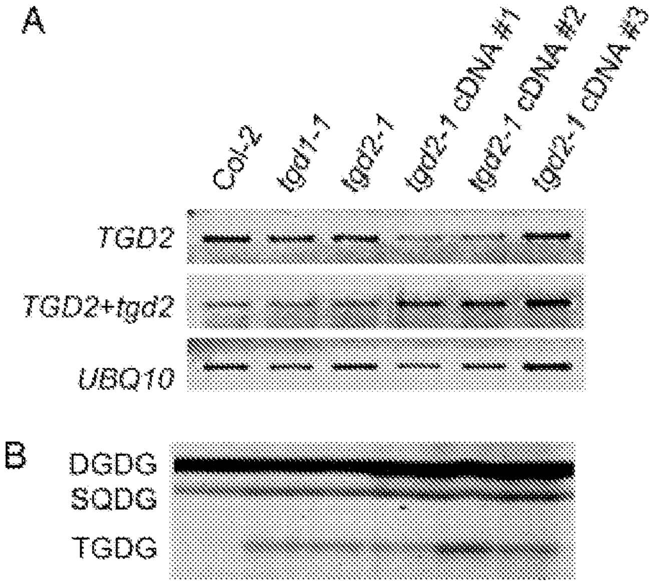
FIG. 12 presents exemplary data showing an expression of the tgd2-1 mutant cDNA in the Col-2 wild type. The untransformed wild type (Col-2) and the untransformed tgd1-1 and tgd2-1 mutants are included for comparison. Three independent transformants are shown.

Semiquantitative RT-PCR confirmed that this effect was not due to cosuppression of the genomic wild-type TGD2 gene and the tgd2-1 cDNA expression construct, because RNA derived from both genes was abundant in the transgenic lines, see, FIG. 12A. One interpretation of this dominant negative effect is that the tgd2−/−encoded mutant protein is impaired in its activity but can still become part of its native protein complex, thereby disrupting overall function of the process involving the complex. In addition, this result provided independent corroboration for the identity of TGD2 with At3g20320.

VI. TGD2 Intracellular Localization.

To determine the subcellular localization of the TGD2 protein, a construct encoding a full-length C-terminal fusion between the TGD2 protein and a GFP was transiently expressed in tobacco the periphery of chloroplasts. See, FIG. 13A. It should be noted that the equivalent experiment for the TGD1-GFP fusion construct showed a similar punctate fluorescence pattern at the chloroplast surface, Xu et al., (2005) *Plant Cell* 17:3094-3110.

Figure 13:
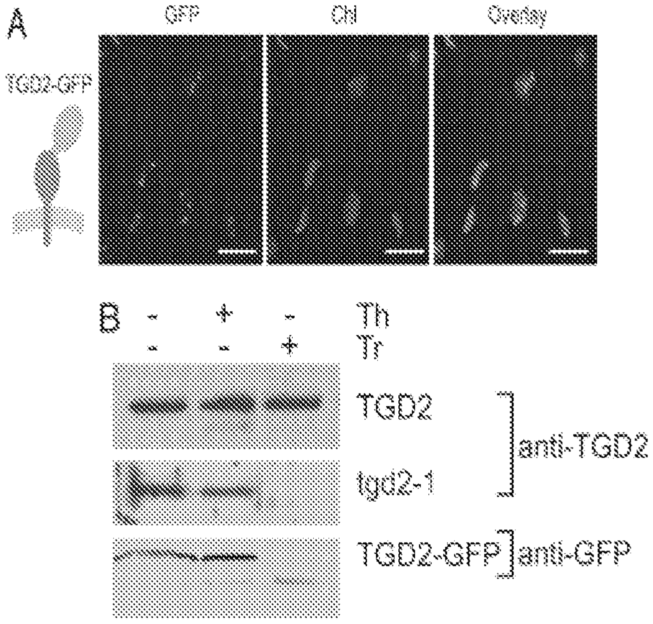
FIG. 13 presents exemplary data showing a subcellular localization and topology of TGD2 after transient expression in tobacco leaves.
Figure 14:
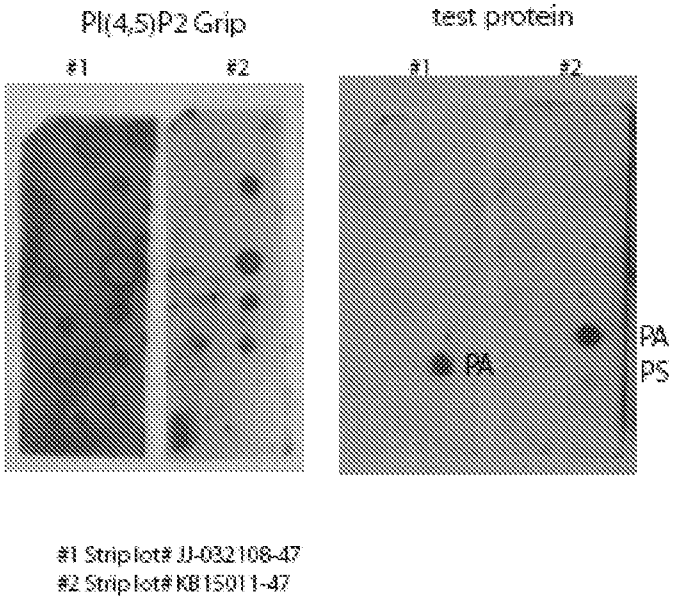
FIG. 14 presents one embodiment of a test strip that identifies a phosphatidic acid. Phosphatidylinositol 4,5 bis phosphate was chromatographed and compared to standard chromatograms of phosphatidic acid (PA) and phosphatidylserine (PS). Slides #1=Strip lot #JJ-032108-47 (#1 Left slide pair); Slides #2=Strip lot #KB15011-47 (#2 Left slide pair).

To further explore the association of the TGD2 protein with one of the two chloroplast envelope membranes and to determine its topology, chloroplasts were isolated from tobacco leaves expressing a wild-type TGD2 cDNA or the tgd2-1 mutant cDNA, see, FIG. 13B. The TGD2 wild type and the tgd2-1 mutant proteins were detected with a polyclonal antibody against TGD2. The chloroplasts were either untreated or treated with thermolysin, a protease unable to penetrate the outer envelope membrane, or trypsin, a protease able to penetrate the outer envelope but not the inner envelope membrane. Interestingly, the wild-type TGD2 protein was resistant to both proteases, whereas the mutant protein tgd2-1 was resistant to thermolysin but not trypsin. See, FIG. 13B, top and middle.

When the full-length wild-type TGD2 protein C-terminally fused to GFP was tested, the GFP tag detected by a GFP-specific antibody was resistant to thermolysin but not to trypsin. See, FIG. 13B, bottom. With the exception of the TGD2 wild-type protein, the result suggests that the TGD2 protein is associated with the inner envelope membrane with the C terminus facing the intermembrane space. The wild-type TGD2 is trypsin-resistant either because it is inside the plastid or, more likely, because it is in a complex or a membrane domain inaccessible to trypsin.

VII. Phosphatidic Acid-Binding Proteins.

A. Trigalactosyldiacylglycerol 2 (TGD2).

The TGD2 protein of *Arabidopsis* is proposed to be the substrate binding component of a lipid transfer complex in the inner chloroplast envelope. Loss of function of this protein or other components of this complex disrupts the ER-pathway of thylakoid lipid biosynthesis. Previous studies demonstrated that the C-terminal 6×-His tag-fused protein of TGD2 (TGD2C, with removal of the N-terminal transit peptide and transmembrane domain) interacts selectively with phosphatidic acid (PtdOH), Awai et al., (2006) "A phosphatidic acid-binding protein of the chloroplast inner envelope membrane involved in lipid trafficking" *Proc Natl Acad Sci USA* 103:10817-10822).

To improve expression and solubilization of this protein, the open reading frame encoding the TGD2C truncated protein C-terminally was fused to the *Discosoma* sp. red fluorescent protein (DsRed) open reading frame and expressed the fused open reading frame under the control of the T7 promoter. Like its predecessor, the DsRed-TGD2C fusion protein was shown to specifically bind PtdOH. By deletion and truncation mutagenesis, the PtdOH binding site within TGD2C was further narrowed down to a 25-amino-acid segment. Experimental results indicated this segment was necessary and sufficient for PtdOH binding. Crystallization of the DsRed-fusion protein would provide the basis for a stereochemical analysis of the binding interaction.

Various TGD2 fusion proteins may be made by polymerase chain reaction (PCR) using primers identified in Table 1:

TABLE 1

PCR primers used for generation of dsRed-TGD2 fusion proteins.

| dsRed-TGD2 protein | mutation | 5' primer | 3' primer |
|---|---|---|---|
| TGD2C WT (SEQ ID NO: 13) (119-391) | WT | 5'-CCG GAG CTC GGT TTT CAA ATG CGG TC-3' (SEQ ID NO: 14) | 5'-CGG CTC GAG TAG TAG CCT GCT TAG GG-3' (SEQ ID NO: 15) |
| TGD2C T1 (SEQ ID NO: 11) (119-250) | 119-250 | 5'-CCG GAG CTC GGT TTT CAA ATG CGG TC-3' (SEQ ID NO: 14) | 5'-GCG CTC GAG AAT ACG AGT GAA AAT TCC-3' (SEQ ID NO: 18) |
| TGD2C T2 (SEQ ID NO: 19) (171-300) | 171-300 | 5'-CCG GAG CTC GCT GAG ATA GAA GAT G-3' (SEQ ID NO: 20) | 5'-CGA CTC GAG GCT ATC ACG AA CTC AG-3' (SEQ ID NO: 21) |
| TGD2C T3 (SEQ ID NO: 22) (221-350) | 221-350 | 5'-CAG GAG CTC AAG GAA GGT CTG ATC G-3' (SEQ ID NO: 23) | 5'-CGG CTC GAG GAC GTT CTT CAA AGT AT-3' (SEQ ID NO: 24) |
| TGD2C T4 (SEQ ID NO: 25) (201-381) | 201-381 | 5'-CCG GAG CTC ATT ATG CCT AGG AAT CCG-3' (SEQ ID NO: 26) | 5'-CGG CTC GAG TAG TAG CCT GCT TAG GG-3' (SEQ ID NO: 27) |
| TGD2C T5 (SEQ ID NO: 28) (119-300) | 119-300 | 5'-CCG GAG CTC GGT TTT CAA ATG CGG TC-3' (SEQ ID NO: 17) | 5'-CGA CTC GAG GCT ATC ACG AA CTC AG-3' (SEQ ID NO: 21) |
| TGD2C T6 (SEQ ID NO: 31) (119-225) | 119-225 | 5'-CCG GAG CTC GGT TTT CAA ATG CGG TC-3' (SEQ ID NO: 17) | 5'-CGG CTC GAG GAT CAG ACC TTC CTT AC-3' (SEQ ID NO: 33) |
| TGD2C T7 (SEQ ID NO: 34) (171-225) | 171-225 | 5'-CCG GAG CTC GCT GAG ATA GAA GAT G-3' (SEQ ID NO: 35) | 5'-CGG CTC GAG GAT CAG ACC TTC CTT AC-3' (SEQ ID NO: 33) |
| TGD2C T8 (SEQ ID NO: 12) (201-225) | 201-225 | 5'-CCG GAG CTC ATT ATG CCT AGG AAT CCG-3' (SEQ ID NO: 26) | 5'-CGG CTC GAG GAT CAG ACC TTC CTT AC-3' (SEQ ID NO: 33) |
| TGD2C T9 (SEQ ID NO: 40) (221-250) | 221-250 | 5'-CAG GAG CTC AAG GAA GGT CTG ATC G-3' (SEQ ID NO: 23) | 5'-GCG CTC GAG AAT ACG AGT GAA AAT TCC-3' (SEQ ID NO: 18) |
| TGD2C D1 (SEQ ID NO: 43) (Δ221-250) | 221-250 deleted | 5'-CTG CAT CCT GAA TGT GGT GGA CGC GAA GTT GAG GCC-3' (SEQ ID NO: 44) | 5'-GGC CTC AAC TTC GCG TCC ACC ACA TTC AGG ATG CAG-3' (SEQ ID NO: 45) |
| TGD2C D2 (SEQ ID NO: 46) (Δ221-225) | 221-225 deleted | 5'-CTG CAT CCT GAA TGT GGT GTT TGT GAT AGG CAG ACA-3' (SEQ ID NO: 47) | 5'-TGT CTG CCT ATC ACA AAC ACC ACA TTC AGG ATG CAG-3' (SEQ ID NO: 48) |

Figure 17A:
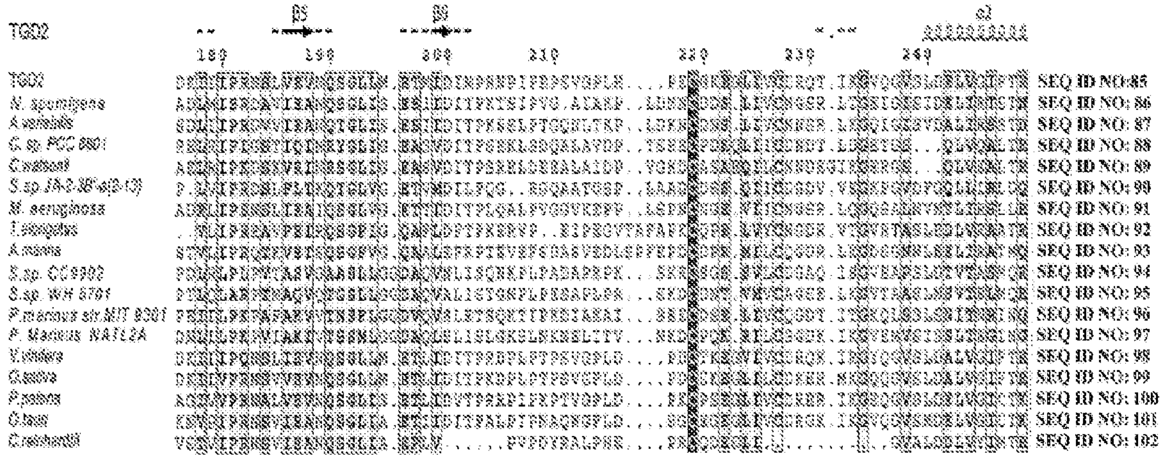
FIG. 17A: A partial sequence alignment of TGD2 (SEQ ID NO: 85) and TGD2 orthologs (SEQ ID NOs:86-102) showing the region of minimal PA binding domain. Conserved residues are highlighted in red, similar residues are boxed in yellow.
Figure 17B:
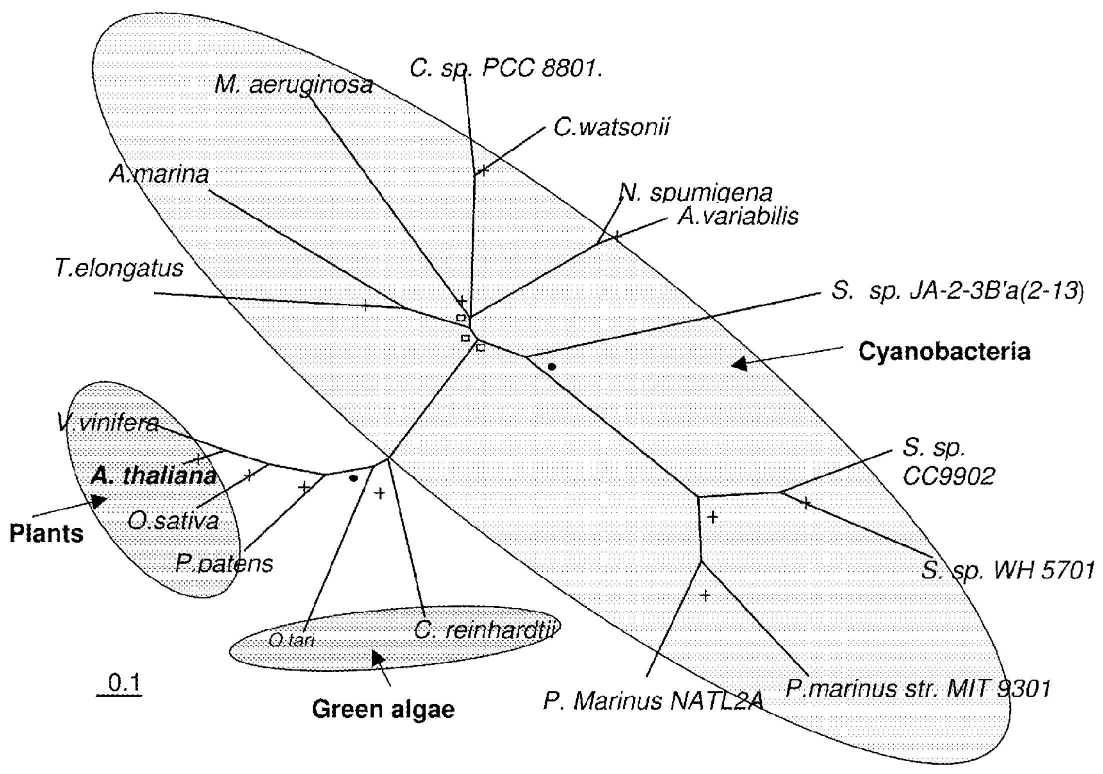
FIG. 17B: An unrooted phylogenetic tree showing the relatedness of predicted TGD2 orthologs in plants and Cyanobacteria. Boot strapping values>950 are marked by +, those between 500 and 950 are marked with a solid circle, and those under 500 are marked by open square.

The TGD2 protein is N-terminally truncated lacking the TMD and C-terminally fused to the *Discosoma* sp. red fluorescent protein (DsRed, dR) open reading frame. Fusion protein was expressed and protein-lipid overlay assay was conducted with commercial phospholipid—containing membrane strip. LPA, lysophosphatidic acid; LPC, lysophosphatidylcholine; Ptdlns, phosphatidylinositol; Ptdlns(3)P, phosphatidylinositol 3-phosphate; Ptdlns(4)P, phosphatidylinositol 4-phosphate; Ptdlns(5)P, phosphatidylinositol 5-phosphate; PE, phosphatidylethanolamine; PC, phosphatidylcholine; S1P, sphingosine 1-phosphate; Ptdlns(3,4)P2, phosphatidylinositol 3,4-bisphosphate; Ptdlns(3,5)P2, phosphatidylinositol 3,5-bisphosphate; Ptdlns(4,5)P2, phosphatidylinositol 4,5-bisphosphate; Ptdlns(3,4,5)P3, phosphatidylinositol 3,4,5-bisphosphate; PA, phosphatidic acid; PS, phosphatidylserine, see, FIG. 7. Gene bank accession numbers for representative TGD2 ortholog sequences include, but are not limited to: *Arabidopsis thalina*, NP_566659.1 (SEQ ID NO:5); *Vitis vinifera*, CAN71395.1 (SEQ ID NO:6); *Oryza sativa*, EAY77419.1 (SEQ ID NO:7); *Physcomitrella patens*, XP_001778862.1 (SEQ ID NO:8); *Ostreococcus tauri*, CAL53419.1 (SEQ ID NO:9); *Chlamydomonas reinhardtii*, XP_001699315.1 (SEQ ID NO:10); *Prochlorococcus marinus* str. NATL2A, YP_292846.1 (SEQ ID NO:115); *Prochlorococcus marinus* str. MIT 9301, YP_001090537.1 (SEQ ID NO:116); *Synechococcus* sp. WH 5701, ZP_01083418.1 (SEQ ID NO:117); *Synechococcus* sp. CC9902, YP_376253.1 (SEQ ID NO:118); *Synechococcus* sp. JA-2-3B'a(2-13), YP_477327.1 (SEQ ID NO:119); *Anabaena variabilis*, YP_323182.1 (SEQ ID NO:120); *Nodularia spumigena*, ZP_01630545.1 (SEQ ID NO:121); *Crocosphaera watsonii*, ZP_00516249.1 (SEQ ID NO:122); *Cyanothece* sp. PCC 8801, ZP_02940544.1 (SEQ ID NO:123); *Microcystis aeruginosa*, CA090615.1 (SEQ ID NO:124); *Acaryochloris marina*, YP_001516641.1 (SEQ ID NO:125); *Thermosynechococcus elongatus*, NP_683197.1 (SEQ ID NO:126), see, FIG. 17.

B. Trigalactosyldiacylglycerol 4 (TGD4) Genes were Isolated and Used for Making Recombinant Constructs.

A genetic mutant screen used to discover genes subsequently designated to encode TGD1, 2, and 3 additionally revealed a gene subsequently designated to encode Trigalactosyldiacylglycerol 4 (TGD4). The inventors unexpectedly discovered that TGD4 did not have a known function and showed no high level of identity to any known gene.

1. TGD4 Genes were Isolated and Analyzed.

A protein named TGD4 was encoded by At3g06960.1 (SEQ ID NO: 136) did not contain any functional domains with similarity to known functional domains. However, after a BLAST comparison to known sequences, similar sequences were found in green algae up to higher plants (Xu et al., 2008, herein incorporated by reference). TGD4 sequences were also found distantly related to the bacterial LptD protein that is an outer membrane β-barrel protein in *E. coli*. This outer membrane β-barrel protein was involved in Lipid A transport (Sperandeo et al., 2008, herein incorporated by reference). In fact, the TGD4 C-terminal fragment was predicted to adopt a secondary structure of hydrophobic β-sheets possibly forming a β-barrel. However, in addition to a lack of knowledge of the function of TGD4, conflicting evidence arose with regard to the cellular localization of TGD4 thus hindering a direct comparison to the bacterial LptD protein. Further, cellular location of a protein often provided clues to the function of a protein with unknown function. When TGD4 was overexpressed, i.e. a functional TGD4 with the N-terminus fused to Green Fluorescent Protein (GFP), TGD4 localization was at the Endoplasmic Reticulum (ER). However, chloroplast proteomic studies indicated chloroplast localization of TGD4 (Ferro et al., 2003, Zybailov et al., 2008, all of which are herein incorporated by reference). Therefore goals of the experiments described herein were to determine the molecular function of TGD4 while resolving the conflicting data regarding the cellular localization of the TGD4 protein, in vivo.

In order to identify a binding partner for TGD4, the inventors applied the following information. Because seed plants have biogenesis of thylakoid lipids that required the import of lipid precursors from the ER, the inventors contemplated the identity of several lipid precursors for generating thylakoid lipids that might bind to TGD4 in vivo. Synthesis of galactoglycerolipids, molecules that are prevalent in photosynthetic membranes, involved enzymes at the membranes of the ER and the chloroplast envelope. Genetic analysis of TGD proteins in *Arabidopsis* demonstrated their role in polar lipid transfer from the ER to the chloroplast. The TGD1, 2, and 3 proteins resemble components of a bacterial-type ATP-Binding Cassette (ABC) transporter, with TGD1 representing a permease, TGD2 as a substrate binding protein, and TGD3 having ATPase activity. In contrast, TGD4 protein showed little sequence similarity to TGDs1-3, additionally was predicted to have a C-terminal β-barrel structure and showed weak similarity to proteins of the outer cell membrane of Gram-negative bacteria, see above. After screening numerous lipids, the inventors showed herein that an exemplary TGD4 protein fused to DsRED unexpectedly (in part due to a lack of sequence similarity to TGD2) and specifically bound phosphatidic acid (PtdOH). With the use of highly purified and specific antibodies to probe specific cell fractionations, the TGD4 proteins were found in vivo as part of the outer envelope membrane of the chloroplast, where portions of it appeared to be deeply buried within the membrane. Thus it was contemplated that TGD4 was either directly involved in the transfer of polar lipids, of which one candidate was PtdOH, from the ER to the outer chloroplast envelope membrane or in the transfer of a lipid, such as PtdOH, through the outer envelope membrane. In another embodiment, phosphatidylcholine (PtdCho) was contemplated to bind to TGD4, such that PtdCho was contemplated to be converted at the outer envelope membrane to PtdOH through the activity of a phospholipase D making PtdOH available for further transfer by the TGD1, 2, 3 complex. Therefore, the inventors made constructs comprising recombinant TGD4 proteins used for testing a variety of lipid samples in order to determine whether TGD4 would bind to any of the sample lipid molecules.

2. Recombinant TGD4 Proteins were Made and Discovered to Bind to Phosphatidic Acid (PtdOH).

In one embodiment, a TGD4 gene was used to make a DsRED-TGD4-His protein expressed in *E. coli* strain BL21 (DE3) transformed with pLW01/DsRED-TGD4-His plasmid using standard culture methods for *E. coli* and as described herein. The recombinant protein expressed by the bacterial was harvested by centrifuging culture media containing bacteria then the pellet was resuspended in lysis buffer. The recombinant protein was purified by Ni-NTA column and used in detection methods and experiments described herein. See for example, Example 12, and exemplary FIG. 25.

In another embodiment, lipid extracts from animals, plants or humans are prepared, for example, from tissues, cells, etc., and spotted onto membranes, such as nitrocellulose, typically as a dilution series, or at a specified concentration. In a further embodiment, the spotted membrane is incubated in the purified recombinant protein then detected with anti-HIS antibodies then visualized and quantitated by using known methods.

Figure 18:
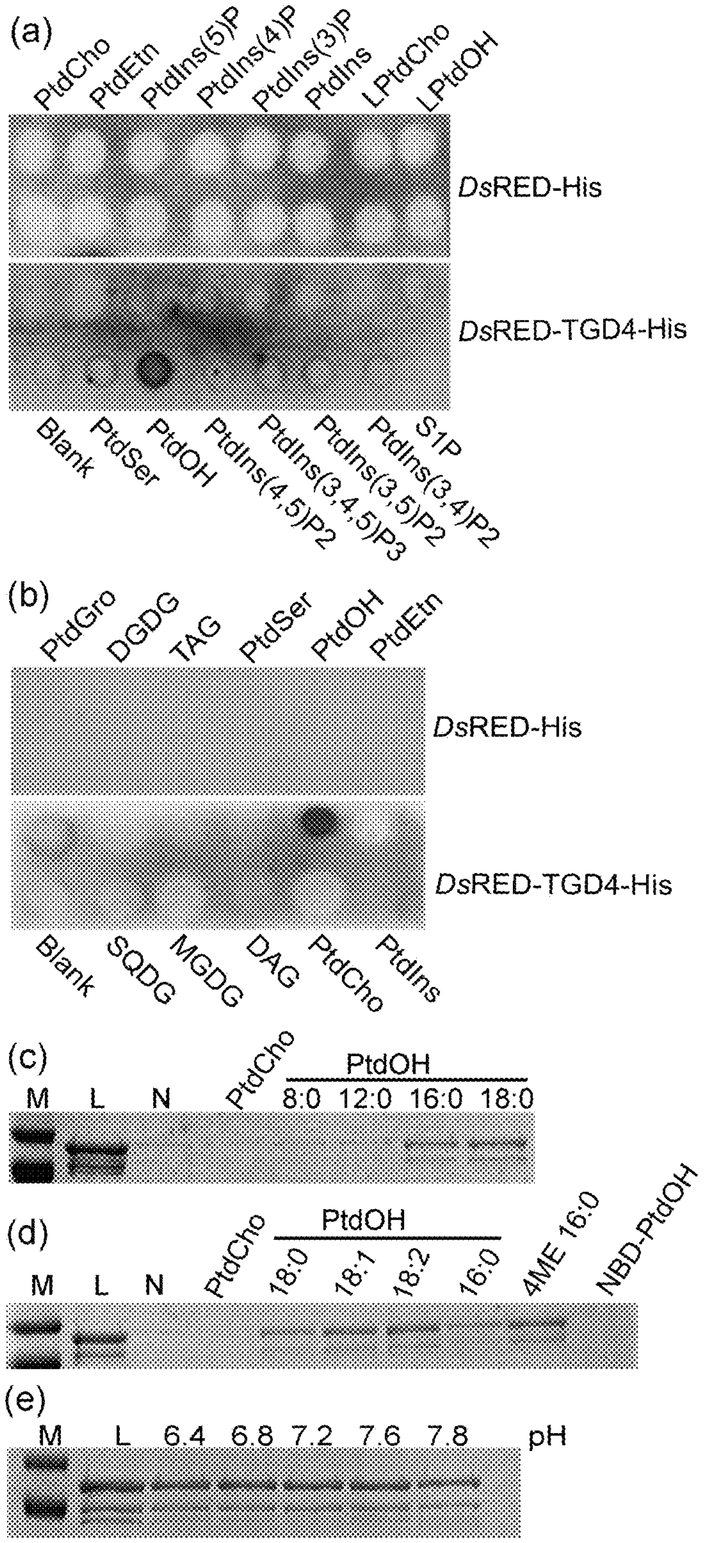
FIG. 18 shows an exemplary TGD4 protein bound to phosphatidic acid in vitro.
Figure 25:
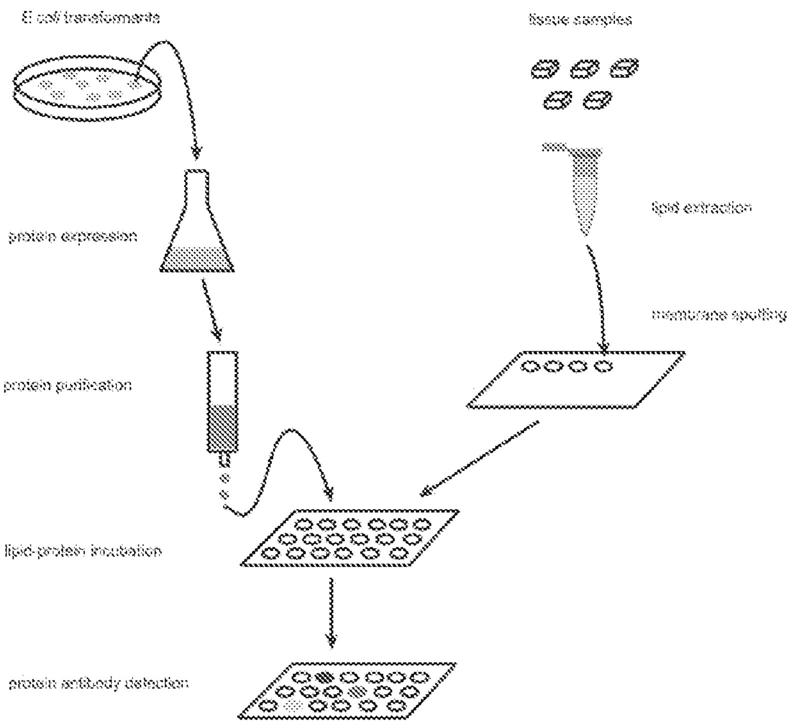
FIG. 25 shows an exemplary flow chart of one embodiment of the present inventions for the use of a TGD4 recombinant protein or fragment thereof in an ELISA assay for identifying a molecule or compound comprising phosphatidic acid.
Figure 26:
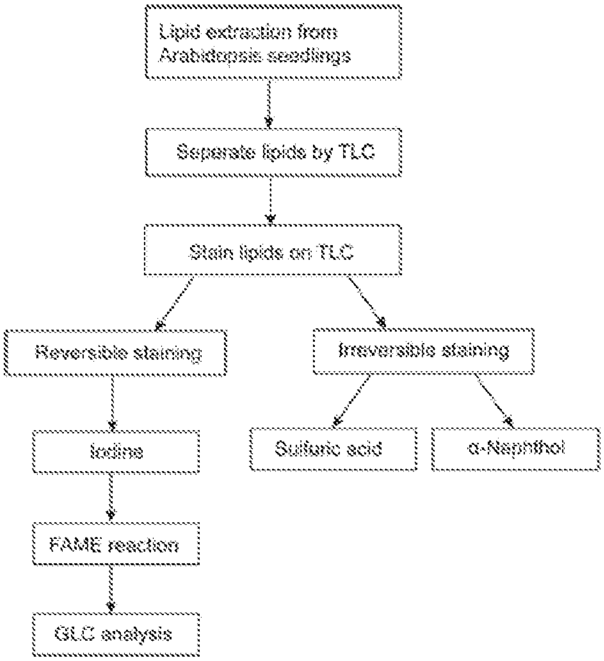
FIG. 26 shows an exemplary flow chart of polar lipid isolation and analysis using *Arabidopsis* seedlings. Total lipids are extracted from 4-week-old *Arabidopsis* seedlings and separated by TLC. The separated lipids were scraped from TLC plate for transesterification followed by GLC analysis.

In one embodiment, the results are quantified by ImageJ software, see, FIG. 18, for example, and FIG. 25 for an exemplary method flow chart.

In lipid-protein overlay assays, which used the general compositions and methods described above and in the Experimental section, recombinant purified TGD4 proteins were used to probing lipid samples spotted onto commercially available membranes (FIG. 18A), DsRED-TGD4-His was found to specifically bind to PtdOH, but not to any other phospholipids tested. Moreover, when probing different chloroplast lipids manually spotted onto membranes, DsRED-TGD4-His did not bind to any other lipids but PtdOH (FIG. 18B). The DsRED-His protein itself was not observed to bind to any of the lipids on either membrane tested. Thus in one embodiment, recombinant purified TGD4 proteins were used to identify PtdOH contained on nitrocellulose membranes.

As a method to independently verify PtdOH binding in a different assay and to test whether the protein showed preferences for different molecular species of PtdOH with regard to the acyl composition of the DAG moiety, a liposome binding assay was developed in which binding of the protein to liposomes containing different species of PtdOH was tested by co-precipitation (FIG. 18C, D). During the development of this liposome binding assay the inventors' discovered that in order for the assay to work there was a prerequisite for the exclusion of detergent while at the same time stabilizing the DsRED-TGD4-His fusion protein by adding choline chloride. Thus, choline chloride was a necessary addition to the buffer used for the liposome binding assay. Using this assay, DsRED-TGD4-His was found to bind to dipalmitoyl PtdOH and distearoyl PtdOH although the binding of distearoyl PtdOH appeared to be stronger. Thus in one embodiment, recombinant purified TGD4 proteins were used to identify dipalmitoyl PtdOH in a liposome sample. In one embodiment, recombinant purified TGD4 proteins were used to identify distearoyl PtdOH in a liposome sample.

The following is a summary of chloroplast lipid synthesis related to TGD4 of the present inventions. Plant chloroplasts are unique organelles of plant cells that function to harness solar energy and convert it to chemical energy by conducting photosynthesis thereby providing food and oxygen for most of the living organisms on earth. The thylakoid lipids provide the structural matrix for the photosynthetic membrane into which the electron transport chain components were embedded. Thylakoid lipids were observed in the crystal structures of both photosystem I and II (Guskov et al., 2009, Jordan et al., 2001; all of which are herein incorporated by reference) consistent with their possible roles in the proper assembly or function of photosynthetic complexes.

Unlike extraplastidic membranes, such as the endoplasmic reticulum (ER) or the plasma membrane, in which phosphoglycerolipids predominate, chloroplast membranes contain primarily galactoglycerolipids, which account for approximately 70% of total lipids in leaf tissue (Dormann and Benning, 2002, herein incorporated by reference). Of the galactoglycerolipids, monogalactosyldiacylglycerol (MGDG) and digalactosyldiacylglycerol (DGDG) represent the two most abundant classes. The amount of DGDG increases further during phosphate deprivation in leaves in order to substitute for the shortage of phospholipids in extraplastidic membranes (Hartel et al., 2000, herein incorporated by reference).

Galactolipids were synthesized at the chloroplast envelope membranes (Benning and Ohta, 2005, herein incorporated by reference). Several enzymes are involved with galactolipid synthesis such as monogalactosyldiacylglycerol (MGDG) synthase and digalactosyldiacylglycerol (DGDG) synthase. MGDG synthase was encoded by MGD1 in *Arabidopsis* and functions to transfer a galactosyl residue from UDP-Gal to diacylglycerol (DAG) generating an MGDG (Awai et al., 2001, Jarvis, 2008, all of which are herein incorporated by reference). MGD1 is localized at the inner envelope facing the intermembrane space (Xu et al., 2005, herein incorporated by reference). Transfer of a second galactosyl residue from UDP-Gal to MGDG is catalyzed by the DGDG synthase encoded by DGD1 (Dormann et al., 1999, herein incorporated by reference), which is localized at the outer envelope of the chloroplast facing the cytosol (Froehlich et al., 2001, herein incorporated by reference).

There are two pathways contributing to the DAG precursor pool for galactoglycerolipid synthesis (Benning, 2009, herein incorporated by reference). In the "prokaryotic pathway", DAG assembly from de novo synthesized fatty acids takes place within the chloroplast. In the "eukaryotic pathway," acyl groups are exported from the plastid to be available for polar lipid assembly at the ER where most of the extraplastidic phosphoglycerolipids are synthesized. DAG moieties transferred from the ER to the chloroplast serve as precursors in the synthesis of galactoglycerolipids. Thylakoid lipids derived from the prokaryotic pathway carry a 16-carbon acyl chain at the sn-2 position of the glycerol backbone, the lipids derived from the eukaryotic pathway an 18-carbon acyl chain at the same position (Heinz and Roughan, 1983, herein incorporated by reference). A precursor lipid is phosphatidic acid (PtdOH). As discussed below, results discovered during the development of the present inventions showed TGD4 recombinant protein binding to PtdOH with 16 and 18 carbon chains, see, FIG. 18C. Visual observation of the results showed little binding to PtdOH with 8 or 12 carbon chains. Thus recombinant TGD4 is contemplated to have a significantly higher affinity for PtdOH with longer carbon chains, such as 16 and 18 carbon chains over PtdOH having shorter carbon chains, such as 8 or 12 carbon chains. Further, purified TGD4 recombinant protein bound to PtdOH with 1 and 2 double bonds, see, FIG. 18D, indicating a broad binding capability for PtdOH comprising single and up to at least 2 double bounds.

Thus, PtdOH species of the same acyl chain length but different desaturation levels, DsRED-TGD4-His showed higher affinity for PtdOH with an increasing number of double bonds. Additionally, DsRED-TGD4-His appeared to have an even higher affinity to diphytanoyl PtdOH that carried branched acyl chains with four methyl groups.

However, DsRED-TGD4-His did not bind PtdOH carrying fluorescently labeled acyl substituents. The secondary band visible for the DsRED fusion proteins on the gels (FIG. 18C-E, and FIG. 19) was a result of DsRED self-cleavage during denaturation prior to electrophoresis (Gross et al., 2000, herein incorporated by reference). Because pH affects protonation of PtdOH and in some instances also PtdOH binding to proteins the effect of pH was tested. However, the binding of DsRED-TGD4-His to PtdOH was not affected over a pH range of 6.4-7.8 (FIG. 18E).

Moreover, the inventors' were surprised that TGD4 was involved with PtdOH binding because although it was found in the chloroplast TGD4 sequences lacked a recognizable chloroplast transit peptide. Further TGD4 was apparently localized to the ER by transiently over-producing a functional GFP-TGD4 fusion protein in tobacco (Xu et al., 2008, herein incorporated by reference). Thus TGD4 appeared to not have a mechanism for moving from the ER to the chloroplast with any lipid no less an important PtdOH. However, the inventors further contemplated that mistargeting of the majority of the recombinant protein visible by fluorescence microscopy was possible. This mistargeting would be possible because GFP fused to TGD4 was contemplated to sequester or expose a signal peptide involved with directing the movement of TGD4 from the ER to the chloroplast due to altered folding (Hanson and Kohler, 2001, herein incorporated by reference). Furthermore, overproduction of the recombinant protein was contemplated to lead to saturation of the cellular protein-sorting machinery causing mistargeting of the majority of the recombinant protein visible by fluorescence microscopy.

In order to avoid this problem the inventors' used TGD4 specific antibodies for identifying TGD4 protein in isolated microsomes and found that the native TGD4 protein was primarily associated with the outer chloroplast envelope membrane fractions. However, this new result does still did not exclude the possibility that a subfraction of TGD4 was associated with the ER as the microsome preparations were found to also contain microsomes derived from both the outer envelope membrane and the ER. Moreover, physical membrane contacts between the ER and the chloroplast were visualized and contemplated as the sites of lipid trafficking between the ER and the chloroplast (Andersson et al., 2007, herein incorporated by reference). Further, isolated chloroplasts of the tgd4-1 mutant did not have a reduced number of ER-fragments attached compared to wild-type chloroplasts which indicated that TGD4 was not directly involved in the tethering of the two membranes (Xu et al., 2008, herein incorporated by reference). However, this result did not exclude the possibility that TGD4 was enriched in ER-outer envelope membrane contact sites. This type of result was also found, for example, using the yeast protein Mmml, an essential component of the tethering complex in ER-mitochondrion contact sites (Kornmann et al., 2009, herein incorporated by reference). Mmml was first localized to the outer envelope of mitochondria by cellular fractionation (Burgess et al., 1994, herein incorporated by reference). However, more recent evidence indicted that without interaction partners, Mmml redistributed to the entire ER network (Kornmann et al., 2009, herein incorporated by reference).

In summary, based on results described herein, TGD4 was contemplated as a lipid transporter carrying lipids from the ER to and through the outer envelope of the chloroplast. Further, after the lipid screening studies described herein, PtdOH was determined as the primary lipid transported by TGD4.

3. Recombinant Truncation Mutants of TGD4 Proteins were Made and Discovered to Bind to Phosphatidic Acid (PtdOH).

The discovery that TGD4 specifically bound PtdOH in vitro as shown herein, indicated that functional transport of PtdOH occurred from the ER to the stroma face of the inner thylakoid envelope membrane. Thus the inventors' tested for the location of the PtdOH binding site by making truncation mutants. In one embodiment, a truncation mutant was made from a N-terminal coding region of a TGD4 gene. Thus, in one embodiment, a recombinant TGD4 protein, at least 90% up to 100% identical to SEQ ID NO: 130 is contemplated for use in the present inventions. In other embodiments, a recombinant TGD4 protein, is at least 91%, 92%, 95%, 98%, 99% identical to SEQ ID NO: 130. In one embodiment, a truncation mutant was made from a C-terminal coding region of a TGD4 gene. Thus, in one embodiment, a recombinant TGD4 protein, at least 90% up to 100% identical to SEQ ID NO: 131 is contemplated for use in the present inventions. In other embodiments, a recombinant TGD4 protein, is at least 91%, 92%, 95%, 98%, 99% identical to SEQ ID NO: 131. In another embodiment, a truncation mutant was made from fusing a N-terminal coding region with the C-terminal coding region of a TGD4 gene by removing a predicted hydrophobic region. Thus, in one embodiment, a recombinant TGD4 protein, at least 90% up to 100% identical to SEQ ID NO: 133 is contemplated for use in the present inventions. In other embodiments, a recombinant TGD4 protein, is at least 91%, 92%, 95%, 98%, 99% identical to SEQ ID NO: 133. These truncation mutants were tested for binding to PtdOH, see, FIG. 19.

In contrast to the expected single PtdOH binding region, as found in TGD2, the inventors were surprised to discover the presence of at least two TGD4 binding regions. However, stronger PtdOH binding activity of TGD4 was primarily attributed to its N-terminal fragment (1-286 aa (SEQ ID NO:130)) over the C-terminal fragment because the N-terminal fragment showed binding to PtdOH at lower concentrations than the C-terminal fragment, see, FIG. 19.

Functionally, after obtaining the results described above, the inventors' further contemplated that the N-terminal portion of TGD4 was responsible for binding to PtdOH at the ER then transferred PtdOH through the predicted C-terminal β-barrel structure to the intermembrane face of the outer chloroplast envelope membrane. Thus TGD4 was contemplated as having a function related to the discovery of two PtdOH binding sites, one each, encoded at the end of the nucleic acid sequence with different binding affinities.

TGD2, another PtdOH binding protein involved in vivo with thylakoid membranes is further contemplated to accept PtdOH from TGD4 then transfer it to the TGD1/TGD3 ABC transporter complex, which facilitates PtdOH transfer across the inner envelope membrane hydrolyzing ATP. On the stroma face of the inner envelope membrane PtdOH is dephosphorylated to DAG, the ER-derived substrate for thylakoid lipid synthesis by the ER-pathway.

Thus in one embodiment, truncated TGD4 proteins are contemplated for differential binding of lipids comprising PtdOH. In one embodiment, a truncated TGD4 N-terminal region was used for identifying low quantities of PtdOH lipids, including but not limited to PtdOH, dipalmitoyl PtdOH and distearoyl PtdOH, see, Examples.

VII. Kits.

In one embodiment, the present invention contemplates a kit, comprising: a) a first container comprising a test strip comprising a phosphatidic acid binding protein; b) a second container comprising a plurality of buffers and a plurality of reagents, wherein said protein is soluble; and c) a set of instructions for determining a phosphatidic acid. In one embodiment, the protein further comprises a label. In one embodiment, the phosphatidic acid is derived from a sample. In one embodiment, the protein further comprises at least one accessory binding protein.

In another embodiment, the present invention contemplates kits for the practice of the methods of this invention. The kits preferably include one or more containers containing a phosphatidic acid determination method of this invention. The kit can optionally include a TGD2 protein comprising a phosphatidic acid binding domain, wherein said domain encompasses amino acid residues 201-225 (SEQ ID NO:12), wherein at least one of said residues is a proline. The kit can optionally include a plurality of buffers as described herein.

In one embodiment, a kit comprises a TGD4 expression construct, for example a pLW01/DsRED TGD4-HIS plasmid. In one embodiment, a kit comprises a TGD4 recombinant protein, for example, a truncated TGD4 protein further comprising a HIS tag.

The kit can optionally include a plurality of reagents as described herein. The kit can optionally include enzymes as described herein. The kit can optionally include enzymes capable of performing PCR (i.e., for example, DNA polymerase, Taq polymerase and/or restriction enzymes). The kit can optionally include a pharmaceutically acceptable excipient and/or a delivery vehicle (e.g., a liposome). The reagents may be provided suspended in the excipient and/or delivery vehicle or may be provided as a separate component which can be later combined with the excipient and/or delivery vehicle.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in the determination of phosphatidic acid for one of many plant disorders. In particular a plant disease, wounding and/or stress can include any one or more of the disorders described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

The following are examples that further illustrate embodiments contemplated by the present invention. It is not intended that these examples provide any limitations on the present invention.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Example I

Expression and Purification of DsRed-TGD2 Fusion Proteins

TGD2 truncated proteins used in this example were obtained from DNA generated by PCR using a TGD2-dTMD-pQE31 (also known as TGD2C-pQE31) plasmid template (22). Following digestion with NcoI and XhoI, the fragment was ligated into DsRed-plw01-His (a gift from Dr. Michael Garavito, Michigan State University, East Lansing, Mich.). Internal deletion mutants and/or point mutants were generated by site-directed mutagenesis approach on TGD2CDsRed-plw01 via PCR, with the primers and mutation sites listed in Table 1 (supra).

Fusion proteins were expressed in the *Escherichia coli* strain, BL21 (DE3) (Novagen, Madison, Wis.). An overnight pre-culture of LB medium (5 mL) was used to start a 200 mL culture in LB medium. The protein was induced with 50 μM IPTG (isopropyl-β-D-thiogalactopyranoside) at OD600 0.6-0.8, 16° C. and growth was continued overnight. Cultures were cooled to 4° C., washed twice and resuspended in lysis buffer (50 mM Tris-HCl, pH7.5, 300 mM NaCl, 10 mM imidazole). The suspensions were lysed by sonication, followed by centrifugation at 18,000 gram.

The resultant supernatant was applied to Ni-NTA agarose column (Qiagen, Valencia, Calif.). Non-specific binding proteins were washed off the column by lysis buffer containing 20 mM imidazole. The His-tagged protein was then eluted with lysis buffer containing 250 mM imidazole.

Samples were concentrated and dialyzed into assay buffer (10 mM $KH_2PO_4$, pH approximately 7.4), using Amicon centrifugal filter devices (Millipore, Billerica, Mass.). Protein concentration was determined according to Bradford (27) using bovine serum albumin as a standard. The fusion proteins were analyzed for purity by SDS-PAGE (28) and stored at 4° C. for a few weeks without significant loss of activity.

Phylogenetic Analysis of TGD2-full-length TGD2 amino acid sequences were BLASTed against non-redundant protein database (29) and the resulted sequences with high similarities and identities were aligned using Clustalx® software (version 1.81). Generation of the bootstrapped phylogenetic tree was performed using the PHYLIP software package as previously described (30).

Example II

Protein-Lipid Overlay Assay

Membrane lipid strips were purchased from Echelon Biosciences (Salt Lake City, Utah). The strips were first blocked with 3% bovine serum albumin in TBST (10 mM Tris-HCl, pH 8.0, 150 mM NaCl, and 0.25% Tween-20) for two hours and incubated in 0.5 μg/mL DsRed-TGD2 fusion protein solution in the blocking buffer at 4° C. overnight. The strips were washed 10 min for 3 times with TBST the next day and soaked in 3% bovine serum albumin in TBST with a Penta-His mouse monoclonal antibody (Sigma-Aldrich, St. Louis, Mo.) at 1:2,000 dilution at 4° C. overnight. The strips were washed twice with TBST and soaked in 3% bovine serum albumin in TBST with horseradish peroxidase-conjugated anti mouse antibody (Bio-Rad, Hercules, Calif.) at 1:20,000 dilution for an hour at room temperature. Following washing with TBST for 1 hour, the protein was detected by using the chemiluminescent detection system (Sigma-Aldrich).

Example III

Liposome-Association Assay

The liposome association assay was performed as previously reported. (31). Briefly, lipids (dioleoyl-phosphatidylcholine, DOPC or dioleoyl-PA, DOPA) were incubated in TBS (50 mM Tris-HCl, pH 7; 0.1 M NaCl) at 37° C. for an hour followed by vigorous vortexing for 5 min. The liposomes were precipitated at 20,000 g and washed twice with ice-cold TBS.

Liposomes (200 μg) were mixed with purified DsRed-TGD2 fusion protein and TBS to make a final 100 μL solution. The mixture was incubated at 30° C. for 30 min and washed twice with ice-cold TBS by centrifugation at 20,000 g at 4° C. The liposome pellet mixed with sample buffer was analyzed by SDS-PAGE (28). Immuno-detection of the His-tagged protein was accomplished using the above mentioned Penta-His antibody at 1:15,000 and the anti mouse antibody at 1:75,000 dilution.

The protein band was visualized by chemiluminescent detection kit from Sigma. The autoradiography film was scanned, distinct protein bands were quantified using computer software Multi Gauge V3.0 (Fujifilm USA, Valhalla, N.Y.) and resulted data were plotted and analyzed by Origin-Pro8 (Origin lab corporation, Northampton, Mass.).

Example IV

Plant Material

*Arabidopsis thaliana* plants were of the ecotypes Columbia-2 (Col-2) or Landsberg erecta (Ler). The tgd1-1 and dgd1 mutants were previously isolated, Xu et al., (2003) *EMBO J.* 22:2370-2379; and Dormann et al., (1995) *Plant Cell* 7:1801-1810. Standard growth conditions were used for surface-sterilized seeds on agar-solidified MS medium supplemented with 1% (wt/vol) sucrose or for plants grown on soil. Murashige et al., (1962) *Physiol. Plant.* 15, 473-497; and Xu et al., (2002) *Plant Physiol.* 129:594-604.

Example V

Lipid Analysis

Lipids were extracted, and fatty acid methylesters were prepared and quantified by gas chromatography as previously Mallinckrodt, Baker, N.J.) by using a solvent system of acetone/toluene/water (90/30/7, vol/vol). Neutral lipids were separated on untreated TLC plates and developed with petroleum ether/ether/acetic acid (70/30/1, vol/vol). Polar lipids were analyzed on activated ammonium sulfate-impregnated silica gel TLC plates (Si250PA; Mallinckrodt, Baker, N.J.) by using a solvent system of acetone/toluene/water (90/30/7, vol/vol). Neutral lipids were separated on untreated TLC plates and developed with petroleum ether/ether/acetic acid (70/30/1, vol/vol). Lipids were visualized by brief exposure to iodine vapor or staining with α-naphthol to detect glycolipids. Benning et al., (1995) *Arch. Biochem. Biophys.* 317:103-111.

Example VI

Markers for Genetic Mapping and Genotyping

For fine mapping, 10 CAPS markers (Konieczny et al., (1993) *Plant J.* 4, 403-410) and 1 dCAPS (MQC12-4) marker (Neff et al., (1998) *Plant J.* 14:387-392) were generated, taking advantage of the Monsanto Polymorphism and Ler Sequence Collection (arabidopsis.org/Cereon/index.jsp). Primers and restriction enzymes were as follows:

```
MYF24:
                                          (SEQ ID NO: 49)
5'-GACAGCCCACAAATTGATGG-3'
and

                                          (SEQ ID NO: 50)
5'-ACCAACGCTCAATGCCTAC-3'
cut with HinfI.

MLD14:
                                          (SEQ ID NO: 51)
5'-GGGGTCCTTAAAATAGAGAC-3'
and

                                          (SEQ ID NO: 52)
5'-GGCCTTTTGAGTTGGGAAAAG-3'
cut with HindIII.

MIL23:
                                          (SEQ ID NO: 53)
5'-GGGGGTGATATCTATCGTAG-3'
and

                                          (SEQ ID NO: 54)
5'-GCACCCTGGATATTCTTTCG-3'
cut with HinfI.

MPN9:
                                          (SEQ ID NO: 55)
5'-CGGTCATATGCTGGCTGAAG-3'
and

                                          (SEQ ID NO: 56)
5'-GACAGCACACAAGTTCCAGG-3'
cut with AluI.

MPN9-2:
                                          (SEQ ID NO: 57)
5'-GTGCTATGGTTCAGGAGTTC-3'
and

                                          (SEQ ID NO: 58)
5'-CTTACCAGCCATGACGATTC-3'
cut with AccI.

MAL21:
                                          (SEQ ID NO: 59)
5'-GAGAAGAAACACCGATTCCG-3'
and

                                          (SEQ ID NO: 60)
5'-GTTGTGATACGAATGGTGGC-3'
cut with RsaI.

K10D20:
                                          (SEQ ID NO: 61)
5'-GGACCTGCCTTTCCCATATC-3'
and

                                          (SEQ ID NO: 62)
5'-GCCCAAGCCTCAAGATGTTG-3'
cut with HindIII.

MSA6:
                                          (SEQ ID NO: 63)
5'-GGAAGAGGGAGGTTTTGTTC-3'
and

                                          (SEQ ID NO: 64)
5'-CCAATTCGTCTCCTTTTCACC-3'
cut with SpeI.

MQC12-2:
                                          (SEQ ID NO: 65)
5'-GTGAGACCAACAGTGTCAAC-3'
and

                                          (SEQ ID NO: 66)
5'-CCAC AATACACCACCACTTG-3'
cut with HinfI.

MQC12-3:
                                          (SEQ ID NO: 67)
5'-CCTCCGTCTCATACATCTAC-3'
and

                                          (SEQ ID NO: 68)
5'-CCAATTCGGTTTCATCCAATCCTCT-3'
cut with BfaI.

MQC12-4:
                                          (SEQ ID NO: 69)
5'-CATATGCATTGATGATAACTGAAATCGA-3'
and

                                          (SEQ ID NO: 70)
5'-CTTCTAGATCTCCTCCTTTC-3'
cut with EcoRI.
```

For genotyping of the tgd2-1 mutant, a dCAPS marker was generated:

```
(SEQ ID NO: 71)
5'-TGATCGTTTGTGATAGGCAGCCTATAAAA-3'
and

(SEQ ID NO: 72)
5'-CCTTGCTTCCTCAATAACCG-3',
cut with EcoNI.
```

The dgd1 dCAPS marker was made as previously described. Xu et al., (2003) EMBO J. 22:2370-2379.

Example VII

Complementation and Dominant-Negative Mutation Analysis

The ORFs for TGD2 and tgd2-1 were isolated by RT-PCR from mRNA preparations by using RNeasy and Omniscript kits (Qiagen, Valencia, Calif.) and standard PCR conditions. The following primers were used:

5'-GTCGACATGATTGGGAATCCAGTAATTCAAG-3' (SEQ ID NO: 73) and

5'-GTCGACTCATAGTAGCCTGCTTAGGG-3' (SEQ ID NO: 74).

The fragments were ligated into pGEM-T Easy (Promega) and sequenced at the Michigan State University Genomics and Technology Facility. The resulting plasmids were digested with SalI and inserted into pCAMBIAmcs1300 followed by transformation into *Agrobacterium*. Plants were transformed by the floral-dip method (22) and screened by resistance to hygromycin (25 μg/ml) on agarsolidified MS medium. Clough et al., (1998) *Plant J.* 16:735-743. For semi-quantitative PCR of TGD2 and tgd2 transcripts the following primers were used: TGD2-specific:

```
(SEQ ID NO: 75)
5'-CGGCTTGCTCAAGGAAGTTG-3'
and

(SEQ ID NO: 76)
5'-CCAGTCTAAAATCTACAGGCTG-3';
```

TGD2 and tgd2-1:

```
(SEQ ID NO: 77)
5'-TGATCGTTTGTGATAGGCAGCCTATAAAA-3'
and

(SEQ ID NO: 78)
5'-CCTTGCTTCCTCAATAACCG-3';
```

UBQ10:

```
(SEQ ID NO: 79)
5'-TCAATTCTCTCTACCGTGATCAAGATGCA-3'
and

(SEQ ID NO: 80)
5'-GTGTCAGAACTCTCCACCTCAAGAGTA-3'.
```

Isolation of RNA and reverse transcription were done as described above. Amplification conditions were as follows: 94° C. for 3 min followed by 25 cycles at 94° C. for 0.5 min, 55° C. for 0.5 min, and 72° C. for 0.5 min followed by 3 min at 72° C.

Example VIII

TGD2-GFP Fusion and In Vivo Chloroplast Import Assay

The sequence encoding the full-length TGD2 protein was amplified from the pCAMBIAmcs 1300 plasmid derivative mentioned above by PCR using the following primers: forward, 5'-GTCGACATGATTGGGAATCCAGTAATTCAAG-3' (SEQ ID NO: 81); reverse, 5'-GTCGACTAGTAGCCTGCTTAGGGATTTG-3' (SEQ ID NO: 82). The fragment was inserted into the pGEM-T Easy vector, sequenced and digested with SalI, and inserted into pCAMBIAmcsGFP. In vivo analysis of the GFP-tagged protein was done by confocal fluorescence microscopy.

In vivo chloroplast import analysis was performed using transient expression of the constructs in tobacco leaves. Xu et al., (2005) *Plant Cell* 17:3094-3110. For immunodetection of the TGD2 or tgd2-1 proteins, a polyclonal antibody was raised in rabbits (Cocalico Biologicals, Reamstown, Pa.) against the truncated TGD2 protein used also for the lipid binding assay. The anti-serum was purified with a Melon Gel IgG Purification Kit (Pierce). For TGD2 immunodetection, the purified anti-TGD2 antibody was used at a 1:2,000 dilution. For GFP immunodetection, a rabbit anti-GFP antibody (Molecular Probes) was used at a 1:3,000 dilution. The antibodies were detected with an anti-rabbit horseradish peroxidase-coupled antibody (Bio-Rad) at a dilution of 1:60,000 followed by development with Chemiluminescent Peroxidase Substrate (Sigma).

Example IX

Recombinant TGD2 Protein Production and Purification

The sequence encoding N-terminally truncated TGD2-dTMD protein (from Gly-119 to stop codon) lacking the targeting peptide and the TMD was PCR-amplified by using primers:

```
(SEQ ID NO: 83)
5'-GTCGACGGTTTTCAAATGCGGTCGAAG-3'
and

(SEQ ID NO: 84)
5'-GTCGACTCATAGTAGCCTGCTTAGGG-3'.
```

This fragment was inserted into pPICT2 plasmid and sequenced. Kawaguchi et al., (2001) *J. Bone Miner. Res.* 16, 260-269. After digestion with SalI, the insert was ligated into pQE31 (Qiagen). An overnight preculture of LB medium (1 ml) was used to start a 500-ml culture in M9 medium. Duffieux et al., (2000) *Eur. J. Biochem.* 267:5306-5312. The protein was induced with 0.1 mM isopropyl-β-D-thiogalactopyranoside at an $OD_{600}$ of 0.4 at 22° C., and growth was continued overnight. Cultures were cooled to 4° C., washed twice, and resuspended in lysis buffer (50 mM Tris-HCl, pH 7.5/600 mM NaCl/20 mM imidazole). The suspensions were lysed by sonication followed by brief centrifugation at 1,500×g to eliminate cell debris. The supernatants were centrifuged at 20,000×g and applied to a Ni-NTA agarose column (Qiagen). The His-tagged protein was eluted with lysis buffer containing 250 mM imidazole. Samples were dialyzed in the lysis buffer lacking imidazole. Protein concentration was determined by using BSA as a standard. Bradford, M. M. (1976) *Anal. Biochem.* 72, 248-254.

Example X

Lipid Binding Assays

Commercially available membrane strips prespotted with lipids were purchased. (Echelon Biosciences, Salt Lake City, Utah). Prokaryotic phosphatidylcholine and PA were also purchased (Avanti Polar Lipids). Prokaryotic monogalactolipid, digalactolipid, sulfolipid, and phosphatidylglycerol were purified from *Synechocystis* PCC6803 by TLC of lipid extracts. Eukaryotic monogalactolipid and digalactolipid was isolated from pea leaves.

Approximately 5 μg of lipids were spotted onto a Hybond-C membrane (Amersham Pharmacia Biosciences). The membranes were first blocked with 3% BSA in TBST (10 mM Tris-HCl, pH 8.0/150 mM NaCl/0.1% Tween 20) for 1 h and incubated in 0.5 μg/ml TGD2 protein solution in the blocking buffer at 4° C. overnight. The blots were washed five times with TBST and soaked in 3% BSA in TBST with a Penta-His mouse monoclonal antibody (Qiagen) at a 1:1,000 dilution at room temperature overnight. The membranes were washed twice with TBST and soaked in 3% BSA in TBST with alkaline phosphatase-conjugated anti-mouse antibody (Jackson ImmunoResearch) at a 1:5,000 dilution for 1 hour at room temperature. After washing with TBST twice, the protein was detected by using the Immun-Star AP detection system (Bio-Rad).

The liposome binding assay was performed as previously reported. Sano et al., (1998) *J. Biol. Chem.* 273:4783-4789. Lipids (i.e., for example, phosphatidylcholine or a mixture of phosphatidylcholine and PA at 6:4 wt/wt) were incubated in TBS (50 mM Tris/HCl, pH 7/0.1M NaCl) at 37° C. for 1 hour followed by vigorous vortexing for 5 min. The liposomes were precipitated at 20,000×g and washed twice with ice-cold TBS.

Liposomes (200 μg) were mixed with purified TGD2 protein lacking the TMD (10 μg/ml) and TBS to make 100 μl of solution. The mixture was incubated at 30° C. for 30 min and washed twice with ice-cold TBS by centrifugation at 20,000×g at 4° C. The liposome pellet mixed with sample buffer was analyzed by SDS/PAGE. Laemmli, U. K. (1970) *Nature* 227, 680-685. Immunodetection of the His-tagged protein was accomplished by using the above-mentioned Penta-His antibody at 1:6,000 and the anti-mouse antibody at 1:10,000 dilutions. The BCIP/NBT Kit from Bio-Rad was used for color detection.

Example XI

Materials and Methods

Plant Materials and Growth Conditions:

*Arabidopsis thaliana* ecotype Col 2 and tgd4 mutant plants were grown as previously described (Xu et al., 2005). Surface-sterilized seeds were germinated on 0.5% (w/v) agar-solidified MS medium (Murashige and Skoog, 1962a) supplemented with 1% sucrose and transferred to soil after 10 days for propagation. Aerial parts of 4-week-old plants grown on agar-solidified MS medium were harvested for chloroplast isolation and lipid analysis.

Expression and Purification of DsRED-TGD4 Fusion Proteins:

The TGD4 cDNA was initially cloned into the pMalc2x vector (New England Biolabs, Ipswich, Mass.). The pMalc2x/TGD4 construct was modified to give rise to pMalc2x/ΔTGD4 by deleting the 859-924 nt (referring to coding sequence NM_111576) fragment encoding the hydrophobic region using site-directed mutagenesis. pMalc2x/TGD4 and pMalc2x/ΔTGD4 were used as PCR templates for the amplification of TGD4 (SacI, Nod), TGD4N (NcoI) and ΔTGD4 (SacI, Nod), TGD4C (SacI, NotI) respectively. The restriction sites were included in the primers (Table 4). Following restriction digestion, the PCR fragments were ligated into the pLW01/DsRED-His vector (Lu and Benning, 2009). Sequence identities were confirmed by sequencing at the MSU Research Technology Support Facility. To express DsRED-TGD4-His proteins, constructs pLW01/DsRED-TGD4-His, pLW01/DsRED-ΔTGD4-His, pLW01/TGD4N-DsRED-His and pLW01/dsRED-TGD4C-His were transformed into *E. coli* strain BL21 (DE3) (Novagen, Madison, Wis.). A 5 ml overnight culture was used to inoculate a 200 ml culture. When the cell density reached $A_{600}$=0.6 to approximately 0.8, isopropyl-β-D-thiogalactopyranoside was added at a final concentration of 0.1 mM to induce protein expression at 16° C. overnight. The cells were centrifuged at 5,000×g for 10 minutes, and resuspended in lysis buffer (50 mM $NaH_2PO_4$, 300 mM NaCl, 10 mM imidazole, pH 8.0, 1% (w/v) foscholine-12 and protease inhibitor cocktail (Roche, Indianapolis, Ind.)) with 0.2 mg/ml lysozyme (Sigma, St. Louis, Mo.). After incubating on ice for 30 minutes, cells were lysed by sonication followed by centrifugation at 10,000×g for 20 minutes. The supernatant was filtered through a 0.45 μm filter and was loaded onto a Ni-NTA column (Qiagen, Valencia, Calif.). Protein purification was carried out according to manufacturer's instructions except of the addition of 0.1% foscholine-12 to the wash and elution buffers. The purified proteins were concentrated with an Amicon centrifugal filter device (Millipore, Billerica, Mass.) and the buffer was changed to Tris-buffered saline (TBS; 10 mM Tris-HCl, pH 8.0, 150 mM NaCl,) with 2 M choline chloride, which stabilizes DsRED-TGD4 proteins. Protein concentration was determined by Bradford assay and protein purity was assessed by SDS-PAGE. The fusion proteins were then frozen in 10 μl aliquots at −80° C.

Protein-Lipid Overlay Assay:

The protein-lipid overlay assay was modified from (Awai et al., 2006, Lu and Benning, 2009). Phosphoinositol-4,5-bisphosphate PIP2) lipid strips were purchased from Echelon Biosciences (Salt Lake City, Utah). Lipids spotted onto membranes were purchased from Avanti Polar Lipids (Alabaster, Al.) as well as Larodan Fine Chemicals (Malmo, Sweden). Lipids (10 nmol) were suspended in 20 μl spotting buffer (250 μl chloroform, 500 μl methanol, 200 μl 50 mM HCl, 2 μl 1% (w/v) Ponseau S (Sigma, St. Louis, Mo.)) and spotted onto Amersham Hybond-C Extra membranes (GE Healthcare, Piscataway, N.J.) followed by drying for 1 hour in a fume hood. The lipid membranes were then blocked in 3% (w/v) bovine serum albumin (BSA) in TBST buffer (TBS with 0.25% (v/v) Tween 20) for 2 hours at room temperature. Purified DsRED-TGD4-His fusion proteins were added at 1 μg/ml final concentration and incubated overnight at 4° C. followed by washing 3 times in TBST. Lipid membranes were then incubated with 1:2000 diluted His antibody (Sigma) in blocking buffer for 2 hours at room temperature followed by 2 washes with TBST. The membranes were processed for immunoblotting as described below.

Liposome Association Assay:

The liposome association assay was adapted from (Awai et al., 2006, Lu and Benning, 2009) with minor modifications. Dioleoyl-PtdCho and PtdOH with different acyl chain lengths and desaturation levels were used for making liposomes. In other liposomes 1-palmitoyl-2-(12-((7-nitro-2-1,3-benzoxadiazol-4-yl)amino)dodecanoyl)-sn-glycero-3-phosphate (NBD-PtdOH; Avanti, Alabaster, Ala.) was used. The lipids were mixed at indicated ratios to give a total lipid amount of 250 μg. The lipids were dried under a stream of nitrogen, resuspended in 0.5 ml TBS buffer with 0.2 M choline chloride and hydrated at 37° C. for 1 hour followed by vigorous vortexing for 2 minutes. The resulting multi-lamellar vesicles were centrifuged at 13,000×g for 10 minutes and then washed once with TBS buffer containing 0.2 M choline chloride. The liposomes were resuspended into 100 μl TBS buffer with 0.2 M choline chloride and incubated with 2 μg purified DsRED-TGD4-His protein and its derivatives. The protein liposome mixture was incubated on ice for 30 minutes followed by centrifugation at 13,000×g for 10 minutes and two washes with 500 μl TBS containing 0.2 M choline chloride. The resulting protein-liposome pellet was resuspended in 20 μl 2× Laemmli buffer (Laemmli, 1970) and processed by SDS-PAGE (Shapiro and Maizel, 1969).

Lipid Analysis by Two-Dimensional TLC and GC:

Total lipids were extracted from 300 mg fresh weight seedlings as described herein and separated on TLC silica gel plates (EMD Chemicals, Gibbstown, N.J.). The first-dimension solvent contained chloroform:methanol: 7 M ammonium hydroxide (65:30:4, v/v/v) and the second-dimension solvent contained chloroform:methanol:acetic acid:water (170:25:25:6, v/v/v/v). Lipids were visualized either by 50% sulfuric acid or by iodine vapor. The iodine-stained lipids were scraped from TLC plates and quantified as described herein.

*Arabidopsis thaliana* Polar Glycerolipid Profiling by Thin Layer Chromatography (TLC) Coupled with Gas-Liquid Chromatography (GLC).

TLC coupled with GLC provided a robust and rapid tool for quantitative analysis of polar lipids in plants. Small changes in lipid composition were identified as shown herein; therefore, this method was used for large scale screening of mutants impaired in polar lipid metabolic pathways (for example, Xu, *EMBO J.* 2003; 22:2370-2370, herein incorporated by reference). This method was also widely used for monitoring activities of enzymes utilizing polar lipids as substrate (Andersson, et al., *Biochim. Biophys. Acta.* 2004; 1684: 46-46, Dormann, et al., *Science.* 1999; 284:2181-2181, and Gaude, et al., Plant J. 2008 56(1):28-39, all of which are herein incorporated by reference). Besides leaves, the lipid composition of other plant tissues such as roots and seeds or subcellular fractions such as chloroplasts and mitochondria can also be determined in the same way.

The solvent system (acetone, toluene, water) used here was originally optimized for the separation of glycolipids and phospholipids in plants. However, in tgd1,2,3,4 mutants and isolated chloroplasts, TGDG ran together with PE while tetragalactosyldiacylglycerol ran with PC. In this case a solvent system with chloroform, methanol, acetic acid and water (85:20:10:4, v/v/v/v) was used (Lu, *J. Biol. Chem.* 2007, 282:35945-35945, herein incorporated by reference) Sometimes two-dimensional TLC using two different solvent systems was performed to further separate glycolipids and phospholipids (Xu, *Plant Cell.* 2005, 17:3094-3094, herein incorporated by reference). In addition, plant tissues were directly subjected to the FAME reaction followed by GLC to determine the total fatty acid profile without initial separation on TLC (Browse, et al., *Anal. Biochem.* 1986, 152:141-141, herein incorporated by reference). Beside the demonstrated TLC-GLC system, another method used for lipid profiling is based on direct electrospray ionization tandem mass spectrometry (Welti, et al., *Anal. Biochem.* 2003; 314:149-149, herein incorporated by reference). In tandem mass spectrometry methods the initial chromatographic separation of lipids in the extract was omitted. However, this latter method requires expensive equipment and experienced personnel, which makes it less useful for routine analyses in the lab or for mutant screening.

The following steps were done with exemplary materials in Table 3:

TABLE 3

Exemplary materials used in TLC and GLC analysis.

| Material Name | Company | Catalogue Number | Comment |
|---|---|---|---|
| α-naphthol | Sigma-Aldrich | N1000 | nc |
| Methanolic HCL 3N | Sigma-Aldrich | 33050-U | Dilute to 1N by methanol |
| Si250-PA TLC plates | J.T. Baker | 7003-04 | With pre-absorbent |
| TLC chamber | Sigma-Aldrich | Z266000 | nc |
| Screw cap tubes | VWR | 53283-800 | nc |
| Scew caps | Sun Sri | 13-425 | nc |
| PTFE disk | Sun Sri | 200 608 | nc |
| GLC system | Hewlett Packard | HP6890 | nc |
| DB-23 column | J&W Scientific | 122-2332 | nc |
| GLC vials | Sun Sri | 500 132 | nc |
| Caps of GLC vials | Sun Sri | 201 828 | nc |
| Chemstation software | Agilent | G2070AA | nc |

Nc = no comment

Lipid Extraction

1. Lipid extraction was started by harvesting 30 mg 4-week-old *Arabidopsis* leaves from plants grown on agar solidified medium or soil and transfer them into 1.5 mL polypropylene reaction tubes. Fresh leaves can be flash frozen in liquid nitrogen and stored at −80° C.
2. 300 μL extraction solvent was added composed of methanol, chloroform and formic acid (20:10:1, v/v/v) to each sample. Shake vigorously (using a paint shaker or similar) for 5 minutes.
3. 150 μL of 0.2 M phosphoric acid ($H_3PO_4$), 1 M potassium chloride (KCl) was added and vortexed briefly.
4. Centrifuged at 13,000×g at room temperature for 1 minute. Lipids dissolved in the lower chloroform phase were spotted onto TLC plates.

Thin Layer Chromatography (TLC) (Stahl, et al., Pharmazie 11(10):633 (1956), herein incorporated by reference).

1. To prepare TLC plates, submerged a 20 cm×20 cm silica gel coated TLC plate with loading strip for 30 sec into 0.15 M ammonium sulfate ($(NH_4)_2SO_4$) solution, After submerging for 30 seconds, the plate was dried for at least 2 days in a covered container. During activation the sublimation of ammonium leaves behind sulfuric acid, which protonates phosphatidylglycerol necessary for its separation from other glycerolipids.
2. On the day of experiment, activate TLC plates by baking in an oven at 120° C. for 2.5 hours.
3. After cooling down the activated plates to room temperature, used a pencil to draw a straight line (1.5 cm from the edge of the plate) across the plate at the origin of the chromatogram.
4. In a fume hood, slowly delivered 3×20 μL of lipid extract in the lower chloroform phase using a 20 μL pipette with 200 μL yellow plastic tips under a slow stream of $N_2$. For this purpose, a Tygon Tubing was connected to the regulator of the $N_2$ tank. Kept the spot smaller than 1 cm in diameter. Each plate can hold up to 10 samples (when subsequent GLC analysis is planned).

5. As the lipid spots completely dried in the fume hood, prepared the developing solvent composed of acetone, toluene, water (91 mL:30 mL:7.5 mL). When the ambient relative air humidity was high, separation was affected. In this case water was reduced to give (91 mL:30 mL:7.0 mL) to achieve the desired separation.
6. Poured 80 mL developing solvent into a sealable TLC developing chamber (L:H:W=27.0:26.5:7.0, cm/cm/cm) and placed the plate into the tank with the sample end facing down. Seal the tank using the clamp. The solvent ascended the plate and lipids were separated. The development time was approximately 50 minutes at room temperature.
7. When the solvent front reached 1 cm from the top of the plate, carefully removed the plate from the tank and completely dried in the fume hood for approximately 10 minutes.
8. Lipids separated by TLC were either reversibly stained briefly with iodine for quantitative analysis or irreversibly stained with sulfuric acid or α-naphthol.
    1. Sulfuric acid charring: sprayed the plate with 50% sulfuric acid in water in a glass spray bottle in the fume hood and bake at 120° C. for 15 minutes (FIG. 27A).
    2. α-naphthol staining for glycolipids: sprayed the plate with 2.4% (w/v) α-naphthol in 10% (v/v) sulfuric acid, 80% (v/v) ethanol and baked at 120° C. for 3-5 minutes until glycolipid bands were stained pink (mid MGDG bands) or purple (lower DGDG bands) (FIG. 27B). Overtreatment led to charring of lipids due to presence of sulfuric acid in the reagent.
    3. Iodine staining (FIG. 27C): in a fume hood, place the plate into a closed TLC tank with iodine crystals (in a tray on the bottom leading to saturation of the atmosphere with iodine vapor until lipids were visible). Care was taken to not expose the plate to iodine too long as iodine covalently modified polyunsaturated fatty acids. Alternatively, to avoid oxidation of lipids, standard lanes interspersed with sample lanes were stained using a glass wool plugged Pasteur pipette with iodine crystals through which $N_2$ was blown over individual standard lanes.

Fatty Acyl Methylester (FAME) Reaction (Stoffel, et al., Proc. Soc. Exp. Biol. Med. 99(1):238 (1958), herein incorporated by reference.

1. Removed silica surrounding identified lipid spots from the TLC plate with a razor blade. Scraped the lipid containing silica and transfer the silica powder using a funnel into a glass tube with a Teflon (PTFE)-lined screw cap.
2. Added 1 mL 1 N hydrochloric acid (HCl) in anhydrous methanol to each sample by glass pipette.
3. Added 100 μL 50 μg $mL^{-1}$ pentadecanoic acid (15:0) using 200 μL pipette to each sample as internal standard using a 200 μL pipette with 200 μL yellow plastic tip. Keep a tube with pentadecenoic acid in methanolic HCl as a control. Glass tubes were closed tightly with Teflon-lined caps.
4. Incubated glass tubes in an 80° C. water bath for 25 minutes. Tubes were sealed so that the solvent did not evaporate.
5. After tubes cooled down, add 1 mL 0.9% sodium chloride followed by 1 mL hexane and vortex vigorously. Centrifuged samples at 1000×g for 3 minutes.
6. In the fume hood, removed the hexane/upper layer of the sample with Pasteur pipette and placed it into a new 13×100 mm glass tube.
7. Evaporated hexane under a slow stream of $N_2$ without drying completely.
8. Dissolved the resulting fatty acyl methylesters s in 60 μL hexane. Transfered samples into autosampler vials and cap tightly. Samples can be stored at 4° C. for short term and −20° C. for a few days.

Gas-Liquid Chromatography (GLC) (James and Martin, Biochem. J. 50(5):679 (1952), herein incorporated by reference).

1. Before beginning GLC, Ensure that the helium, hydrogen and air cylinders are filled.
2. Sufficient hexane must be added to the solvent reservoir and the waste container must be empty. For fatty acyl methylesters separation, attach a DB-23 column to the machine.
3. Place vials into the autosampler. Start the Chemstation software for GLC on the system computer.
4. Set the inlet temperature at 250° C. with helium flow rate at 48.6 mL $min^{-1}$ and the pressure at 21.93 psi. The split ratio is 30.0:1.
5. The oven temperature was set initially at 140° C. for 2 min then raised to 160° C. at a rate of 25° C. $min^{-1}$. The temperature was set to increase from 160° C. to 250° C. at a rate of 8° C. $min^{-1}$ and hold at 250° C. for 4 min followed by a decrease to 140° C. at a rate of 38° C. $min^{-1}$. One run took approximately 21 minutes.
6. The temperature of the flame ionization detector was 270° C. with a hydrogen flow rate of 30.0 mL $min^{-1}$, air flow rate at 400 mL $min^{-1}$ and helium flow rate at 30.0 mL $min^{-1}$.
7. Entered the number of vials and sample names into the run sequence table. Set the 10 μL injector to inject 2 μL sample per vial.
8. When the instrument was ready, initiate the run sequence.

Figure 27:
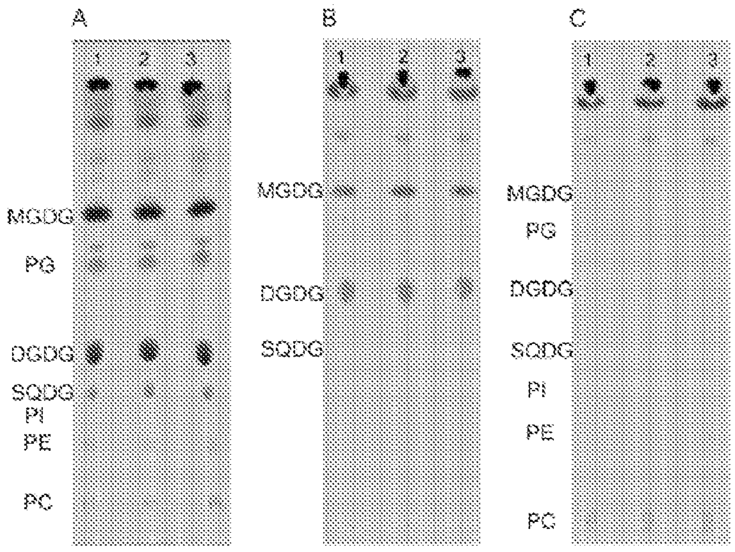
FIG. 27 shows an exemplary separation of lipids on TLC plates. Lipid extracts of 35 mg (fresh weight) wild type seedlings were separated by TLC and stained by sulfuric acid.

Representative Results:

Examples of irreversible staining of TLC-separated lipids from 4-week-old *Arabidopsis* seedlings are shown in FIG. 27. The sulfuric acid stained lipids (FIG. 27A) are charred and appear as brown spots. α-naphthol is preferred to stain glycolipids such as MGDG, DGDG, SQDG etc. Glycolipids stained with α-naphthol carry a pink-purple color while other polar lipids stain yellow (FIG. 27B). The iodine staining is reversible and gives lipids a yellowish color that will disappear over a short time as iodine evaporates (FIG. 27C). Briefly iodine stained lipids can be subjected to GLC analysis although unstained lipids are preferable to reduce break down of lipids.

Figure 28:
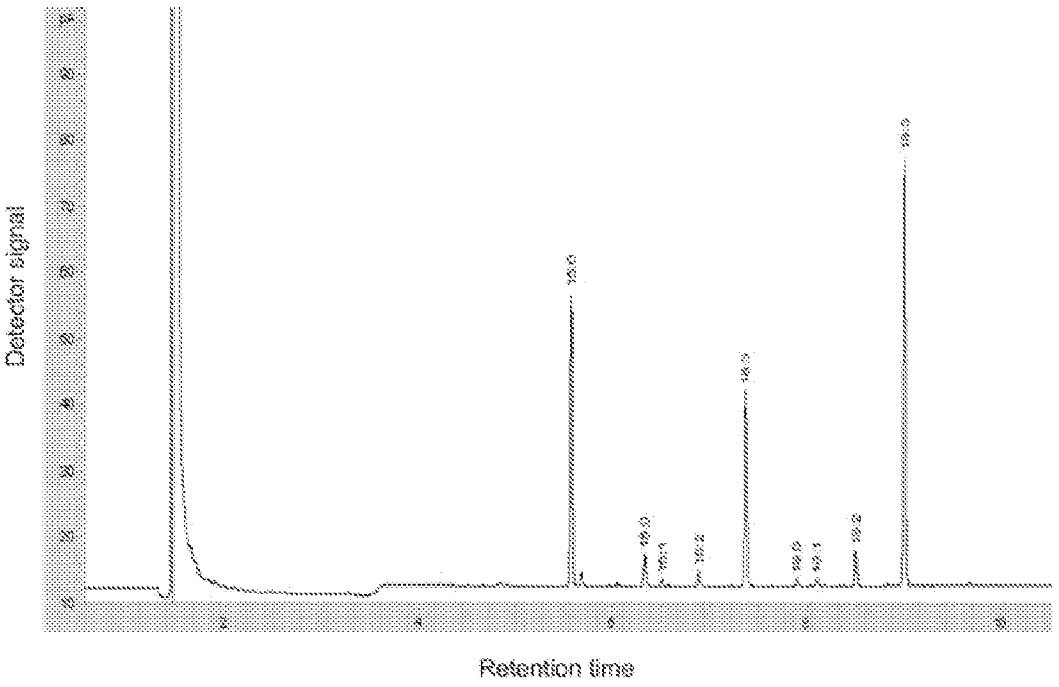
FIG. 28 shows an exemplary GLC analysis of Fatty Acid Methylesters (FAMEs) derived from MGDG of the wild type. FAMEs are separated on a 30 m capillary column and detected by flame ionization. Pentadecanoic acid (15:0) was used as an internal standard.

Distinctive signals representing different Fatty acyl methylester were observed after GLC (FIG. 28). Fatty acyl methylester with shorter carbon chain and fewer double bonds have shorter retention time using the DB-23 column. Fatty acyl methylester profiling is a sensitive tool to identify mutants with altered lipid composition. In FIG. 29, the MGDG18:3 fatty acid molar ratio was decreased in the tgd4-1 mutant compared to the wild type Xu, Plant Cell 20(8):2190 (2008), herein incorporated by reference. By dividing the moles of Fatty acyl methylester for one lipid class with the moles of all lipid classes, the molar ratio of each lipid was calculated. For example, to calculate the molar ratio of MGDG:

$$(MGDG)\text{mol }\% = \Sigma[FAMEs_{(MGDG)}]/\Sigma[FAMEs_{(total)}]\times 100\%.$$

The resulting molar ratios of each lipid class from both the wild type and the mutant can be compared. For instance, the tgd4-1 mutant has increased relative amounts of MGDG and PG but decreased amounts of DGDG and PE (FIG. 30) Xu, Plant Cell 20(8):2190 (2008), herein incorporated by reference.

Production and Purification of TGD4-Antibodies:

For the generation of polyclonal antibodies 100 μg purified DsRED-ΔTGD4-His was injected three times to immunize rabbits (Cocalico Biologicals, Pennsylvania). To purify the antibodies from the serum, DsRED-TGD4C-His was conjugated with Affi-Gel 15 (Bio-Rad, Hercules, Calif.) beads in 0.1 M HEPES, 8 M Urea according to the manufacturer's instruction. Anti-TGD4 crude serum was incubated with the antigen-coupled beads overnight at 4° C. After washing seven times with 5 ml phosphate buffered saline each, antibodies were eluted with 0.1 M glycine, pH 2.7 and were immediately neutralized with 1 M Tris-HCl, pH 9.0.

Immunoblot Analysis:

*Arabidopsis* total leaf extracts or isolated chloroplasts were dissolved in 2× Laemmli buffer and the proteins were separated on SDS-PAGE followed by transfer to the PVDF membrane (Bio-Rad) that was then blocked with 5% (w/v) non-fat dry milk in TBST buffer at room temperature for 1 hour. Primary antibodies were added to the blocking solution at various dilutions and incubation was continued overnight at 4° C. The PVDF membrane was then incubated with horseradish peroxidase (HRP)-conjugated goat anti-mouse (diluted 1:20,000, Bio-Rad) or goat anti-rabbit (diluted 1:75,000, Bio-Rad) for 30 minutes at room temperature followed by 6 washes with TBST and detection using a chemiluminescence kit (Sigma). The TGD4 antibodies were diluted 1:500. BIP antibodies (diluted 1:500) and HA-antibodies (diluted 1:5,000) were purchased from Santa Cruz Biotechnology and Sigma Aldrich respectively. SMT1 antibodies (diluted 1:200) were purchased from Agrisera (Vannas, Sweden). TOC75 (diluted 1:3,000) and TIC110 (diluted 1:3,000) antibodies were kindly provided by Dr. John Froehlich, Michigan State University while the TOC159 (diluted 1:2000) antibody was kindly provided by Dr. Masato Nakai, Osaka University.

Chloroplast Isolation and Proteinase Digestion:

Intact *Arabidopsis* chloroplasts were purified by discontinuous Percoll (Sigma) gradient (Arons son and Jarvis, 2002). To perform Thermolysin and Trypsin digestions, 10 μg chlorophyll equivalent chloroplasts were incubated with 0 to approximately 4 mg/ml Thermolysin (Sigma) or 0 to approximately 0.8 mg/ml Trypsin (Sigma) in digestion buffer (330 mM sorbitol, 50 mM Hepes-KOH pH 8.0, 5 mM $MgCl_2$) at 100 μl total volume on ice for 30 minutes. 1% (v/v) TritonX-100 was added to the sample containing the lowest amount of either proteinase as the positive control. The digestion was terminated by adding 50 μl 20 mM EDTA or 50 μl 0.2 mg/ml Trypsin inhibitor. After re-purifying by 40% Percoll and washing with digestion buffer once, proteinase digested intact chloroplasts were dissolved in 10 μl 2× Laemmli buffer and processed for SDS-PAGE and immunoblotting.

Figure 22:
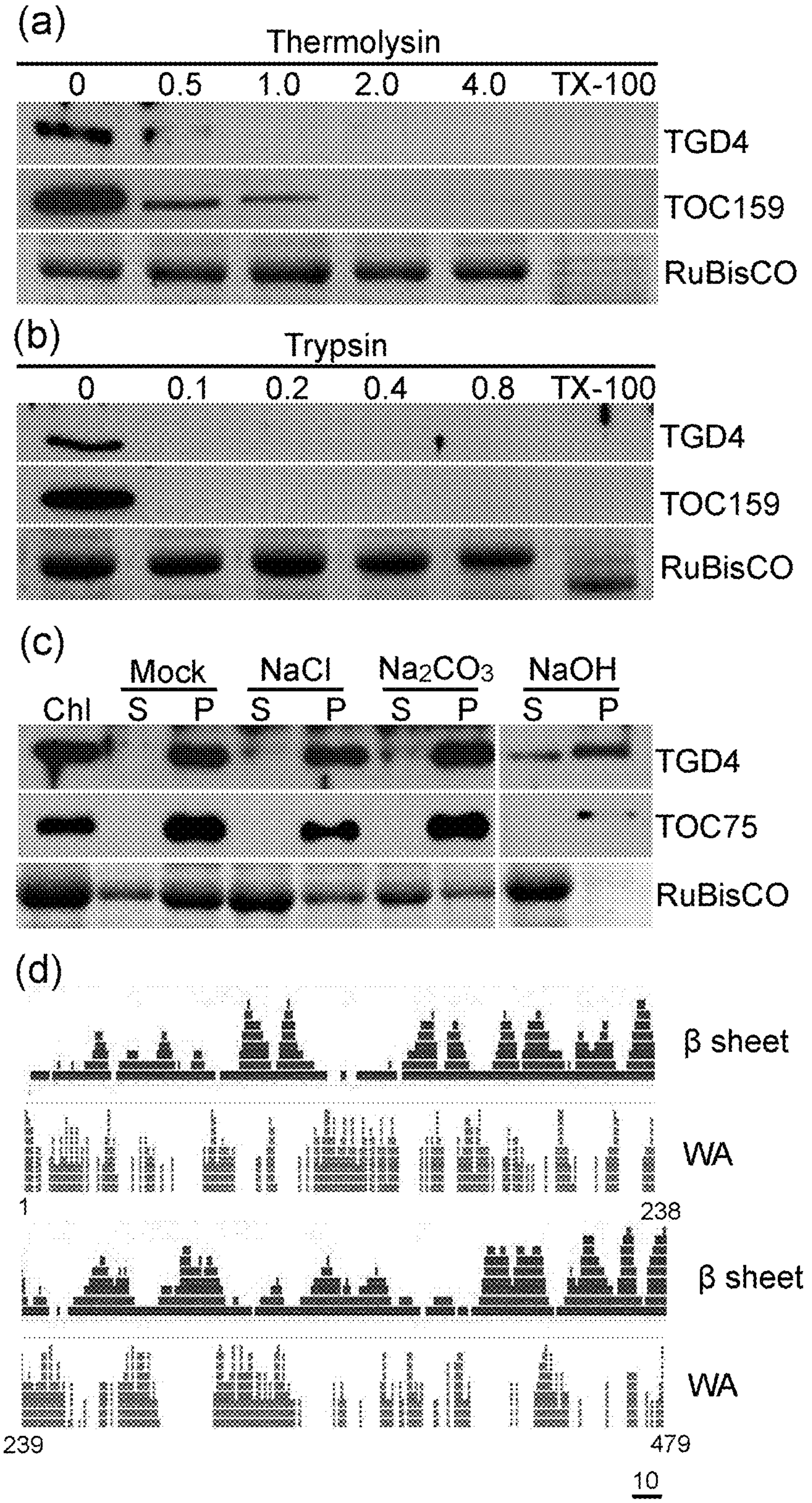
FIG. 22 shows exemplary TGD4 as a membrane embedded protein of the outer chloroplast envelope.
Figure 23:
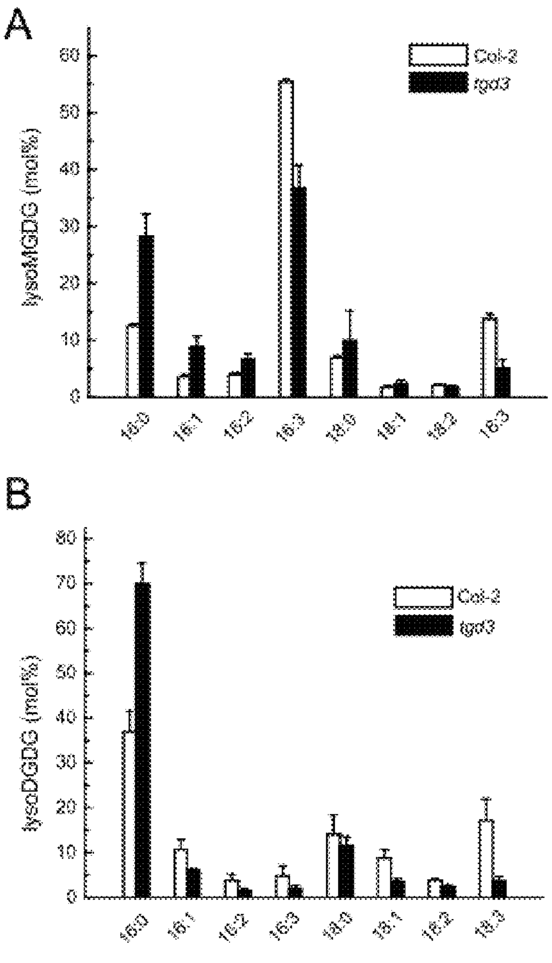
FIG. 23 shows exemplary choline chloride stabilized DsRED-TGD4-His.
Figure 24:
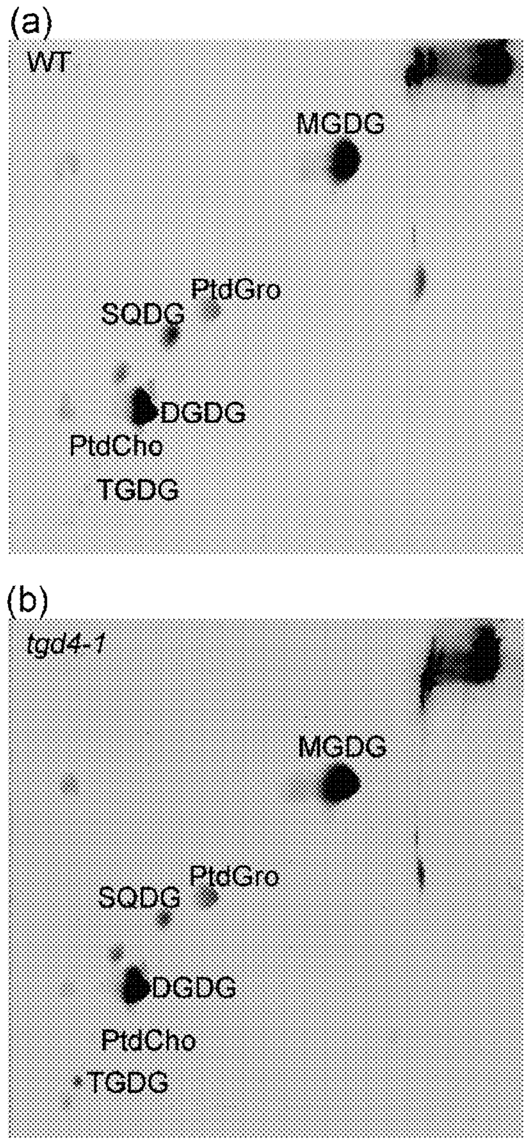
FIG. 24 shows exemplary experiments where PtdOH was not detectable in the chloroplast. Lipid extracts made from isolated chloroplasts were separated by two-dimensional thin layer chromatography (TLC).

To test the interaction strength between TGD4 and the outer envelope, 10 μg chlorophyll equivalent chloroplasts of the wild type were treated with hypotonic buffer (10 mM MOPS-NaOH, 4 mM $MgCl_2$) or reagents as indicated in FIG. 22C on ice for 30 minutes followed by centrifugation at 100,000×g for 1 hour. The protein compositions of both the supernatant and the pellet were examined by SDS-PAGE.

Membrane Fractionation:

*Arabidopsis* ER enriched microsomes were isolated from 4-week-old seedlings as described (Chen et al., 2002, herein incorporated by reference). Briefly, seedlings were homogenized employing pre-chilled mortar and pestle in grinding buffer containing 50 mM Tris-HCl, pH 8.2, 20% (v/v) glycerol, 5 mM $MgCl_2$, 1 mM dithiothreitol, 2 mM EDTA and protease inhibitor cocktail (Roche). The homogenate was then filtered through Miracloth and centrifuged at 12,000×g for 15 minutes. The supernatant was centrifuged again at 100,000×g for 1 hour. The resulting microsomes were resuspended in 0.5 ml buffer containing 10 mM Tris-HCl, pH7.5, 10% (w/v) sucrose, 5 mM $MgCl_2$, 2 mM EDTA, 1 mM dithiothreitol and protease inhibitor cocktail. The microsome suspension was separated on a 20%-50% (w/v) continuous sucrose gradient at 100,000×g for 16 hours at 4° C. Fractions of 1 ml were collected and processed for SDS-PAGE and Immunoblotting.

Example XII

TGD4 Binds PtdOH In Vitro

Trigalactosyldiacylglycerol 4 (TGD4) mutant plant phenotypes indicated that TGD4 was involved in the transfer of lipids from the ER-to-the plastid. Lipid binding properties of TGD4 were investigated by producing TGD4 fused to DsRED. The DsRED protein is a red fluorescent protein of the coral *Discosoma* sp. (Gross et al., 2000, herein incorporated by reference). DsRED protein was chosen because fusions of DsRED protein with TGD2 (recombinant TGD2) were successfully used to produce soluble protein used in lipid binding assays. Initially, the DsRED protein was fused to the N-terminus of the full-length TGD4 protein (such as with the ligation of a coding region for the N-terminus regions, for example, SEQ ID NO: 134, into DsRED nucleic acids (SEQ ID NO:137), such that the encoded truncated TGD4 has a C-terminal His-tag (DsRED-TGD4-His) giving rise to a fusion protein capable of being membrane associated. The DsRED-TGD4-His protein and later its derivatives (i.e. DsRED comprising truncation mutants of TGD4, i.e. SEQ ID NOs:130 and 131) were solubilized and purified on a nickel-chelate column in the presence of the zwitter-ionic detergent foscholine-12. Removal of detergent from the DsRED-TGD4-His protein preparation unexpectedly resulted in protein precipitation, unlike TGD2-His protein preparations. Because precipitated protein would interfere with the lipid assay, several compounds were then tested in order to reduce precipitation. Choline chloride was found to minimize precipitation and found use as a suitable stabilizer for this assay (FIG. 28). Choline chloride was then routinely added to the purified protein prior to assay experiments.

TABLE 4

Primers for producing the pLW01/dsRED-TGD4-His protein construct series. The pLW01/DsRED-His vector was used as cloning template. Primers have a SacI restriction site on the forward primer and a NotI site on the reverse primer except for pLW01/TGD4N-DsRED-His construct. Both primers for cloning pLW01/TGD4N-DsRED-His contain a NotI restriction site. The 5'-end is on the left.

| Construct | Forward Primer | Reverse Primer |
|---|---|---|
| pLW01/dsRED-TGD4-His | 5' CGAGCTCATGAACAGAATGAGATGGTC (SEQ ID NO: 139) | 5' ATAGTTTAGCGGCCGCTGTCTCAAAGAAACGAAGCTC (SEQ ID NO: 140) |
| pLW01/dsRED-ΔTGD4-His | 5' CGAGCTCATGAACAGAATGAGATGGTC (SEQ ID NO: 141) | 5' ATAGTTTAGCGGCCGCTGTCTCAAAGAAACGAAGCTC (SEQ ID NO: 142) |

TABLE 4-continued

Primers for producing the pLW01/dsRED-TGD4-His protein construct series. The pLW01/DsRED-His vector was used as cloning template. Primers have a SacI restriction site on the forward primer and a NotI site on the reverse primer except for pLW01/TGD4N-DsRED-His construct. Both primers for cloning pLW01/TGD4N-DsRED-His contain a NotI restriction site. The 5'-end is on the left.

| Construct | Forward Primer | Reverse Primer |
| --- | --- | --- |
| pLW01/TGD4N-dsRED-His | 5' CATGCCATGGATATGAACAGAATGAGATGGGTC (SEQ ID NO: 143) | 5' CATGCCATGGTATAGGGCTTGCAAGTTTCG (SEQ ID NO: 144) |
| pLW01/dsRED-TGD4C-His | 5' CGAGCTCGGTGAAAATTCAATCAGATCAAA (SEQ ID NO: 145) | 5' ATAGTTTAGCGGCCGCTGTCTCAAAGAAACGAAGCTC (SEQ ID NO: 146) |

In lipid-protein overlay assays probing lipids on commercially available membranes (FIG. 18A), DsRED-TGD4-His was found to specifically bind to PtdOH, but not to any other phospholipids tested. Moreover, when probing different chloroplast lipids manually spotted onto membranes, DsRED-TGD4-His did not bind to any other lipids but PtdOH (FIG. 18B). The DsRED-His protein itself was not observed to bind to any of the lipids on either membrane tested.

To independently verify PtdOH binding in a different assay and to test whether the protein showed preferences for different molecular species of PtdOH with regard to the acyl composition of the DAG moiety, a liposome binding assay was developed in which binding of the protein to liposomes containing different species of PtdOH was tested by co-precipitation (FIG. 18C, D). During the development of this liposome binding assay the inventors' discovered that in order for the assay to work there was a prerequisite for the exclusion of detergent while at the same time stabilizing the DsRED-TGD4-His fusion protein by adding choline chloride. Thus, choline chloride was a necessary addition to the buffer used for the liposome binding assay. Using this assay, DsRED-TGD4-His was found to bind to dipalmitoyl PtdOH and distearoyl PtdOH although the binding of distearoyl PtdOH appeared to be stronger. For PtdOH species of the same acyl chain length but different desaturation levels, DsRED-TGD4-His showed higher affinity for PtdOH with an increasing number of double bonds. Interestingly, DsRED-TGD4-His appeared to have an even higher affinity to diphytanoyl PtdOH that carried branched acyl chains with four methyl groups. However, DsRED-TGD4-His did not bind PtdOH carrying fluorescently labeled acyl substituents. The secondary band visible for the DsRED fusion proteins on the gels (FIG. 18C-E, and FIG. 19) was a result of DsRED self-cleavage during denaturation prior to electrophoresis (Gross et al., 2000). Because pH affects protonation of PtdOH and in some instances also PtdOH binding to proteins the effect of pH was tested. However, the binding of DsRED-TGD4-His to PtdOH was not affected over a pH range of 6.4-7.8 (FIG. 18E).

Example XIII

PtdOH Binding is Primarily a Function of the N-Terminal Half of TGD4

Figure 19:
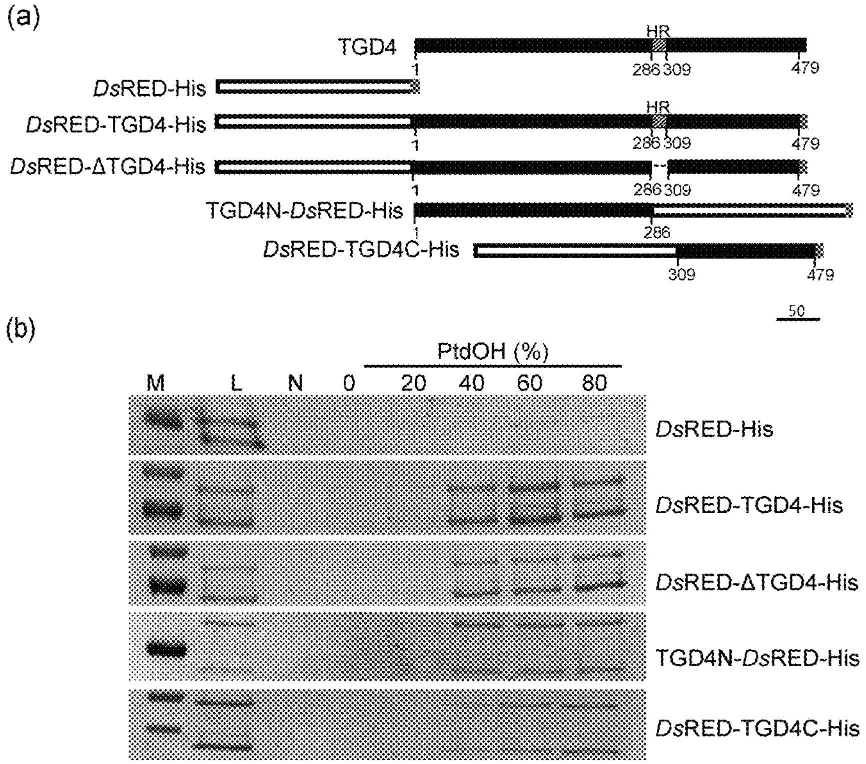
FIG. 19 shows an exemplary PtdOH bound to the N-terminal domain of DsRED-TGD4-His.

To determine the possible location of a PtdOH binding site in TGD4, a series of DsRED-TGD4-His truncation mutants was constructed as shown in FIG. 19. TGD4 contains a hydrophobic region of 23 amino acids (287D-309F) predicted by Aramemnon (Schwacke et al., 2003, herein incorporated by reference). To test whether this region is involved it was deleted in the DsRED-ΔTGD4-His protein (SEQ ID NO:133) (FIG. 19*a*). The N-terminal portion of TGD4 up to the mentioned hydrophobic region (SEQ ID NO:134) was fused to the N-terminus of DsRED giving rise to TGD4N-DsRED-His (FIG. 19*a*). The TGD4 C-terminal region (SEQ ID NO:135) was fused to the C-terminus of DsRED giving rise to DsRED-TGD4C-His (FIG. 19*a*). Except for DsRED-His alone, tested recombinant fusion proteins bound to PtdOH-containing liposomes, more so as the fraction of PtdOH in the liposomes increased. The TGD4N-DsRED-His protein showed an affinity to PtdOH liposomes comparable to the full-length protein DsRED-TGD4-His, indicating that a major PtdOH binding region resides within the N-terminal part of TGD4. In contrast, the DsRED-TGD4C-His protein had much lower affinity compared to the wild-type protein DsRED-TGD4-His but still bound PtdOH. Thus PtdOH binding activity did not require the central hydrophobic region of TGD4 and resided primarily, although not exclusively, in the N-terminal portion of TGD4.

Example XIV

PtdOH Accumulates in the tgd4 Mutants

Figure 20:
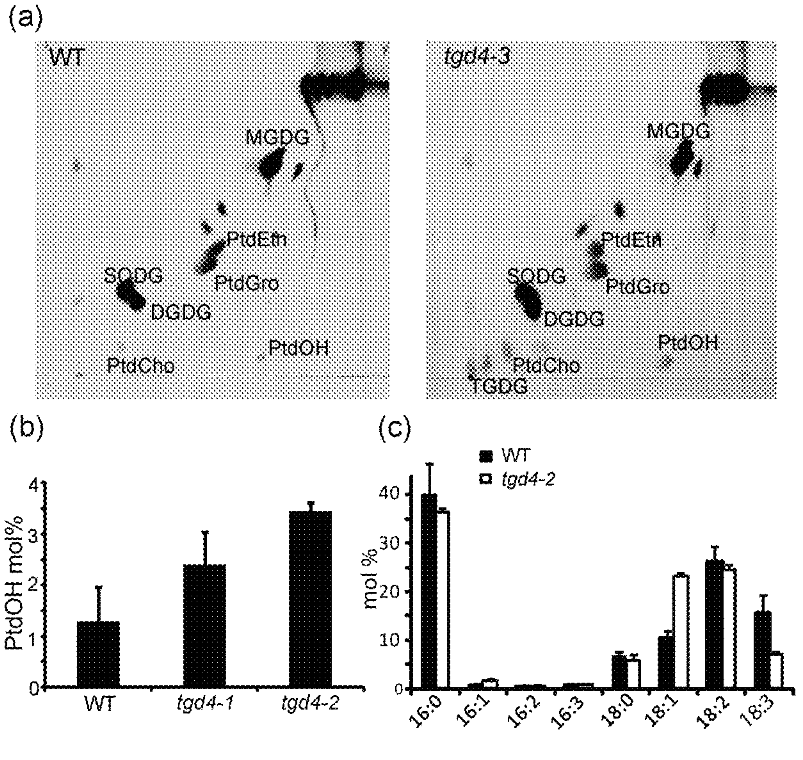
FIG. 20 shows an exemplary tgd4 mutant that accumulated phosphatidic acid in vivo.

Previous lipid profiling of the tgd4 mutant plants did not extend to PtdOH (Xu et al., 2008, herein incorporated by reference) therefore it was a surprise that TGD4 was involved with PtdOH binding, especially because TGD2 was found to bind to PtdOH and because PtdOH was found to accumulate in the tgd1 mutant plants (Xu et al., 2005, herein incorporated by reference). Therefore the inventors' determined whether tgd4 mutant plants also accumulated PtdOH. In plants, the tgd4-1 allele carried a one amino acid substitution (P20L) while tgd4-2 and tgd4-3 mutant plants were T-DNA knockout lines (Xu et al., 2008, herein incorporated by reference). Total lipid extracts were isolated from wild type and each of the tgd4 different mutant plants, each expressing a tgd4 mutant allele, then separated by two-dimensional thin-layer chromatography (TLC), which allowed clean isolation of PtdOH (FIG. 20*a*), and subsequent quantification (FIG. 20*b*). tgd4 mutant alleles showed increased relative amounts of PtdOH, approximately double in the weak tgd4-1 point mutant allele and triple in the strong tgd4-2 allele (FIG. 20*b*) compared to wild type. Probing lipids in chloroplasts isolated from the weaker tgd4-1 mutant allele, which was not possible for the stronger T-DNA-alleles due to the limited availability of material, did not reveal an accumulation of PtdOH in mutant chloroplasts compared to the wild type (FIG. 30). Thus it is likely that PtdOH accumulating in the tgd4-1 mutant was associated with extraplastidic membranes. Analysis of the fatty acid composition of PtdOH in the tgd4-2 mutant revealed an elevated 18:1 and decreased 18:3 acyl group content, similar to observations previously made for the tgd1 mutant (Xu et al., 2005, herein incorporated by reference).

Example XV

TGD4 Protein was Localized in the Outer Chloroplast Envelope Membrane

Figure 21:
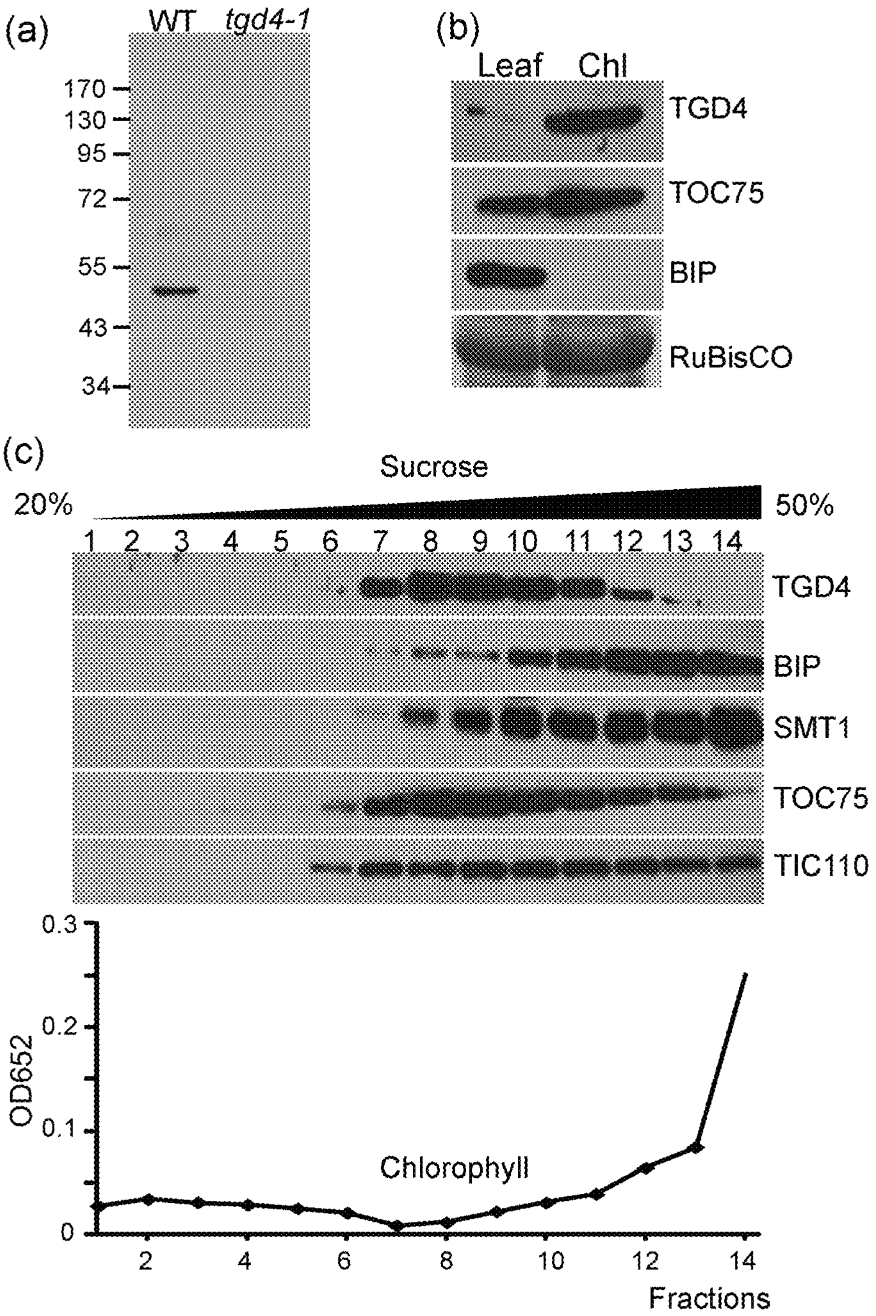
FIG. 21 shows exemplary TGD4 localized to the chloroplast.

In order to determine the location of the native TGD4 protein, a polyclonal TGD4-antiserum was produced in rabbits using purified DsRED-ΔTGD4-His as antigen. From the crude serum, TGD4 antibodies were highly purified. Using immunoblotting, a signal corresponding to the TGD4 protein with a calculated molecular weight of 52.8 kDa, was detected in leaf-extract of the wild type but not of the tgd4-1 mutants (FIG. 21*a*). Note that TGD4 protein was not detectable in this point mutant suggesting that the respective mutation affects the stability of TGD4 in vivo.

Cell fractionation in combination with protein immunoblotting and detection with the purified TGD4 antibody was employed to localize TGD4. The TGD4 protein was enriched in isolated chloroplasts in wild-type plants (FIG. 21*b*) in parallel with the chloroplast outer envelope marker TOC75 (Tranel et al., 1995, herein incorporated by reference). However, the ER luminal binding protein marker (BIP) (Oliver et al., 1995, herein incorporated by reference), was absent from the isolated chloroplasts. To determine whether TGD4 might also be present in the ER, an *Arabidopsis* wild-type microsomal preparation was fractionated by a continuous sucrose gradient to separate ER from other membranes (FIG. 21*c*). ER microsomes represented by BIP and SMT1, an ER membrane protein (Boutte and Grebe, 2009, herein incorporated by reference), were present in the denser fractions, which also contained thylakoid membrane fragments as indicated by the presence of chlorophyll. TOC75 was enriched in the medium dense fractions while TIC110, an inner envelope marker (Inaba et al., 2005, herein incorporated by reference), was found in both medium dense and dense fractions. The fractionation profile for TGD4 was similar to that of TOC75 suggesting that TGD4 was primarily associated with the chloroplast.

To further refine the localization of the native TGD4 protein, chloroplasts isolated from the wild-type leaves were subjected to protease digestion. The protease thermolysin did not penetrate the chloroplast outer envelope membrane and, therefore, digests proteins of the outer envelope membrane exposed to the cytosol but not inner envelope membrane proteins. On the other hand Trypsin, which is smaller in size, was able to penetrate the outer envelope membrane but not the inner envelope membrane and digests proteins associated with the inner envelope membrane facing the intermembrane space (Joyard et al., 1983, herein incorporated by reference). As shown in FIG. 22*a* and *b*, TGD4 protein was susceptible to Thermolysin and Trypsin digestion as was TOC159, an outer envelope membrane protein (Hiltbrunner et al., 2001, herein incorporated by reference), while the stroma protein RuBisCo was resistant to both. The addition of TritonX-100 disrupts chloroplast envelopes allowing complete accessibility by both proteases. Based on these results it is concluded that TGD4 is located in the outer envelope membrane of the chloroplast and at least partially exposed to the cytosol.

To determine the strength of the interaction between TGD4 and the outer envelope, isolated wild-type chloroplasts were extracted with sodium chloride, sodium carbonate, or sodium hydroxide (FIG. 22*c*). Peripheral or monotopic membrane proteins can be extracted by sodium chloride or sodium carbonate respectively, while transmembrane proteins are resistant to strongly basic sodium hydroxide (Miege et al., 1999, herein incorporated by reference). TGD4, like TOC75, which is a β-barrel protein, could not be extracted by any of the three reagents. In contrast, RuBisCo, most of which is peripheral to the thylakoid membrane (Irving and Robinson, 2006, herein incorporated by reference), was extracted by three reagents. Secondary structure prediction of TGD4 by PROF (Rost et al., 2004, herein incorporated by reference) suggested that the TGD4 protein most likely forms multiple β-sheets especially at the C-terminus corresponding well with regions not accessible to water indicative of a possible β-barrel conformation (FIG. 22*d*). Taken together, TGD4 is a transmembrane protein, contemplated as comprising a β-barrel shape, localized in the outer envelope membrane of the chloroplast and partially exposed to the cytosol.

REFERENCES

1. Meijer, H. J. G. and Munnik T. Phospholipid-based signaling in plants. Annu. Rev. Plant Biol. 54, 265-306. 2003.
2. Wang, X. Lipid signaling. Curr. Opin. Plant Biol. 7, 329-336. 2004.
3. Mueller-Roeber, B. and Pical C. Inositol phospholipids metabolism in *Arabidopsis*. Charaterized and putative isoforms of inositol phospholipids kinase and phosphaoniositide-specific phospholipase C. Plant Physiol. 130, 22-46. 2002.
4. Ryu, S. B. Phospholipid-derived signaling mediated by phospholipase A in plants. 9, 229-235. Trends Plant Sci. 9, 229-235. 2004.
5. van Leeuwen, W. et al. Learning the lipid language of plant signaling. Trends Plant Sci. 9, 378-384. 2004.
6. Zonia, L. and Munnik T. Cracking the green paradigm: functional coding of phosphoinositide signals in plant stress responses. In Subcellular Biochemistry: Biology of Inositols and Phosphoinositides (Vol. 39) (Majunder, A. and Biswas, B., eds), Kluwer/Plenum Publishers (in press). 2008.
7. Laxalt, A. M. and Munnik T. Phospholipid signaling in plant defense. Curr. Opin. Plant Biol. 5, 332-338. 2002.
8. Munnik, T. Phosphatidic acid: an emerging plant lipid second messenger. Trends Plant Sci. 6, 227-233.2001.
9. Wang, X. Phospholipase D in hormonal and stress signaling. Curr. Opin. Plant Biol. 5, 408-414. 2002.
10. Munnik T, Testerink C. Phosphotidic acid: a multifunctional stress signaling lipid in plants. Trends Plant Sci. 10, 368-375. 2005.
11. Ghosh, S. et al. Raf-1 kinase possesses distinct binding domains for phosphatidylserine and phosphatidic acid. J. Biol. Chem. 271, 8472-8480. 1996.
12. Ghosh, S. et al. Functional anslysis of a phosphatidic acid binding domain in human Raf-1 kinase. J. Biol. Chem. 278, 45690-45696. 2003.
13. Frank, C. et al. Binding of phosphatidc acid to the protein-tyrosine phosphatase SHP-1 as a basis for activity modulation. Biochemisty 38, 11993-12002. 1999.
14. Jones, J. A. and Hannun Y. A. Tight binding inhibition of protein phosphatase-1 by phosphatidic acid. J. Biol. Chem. 277, 15530-15538. 2002.
15. Jose Lopez-Andreo, M. et al. The simultaneous production of phosphatidic acid and diacylglycerol is essential for the translocation of protein kinase Ca to the plasma membrane in RBL-2H3 cells. Mol. Biol. Cell 14, 4885-4895. 2003.

16. Nakanishi, H. et al. Positive and negative regulation of a SNARE protein by control of intracellular localization. Mol. Biol. Cell 15, 1802-1815. 2004.

17. Loewen, C. J. R. et al. Phospholipid metabolism regulated by a transcription factor sensing phosphatidic acid. Science 204, 1644-1647. 2004.

18. Zhang, W. et al. Phospholipase Dal-derived phosphatidic acid interacts with ABI1 phosphatase 2C and regulates abscisic acid signaling. Proc. Natl. Acad. Sci. U.S.A. 101, 9508-9513. 2004.

19. Anthony, R. G. et al. A protein kinase target of a PDK1 signaling pathway is involved in root hair growth in *Arabidopsis*. EMBO J. 23, 572-581. 2004.

20. Deak, M. et al. Characterization of a plant 3-phosphoinositide-dependent protein kinae-1 homologue which contains a pleckstrin homology domain. FEBS Lett. 451, 220-226. 1999

21. Testerink C. et al. Isolation and identification of phosphatidic acid targets from plants. Plant J. 39, 527-536. 2004.

22. Awai K, Xu C Tamot B Benning C. A phosphatidic acid-binding protein of the chloroplast inner envelope membrane involved in lipid trafficking. Proc Natl Acad Sci USA 103, 10817-10822. 2006.

23. Xu C, Fan J Froehlich J Awai K Benning C. Mutation of the TGD1 chloroplast envelope protein affects phosphatidate metabolism in *Arabidopsis*. Plant Cell 17, 3094-3110. 2005.

24. Xu C, Fan J RiekhofW Froehlich J E Benning C. A permease-like protein involved in ER to thylakoid lipid transfer in *Arabidopsis*. EMBO J 22, 2370-2379. 2003.

25. Karathanassis, D. et al. Binding of the PX domain of P47phox to phosphatidylinositol 3,4-bisphosphate and phosphatidic acid is masked by an intramolecular interactions. EMBO J. 21, 5057-5068. 2002.

26. Lindsay, A. J. and McCaffrey M. W. The C2 domains of the class I Rab11 family of interacting proteins target recycling vesicles to the plasma membrane. J. Cell Sci. 117, 4365-4375. 2004.

27. Bradford, M. M. Anal. Biochem. 72, 248-254. 1976. Ref Type: Generic 28. Laemmli, U. K. Nature 227, 680-685. 1970.

29. Stephen F. Altschul, Thomas L. Madden Alejandro A. Schäffer Jinghui Zhang Zheng Zhang Webb Miller and David J. Lipman. Gapped BLAST and PSI-BLAST: a new generation of protein database search programs. Nucleic Acids Res 25, 3389-3402. 1997.

30. Mamedov, T. G. Moellering E. R. and Chollet R. Identification and expression analysis of two inorganic C- and N-responsive genes encoding novel and distinct molecular forms of eukaryotic phosphoenolpyruvate carboxylase in the green microalga *Chlamydomonas reinhardtii*. Plant J. 42, 832-843. 2005.

31. Sano, H. Kuroki Y. Honma T. Ogasawara Y. Sohma H. Voelker D. R. & Akino T. J. Biol. Chem. 273, 4783-4789. 1998.

32. Chitale, S. Ehrt S. Kawamura I. Fujimura T. Shimono N. Anand N. Lu S. Cohen-Gould L. & Riley L. W. Cell. Microbiol. 3, 247-254. 2001.

33. Kooijman E, Tieleman D Testerink C Munnik T Rijkers D Burger K and Kruijff B. An electrostatic/hydrogen bond switch as the basis for the specific interaction of phosphatidic acid with proteins. J. Biol. Chem. 282(15), 11356-11364. 2007.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in chemistry, plant biology, molecular biology, biochemistry, botany, and medicine, or related fields are intended to be within the scope of the following claims.

The invention claimed is:

1. A truncated trigalactosyldiacylglycerol 4 protein consisting of a polypeptide sequence selected from the group consisting of SEQ ID NO: 130, SEQ ID NO: 131, and SEQ ID NO: 133, wherein said polypeptide sequence comprising a phosphatidic acid binding domain.

2. The truncated trigalactosyldiacylglycerol 4 protein of claim 1, wherein said protein has a C-terminally attached label.

3. The truncated trigalactosyldiacylglycerol 4 protein of claim 2, wherein said C-terminally attached label is a histidine tag.

4. The truncated trigalactosyldiacylglycerol 4 protein of claim 1, wherein said protein lacks a transit peptide domain.

5. The truncated trigalactosyldiacylglycerol 4 protein of claim 1, wherein said protein lacks membrane associated domain.

6. The truncated trigalactosyldiacylglycerol 4 protein of claim 1, labeled with a fluorescent label.

7. A method, comprising:

a) providing:

i) a truncated trigalactosyldiacylglycerol 4 protein consisting of a polypeptide sequence selected from the group consisting of SEQ ID NO: 130, SEQ ID NO:

131, and SEQ ID NO: 133, wherein said polypeptide sequence comprising a phosphatidic acid binding domain, ii) a sample suspected of containing a lipid comprising a phosphatidic acid capable of binding to said trigalactosyldiacylglycerol 4 protein; and b) contacting said sample with said protein under conditions such that said phosphatidic acid binds to said trigalactosyldiacylglycerol 4 protein; and c) determining an amount of said phosphatidic acid binding to said trigalactosyldiacylglycerol 4 protein.

8. The method of claim 7, wherein said phosphatidic acid is selected from the group consisting of a phosphatidic acid, a dipalmitoyl phosphatidic acid and distearoyl phosphatidic acid.

9. The method of claim 7, wherein said trigalactosyldiacylglycerol 4 protein is a truncated protein.

10. The method of claim 7, wherein said sample is immobilized on a membrane.

11. The method of claim 7, wherein said sample comprises a liposome.

12. The method of claim 11, wherein said liposome comprises a lipid selected from the group consisting of a dipalmitoyl phosphatidic acid and distearoyl phosphatidic acid.

13. The method of claim 7, wherein said phosphatidic acid has a carbon chain length selected from the group consisting of 16 carbons and 18 carbons.

14. The method of claim 7, wherein said sample comprises a plant sample.

15. The method of claim 14, further comprising identifying a plant disease with said phosphatidic acid-domain binding amount.

16. The method of claim 14, further comprising identifying a plant wound with said phosphatidic acid-domain binding amount.

17. The method of claim 14, further comprising identifying a plant stress with said phosphatidic acid-domain binding amount.

18. The method of claim 17, wherein said plant stress is selected from the group consisting biotic stress, abiotic stress, pathogen infection, drought, salinity, and cold.

19. The method of claim 7, wherein said sample comprises a patient sample.

20. The method of claim 19, further comprising identifying a patient at risk for a disease with said amount of phosphatidic acid-domain binding.

21. The method of claim 19, further comprising identifying a patient disease with said amount of phosphatidic acid-domain binding.

22. The method of claim 19, wherein said patient is a human patient.

23. The method of claim 22, wherein said patient disease is polycystic kidney disease.

24. The method of claim 7, wherein said sample is immobilized on a plastic plate.

25. The method of claim 24, further comprising an enzyme-linked immunosorbent assay capable of providing an optical density read out, wherein said determining an amount is measuring said optical density.

26. The method of claim 7, further comprising a test strip, wherein said determining an amount is observed on said test strip.

27. The method of claim 7, wherein said determining an amount is determining an amount of phosphatidic acid-domain binding for use as a medical diagnostic.

28. The method of claim 7, further comprising a step before step b of treating the lipid under conditions that release a phosphatidic acid from said lipid.

29. A kit, comprising:

a) a first container comprising a truncated trigalactosyldiacylglycerol 4 protein consisting of a polypeptide sequence selected from the group consisting of SEQ ID NO: 130, SEQ ID NO: 131, and SEQ ID NO: 133, wherein said polypeptide sequence comprising a phosphatidic acid binding domain, b) a second container comprising a plurality of buffers and a plurality of reagents, c) a set of instructions for determining the presence of a phosphatidic acid.

30. The kit of claim 29, wherein said protein is soluble.

31. The kit of claim 29, wherein said protein is labeled.

32. The kit of claim 29, wherein said kit further comprises choline chloride.

33. The kit of claim 29, wherein said phosphatidic acid is derived from a sample.

34. The kit of claim 29, wherein said instructions describe determining the amount of a phosphatidic acid.

35. The kit of claim 29, wherein said instructions further comprise a method for releasing a phosphatidic acid from a lipid comprising a phosphatidic acid.

36. The kit of claim 29, wherein said instructions further comprise a method for determining the presence of a lipid selected from the group consisting of a dipalmitoyl phosphatidic acid and distearoyl phosphatidic acid.

* * * * *

UNITED STATES PATENT AND TRADEMARK OFFICE

CERTIFICATE OF CORRECTION

PATENT NO. : 8,629,251 B2
APPLICATION NO. : 13/350287
DATED : January 14, 2014
INVENTOR(S) : Benning et al.

It is certified that error appears in the above-identified patent and that said Letters Patent is hereby corrected as shown below:

In the Claims

In column 246, line 28, in Claim 29, after "reagents,", insert --and--, therefor Signed and Sealed this
Twenty-fourth Day of June, 2014

Michelle K. Lee
*Deputy Director of the United States Patent and Trademark Office*

SEQUENCE LISTING

```
<160> NUMBER OF SEQ ID NOS: 146

<210> SEQ ID NO 1
<211> LENGTH: 381
<212> TYPE: PRT
<213> ORGANISM: Arabidopsis thaliana

<400> SEQUENCE: 1

Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
        35                  40                  45

Asn Ser Asp Ala Ala His Gly Gln Pro Ser Ser Asp Gly Gly Lys Asn
    50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
            100                 105                 110
```

```
Ser Trp Ala Trp Leu Arg Gly Phe Gln Met Arg Ser Lys Phe Arg Lys
        115                 120                 125

Tyr Gln Thr Val Phe Glu Leu Ser His Ala Ser Gly Ile Cys Thr Gly
    130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
            180                 185                 190

Leu Leu Met Glu Thr Met Ile Asp Ile Met Pro Arg Asn Pro Ile Pro
        195                 200                 205

Glu Pro Ser Val Gly Pro Leu His Pro Glu Cys Gly Lys Glu Gly Leu
    210                 215                 220

Ile Val Cys Asp Arg Gln Thr Ile Lys Gly Val Gln Gly Val Ser Leu
225                 230                 235                 240

Asp Glu Leu Val Gly Ile Phe Thr Arg Ile Gly Arg Glu Val Glu Ala
                245                 250                 255

Ile Gly Val Ala Asn Thr Tyr Ser Leu Ala Glu Arg Ala Ala Ser Val
            260                 265                 270

Ile Glu Glu Ala Arg Pro Leu Leu Lys Lys Ile Gln Ala Met Ala Glu
        275                 280                 285

Asp Ala Gln Pro Leu Leu Ser Glu Phe Arg Asp Ser Gly Leu Leu Lys
    290                 295                 300

Glu Val Glu Cys Leu Thr Arg Ser Leu Thr Gln Ala Ser Asp Asp Leu
305                 310                 315                 320

Arg Lys Val Asn Ser Ser Ile Met Thr Pro Glu Asn Thr Glu Leu Ile
                325                 330                 335

Gln Lys Ser Ile Tyr Thr Leu Val Tyr Thr Leu Lys Asn Val Glu Ser
            340                 345                 350

Ile Ser Ser Asp Ile Leu Gly Phe Thr Gly Asp Glu Ala Thr Arg Lys
        355                 360                 365

Asn Leu Lys Leu Leu Ile Lys Ser Leu Ser Arg Leu Leu
    370                 375                 380


<210> SEQ ID NO 2
<211> LENGTH: 91
<212> TYPE: PRT
<213> ORGANISM: Arabidopsis thaliana

<400> SEQUENCE: 2

Arg Lys Tyr Gln Thr Val Phe Glu Leu Ser His Ala Ser Gly Ile Cys
1               5                   10                  15

Thr Gly Thr Pro Val Arg Ile Arg Gly Val Thr Val Gly Thr Ile Ile
            20                  25                  30

Arg Val Asn Pro Ser Leu Lys Asn Ile Glu Ala Val Ala Glu Ile Glu
        35                  40                  45

Asp Asp Lys Ile Ile Ile Arg Asn Pro Ile Pro Glu Pro Ser Val Gly
    50                  55                  60

Pro Leu His Pro Glu Cys Gly Lys Glu Gly Leu Ile Val Cys Asp Arg
65                  70                  75                  80

Gln Thr Ile Lys Gly Val Gln Gly Val Ser Leu
                85                  90


<210> SEQ ID NO 3
```

```
<211> LENGTH: 23
<212> TYPE: PRT
<213> ORGANISM: Arabidopsis thaliana

<400> SEQUENCE: 3

Glu Gly Gly Val Gly Leu Phe Ile Val Ser Gly Ala Thr Leu Leu Ala
1               5                   10                  15

Leu Ser Trp Ala Trp Leu Arg
            20


<210> SEQ ID NO 4
<211> LENGTH: 45
<212> TYPE: PRT
<213> ORGANISM: Arabidopsis thaliana

<400> SEQUENCE: 4

Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg
        35                  40                  45


<210> SEQ ID NO 5
<211> LENGTH: 381
<212> TYPE: PRT
<213> ORGANISM: Arabidopsis thaliana

<400> SEQUENCE: 5

Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
        35                  40                  45

Asn Ser Asp Ala Ala His Gly Gln Pro Ser Ser Asp Gly Gly Lys Asn
    50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
            100                 105                 110

Ser Trp Ala Trp Leu Arg Gly Phe Gln Met Arg Ser Lys Phe Arg Lys
        115                 120                 125

Tyr Gln Thr Val Phe Glu Leu Ser His Ala Ser Gly Ile Cys Thr Gly
    130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
            180                 185                 190

Leu Leu Met Glu Thr Met Ile Asp Ile Met Pro Arg Asn Pro Ile Pro
        195                 200                 205

Glu Pro Ser Val Gly Pro Leu His Pro Glu Cys Gly Lys Glu Gly Leu
    210                 215                 220

Ile Val Cys Asp Arg Gln Thr Ile Lys Gly Val Gln Gly Val Ser Leu
```

```
225                 230                 235                 240

Asp Glu Leu Val Gly Ile Phe Thr Arg Ile Gly Arg Glu Val Glu Ala
                245                 250                 255

Ile Gly Val Ala Asn Thr Tyr Ser Leu Ala Glu Arg Ala Ala Ser Val
            260                 265                 270

Ile Glu Glu Ala Arg Pro Leu Leu Lys Lys Ile Gln Ala Met Ala Glu
        275                 280                 285

Asp Ala Gln Pro Leu Leu Ser Glu Phe Arg Asp Ser Gly Leu Leu Lys
    290                 295                 300

Glu Val Glu Cys Leu Thr Arg Ser Leu Thr Gln Ala Ser Asp Asp Leu
305                 310                 315                 320

Arg Lys Val Asn Ser Ser Ile Met Thr Pro Glu Asn Thr Glu Leu Ile
                325                 330                 335

Gln Lys Ser Ile Tyr Thr Leu Val Tyr Thr Leu Lys Asn Val Glu Ser
            340                 345                 350

Ile Ser Ser Asp Ile Leu Gly Phe Thr Gly Asp Glu Ala Thr Arg Lys
        355                 360                 365

Asn Leu Lys Leu Leu Ile Lys Ser Leu Ser Arg Leu Leu
    370                 375                 380


<210> SEQ ID NO 6
<211> LENGTH: 408
<212> TYPE: PRT
<213> ORGANISM: Vitis vinifera

<400> SEQUENCE: 6

Met Val Gly Asn Pro Ile Val Gln Val Pro Thr Cys Pro Ala Ala Leu
1               5                   10                  15

Ser Ser Ala Leu Ala Thr Leu Pro Trp Gly Ser Gly Asn Phe Met Pro
            20                  25                  30

Cys Leu Pro Pro Arg Ser Arg Lys Lys Leu Leu Leu Val Arg Ala Asn
        35                  40                  45

Ser Ala Asp Ala Gly His Ser Gln Pro Pro Ser Pro Ser Lys Thr Lys
    50                  55                  60

Asn Pro Leu Ala Val Ile Leu Asp Phe Pro Arg Asn Val Trp Lys Gln
65                  70                  75                  80

Thr Leu Arg Pro Leu Ser Asp Phe Gly Phe Gly Arg Arg Ser Ile Trp
                85                  90                  95

Glu Gly Gly Val Gly Leu Phe Leu Val Ser Gly Thr Val Leu Leu Val
            100                 105                 110

Leu Ser Leu Ala Trp Leu Arg Gly Phe Gln Leu Arg Ser Lys Phe Arg
        115                 120                 125

Lys Tyr Leu Ala Val Phe Glu Phe Thr Gln Ala Cys Gly Ile Cys Lys
    130                 135                 140

Gly Thr Pro Val Arg Ile Arg Gly Val Thr Val Gly Asn Val Ile Gln
145                 150                 155                 160

Val Asn Pro Ser Leu Lys Ser Ile Glu Ala Val Val Glu Val Glu Asp
                165                 170                 175

Asp Lys Ile Ile Ile Pro Gln Asn Ser Leu Ile Glu Val Asn Gln Ser
            180                 185                 190

Gly Leu Leu Met Glu Thr Leu Ile Asp Ile Thr Pro Arg Asp Pro Leu
        195                 200                 205

Pro Thr Pro Ser Val Gly Pro Leu Asp Pro Asp Cys Thr Lys Glu Gly
    210                 215                 220

Val Ile Val Cys Asp Arg Gln Lys Ile Arg Gly Tyr Gln Gly Val Ser
```

-continued

```
225                 230                 235                 240

Leu Asp Ala Leu Val Gly Ile Phe Thr Arg Leu Gly Arg Glu Val Glu
                245                 250                 255

Glu Ile Gly Ile Ala Gln Gly Tyr Ser Met Ala Glu Arg Ala Leu Ser
            260                 265                 270

Ile Ile Glu Glu Ala Arg Pro Leu Leu Ala Lys Ile Asn Asn Gln Arg
        275                 280                 285

Gly Met Gln Asn Arg Val Gly Thr Ser Asp Val Leu Phe Leu Val Trp
    290                 295                 300

Asp Trp Thr Phe Pro Ile Lys Ala Met Ala Glu Asp Val Gln Pro Leu
305                 310                 315                 320

Val Thr Glu Phe Arg Asp Thr Gly Leu Leu Lys Glu Val Glu Ser Leu
                325                 330                 335

Thr Lys Ser Leu Ala Gln Ala Thr Glu Glu Leu Arg Arg Val His Ser
            340                 345                 350

Ser Ile Leu Thr Pro Glu Asn Thr Glu Leu Ile Gln Lys Ser Ile Tyr
        355                 360                 365

Thr Leu Ile Phe Thr Leu Lys Asn Ile Glu Asn Ile Ser Ser Asp Ile
    370                 375                 380

Leu Gly Phe Thr Gly Asp Glu Ala Thr Arg Arg Asn Leu Lys Leu Leu
385                 390                 395                 400

Ile Lys Ser Leu Ser Arg Leu Leu
                405


<210> SEQ ID NO 7
<211> LENGTH: 370
<212> TYPE: PRT
<213> ORGANISM: Oryza sativa

<400> SEQUENCE: 7

Met Ala Thr Thr Lys Ser Phe Leu Pro Pro Pro Phe Ile Ala Leu Ser
1               5                   10                  15

Ser Asn Pro Arg Pro Thr Thr Leu Ala Pro Thr Pro Asn Pro Arg Pro
            20                  25                  30

Arg Arg Arg Asn Ser Leu Ala Ile Cys Ser Ala Ser Ala Ser Gly Asp
        35                  40                  45

Pro Ser Pro Pro Pro Glu Ala Glu Gly Gly Ser Asn Pro Leu Leu Ala
    50                  55                  60

Leu Trp Arg Arg Thr Leu His Pro Leu Gly Asp Tyr Gly Phe Gly Lys
65                  70                  75                  80

Arg Ser Val Trp Glu Gly Gly Val Gly Leu Phe Met Val Ser Gly Ala
                85                  90                  95

Ala Leu Leu Ala Leu Ala Leu Ala Trp Leu Arg Gly Phe Gln Leu Arg
            100                 105                 110

Ala Arg Phe Arg Lys Tyr Gln Ala Val Phe Glu Phe Thr Gln Ala Cys
        115                 120                 125

Gly Ile Cys Val Gly Thr Pro Val Arg Ile Arg Gly Val Thr Val Gly
    130                 135                 140

Asn Val Val Arg Val Asp Ser Ser Leu Lys Ser Ile Asp Ala Tyr Val
145                 150                 155                 160

Glu Val Glu Asp Asp Lys Ile Ile Val Pro Arg Asn Ser Val Val Glu
                165                 170                 175

Val Asn Gln Ser Gly Leu Leu Met Glu Thr Leu Ile Asp Ile Thr Pro
            180                 185                 190

Lys Asp Pro Leu Pro Thr Pro Ser Val Gly Pro Leu Asp Pro Asp Cys
```

```
        195                 200                 205

Ser Lys Glu Gly Leu Ile Leu Cys Asp Lys Glu Arg Met Lys Gly Gln
    210                 215                 220

Gln Gly Val Ser Leu Asp Ala Leu Val Gly Ile Phe Thr Arg Leu Gly
225                 230                 235                 240

Arg Glu Met Glu Glu Ile Gly Val His Lys Ser Tyr Lys Leu Ala Glu
                245                 250                 255

Lys Val Ala Ser Ile Met Glu Glu Ala Gln Pro Leu Leu Ser Arg Ile
            260                 265                 270

Glu Ala Leu Ala Glu Glu Ile Gln Pro Leu Leu Ser Glu Val Arg Asp
        275                 280                 285

Ser Asp Leu Val Lys Asp Val Glu Ile Ile Ala Lys Gly Leu Ala Asp
    290                 295                 300

Ala Ser Gly Asp Leu Arg Arg Leu Lys Ser Ser Met Leu Thr Pro Glu
305                 310                 315                 320

Asn Thr Asp Leu Ile Lys Gln Ser Ile Phe Thr Leu Ile Phe Thr Leu
                325                 330                 335

Lys Asn Ile Glu Ser Ile Ser Ser Asp Ile Ser Gly Phe Thr Gly Asp
            340                 345                 350

Asp Ala Thr Arg Arg Asn Ile Lys Leu Leu Ile Lys Ser Leu Ser Arg
        355                 360                 365

Leu Leu
    370


<210> SEQ ID NO 8
<211> LENGTH: 321
<212> TYPE: PRT
<213> ORGANISM: Physcomitrella patens

<400> SEQUENCE: 8

Met Ser Val Thr Glu Lys Leu Val Ser Leu Pro Gly Ala Ile Trp Lys
1               5                   10                  15

Gln Ile Leu Gly Pro Leu Ser Asn Phe Gly Phe Gly Lys Arg Ser Leu
            20                  25                  30

Trp Glu Gly Gly Val Gly Leu Phe Ile Met Ser Gly Val Leu Leu Leu
        35                  40                  45

Ala Ile Thr Leu Val Trp Val Lys Gly Lys Gln Ile Arg Ala Gln Thr
    50                  55                  60

Arg Lys Tyr Glu Ala Val Phe Glu Phe Gln Leu Ala Gln Gly Ile Thr
65                  70                  75                  80

Val Gly Thr Pro Val Arg Ile Arg Gly Val Asp Val Gly Asn Val Val
                85                  90                  95

Gln Val Arg Pro Ser Leu Glu Lys Ile Asp Val Val Val Glu Leu Ser
            100                 105                 110

Asp Ala Gly Ile Val Val Pro Arg Asn Ala Leu Val Glu Val Asn Gln
        115                 120                 125

Ser Gly Leu Ile Ser Glu Thr Leu Ile Asp Val Thr Pro Arg Arg Pro
    130                 135                 140

Ile Pro Lys Pro Thr Val Gly Pro Leu Asp Pro Lys Cys Pro Ser Glu
145                 150                 155                 160

Gly Leu Ile Val Cys Asp Arg Glu Arg Ile Lys Gly Glu Gln Gly Val
                165                 170                 175

Ser Leu Asp Glu Leu Val Gly Ile Cys Thr Lys Ile Ala Arg Gln Ile
            180                 185                 190

Asp Gly Leu Gly Val Glu Arg Met Ala Ser Met Ala Glu Arg Leu Gly
```

```
        195                 200                 205

Asp Ala Val Gln Glu Ala Arg Pro Leu Leu Leu Lys Val Gln Ser Met
    210                 215                 220

Ala Glu Asp Val Glu Pro Leu Leu Lys Glu Val Arg Glu Gly Gly Leu
225                 230                 235                 240

Leu Lys Asp Phe Glu Lys Leu Thr Lys Val Ala Ala Glu Ala Gly Arg
                245                 250                 255

Asp Leu Ser Asn Leu Asn Lys Val Val Leu Thr Ser Asp Asn Thr Glu
            260                 265                 270

Leu Leu Arg Asp Ser Val Ser Thr Leu Thr Lys Thr Leu Lys His Val
        275                 280                 285

Glu Ser Ile Ser Lys Asp Val Ser Gly Val Thr Gly Asp Ala Lys Thr
    290                 295                 300

Arg Asn Asn Leu Arg Gln Leu Ile Glu Ser Leu Ser Arg Leu Val Thr
305                 310                 315                 320

Asp


<210> SEQ ID NO 9
<211> LENGTH: 449
<212> TYPE: PRT
<213> ORGANISM: Ostreococcus tauri

<400> SEQUENCE: 9

Met Ala Ala Pro Ser Ala Thr Cys Ala Arg Gly Cys Ala Arg Ser Thr
1               5                   10                  15

Thr Thr Ser Ala Ser Gly Ile Asn Gly Tyr Val Arg Ala Ser Arg Ala
            20                  25                  30

Arg Ala Thr Arg Ile Ala Cys Ser Ser Leu Gly Glu Gly Glu Arg Gly
        35                  40                  45

Arg Glu Gly Gly Asp Val Arg Gly Glu Ile Gly Leu Ala Arg Leu Pro
    50                  55                  60

Arg Pro Ser Val Arg Arg Ala Val Val Arg Arg Asp Ala Arg Thr Ser
65                  70                  75                  80

Gly Thr Ser Gly Arg Ile Gln Gly Asn Val Ala Gly Asp Asp Gly Arg
                85                  90                  95

Ala Trp Trp Arg Asn Val Thr Ala Lys Ala Ala Val Asp Gly Gly Ser
            100                 105                 110

Glu Ser Ala Asp Ala Ser Ala Ser Glu Asp Phe Gly Ser Glu Asp Glu
        115                 120                 125

Gly Thr Ala Gly Lys Pro Val Asn Val Leu Lys Thr Phe Leu Arg Arg
    130                 135                 140

Leu Val Lys Pro Leu Gln Asp Phe Gly Phe Gly Arg Thr Arg Leu Trp
145                 150                 155                 160

Glu Gly Gly Val Gly Leu Phe Ile Ile Ser Gly Val Ala Val Thr Phe
                165                 170                 175

Ile Ile Trp Gly Trp Ile Gln Gly Leu Leu Ser Phe Ala Arg Lys Asn
            180                 185                 190

Ser Tyr Gln Ala Phe Ile Glu Phe Pro Val Ala Cys Gly Ile Gln Val
        195                 200                 205

Gly Thr Asn Val Arg Val Arg Gly Val Lys Ala Gly Thr Val Leu Ser
    210                 215                 220

Val Gln Pro Ser Leu Glu Lys Val Asp Val Leu Val Glu Met Asp Asp
225                 230                 235                 240

Lys Asn Val Pro Ile Pro Arg Asn Ser Val Ile Glu Ala Asn Gln Ser
                245                 250                 255
```

```
Gly Leu Ile Ala Glu Thr Ile Ile Asp Ile Thr Pro Ala Leu Pro Ile
            260                 265                 270

Pro Asn Ala Gln Trp Gly Pro Leu Asp Ser Gly Cys Glu Gly Glu Gly
        275                 280                 285

Leu Ile Val Cys Asp Arg Gly Lys Ile Lys Gly Val Gln Gly Val Ser
    290                 295                 300

Met Asp Glu Leu Val Gly Ile Cys Thr Lys Leu Ala Arg Glu Met Glu
305                 310                 315                 320

Arg Gln Asn Gly Val Gln Gln Met Phe Ala Thr Thr Glu Ser Ala Gln
                325                 330                 335

Arg Leu Met Thr Thr Leu Gln Pro Leu Leu Arg Glu Ala Ala Gln Ile
            340                 345                 350

Ala His Glu Leu Arg Pro Met Met Gln Asn Val Asn Glu Gln Gly Thr
        355                 360                 365

Leu Asp Thr Leu Glu Asp Leu Ala Gly Lys Thr Ser Ala Thr Val Glu
    370                 375                 380

Asp Ile Arg Arg Leu Lys Thr Thr Ile Leu Thr Asp Glu Asn Gln Glu
385                 390                 395                 400

Leu Leu Arg Gln Ser Ile Ser Thr Leu Thr Lys Thr Leu Gln His Val
                405                 410                 415

Glu Lys Val Ser Gly Asp Ile Ser Ser Val Ser Gly Asp Pro Ser Thr
            420                 425                 430

Arg Thr Asn Leu Arg His Leu Ile Gln Ser Leu Ser Arg Leu Val Asp
        435                 440                 445

Ala


<210> SEQ ID NO 10
<211> LENGTH: 278
<212> TYPE: PRT
<213> ORGANISM: Chlamydomonas reinhardtii

<400> SEQUENCE: 10

Met Val Ile His Ala Ser Ala Ser Gln Gly Asp Ala Glu Ser Gln Pro
1               5                   10                  15

Gly Phe Lys Gln Gly Leu Phe Gly Ser Ile Ala Lys Ser Leu Ser Asp
            20                  25                  30

Tyr Gly Ile Gly Lys Lys Ser Ile Trp Glu Gly Gly Val Gly Leu Phe
        35                  40                  45

Val Leu Ala Gly Gly Gly Ala Ala Val Ala Leu Val Ala Trp Ala Arg
    50                  55                  60

Gly Asn Ala Leu Arg Thr Gly Thr Pro Tyr Gln Ala Thr Ile Glu Phe
65                  70                  75                  80

Pro Leu Ala Cys Gly Ile Gln Ile Gly Thr Pro Val Arg Ile Arg Gly
                85                  90                  95

Val Gln Val Asn Asp Val Ser Thr Val Ile Pro Arg Asn Ser Val Ile
            100                 105                 110

Glu Ala Asn Gln Ser Gly Leu Ile Ala Glu Pro Leu Val Pro Val Pro
        115                 120                 125

Asp Tyr Arg Ala Leu Pro His Glu Pro Arg Cys Gln Asp Glu Ser Leu
    130                 135                 140

Ile Gly Val Ala Leu Asp Asp Leu Val Tyr Ile Met Thr Arg Cys Glu
145                 150                 155                 160

Leu Cys Glu Cys Ala Glu Asn Asp Gly Val Asp Lys Val Phe Ala Ala
                165                 170                 175
```

```
Ala Glu Ser Ala Thr Gln Leu Met Glu Lys Ala Ala Pro Leu Val Ser
            180                 185                 190

Ser Ala Ala Glu Leu Val Gly Asn Ile Glu Ala Leu Thr Arg Thr Ala
        195                 200                 205

Ala Asp Ala Ala Ala Asp Ile Arg Arg Leu Gln Gly Ser Val Leu Thr
    210                 215                 220

Glu Asp Asn Val Arg Ala Leu Arg Gln Ala Val Leu Thr Leu Cys Lys
225                 230                 235                 240

Thr Leu Asp His Val Glu Ser Ile Ser Ala Asp Val Ser Ile Leu Ala
                245                 250                 255

Arg Asp Ser Gly Val Gln Arg Asn Leu Lys Thr Leu Val Gln Ala Leu
            260                 265                 270

Ser Arg Leu Leu Asp Asp
        275


<210> SEQ ID NO 11
<211> LENGTH: 132
<212> TYPE: PRT
<213> ORGANISM: Arabidopsis thaliana

<400> SEQUENCE: 11

Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
        35                  40                  45

Ile Glu Ala Val Ala Glu Ile Glu Asp Asp Lys Ile Ile Ile Pro Arg
    50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile Val Cys Asp Arg Gln
            100                 105                 110

Thr Ile Lys Gly Val Gln Gly Val Ser Leu Asp Glu Leu Val Gly Ile
        115                 120                 125

Phe Thr Arg Ile
    130


<210> SEQ ID NO 12
<211> LENGTH: 25
<212> TYPE: PRT
<213> ORGANISM: Arabidopsis thaliana

<400> SEQUENCE: 12

Ile Met Pro Arg Asn Pro Ile Pro Glu Pro Ser Val Gly Pro Leu His
1               5                   10                  15

Pro Glu Cys Gly Lys Glu Gly Leu Ile
            20                  25


<210> SEQ ID NO 13
<211> LENGTH: 263
<212> TYPE: PRT
<213> ORGANISM: Arabidopsis thaliana

<400> SEQUENCE: 13

Gly Phe Gln Met Arg Ser Lys Phe Arg Lys Tyr Gln Thr Val Phe Glu
1               5                   10                  15
```

-continued

```
Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
        35                  40                  45

Ile Glu Ala Val Ala Glu Ile Glu Asp Asp Lys Ile Ile Ile Pro Arg
    50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile Val Cys Asp Arg Gln
            100                 105                 110

Thr Ile Lys Gly Val Gln Gly Val Ser Leu Asp Glu Leu Val Gly Ile
        115                 120                 125

Phe Thr Arg Ile Gly Arg Glu Val Glu Ala Ile Gly Val Ala Asn Thr
    130                 135                 140

Tyr Ser Leu Ala Glu Arg Ala Ala Ser Val Ile Glu Glu Ala Arg Pro
145                 150                 155                 160

Leu Leu Lys Lys Ile Gln Ala Met Ala Glu Asp Ala Gln Pro Leu Leu
                165                 170                 175

Ser Glu Phe Arg Asp Ser Gly Leu Leu Lys Glu Val Glu Cys Leu Thr
            180                 185                 190

Arg Ser Leu Thr Gln Ala Ser Asp Asp Leu Arg Lys Val Asn Ser Ser
        195                 200                 205

Ile Met Thr Pro Glu Asn Thr Glu Leu Ile Gln Lys Ser Ile Tyr Thr
    210                 215                 220

Leu Val Tyr Thr Leu Lys Asn Val Glu Ser Ile Ser Ser Asp Ile Leu
225                 230                 235                 240

Gly Phe Thr Gly Asp Glu Ala Thr Arg Lys Asn Leu Lys Leu Leu Ile
                245                 250                 255

Lys Ser Leu Ser Arg Leu Leu
            260


<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14

ccggagctcg gttttcaaat gcggtc                                          26


<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15

cggctcgagt agtagcctgc ttaggg                                          26


<210> SEQ ID NO 16

<400> SEQUENCE: 16

000
```

<210> SEQ ID NO 17

<400> SEQUENCE: 17

000

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
gcgctcgaga atacgagtga aaattcc 27

<210> SEQ ID NO 19
<211> LENGTH: 130
<212> TYPE: PRT
<213> ORGANISM: Arabidopsis thaliana

<400> SEQUENCE: 19

```
Ala Glu Ile Glu Asp Asp Lys Ile Ile Ile Pro Arg Asn Ser Leu Val
1               5                   10                  15

Glu Val Asn Gln Ser Gly Leu Leu Met Glu Thr Met Ile Asp Ile Met
            20                  25                  30

Pro Arg Asn Pro Ile Pro Glu Pro Ser Val Gly Pro Leu His Pro Glu
        35                  40                  45

Cys Gly Lys Glu Gly Leu Ile Val Cys Asp Arg Gln Thr Ile Lys Gly
    50                  55                  60

Val Gln Gly Val Ser Leu Asp Glu Leu Val Gly Ile Phe Thr Arg Ile
65                  70                  75                  80

Gly Arg Glu Val Glu Ala Ile Gly Val Ala Asn Thr Tyr Ser Leu Ala
                85                  90                  95

Glu Arg Ala Ala Ser Val Ile Glu Glu Ala Arg Pro Leu Leu Lys Lys
            100                 105                 110

Ile Gln Ala Met Ala Glu Asp Ala Gln Pro Leu Leu Ser Glu Phe Arg
        115                 120                 125

Asp Ser
    130
```

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
ccggagctcg ctgagataga agatg 25

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
cgactcgagg ctatcacgaa actcag 26

<210> SEQ ID NO 22

<211> LENGTH: 130
<212> TYPE: PRT
<213> ORGANISM: Arabidopsis thaliana

<400> SEQUENCE: 22

Lys Glu Gly Leu Ile Val Cys Asp Arg Gln Thr Ile Lys Gly Val Gln
1 5 10 15

Gly Val Ser Leu Asp Glu Leu Val Gly Ile Phe Thr Arg Ile Gly Arg
20 25 30

Glu Val Glu Ala Ile Gly Val Ala Asn Thr Tyr Ser Leu Ala Glu Arg
35 40 45

Ala Ala Ser Val Ile Glu Glu Ala Arg Pro Leu Leu Lys Lys Ile Gln
50 55 60

Ala Met Ala Glu Asp Ala Gln Pro Leu Leu Ser Glu Phe Arg Asp Ser
65 70 75 80

Gly Leu Leu Lys Glu Val Glu Cys Leu Thr Arg Ser Leu Thr Gln Ala
85 90 95

Ser Asp Asp Leu Arg Lys Val Asn Ser Ser Ile Met Thr Pro Glu Asn
100 105 110

Thr Glu Leu Ile Gln Lys Ser Ile Tyr Thr Leu Val Tyr Thr Leu Lys
115 120 125

Asn Val
130

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
caggagctca aggaaggtct gatcg 25

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
cggctcgagg acgttcttca aagtat 26

<210> SEQ ID NO 25
<211> LENGTH: 181
<212> TYPE: PRT
<213> ORGANISM: Arabidopsis thaliana

<400> SEQUENCE: 25

Ile Met Pro Arg Asn Pro Ile Pro Glu Pro Ser Val Gly Pro Leu His
1 5 10 15

Pro Glu Cys Gly Lys Glu Gly Leu Ile Val Cys Asp Arg Gln Thr Ile
20 25 30

Lys Gly Val Gln Gly Val Ser Leu Asp Glu Leu Val Gly Ile Phe Thr
35 40 45

Arg Ile Gly Arg Glu Val Glu Ala Ile Gly Val Ala Asn Thr Tyr Ser
50 55 60

Leu Ala Glu Arg Ala Ala Ser Val Ile Glu Glu Ala Arg Pro Leu Leu
65 70 75 80

```
Lys Lys Ile Gln Ala Met Ala Glu Asp Ala Gln Pro Leu Leu Ser Glu
                85                  90                  95

Phe Arg Asp Ser Gly Leu Leu Lys Glu Val Glu Cys Leu Thr Arg Ser
            100                 105                 110

Leu Thr Gln Ala Ser Asp Asp Leu Arg Lys Val Asn Ser Ser Ile Met
        115                 120                 125

Thr Pro Glu Asn Thr Glu Leu Ile Gln Lys Ser Ile Tyr Thr Leu Val
    130                 135                 140

Tyr Thr Leu Lys Asn Val Glu Ser Ile Ser Ser Asp Ile Leu Gly Phe
145                 150                 155                 160

Thr Gly Asp Glu Ala Thr Arg Lys Asn Leu Lys Leu Leu Ile Lys Ser
                165                 170                 175

Leu Ser Arg Leu Leu
            180
```

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26

```
ccggagctca ttatgcctag gaatccg                                          27
```

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27

```
cggctcgagt agtagcctgc ttaggg                                           26
```

<210> SEQ ID NO 28
<211> LENGTH: 182
<212> TYPE: PRT
<213> ORGANISM: Arabidopsis thaliana

<400> SEQUENCE: 28

```
Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
        35                  40                  45

Ile Glu Ala Val Ala Glu Ile Glu Asp Asp Lys Ile Ile Pro Arg
    50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile Val Cys Asp Arg Gln
            100                 105                 110

Thr Ile Lys Gly Val Gln Gly Val Ser Leu Asp Glu Leu Val Gly Ile
        115                 120                 125

Phe Thr Arg Ile Gly Arg Glu Val Glu Ala Ile Gly Val Ala Asn Thr
    130                 135                 140
```

```
Tyr Ser Leu Ala Glu Arg Ala Ala Ser Val Ile Glu Glu Ala Arg Pro
145                 150                 155                 160

Leu Leu Lys Lys Ile Gln Ala Met Ala Glu Asp Ala Gln Pro Leu Leu
                165                 170                 175

Ser Glu Phe Arg Asp Ser
            180
```

<210> SEQ ID NO 29

<400> SEQUENCE: 29

000

<210> SEQ ID NO 30

<400> SEQUENCE: 30

000

<210> SEQ ID NO 31
<211> LENGTH: 107
<212> TYPE: PRT
<213> ORGANISM: Arabidopsis thaliana

<400> SEQUENCE: 31

```
Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
        35                  40                  45

Ile Glu Ala Val Ala Glu Ile Glu Asp Asp Lys Ile Ile Ile Pro Arg
    50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile
            100                 105
```

<210> SEQ ID NO 32

<400> SEQUENCE: 32

000

<210> SEQ ID NO 33
<211> LENGTH: 26
<212> TYPE: DNA
<213> ORGANISM: Artificial Sequence
<220> FEATURE:
<223> OTHER INFORMATION: Synthetic

<400> SEQUENCE: 33
cggctcgagg atcagacctt ccttac 26

<210> SEQ ID NO 34
<211> LENGTH: 55
<212> TYPE: PRT
<213> ORGANISM: Arabidopsis thaliana

<400> SEQUENCE: 34

```
Ala Glu Ile Glu Asp Asp Lys Ile Ile Ile Pro Arg Asn Ser Leu Val
```

```
1               5                   10                  15

Glu Val Asn Gln Ser Gly Leu Leu Met Glu Thr Met Ile Asp Ile Met
            20                  25                  30

Pro Arg Asn Pro Ile Pro Glu Pro Ser Val Gly Pro Leu His Pro Glu
        35                  40                  45

Cys Gly Lys Glu Gly Leu Ile
    50                  55


<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35

ccggagctcg ctgagataga agatg                                           25


<210> SEQ ID NO 36

<400> SEQUENCE: 36

000


<210> SEQ ID NO 37

<400> SEQUENCE: 37

000


<210> SEQ ID NO 38

<400> SEQUENCE: 38

000


<210> SEQ ID NO 39

<400> SEQUENCE: 39

000


<210> SEQ ID NO 40
<211> LENGTH: 30
<212> TYPE: PRT
<213> ORGANISM: Arabidopsis thaliana

<400> SEQUENCE: 40

Lys Glu Gly Leu Ile Val Cys Asp Arg Gln Thr Ile Lys Gly Val Gln
1               5                   10                  15

Gly Val Ser Leu Asp Glu Leu Val Gly Ile Phe Thr Arg Ile
            20                  25                  30


<210> SEQ ID NO 41

<400> SEQUENCE: 41

000


<210> SEQ ID NO 42

<400> SEQUENCE: 42

000
```

-continued

<210> SEQ ID NO 43
<211> LENGTH: 351
<212> TYPE: PRT
<213> ORGANISM: Artificial Sequence
<220> FEATURE:
<223> OTHER INFORMATION: Synthetic

<400> SEQUENCE: 43

```
Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
        35                  40                  45

Asn Ser Asp Ala Ala His Gly Gln Pro Ser Ser Asp Gly Gly Lys Asn
    50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
            100                 105                 110

Ser Trp Ala Trp Leu Arg Gly Phe Gln Met Arg Ser Lys Phe Arg Lys
        115                 120                 125

Tyr Gln Thr Val Phe Glu Leu Ser His Ala Ser Gly Ile Cys Thr Gly
    130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
            180                 185                 190

Leu Leu Met Glu Thr Met Ile Asp Ile Met Pro Arg Asn Pro Ile Pro
        195                 200                 205

Glu Pro Ser Val Gly Pro Leu His Pro Glu Cys Gly Gly Arg Glu Val
    210                 215                 220

Glu Ala Ile Gly Val Ala Asn Thr Tyr Ser Leu Ala Glu Arg Ala Ala
225                 230                 235                 240

Ser Val Ile Glu Glu Ala Arg Pro Leu Leu Lys Lys Ile Gln Ala Met
                245                 250                 255

Ala Glu Asp Ala Gln Pro Leu Leu Ser Glu Phe Arg Asp Ser Gly Leu
            260                 265                 270

Leu Lys Glu Val Glu Cys Leu Thr Arg Ser Leu Thr Gln Ala Ser Asp
        275                 280                 285

Asp Leu Arg Lys Val Asn Ser Ser Ile Met Thr Pro Glu Asn Thr Glu
    290                 295                 300

Leu Ile Gln Lys Ser Ile Tyr Thr Leu Val Tyr Thr Leu Lys Asn Val
305                 310                 315                 320

Glu Ser Ile Ser Ser Asp Ile Leu Gly Phe Thr Gly Asp Glu Ala Thr
                325                 330                 335

Arg Lys Asn Leu Lys Leu Leu Ile Lys Ser Leu Ser Arg Leu Leu
            340                 345                 350
```

<210> SEQ ID NO 44
<211> LENGTH: 36
<212> TYPE: DNA
<213> ORGANISM: Artificial Sequence
<220> FEATURE:
<223> OTHER INFORMATION: Synthetic

<400> SEQUENCE: 44
ctgcatcctg aatgtggtgg acgcgaagtt gaggcc 36

<210> SEQ ID NO 45
<211> LENGTH: 36
<212> TYPE: DNA
<213> ORGANISM: Artificial Sequence
<220> FEATURE:
<223> OTHER INFORMATION: Synthetic

<400> SEQUENCE: 45
ggcctcaact tcgcgtccac cacattcagg atgcag 36

<210> SEQ ID NO 46
<211> LENGTH: 376
<212> TYPE: PRT
<213> ORGANISM: Artificial Sequence
<220> FEATURE:
<223> OTHER INFORMATION: Synthetic

<400> SEQUENCE: 46

Met Ile Gly Asn Pro Val Ile Gln Val Pro Ser Ser Leu Met Pro Ser
1 5 10 15

Ser Ser Met Ile Ala Cys Pro Arg Val Ser Pro Asn Gly Val Pro Tyr
20 25 30

Leu Pro Pro Lys Pro Arg Thr Arg His Leu Val Val Arg Ala Ala Ser
35 40 45

Asn Ser Asp Ala Ala His Gly Gln Pro Ser Ser Asp Gly Gly Lys Asn
50 55 60

Pro Leu Thr Val Val Leu Asp Val Pro Arg Asn Ile Trp Arg Gln Thr
65 70 75 80

Leu Lys Pro Leu Ser Asp Phe Gly Phe Gly Lys Arg Ser Ile Trp Glu
85 90 95

Gly Gly Val Gly Leu Phe Ile Val Ser Gly Ala Thr Leu Leu Ala Leu
100 105 110

Ser Trp Ala Trp Leu Arg Gly Phe Gln Met Arg Ser Lys Phe Arg Lys
115 120 125

Tyr Gln Thr Val Phe Glu Leu Ser His Ala Ser Gly Ile Cys Thr Gly
130 135 140

Thr Pro Val Arg Ile Arg Gly Val Thr Val Gly Thr Ile Ile Arg Val
145 150 155 160

Asn Pro Ser Leu Lys Asn Ile Glu Ala Val Ala Glu Ile Glu Asp Asp
165 170 175

Lys Ile Ile Ile Pro Arg Asn Ser Leu Val Glu Val Asn Gln Ser Gly
180 185 190

Leu Leu Met Glu Thr Met Ile Asp Ile Met Pro Arg Asn Pro Ile Pro
195 200 205

Glu Pro Ser Val Gly Pro Leu His Pro Glu Cys Gly Val Cys Asp Arg
210 215 220

Gln Thr Ile Lys Gly Val Gln Gly Val Ser Leu Asp Glu Leu Val Gly
225 230 235 240

Ile Phe Thr Arg Ile Gly Arg Glu Val Glu Ala Ile Gly Val Ala Asn
245 250 255

Thr Tyr Ser Leu Ala Glu Arg Ala Ala Ser Val Ile Glu Glu Ala Arg
260 265 270

```
Pro Leu Leu Lys Lys Ile Gln Ala Met Ala Glu Asp Ala Gln Pro Leu
        275                 280                 285

Leu Ser Glu Phe Arg Asp Ser Gly Leu Leu Lys Glu Val Glu Cys Leu
    290                 295                 300

Thr Arg Ser Leu Thr Gln Ala Ser Asp Asp Leu Arg Lys Val Asn Ser
305                 310                 315                 320

Ser Ile Met Thr Pro Glu Asn Thr Glu Leu Ile Gln Lys Ser Ile Tyr
                325                 330                 335

Thr Leu Val Tyr Thr Leu Lys Asn Val Glu Ser Ile Ser Ser Asp Ile
            340                 345                 350

Leu Gly Phe Thr Gly Asp Glu Ala Thr Arg Lys Asn Leu Lys Leu Leu
        355                 360                 365

Ile Lys Ser Leu Ser Arg Leu Leu
    370                 375


<210> SEQ ID NO 47
<211> LENGTH: 36
<212> TYPE: DNA
<213> ORGANISM: Artificial Sequence
<220> FEATURE:
<223> OTHER INFORMATION: Synthetic

<400> SEQUENCE: 47

ctgcatcctg aatgtggtgt ttgtgatagg cagaca                              36


<210> SEQ ID NO 48
<211> LENGTH: 36
<212> TYPE: DNA
<213> ORGANISM: Artificial Sequence
<220> FEATURE:
<223> OTHER INFORMATION: Synthetic

<400> SEQUENCE: 48

tgtctgccta tcacaaacac cacattcagg atgcag                              36


<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49

gacagcccac aaattgatgg                                                20


<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50

accaacgctc aatgcctac                                                 19


<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51

ggggtcctta aaatagagac                                                20
```

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52
ggccttttga gttgggaaaa g 21

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gggggtgata tctatcgtag 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gcaccctgga tattctttcg 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
cggtcatatg ctggctgaag 20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gacagcacac aagttccagg 20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
gtgctatggt tcaggagttc 20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
cttaccagcc atgacgattc 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gagaagaaac accgattccg 20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
gttgtgatac gaatggtggc 20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
ggacctgcct ttcccatatc 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gcccaagcct caagatgttg 20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
ggaagaggga ggttttgttc 20

<210> SEQ ID NO 64
<211> LENGTH: 21
<212> TYPE: DNA
<213> ORGANISM: Artificial Sequence
<220> FEATURE:
<223> OTHER INFORMATION: Synthetic

<400> SEQUENCE: 64
ccaattcgtc tccttttcac c 21

<210> SEQ ID NO 65
<211> LENGTH: 20

<212> TYPE: DNA
<213> ORGANISM: Artificial Sequence
<220> FEATURE:
<223> OTHER INFORMATION: Synthetic

<400> SEQUENCE: 65
gtgagaccaa cagtgtcaac 20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
ccacaataca ccaccacttg 20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
cctccgtctc atacatctac 20

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
ccaattcggt ttcatccaat cctct 25

<210> SEQ ID NO 69
<211> LENGTH: 28
<212> TYPE: DNA
<213> ORGANISM: Artificial Sequence
<220> FEATURE:
<223> OTHER INFORMATION: Synthetic

<400> SEQUENCE: 69
catatgcatt gatgataact gaaatcga 28

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
cttctagatc tcctcctttc 20

<210> SEQ ID NO 71
<211> LENGTH: 29
<212> TYPE: DNA
<213> ORGANISM: Artificial Sequence
<220> FEATURE:
<223> OTHER INFORMATION: Synthetic

<400> SEQUENCE: 71
tgatcgtttg tgataggcag cctataaaa 29

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
ccttgcttcc tcaataaccg 20

<210> SEQ ID NO 73
<211> LENGTH: 31
<212> TYPE: DNA
<213> ORGANISM: Artificial Sequence
<220> FEATURE:
<223> OTHER INFORMATION: Synthetic

<400> SEQUENCE: 73
gtcgacatga ttgggaatcc agtaattcaa g 31

<210> SEQ ID NO 74
<211> LENGTH: 26
<212> TYPE: DNA
<213> ORGANISM: Artificial Sequence
<220> FEATURE:
<223> OTHER INFORMATION: Synthetic

<400> SEQUENCE: 74
gtcgactcat agtagcctgc ttaggg 26

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cggcttgctc aaggaagttg 20

<210> SEQ ID NO 76
<211> LENGTH: 22
<212> TYPE: DNA
<213> ORGANISM: Artificial Sequence
<220> FEATURE:
<223> OTHER INFORMATION: Synthetic

<400> SEQUENCE: 76
ccagtctaaa atctacaggc tg 22

<210> SEQ ID NO 77
<211> LENGTH: 29
<212> TYPE: DNA
<213> ORGANISM: Artificial Sequence
<220> FEATURE:
<223> OTHER INFORMATION: Synthetic

<400> SEQUENCE: 77
tgatcgtttg tgataggcag cctataaaa 29

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
ccttgcttcc tcaataaccg 20

<210> SEQ ID NO 79
<211> LENGTH: 29
<212> TYPE: DNA
<213> ORGANISM: Artificial Sequence
<220> FEATURE:
<223> OTHER INFORMATION: Synthetic

<400> SEQUENCE: 79
tcaattctct ctaccgtgat caagatgca 29

<210> SEQ ID NO 80
<211> LENGTH: 27
<212> TYPE: DNA
<213> ORGANISM: Artificial Sequence
<220> FEATURE:
<223> OTHER INFORMATION: Synthetic

<400> SEQUENCE: 80
gtgtcagaac tctccacctc aagagta 27

<210> SEQ ID NO 81
<211> LENGTH: 31
<212> TYPE: DNA
<213> ORGANISM: Artificial Sequence
<220> FEATURE:
<223> OTHER INFORMATION: Synthetic

<400> SEQUENCE: 81
gtcgacatga ttgggaatcc agtaattcaa g 31

<210> SEQ ID NO 82
<211> LENGTH: 28
<212> TYPE: DNA
<213> ORGANISM: Artificial Sequence
<220> FEATURE:
<223> OTHER INFORMATION: Synthetic

<400> SEQUENCE: 82
gtcgactagt agcctgctta gggatttg 28

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
gtcgacggtt ttcaaatgcg gtcgaag 27

<210> SEQ ID NO 84
<211> LENGTH: 26
<212> TYPE: DNA
<213> ORGANISM: Artificial Sequence
<220> FEATURE:
<223> OTHER INFORMATION: Synthetic

<400> SEQUENCE: 84
gtcgactcat agtagcctgc ttaggg 26

<210> SEQ ID NO 85
<211> LENGTH: 74

<212> TYPE: PRT
<213> ORGANISM: Arabidopsis thaliana

<400> SEQUENCE: 85

```
Asp Lys Ile Ile Ile Pro Arg Asn Ser Leu Val Glu Val Asn Gln Ser
1               5                   10                  15

Gly Leu Leu Met Glu Thr Met Ile Asp Ile Met Pro Arg Asn Pro Ile
            20                  25                  30

Pro Glu Pro Ser Val Gly Pro Leu His Pro Glu Cys Gly Lys Glu Gly
        35                  40                  45

Leu Ile Val Cys Asp Arg Gln Thr Ile Lys Gly Val Gln Gly Val Ser
    50                  55                  60

Leu Asp Glu Leu Val Gly Ile Phe Thr Arg
65                  70
```

<210> SEQ ID NO 86
<211> LENGTH: 74
<212> TYPE: PRT
<213> ORGANISM: Nodularia spumigena

<400> SEQUENCE: 86

```
Ala Asp Leu Met Ile Ser Arg Asp Ala Val Ile Glu Ala Asn Gln Ser
1               5                   10                  15

Gly Leu Ile Ser Glu Ser Ile Ile Asp Ile Thr Pro Lys Thr Ser Ile
            20                  25                  30

Pro Val Gly Ala Ile Ala Lys Pro Leu Asp Asn Asn Cys Asp Asp Ser
        35                  40                  45

Leu Ile Val Cys Asn Gly Ser Arg Leu Thr Gly Glu Ile Gly Ile Ser
    50                  55                  60

Ile Asp Glu Leu Ile Arg Thr Ser Thr Asn
65                  70
```

<210> SEQ ID NO 87
<211> LENGTH: 75
<212> TYPE: PRT
<213> ORGANISM: Anabaena variabilis

<400> SEQUENCE: 87

```
Ser Asp Leu Ile Ile Pro Arg Asp Val Val Ile Glu Ala Asn Gln Thr
1               5                   10                  15

Gly Leu Ile Ser Glu Ser Ile Ile Asp Ile Thr Pro Lys Ser Ser Leu
            20                  25                  30

Pro Thr Gly Gln Asn Leu Thr Lys Pro Leu Asp Lys Asn Cys Asp Asn
        35                  40                  45

Ser Leu Ile Val Cys Asn Asn Ser Arg Leu Lys Gly Gln Ile Gly Ile
    50                  55                  60

Ser Val Asp Ala Leu Ile Arg Ser Ser Thr Asp
65                  70                  75
```

<210> SEQ ID NO 88
<211> LENGTH: 73
<212> TYPE: PRT
<213> ORGANISM: Cyanothece sp. PCC 8801

<400> SEQUENCE: 88

```
Arg Glu Leu Arg Ile Pro Ile Gly Ser Thr Ile Gln Ile Asn Arg Tyr
1               5                   10                  15

Gly Leu Ile Gly Glu Ala Ser Val Asp Ile Thr Pro Ser Glu Lys Leu
            20                  25                  30
```

```
Ser Asp Gln Ala Leu Ala Val Asp Pro Thr Ser Glu Glu Cys Pro Asp
        35                  40                  45

Lys Gln Leu Ile Ile Cys Asp Asn Asp Thr Leu Asp Gly Glu Thr Gly
    50                  55                  60

Ser Gln Leu Val Gln Ala Leu Thr Arg
65                  70


<210> SEQ ID NO 89
<211> LENGTH: 74
<212> TYPE: PRT
<213> ORGANISM: Crocosphaera watsonii

<400> SEQUENCE: 89

Ala Glu Leu Arg Ile Pro Lys Asp Ser Lys Val Arg Ile Asn Arg Ser
1               5                   10                  15

Gly Leu Ile Gly Glu Ala Ser Val Asp Ile Thr Pro Ser Arg Glu Leu
            20                  25                  30

Asp Glu Glu Ala Leu Ala Ile Asp Pro Val Gly Lys Asp Cys Ala Ser
        35                  40                  45

Ala Glu Gln Ile Leu Cys Asn Asn Asp Glu Gly Ile Lys Gly Glu Arg
    50                  55                  60

Gly Ser Gln Leu Val Glu Ala Leu Thr Arg
65                  70


<210> SEQ ID NO 90
<211> LENGTH: 72
<212> TYPE: PRT
<213> ORGANISM: Synechococcus sp. JA-2-3B's(213)

<400> SEQUENCE: 90

Pro Leu Val Ile Pro Arg Asp Ser Leu Phe Leu Thr Lys Gln Thr Gly
1               5                   10                  15

Leu Val Gly Glu Thr Val Met Asp Ile Leu Pro Gln Gly Arg Gly Gln
            20                  25                  30

Ala Ala Thr Gly Ser Pro Leu Ala Ala Asp Cys Asp Ser Ser Gln Ile
        35                  40                  45

Ile Cys Asp Gly Asp Val Val Glu Gly Lys Pro Gly Val Asp Phe Gly
    50                  55                  60

Gln Leu Leu Ile Arg Leu Asp Gln
65                  70


<210> SEQ ID NO 91
<211> LENGTH: 75
<212> TYPE: PRT
<213> ORGANISM: Microcystis aeruginosa

<400> SEQUENCE: 91

Ala Asp Arg Leu Ile Pro Ser Asn Ser Leu Ile Glu Ala Ile Gln Ser
1               5                   10                  15

Gly Leu Val Gly Glu Thr Thr Ile Asp Ile Thr Pro Leu Gln Ala Leu
            20                  25                  30

Pro Val Gly Gly Val Lys Glu Pro Pro Leu Ser Pro Asn Cys Asn Gly
        35                  40                  45

Glu Val Ile Ile Cys Asn Gly Ser Arg Leu Gln Gly Gln Ser Ala Leu
    50                  55                  60

Asn Val Asn Thr Leu Ile Arg Ser Leu Leu Arg
65                  70                  75


<210> SEQ ID NO 92
```

<211> LENGTH: 73
<212> TYPE: PRT
<213> ORGANISM: Thermosynechococcus elongatus

<400> SEQUENCE: 92

Val Leu Ile Pro Arg Arg Ala Val Pro Glu Ile Arg Gln Ser Gly Phe
1 5 10 15

Ile Gly Gln Ala Phe Leu Asp Phe Thr Pro Lys Glu Arg Val Pro Glu
20 25 30

Ile Pro Glu Gly Val Thr Ala Phe Ala Pro Lys Cys Gln Pro Glu Leu
35 40 45

Val Tyr Cys Asn Gly Asp Arg Val Thr Gly Val Arg Thr Ala Ser Leu
50 55 60

Glu Asp Leu Val Arg Ala Ala Thr Arg
65 70

<210> SEQ ID NO 93
<211> LENGTH: 77
<212> TYPE: PRT
<213> ORGANISM: Acaryochloris marina

<400> SEQUENCE: 93

Ser Thr Val Leu Ile Pro Arg Gln Thr Lys Val Glu Thr Ser Gln Ser
1 5 10 15

Gly Phe Val Gly Gln Ala Ala Leu Glu Phe Arg Pro Thr Glu Val Glu
20 25 30

Phe Ser Asp Ala Ser Val Glu Asp Leu Ser Pro Phe Glu Pro Asp Cys
35 40 45

Asp Pro Arg Met Ile Leu Cys Gln Gly Asp Arg Leu Glu Gly Asp Ser
50 55 60

Gly Asn Asn Leu Glu Glu Leu Ile Arg Ala Thr Met Gln
65 70 75

<210> SEQ ID NO 94
<211> LENGTH: 75
<212> TYPE: PRT
<213> ORGANISM: Synechococcus sp. CC9902

<400> SEQUENCE: 94

Pro Asp Leu Arg Leu Pro Leu Pro Val Thr Ala Ser Val Gly Ala Ala
1 5 10 15

Ser Leu Leu Gly Gly Asp Ala Gln Val Asn Leu Ile Ser Gln Asn Lys
20 25 30

Pro Leu Pro Ala Asp Ala Pro Arg Pro Lys Ser Lys Arg Cys Ser Gly
35 40 45

Ser Ser Val Leu Cys Asp Gly Ala Gln Ile Ser Gly Val Glu Ala Pro
50 55 60

Ser Leu Asp Thr Val Thr Ala Ser Met Gln Arg
65 70 75

<210> SEQ ID NO 95
<211> LENGTH: 75
<212> TYPE: PRT
<213> ORGANISM: Synechococcus sp. WH 5701

<400> SEQUENCE: 95

Pro Thr Leu Gln Leu Ala Arg Pro Thr Met Ala Gln Val Gln Thr Gly
1 5 10 15

Ser Leu Leu Gly Gly Asp Ala Gln Val Ala Leu Ile Ser Thr Gly Asn
20 25 30

```
Pro Leu Pro Glu Ser Ala Pro Leu Pro Arg Ser Lys Asp Cys Asp Asn
        35                  40                  45

Thr Val Met Val Cys Ala Gly Ser Glu Leu Lys Gly Val Thr Ala Ala
    50                  55                  60

Ser Leu Asn Ser Val Thr Glu Leu Met Gln Arg
65                  70                  75


<210> SEQ ID NO 96
<211> LENGTH: 75
<212> TYPE: PRT
<213> ORGANISM: Prochlorococcus marinus str. MIT 9301

<400> SEQUENCE: 96

Pro Glu Ile Ile Leu Pro Lys Pro Ala Phe Ala Lys Val Val Thr Asn
1               5                   10                  15

Ser Phe Leu Gly Gly Asp Val Gln Val Ser Leu Glu Thr Ser Gln Lys
            20                  25                  30

Thr Ile Pro Lys Asp Ile Ala Lys Ala Ile Ser Glu Glu Cys Asp Ser
        35                  40                  45

Glu Leu Ile Val Cys Gln Gly Asp Thr Ile Thr Gly Lys Gln Leu Ser
    50                  55                  60

Ser Leu Ser Asn Ile Thr Asn Arg Ile Asn Gln
65                  70                  75


<210> SEQ ID NO 97
<211> LENGTH: 75
<212> TYPE: PRT
<213> ORGANISM: Prochlorococcus marinus str. NATL2A

<400> SEQUENCE: 97

Asp Asn Leu Ile Leu Pro Lys Pro Val Ile Ala Lys Ile Val Thr Ser
1               5                   10                  15

Ser Met Leu Gly Gly Asp Ala Gln Leu Ser Leu Ile Ser Leu Gly Lys
            20                  25                  30

Ser Leu Asn Lys Asn Glu Leu Ile Thr Val Asn Lys Asp Cys Pro Gln
        35                  40                  45

Lys Arg Ile Leu Cys Ser Gly Asp Lys Ile Lys Gly Val Glu Met Val
    50                  55                  60

Ser Ile Ser Ser Leu Thr Glu Gly Ile Asn Gly
65                  70                  75


<210> SEQ ID NO 98
<211> LENGTH: 74
<212> TYPE: PRT
<213> ORGANISM: Vitis vinifera

<400> SEQUENCE: 98

Asp Lys Ile Ile Ile Pro Gln Asn Ser Leu Ile Glu Val Asn Gln Ser
1               5                   10                  15

Gly Leu Leu Met Glu Thr Leu Ile Asp Ile Thr Pro Arg Asp Pro Leu
            20                  25                  30

Pro Thr Pro Ser Val Gly Pro Leu Asp Pro Asp Cys Thr Lys Glu Gly
        35                  40                  45

Val Ile Val Cys Asp Arg Gln Lys Ile Arg Gly Tyr Gln Gly Val Ser
    50                  55                  60

Leu Asp Ala Leu Val Gly Ile Phe Thr Arg
65                  70
```

<210> SEQ ID NO 99
<211> LENGTH: 74
<212> TYPE: PRT
<213> ORGANISM: Oryza sativa

<400> SEQUENCE: 99

```
Asp Lys Ile Ile Val Pro Arg Asn Ser Val Val Glu Val Asn Gln Ser
1               5                   10                  15

Gly Leu Leu Met Glu Thr Leu Ile Asp Ile Thr Pro Lys Asp Pro Leu
            20                  25                  30

Pro Thr Pro Ser Val Gly Pro Leu Asp Pro Asp Cys Ser Lys Glu Gly
        35                  40                  45

Leu Ile Leu Cys Asp Lys Glu Arg Met Lys Gly Gln Gln Gly Val Ser
    50                  55                  60

Leu Asp Ala Leu Val Gly Ile Phe Thr Arg
65                  70
```

<210> SEQ ID NO 100
<211> LENGTH: 74
<212> TYPE: PRT
<213> ORGANISM: Physcomitrella patens

<400> SEQUENCE: 100

```
Ala Gly Ile Val Val Pro Arg Asn Ala Leu Val Glu Val Asn Gln Ser
1               5                   10                  15

Gly Leu Ile Ser Glu Thr Leu Ile Asp Val Thr Pro Arg Arg Pro Ile
            20                  25                  30

Pro Lys Pro Thr Val Gly Pro Leu Asp Pro Lys Cys Pro Ser Glu Gly
        35                  40                  45

Leu Ile Val Cys Asp Arg Glu Arg Ile Lys Gly Glu Gln Gly Val Ser
    50                  55                  60

Leu Asp Glu Leu Val Gly Ile Cys Thr Lys
65                  70
```

<210> SEQ ID NO 101
<211> LENGTH: 74
<212> TYPE: PRT
<213> ORGANISM: Ostreococcus tauri

<400> SEQUENCE: 101

```
Lys Asn Val Pro Ile Pro Arg Asn Ser Val Ile Glu Ala Asn Gln Ser
1               5                   10                  15

Gly Leu Ile Ala Glu Thr Ile Ile Asp Ile Thr Pro Ala Leu Pro Ile
            20                  25                  30

Pro Asn Ala Gln Trp Gly Pro Leu Asp Ser Gly Cys Glu Gly Glu Gly
        35                  40                  45

Leu Ile Val Cys Asp Arg Gly Thr Ile Lys Gly Val Gln Gly Val Ser
    50                  55                  60

Met Asp Glu Leu Val Gly Ile Cys Thr Lys
65                  70
```

<210> SEQ ID NO 102
<211> LENGTH: 57
<212> TYPE: PRT
<213> ORGANISM: Chlamydomonas reinhardtii

<400> SEQUENCE: 102

```
Val Ser Thr Val Ile Pro Arg Asn Ser Val Ile Glu Ala Asn Gln Ser
1               5                   10                  15

Gly Leu Ile Ala Glu Pro Leu Val Pro Val Pro Asp Tyr Arg Ala Leu
```

```
            20                  25                  30

Pro His Glu Pro Arg Cys Gln Asp Glu Ser Leu Ile Gly Val Ala Leu
        35                  40                  45

Asp Asp Leu Val Tyr Ile Met Thr Arg
    50                  55


<210> SEQ ID NO 103
<211> LENGTH: 50
<212> TYPE: PRT
<213> ORGANISM: Arabidopsis thaliana

<400> SEQUENCE: 103

Gly Arg Glu Val Glu Ala Ile Gly Val Ala Asn Thr Tyr Ser Leu Ala
1               5                   10                  15

Glu Arg Ala Ala Ser Val Ile Glu Glu Ala Arg Pro Leu Leu Lys Lys
            20                  25                  30

Ile Gln Ala Met Ala Glu Asp Ala Gln Pro Leu Leu Ser Glu Phe Arg
        35                  40                  45

Asp Ser
    50


<210> SEQ ID NO 104
<211> LENGTH: 54
<212> TYPE: PRT
<213> ORGANISM: Arabidopsis thaliana

<400> SEQUENCE: 104

Asn Pro Ser Leu Lys Asn Ile Glu Ala Val Ala Glu Ile Glu Asp Asp
1               5                   10                  15

Lys Ile Ile Ile Pro Arg Asn Ser Leu Val Glu Val Asn Gln Ser Gly
            20                  25                  30

Leu Leu Met Glu Thr Met Ile Asp Ile Met Pro Arg Asn Pro Ile Pro
        35                  40                  45

Glu Pro Ser Val Gly Pro
    50


<210> SEQ ID NO 105
<211> LENGTH: 50
<212> TYPE: PRT
<213> ORGANISM: Arabidopsis thaliana

<400> SEQUENCE: 105

Gln Pro Leu Leu Ser Glu Phe Arg Asp Ser Gly Leu Leu Lys Glu Val
1               5                   10                  15

Glu Cys Leu Thr Arg Ser Leu Thr Gln Ala Ser Asp Asp Leu Arg Lys
            20                  25                  30

Val Asn Ser Ser Ile Met Thr Pro Glu Asn Thr Glu Leu Ile Gln Lys
        35                  40                  45

Ser Ile
    50


<210> SEQ ID NO 106
<211> LENGTH: 51
<212> TYPE: PRT
<213> ORGANISM: Arabidopsis thaliana

<400> SEQUENCE: 106

Gln Thr Val Phe Glu Leu Ser His Ala Ser Gly Ile Cys Thr Gly Thr
1               5                   10                  15

Pro Val Arg Ile Arg Gly Val Thr Val Gly Thr Ile Ile Arg Val Asn
```

```
            20                  25                  30

Pro Ser Leu Lys Asn Ile Glu Ala Val Ala Glu Ile Glu Asp Asp Lys
        35                  40                  45

Ile Ile Ile
    50


<210> SEQ ID NO 107
<211> LENGTH: 261
<212> TYPE: PRT
<213> ORGANISM: Arabidopsis thaliana

<400> SEQUENCE: 107

Gln Met Arg Ser Lys Phe Arg Lys Tyr Gln Thr Val Phe Glu Leu Ser
1               5                   10                  15

His Ala Ser Gly Ile Cys Thr Gly Thr Pro Val Arg Ile Arg Gly Val
            20                  25                  30

Thr Val Gly Thr Ile Ile Arg Val Asn Pro Ser Leu Lys Asn Ile Glu
        35                  40                  45

Ala Val Ala Glu Ile Glu Asp Asp Lys Ile Ile Ile Pro Arg Asn Ser
    50                  55                  60

Leu Val Glu Val Asn Gln Ser Gly Leu Leu Met Glu Thr Met Ile Asp
65                  70                  75                  80

Ile Met Pro Arg Asn Pro Ile Pro Glu Pro Ser Val Gly Pro Leu His
                85                  90                  95

Pro Glu Cys Gly Lys Glu Gly Leu Ile Val Cys Asp Arg Gln Thr Ile
            100                 105                 110

Lys Gly Val Gln Gly Val Ser Leu Asp Glu Leu Val Gly Ile Phe Thr
        115                 120                 125

Arg Ile Gly Arg Glu Val Glu Ala Ile Gly Val Ala Asn Thr Tyr Ser
    130                 135                 140

Leu Ala Glu Arg Ala Ala Ser Val Ile Glu Glu Ala Arg Pro Leu Leu
145                 150                 155                 160

Lys Lys Ile Gln Ala Met Ala Glu Asp Ala Gln Pro Leu Leu Ser Glu
                165                 170                 175

Phe Arg Asp Ser Gly Leu Leu Lys Glu Val Glu Cys Leu Thr Arg Ser
            180                 185                 190

Leu Thr Gln Ala Ser Asp Asp Leu Arg Lys Val Asn Ser Ser Ile Met
        195                 200                 205

Thr Pro Glu Asn Thr Glu Leu Ile Gln Lys Ser Ile Tyr Thr Leu Val
    210                 215                 220

Tyr Thr Leu Lys Asn Val Glu Ser Ile Ser Ser Asp Ile Leu Gly Phe
225                 230                 235                 240

Thr Gly Asp Glu Ala Thr Arg Lys Asn Leu Lys Leu Leu Ile Lys Ser
                245                 250                 255

Leu Ser Arg Leu Leu
            260


<210> SEQ ID NO 108
<211> LENGTH: 5
<212> TYPE: PRT
<213> ORGANISM: Arabidopsis thaliana

<400> SEQUENCE: 108

Lys Glu Gly Leu Ile
1               5


<210> SEQ ID NO 109
```

<211> LENGTH: 118
<212> TYPE: PRT
<213> ORGANISM: Arabidopsis thaliana

<400> SEQUENCE: 109

Val Gly Leu Phe Ile Val Ser Gly Ala Thr Leu Leu Ala Leu Ser Trp
1 5 10 15

Ala Trp Leu Arg Gly Phe Gln Met Arg Ser Lys Phe Arg Lys Tyr Gln
20 25 30

Thr Val Phe Glu Leu Ser His Ala Ser Gly Ile Cys Thr Gly Thr Pro
35 40 45

Val Arg Ile Arg Gly Val Thr Val Gly Thr Ile Ile Arg Val Asn Pro
50 55 60

Ser Leu Lys Asn Ile Glu Ala Val Ala Glu Ile Glu Asp Asp Lys Ile
65 70 75 80

Ile Ile Pro Arg Asn Ser Leu Val Glu Val Asn Gln Ser Gly Leu Leu
85 90 95

Met Glu Thr Met Ile Asp Ile Met Pro Arg Asn Pro Ile Pro Glu Pro
100 105 110

Ser Val Gly Pro Leu His
115

<210> SEQ ID NO 110
<211> LENGTH: 25
<212> TYPE: PRT
<213> ORGANISM: Artificial Sequence
<220> FEATURE:
<223> OTHER INFORMATION: Synthetic

<400> SEQUENCE: 110

Ile Thr Pro Arg Asp Pro Leu Pro Thr Pro Ser Val Gly Pro Leu Asp
1 5 10 15

Pro Asp Cys Thr Lys Glu Gly Val Ile
20 25

<210> SEQ ID NO 111
<211> LENGTH: 25
<212> TYPE: PRT
<213> ORGANISM: Artificial Sequence
<220> FEATURE:
<223> OTHER INFORMATION: Synthetic

<400> SEQUENCE: 111

Ile Thr Pro Lys Asp Pro Leu Pro Thr Pro Ser Val Gly Pro Leu Asp
1 5 10 15

Pro Asp Cys Ser Lys Glu Gly Leu Ile
20 25

<210> SEQ ID NO 112
<211> LENGTH: 25
<212> TYPE: PRT
<213> ORGANISM: Artificial Sequence
<220> FEATURE:
<223> OTHER INFORMATION: Synthetic

<400> SEQUENCE: 112

Val Thr Pro Arg Arg Pro Ile Pro Lys Pro Thr Val Gly Pro Leu Asp
1 5 10 15

Pro Lys Cys Pro Ser Glu Gly Leu Ile
20 25

<210> SEQ ID NO 113

<211> LENGTH: 25
<212> TYPE: PRT
<213> ORGANISM: Artificial Sequence
<220> FEATURE:
<223> OTHER INFORMATION: Synthetic

<400> SEQUENCE: 113

Ile Thr Pro Ala Leu Pro Ile Pro Asn Ala Gln Trp Gly Pro Leu Asp
1 5 10 15

Ser Gly Cys Glu Gly Glu Gly Leu Ile
20 25

<210> SEQ ID NO 114
<211> LENGTH: 20
<212> TYPE: PRT
<213> ORGANISM: Artificial Sequence
<220> FEATURE:
<223> OTHER INFORMATION: Synthetic

<400> SEQUENCE: 114

Pro Val Pro Asp Tyr Arg Ala Leu Pro His Glu Pro Arg Cys Gln Asp
1 5 10 15

Glu Ser Leu Ile
20

<210> SEQ ID NO 115
<211> LENGTH: 281
<212> TYPE: PRT
<213> ORGANISM: Prochlorococcus marinus str. NATL2A

<400> SEQUENCE: 115

Met Arg Arg Ser Leu Arg Asp Ala Phe Val Gly Phe Ser Leu Leu Gly
1 5 10 15

Gly Leu Val Ile Phe Ser Gly Ala Met Leu Trp Leu Arg Asp Phe Arg
20 25 30

Leu Gly Ser Lys Thr Trp Glu Ile Ser Ala Ser Phe Lys Asp Ala Ser
35 40 45

Gly Leu Ala Lys Met Ser Pro Val Thr Tyr Arg Gly Ile Ile Val Gly
50 55 60

Ser Val Gln Asn Ile Ser Phe Thr Pro Asn Thr Val Glu Thr Lys Ile
65 70 75 80

Lys Ile Asn Asn Asp Asn Leu Ile Leu Pro Lys Pro Val Ile Ala Lys
85 90 95

Ile Val Thr Ser Ser Met Leu Gly Gly Asp Ala Gln Leu Ser Leu Ile
100 105 110

Ser Leu Gly Lys Ser Leu Asn Lys Asn Glu Leu Ile Thr Val Asn Lys
115 120 125

Asp Cys Pro Gln Lys Arg Ile Leu Cys Ser Gly Asp Lys Ile Lys Gly
130 135 140

Val Glu Met Val Ser Ile Ser Ser Leu Thr Glu Gly Ile Asn Gly Ile
145 150 155 160

Ile Asp Glu Ala Asp Lys Gln Ala Ile Val Asn Lys Val Ser Glu Ser
165 170 175

Ile Gln Gln Phe Asp Arg Thr Gln Ala Asn Leu Asp Glu Leu Val Leu
180 185 190

Leu Ser Lys Ser Glu Leu Ile Arg Ala Lys Pro Ile Ile Ser Glu Leu
195 200 205

Thr Lys Ala Ser Phe His Leu Asn Asn Ile Leu Glu Ser Leu Asp Asn
210 215 220

-continued

```
Pro Glu Thr Leu Lys Asp Ile Gln Glu Leu Ala Ser Thr Ser Ser Ser
225                 230                 235                 240

Leu Thr Lys Lys Ile Asp Gln Met Ser Ser Asp Met Gly Asn Ile Met
                245                 250                 255

Glu Asp Lys Glu Leu Ile Asn Ala Leu Lys Lys Val Thr Ile Gly Leu
            260                 265                 270

Ser Lys Leu Phe Asp Asp Ile Tyr Pro
        275                 280


<210> SEQ ID NO 116
<211> LENGTH: 281
<212> TYPE: PRT
<213> ORGANISM: Prochlorococcus marinus str. MIT 9301

<400> SEQUENCE: 116

Met Arg Arg Ser Leu Arg Asp Ser Ile Val Gly Phe Ser Leu Leu Gly
1               5                   10                  15

Gly Ile Leu Ile Phe Thr Phe Phe Ser Phe Trp Leu Arg Gly Val Arg
            20                  25                  30

Leu Ser Ser Lys Asn Trp Tyr Leu Phe Ala Glu Phe Asn Asn Ala Ser
        35                  40                  45

Gly Leu Ser Lys Lys Ser Pro Val Thr Tyr Arg Gly Ile Leu Val Gly
    50                  55                  60

Ser Ile Glu Asp Ile Ile Phe Thr Asn Glu Ser Ile Lys Ala Lys Ile
65                  70                  75                  80

Val Leu Asn Asn Pro Glu Ile Ile Leu Pro Arg Pro Ala Phe Ala Arg
                85                  90                  95

Val Val Thr Asn Ser Phe Leu Gly Gly Asp Val Gln Val Ala Leu Glu
            100                 105                 110

Ala Ser Asp Lys Thr Ile Leu Lys Asn Ile Ala Lys Pro Ile Ser Glu
        115                 120                 125

Glu Cys Asp Ala Lys Leu Ile Val Cys Gln Gly Asn Thr Ile Thr Gly
    130                 135                 140

Lys Gln Leu Ser Ser Leu Ser Asn Ile Thr Asn Arg Ile Ser Gln Leu
145                 150                 155                 160

Leu Lys Glu Thr Asn Gln Glu Asn Leu Ile Glu Asn Ile Val Thr Ser
                165                 170                 175

Ile Asp Gln Phe Asp Arg Thr Gln Glu Asn Leu Asp Glu Leu Ile Phe
            180                 185                 190

Leu Ser Lys Gln Glu Leu Gln Arg Val Glu Pro Leu Ile Lys Glu Ile
        195                 200                 205

Thr Ile Ala Ala Asn His Leu Asn Asn Ile Leu Ser Thr Ile Asp Asp
    210                 215                 220

Lys Glu Thr Leu Asn Asp Ile Lys Leu Thr Ile Asn Ala Ala Arg Ser
225                 230                 235                 240

Ile Ser Thr Lys Ile Asp Asn Met Ser Asp Asp Phe Glu Lys Leu Thr
                245                 250                 255

Gln Asp Lys Glu Leu Thr Lys Ser Ile Arg Asp Leu Thr Ile Gly Leu
            260                 265                 270

Ser Lys Phe Leu Asn Glu Ile Tyr Pro
        275                 280


<210> SEQ ID NO 117
<211> LENGTH: 319
<212> TYPE: PRT
<213> ORGANISM: Synechococcus sp. WH 5701
```

<400> SEQUENCE: 117

Met Arg Arg Ser Val Arg Glu Ala Ile Val Gly Phe Ser Leu Leu Ala
1 5 10 15

Ala Val Val Gly Gly Ser Gly Phe Trp Ile Trp Leu Arg Gly Ile Ser
20 25 30

Leu Ser Gln Asn Asn Trp Ile Leu Lys Val Ser Phe Gln Asp Ala Ala
35 40 45

Gly Leu Ala Asp Arg Ser Ala Val Ile Phe Arg Gly Val Gln Val Gly
50 55 60

Ser Val Arg Lys Val Gln Thr Thr Ser Ala Ala Val Leu Ala Glu Leu
65 70 75 80

Glu Ile Ser Asp Pro Thr Leu Gln Leu Ala Arg Pro Thr Met Ala Gln
85 90 95

Val Gln Thr Gly Ser Leu Leu Gly Gly Asp Ala Gln Val Ala Leu Ile
100 105 110

Ser Thr Gly Asn Pro Leu Pro Glu Ser Ala Pro Leu Pro Arg Ser Lys
115 120 125

Asp Cys Asp Asn Thr Val Met Val Cys Ala Gly Ser Glu Leu Lys Gly
130 135 140

Val Thr Ala Ala Ser Leu Asn Ser Val Thr Glu Leu Met Gln Arg Leu
145 150 155 160

Leu Ser Gln Val Asp Glu Lys Gln Ile Val Glu Glu Met Ala Arg Thr
165 170 175

Thr Arg Ser Phe Asp Ala Thr Ser Lys Glu Ala Thr Gln Phe Leu Lys
180 185 190

Arg Ala Gln Val Leu Val Ala Glu Leu Lys Arg Ser Val Gly Lys Ala
195 200 205

Asp Pro Ile Leu Ala Asn Leu Ser Thr Ala Thr Ala Glu Ala Ala Ala
210 215 220

Ala Ser Arg His Val Arg Asn Val Thr Ala Ser Leu Asp Asn Pro Lys
225 230 235 240

Thr Leu Ala Gln Leu Lys Thr Thr Val Gly Asn Ala Glu Arg Leu Thr
245 250 255

Ala Arg Ile Asp Ala Val Gly Gly Asp Val Asn Lys Leu Thr Ser Asp
260 265 270

Ala Glu Phe Met Asp Gly Val Arg Ser Val Ala Ile Gly Leu Gly Gln
275 280 285

Leu Phe Asp Glu Leu Tyr Pro Ala Gln Thr Gly Leu Ala Lys Asp Lys
290 295 300

Ala Glu Lys Glu Ala Gln Lys Lys Ala Ala Pro Lys Pro Pro Arg
305 310 315

<210> SEQ ID NO 118
<211> LENGTH: 286
<212> TYPE: PRT
<213> ORGANISM: Synechococcus sp. CC9902

<400> SEQUENCE: 118

Met Arg Arg Ser Val Arg Asp Ala Ile Val Gly Phe Thr Val Leu Gly
1 5 10 15

Gly Leu Val Gly Phe Ala Ala Thr Gly Met Trp Met Arg Gly Ile Arg
20 25 30

Leu Gly Ser Ser Glu Trp Arg Leu Thr Ala Asn Phe Asn Asp Ala Ser
35 40 45

Gly Leu Ala Glu Arg Ser Pro Val Thr Tyr Arg Gly Ile Leu Val Gly

```
    50                  55                  60

Ser Val Arg Ser Ile Lys Val Thr Ser Ser Ala Val Val Ala Glu Leu
65                  70                  75                  80

Glu Ile Thr Lys Gly Asp Leu Arg Leu Pro Leu Pro Val Thr Ala Thr
                85                  90                  95

Ile Gly Ser Ala Ser Leu Leu Gly Gly Asp Ala Gln Val Ser Leu Met
            100                 105                 110

Ser Arg Gly Lys Pro Leu Pro Glu Asn Ala Pro Leu Pro Lys Ala Val
        115                 120                 125

Thr Cys Gln Pro Lys Ala Gln Leu Cys Asp Gly Ala Thr Val Met Gly
    130                 135                 140

Gln Glu Ala Ser Ser Ile Thr Thr Val Thr Glu Thr Leu Gln Glu Leu
145                 150                 155                 160

Leu Thr Gln Ala Lys Ala Glu Lys Leu Ile Pro Asn Ala Ala Ala Ser
                165                 170                 175

Met Glu Gln Ile Asp Glu Thr Ala Lys Ser Phe Glu Ala Leu Thr Val
            180                 185                 190

Gln Leu Gln Ala Glu Leu Leu Lys Val Asp Pro Val Leu Arg Asn Leu
        195                 200                 205

Gln Ala Ala Thr Ala His Ala Asn Asn Ile Val Ala Ser Leu Asp Asn
    210                 215                 220

Pro Glu Thr Leu Thr Ser Leu Gln Gln Thr Ala Thr Asn Ala Ala Glu
225                 230                 235                 240

Leu Thr Ala Lys Leu Asp Ala Val Gly Gly Asp Val Glu Thr Leu Thr
                245                 250                 255

Ser Asp Pro Ala Phe Met Asp Gly Leu Arg Asn Val Thr Ile Gly Leu
            260                 265                 270

Gly Ala Leu Phe Ser Glu Val Tyr Pro Ala Gln Thr Ser Arg
        275                 280                 285


<210> SEQ ID NO 119
<211> LENGTH: 407
<212> TYPE: PRT
<213> ORGANISM: Synechococcus sp. JA-2-3B'a(2-13)

<400> SEQUENCE: 119

Met Arg Ser Arg Ala Val Arg Glu Gly Ala Val Gly Leu Leu Ile Leu
1               5                   10                  15

Ala Gly Ala Leu Gly Phe Ala Gly Leu Phe Leu Trp Ile Tyr Asn Leu
            20                  25                  30

Arg Phe Gly Ser Arg Gly Phe Gln Phe Thr Val Thr Tyr Thr Asn Val
        35                  40                  45

Val Gly Leu Thr Glu Gly Ser Ser Val Arg Leu Arg Gly Val Thr Ile
    50                  55                  60

Gly Arg Val Glu Arg Ile Val Pro Gln Pro Ser Gln Val Glu Val Gln
65                  70                  75                  80

Val Thr Ile Asp Gln Pro Leu Val Ile Pro Arg Asp Ser Leu Phe Leu
                85                  90                  95

Thr Lys Gln Thr Gly Leu Val Gly Glu Thr Val Met Asp Ile Leu Pro
            100                 105                 110

Gln Gly Arg Gly Gln Ala Ala Thr Gly Ser Pro Leu Ala Ala Asp Cys
        115                 120                 125

Asp Ser Ser Gln Ile Ile Cys Asp Gly Asp Val Val Glu Gly Lys Pro
    130                 135                 140

Gly Val Asp Phe Gly Gln Leu Leu Ile Arg Leu Asp Gln Leu Leu Thr
```

```
145                 150                 155                 160

Arg Ile Asn Asp Asp Glu Leu Phe Asp Thr Leu Asn Ala Thr Leu Glu
                165                 170                 175

Gly Leu Thr Arg Val Ala Asn Ser Val Ala Asp Leu Ser Glu Thr Val
            180                 185                 190

Glu Glu Arg Val Ala Ala Leu Arg Thr Glu Asp Leu Asp Leu Leu Gln
        195                 200                 205

Phe Thr Thr Ala Ala Thr Ala Ile Gln Asp Ala Ala Gly Ala Val Arg
    210                 215                 220

Gly Thr Ala Arg Ser Leu Gln Ala Ala Ala Asp Gln Phe Thr Ala Leu
225                 230                 235                 240

Val Asp Gln Asn Arg Thr Ser Leu Asn Ala Ala Leu Glu Asn Ile Gln
                245                 250                 255

Gln Val Ser Ala Asp Leu Gln Ala Met Ser Ser Ala Val Arg Pro Leu
            260                 265                 270

Val Thr Asp Pro Gln Leu Gln Ala Asp Val Arg Gln Ile Leu Ala Glu
        275                 280                 285

Val Arg Ala Ala Ala Glu Asn Val Ala Gln Ala Thr Glu Asp Leu Gln
    290                 295                 300

Gln Ile Ala Ala Ser Leu Asn Asp Pro Gly Thr Leu Ala Thr Leu Arg
305                 310                 315                 320

Gln Thr Leu Asp Ser Ala Arg Ile Thr Phe Gln Asn Met Gln Lys Ile
                325                 330                 335

Thr Ala Asp Ile Asp Glu Leu Thr Gly Asp Pro Gln Phe Arg Arg Gly
            340                 345                 350

Ile Arg Glu Leu Val Leu Gly Leu Ser Asn Leu Val Ser Ser Val Pro
        355                 360                 365

Gly Glu Asp Gly Ile Gln Pro Ala Val Ala Glu Gly Tyr His Phe Arg
    370                 375                 380

Phe Ala Pro Val Ser Phe Ala Gln Gly Ile Val Ser Gly Ser Gln Gly
385                 390                 395                 400

Trp Gln Pro Gln Thr Ser Pro
                405


<210> SEQ ID NO 120
<211> LENGTH: 470
<212> TYPE: PRT
<213> ORGANISM: Anabaena variabilis

<400> SEQUENCE: 120

Met Arg Asp Leu Ile Thr Asn Arg Phe Thr Ser Gln Arg Thr Leu Arg
1               5                   10                  15

Glu Gly Ser Val Gly Leu Leu Phe Leu Leu Gly Leu Gly Ala Phe Gly
            20                  25                  30

Val Ile Leu Leu Trp Leu Asn Arg Tyr Thr Ala Ala Gly Ser Ser Tyr
        35                  40                  45

Lys Ala Val Val Glu Phe Ala Asn Ala Gly Gly Met Gln Arg Gly Ala
    50                  55                  60

Thr Val Arg Tyr Arg Gly Val Lys Val Gly Arg Ile Ser Gln Ile Gln
65                  70                  75                  80

Pro Gly Pro Asn Ala Val Glu Val Glu Ile Glu Phe Ala Gln Ser Asp
                85                  90                  95

Leu Ile Ile Pro Arg Asp Val Val Ile Glu Ala Asn Gln Thr Gly Leu
            100                 105                 110

Ile Ser Glu Ser Ile Ile Asp Ile Thr Pro Lys Ser Ser Leu Pro Thr
```

-continued

```
        115                 120                 125

Gly Gln Asn Leu Thr Lys Pro Leu Asp Lys Asn Cys Asp Asn Ser Leu
    130                 135                 140

Ile Val Cys Asn Asn Ser Arg Leu Lys Gly Gln Ile Gly Ile Ser Val
145                 150                 155                 160

Asp Ala Leu Ile Arg Ser Ser Thr Asp Phe Ala Asn Thr Tyr Asn Asn
                165                 170                 175

Pro Glu Phe Tyr Gln Arg Val Asn Arg Leu Leu Glu Thr Ser Ala Gln
            180                 185                 190

Ala Ala Thr Gly Val Ala Ala Leu Thr Gln Asp Phe Arg Gly Leu Thr
        195                 200                 205

Lys Ser Phe Gln Gly Gln Leu Gly Thr Phe Ala Ser Thr Ala Asn Thr
    210                 215                 220

Val Gln Arg Ala Thr Asn Glu Leu Thr Val Ser Thr Thr Lys Thr Val
225                 230                 235                 240

Asn Gln Phe Gly Ile Thr Ala Asp Lys Phe Gly Thr Thr Ala Thr Gln
                245                 250                 255

Ala Ser Arg Leu Leu Ser Asp Leu Asn Ser Leu Leu Asn Thr Asn Arg
            260                 265                 270

Ser Ser Leu Val Gly Ala Leu Asn Asn Ile Thr Glu Thr Ser Asn Gln
        275                 280                 285

Leu Arg Leu Thr Val Thr Asn Leu Ser Pro Ser Leu Asn Arg Leu Thr
    290                 295                 300

Gln Gly Glu Leu Ile Lys Asn Leu Glu Thr Leu Ser Ala Asn Ala Ala
305                 310                 315                 320

Gln Ala Ser Ala Asn Leu Arg Asn Ala Thr Glu Ser Leu Asn Asp Pro
                325                 330                 335

Lys Asn Ala Val Leu Leu Gln Gln Thr Leu Asp Ser Ala Arg Leu Thr
            340                 345                 350

Phe Glu Asn Thr Gln Lys Ile Thr Ser Asp Leu Asp Glu Leu Thr Gly
        355                 360                 365

Asp Pro Ser Phe Arg Gln Asn Leu Arg Gln Leu Val Asn Gly Leu Ser
    370                 375                 380

Gly Leu Val Ser Ser Thr Asp Gln Met Glu Gln Gln Ala Lys Leu Ala
385                 390                 395                 400

Thr Val Leu Glu Ser Met Lys Ala Ala Ala Asp Lys Pro Asn Ile Thr
                405                 410                 415

Ile Pro Ser Leu Ala Thr Asn Pro Leu Pro Asn Ala Val Thr Ile Ala
            420                 425                 430

Asn Asn Gln Pro Gln Leu Ser Ser Gln Glu Lys Leu Leu Gln Gln Leu
        435                 440                 445

Arg Asp Tyr Ala Glu Gln Gly Asn Ser Glu Glu Lys Gln Gly Lys Glu
    450                 455                 460

Lys Lys Thr Asn Glu Asn
465                 470


<210> SEQ ID NO 121
<211> LENGTH: 494
<212> TYPE: PRT
<213> ORGANISM: Nodularia spumigena

<400> SEQUENCE: 121

Met Arg Asp Ile Ile Thr Asn Ser Phe Ala Ser Lys Arg Thr Leu Arg
1               5                   10                  15

Glu Gly Ser Val Gly Leu Leu Ile Leu Val Gly Leu Gly Ala Phe Val
```

```
            20                  25                  30

Met Ile Val Leu Trp Leu Asn Arg Phe Thr Ala Gly Thr Asn Ser Tyr
        35                  40                  45

Lys Phe Ile Val Glu Phe Ala Asn Ala Gly Gly Met Gln Arg Gly Ala
    50                  55                  60

Pro Val Arg Tyr Arg Gly Val Lys Val Gly Asn Ile Ser Lys Leu Lys
65                  70                  75                  80

Ala Gly Ser Asn Ala Val Glu Val Glu Ile Glu Ile Ala Pro Ala Asp
                85                  90                  95

Leu Met Ile Ser Arg Asp Ala Val Ile Glu Ala Asn Gln Ser Gly Leu
            100                 105                 110

Ile Ser Glu Ser Ile Ile Asp Ile Thr Pro Lys Thr Ser Ile Pro Val
        115                 120                 125

Gly Ala Ile Ala Lys Pro Leu Asp Asn Asn Cys Asp Asp Ser Leu Ile
    130                 135                 140

Val Cys Asn Gly Ser Arg Leu Thr Gly Glu Ile Gly Ile Ser Ile Asp
145                 150                 155                 160

Glu Leu Ile Arg Thr Ser Thr Asn Leu Ala Thr Thr Tyr Asn Asp Pro
                165                 170                 175

Ala Phe Tyr Gln Asn Leu Asn Arg Leu Leu Glu Ser Ser Thr Ala Ala
            180                 185                 190

Ala Thr Gly Val Ala Ser Leu Thr Gln Asp Phe Gln Val Leu Ser Lys
        195                 200                 205

Ser Phe Gln Gln Gln Leu Gly Thr Phe Ser Thr Thr Ala Asn Ser Val
    210                 215                 220

Gln Gln Ser Thr Asn Lys Leu Thr Val Ser Ala Thr Lys Thr Val Asp
225                 230                 235                 240

Gln Leu Gly Ala Thr Ala Ser Glu Phe Ser Ala Thr Ala Asn Gln Ala
                245                 250                 255

Ser Arg Leu Leu Ser Asn Leu Asp Glu Leu Val Thr Ser Asn Arg Ser
            260                 265                 270

Ser Leu Val Gly Ala Leu Asn Asn Ile Thr Glu Thr Ser Asn Gln Leu
        275                 280                 285

Arg Val Thr Val Ser Ser Leu Ser Pro Ala Val Asn Gln Leu Thr Gln
    290                 295                 300

Gly Glu Leu Leu Asn Asn Leu Glu Ser Leu Ser Ala Asn Ala Ala Gln
305                 310                 315                 320

Ala Ser Ala Asn Leu Arg Asp Ala Ser Lys Thr Leu Asn Asp Pro Gln
                325                 330                 335

Asn Leu Val Leu Met Gln Gln Thr Leu Asp Ser Ala Arg Val Thr Phe
            340                 345                 350

Glu Asn Thr Gln Lys Ile Thr Ser Asp Leu Asp Glu Leu Thr Gly Asp
        355                 360                 365

Pro Ala Phe Arg Gln Asn Leu Leu Gln Leu Val Asn Gly Leu Ser Gly
    370                 375                 380

Leu Val Ser Ser Thr Glu Gln Met Gln Gln Asp Val Lys Val Ala Ala
385                 390                 395                 400

Thr Leu Asp Ser Leu Lys Ile Ala Val Ser Lys Pro Gly Val Lys Gln
                405                 410                 415

Leu Pro Val Lys Lys Pro Phe Val Lys Gln Pro Pro Val Ser Thr Pro
            420                 425                 430

Lys Ile Glu Leu Pro Thr Pro Asn Pro Pro Lys Gln Gln Ala Leu Asn
        435                 440                 445
```

```
Ile Lys Pro Thr Pro Ala Ala Val Ala Ile Phe Glu Pro Asn Pro Gln
    450                 455                 460

Pro Ile Val Asn Pro Ala Ile Pro Asp Ser Ser Gln Asp Lys Leu Leu
465                 470                 475                 480

Gln Gln Leu Arg Lys Tyr Gly Glu Glu Arg Lys Val Asn Glu
                485                 490


<210> SEQ ID NO 122
<211> LENGTH: 465
<212> TYPE: PRT
<213> ORGANISM: Crocosphaera watsonii

<400> SEQUENCE: 122

Met Leu Arg Met Arg Thr Leu Gln Glu Gly Ser Val Gly Leu Phe Ala
1               5                   10                  15

Leu Phe Gly Leu Ile Ile Phe Gly Ser Ile Val Val Trp Leu Arg Gly
            20                  25                  30

Gly Ile Leu Gly Gln Gln Thr Tyr Gln Phe Phe Ala Asp Phe Glu Asn
        35                  40                  45

Val Asp Gly Leu Gln Ile Gly Ala Pro Val Arg Tyr Arg Gly Val Ala
    50                  55                  60

Val Gly Lys Ile Leu Gly Leu Gln Pro Ser Ser Asn Gly Val Thr Val
65                  70                  75                  80

Ala Val Glu Ile Ser Ser Ala Glu Leu Arg Ile Pro Lys Asp Ser Lys
                85                  90                  95

Val Arg Ile Asn Arg Ser Gly Leu Ile Gly Glu Ala Ser Val Asp Ile
            100                 105                 110

Thr Pro Ser Arg Glu Leu Asp Glu Glu Ala Leu Ala Ile Asp Pro Val
        115                 120                 125

Gly Lys Asp Cys Ala Ser Ala Glu Gln Ile Leu Cys Asn Asn Asp Glu
    130                 135                 140

Gly Ile Lys Gly Glu Arg Gly Ser Gln Leu Val Glu Ala Leu Thr Arg
145                 150                 155                 160

Leu Ser Arg Ala Tyr Ser Asp Pro Glu Phe Val Gly Asn Leu Asn Ala
                165                 170                 175

Ala Ala Arg Asn Val Ala Lys Ala Gly Asp Lys Ile Ala Thr Leu Ser
            180                 185                 190

Gln Glu Val Thr Glu Leu Ser Lys Ala Ala Arg Gly Glu Ile Gly Gly
        195                 200                 205

Val Ser Asp Leu Ile Ser Ser Ala Asp Gln Ala Ala Lys Asp Ala Ser
    210                 215                 220

Gln Leu Met Leu Asn Val Asn Thr Val Val Ala Glu Asn Arg Thr Asp
225                 230                 235                 240

Phe Asn Arg Thr Val Ser Ser Ala Ala Asn Leu Val Ser Asn Leu Asp
                245                 250                 255

Gly Leu Val Ser Glu Asn Arg Gly Asn Ile Val Asn Thr Leu Ser Ser
            260                 265                 270

Ile Glu Arg Thr Ser Asp Gln Val Arg Leu Leu Ala Met Asn Phe Asn
        275                 280                 285

Thr Thr Val Asp Arg Val Asn Glu Gly Ile Asp Glu Ile Asp Met Ala
    290                 295                 300

Gln Leu Ala Asn Asp Leu Glu Val Leu Met Ala Asn Ala Ala Gln Thr
305                 310                 315                 320

Ala Gln Asn Leu Gln Asn Leu Ser Gln Ser Leu Asn Asp Pro Glu Val
                325                 330                 335
```

```
Leu Val Thr Ile Gln Lys Thr Leu Asp Ser Ala Arg Val Thr Phe Glu
            340                 345                 350

Asn Thr Gln Lys Ile Thr Ser Asp Val Glu Glu Leu Thr Gly Asp Pro
        355                 360                 365

Thr Phe Arg Gln Asn Ile Arg Lys Leu Ile Asp Gly Leu Gly Asn Leu
    370                 375                 380

Val Ala Tyr Thr Glu Gln Leu Glu Gln Gln Val Tyr Val Gly Gln Val
385                 390                 395                 400

Ile Glu Ser Val Thr Ala Gln Val Glu Tyr Ser Leu Leu Pro Gln Gln
                405                 410                 415

His Leu Lys Ser Phe Ser Pro Glu Gln Lys Val Pro Ala Arg Leu Pro
            420                 425                 430

Lys Arg Leu Ser Pro Ile Asn Lys Pro Val Pro Thr Thr Glu Thr Lys
        435                 440                 445

Ala Ala Pro Thr Pro Val Glu Lys Asp Glu Glu Lys Gln Glu Ser Ser
    450                 455                 460

Arg
465


<210> SEQ ID NO 123
<211> LENGTH: 465
<212> TYPE: PRT
<213> ORGANISM: Cyanothece sp. PCC 8801

<400> SEQUENCE: 123

Met Leu Arg Ser Arg Thr Leu Gln Glu Gly Thr Val Gly Leu Phe Ala
1               5                   10                  15

Leu Ile Gly Leu Val Leu Phe Gly Gly Leu Val Ile Trp Leu Arg Gly
            20                  25                  30

Gly Val Leu Gly Gln Lys Pro Tyr Gln Ile Gln Ala Asn Phe Gln Asp
        35                  40                  45

Val Ser Gly Leu Gln Ile Gly Ala Pro Val Asn Phe Arg Gly Val Ala
    50                  55                  60

Val Gly Lys Ile Thr Ala Leu Gln Ala Ser Ser Asn Gly Val Thr Val
65                  70                  75                  80

Leu Ile Glu Val Ser Ser Arg Glu Leu Arg Ile Pro Ile Gly Ser Thr
                85                  90                  95

Ile Gln Ile Asn Arg Tyr Gly Leu Ile Gly Glu Ala Ser Val Asp Ile
            100                 105                 110

Thr Pro Ser Glu Lys Leu Ser Asp Gln Ala Leu Ala Val Asp Pro Thr
        115                 120                 125

Ser Glu Glu Cys Pro Asp Lys Gln Leu Ile Ile Cys Asp Asn Asp Thr
    130                 135                 140

Leu Asp Gly Glu Thr Gly Ser Gln Leu Val Gln Ala Leu Thr Arg Leu
145                 150                 155                 160

Ser Asn Ala Tyr Ser Asp Pro Glu Phe Val Lys Glu Leu Lys Gly Ala
                165                 170                 175

Phe Thr Ser Val Ala Gln Ala Gly Thr Lys Ile Gly Lys Leu Ser Asp
            180                 185                 190

Glu Ala Ala Ile Phe Ser Lys Thr Ala Arg Arg Glu Ile Gln Gly Thr
        195                 200                 205

Ser Gln Thr Ile Ala Gln Ile Asn Gln Ala Ala Arg Asp Ala Ser Gln
    210                 215                 220

Leu Met Arg Asn Val Asn Thr Val Val Ser Glu Asn Arg Glu Ser Leu
225                 230                 235                 240
```

```
Asn Arg Ala Val Asn Asn Ala Ala Ser Leu Val Asn Asn Leu Asn Gly
                245                 250                 255

Leu Val Ser Glu Asn Arg Gly Asn Val Ile Asn Thr Leu Asn Ser Leu
            260                 265                 270

Glu Arg Thr Ser Asp Glu Val Arg Met Val Ala Ile Gly Leu Gly Lys
        275                 280                 285

Thr Val Asn Lys Val Asn Ser Gly Ile Asp Glu Val Asn Ile Lys Lys
    290                 295                 300

Ile Ala Arg Asp Leu Glu Ile Leu Met Ala Asn Ala Ala Glu Thr Ser
305                 310                 315                 320

Ala Asn Leu Arg Asp Ile Ser Gln Ser Phe Asn Asp Pro Thr Val Ile
                325                 330                 335

Leu Thr Val Gln Lys Thr Leu Asp Ser Ala Arg Ala Thr Phe Glu Asn
            340                 345                 350

Ala Gln Lys Ile Thr Ser Asp Val Glu Glu Leu Thr Gly Asp Pro Ala
        355                 360                 365

Phe Arg Asp Asn Val Arg Lys Leu Ile Asn Gly Leu Ser Asn Leu Leu
    370                 375                 380

Ser Tyr Thr Asn Gln Leu Glu Gln Gln Ile Tyr Thr Ala Gln Leu Met
385                 390                 395                 400

Glu Ser Val Thr Glu Gln Leu Glu Tyr Gln Val Ala Val Gln Gln Arg
                405                 410                 415

Phe Leu Glu Gln Glu Asn Ala Asn Gln Thr Thr Leu Ser Arg Asp Ser
            420                 425                 430

Ser Ile Pro Pro Gln Val Pro Val Lys Glu Thr Pro Lys Pro Val Arg
        435                 440                 445

Val Ile Ala Pro Glu Trp Val Leu Glu Ser Glu Lys Asn Asn Gln Ile
    450                 455                 460

Arg
465


<210> SEQ ID NO 124
<211> LENGTH: 458
<212> TYPE: PRT
<213> ORGANISM: Microcystis aeruginosa

<400> SEQUENCE: 124

Met Glu Ala Gly Gly Ser Gln Arg Gly Ile Ser Pro Thr Leu Arg Gln
1               5                   10                  15

Ser Gly Ile Gly Leu Met Leu Leu Ala Ser Gly Gly Ile Leu Ile Trp
            20                  25                  30

Phe Val Thr Trp Leu Ser Asn Phe Ser Phe Gly Gly Arg Ser Tyr Arg
        35                  40                  45

Ala Ser Phe Leu Phe Pro Asn Val Gly Gly Met Met Val Gly Thr Arg
    50                  55                  60

Val Gly Tyr Arg Gly Val Arg Ile Gly Gln Val Thr Ala Ile Thr Pro
65                  70                  75                  80

Glu Pro Glu Gly Val Ala Val Glu Val Glu Ile Ser Pro Ala Asp Arg
                85                  90                  95

Leu Ile Pro Ser Asn Ser Leu Ile Glu Ala Ile Gln Ser Gly Leu Val
            100                 105                 110

Gly Glu Thr Thr Ile Asp Ile Thr Pro Leu Gln Ala Leu Pro Val Gly
        115                 120                 125

Gly Val Lys Glu Pro Pro Leu Ser Pro Asn Cys Asn Gly Glu Val Ile
    130                 135                 140
```

Ile Cys Asn Gly Ser Arg Leu Gln Gly Gln Ser Ala Leu Asn Val Asn
145 150 155 160

Thr Leu Ile Arg Ser Leu Leu Arg Ile Ser Asn Leu Val Ser Asp Pro
165 170 175

Asp Met Val Ala Gly Phe Arg Ser Phe Thr Gln Arg Ala Ala Asn Ala
180 185 190

Leu Gly Gly Leu Asp Arg Phe Ser Gly Glu Ala Thr Thr Ala Leu Ser
195 200 205

Glu Val Arg Arg Ser Gly Thr Leu Gly Lys Val Asn Ser Gly Met Arg
210 215 220

Ser Leu Glu Ser Leu Pro Gln Val Ser Gly Ser Leu Asp Arg Leu Ser
225 230 235 240

Ser Asp Leu Ser Gly Val Gly Gly Leu Ser Gln Glu Ala Thr Thr Leu
245 250 255

Leu Arg Ser Leu Gln Gly Ser Gly Gly Leu Arg Asn Leu Asp Ala Thr
260 265 270

Leu Val Glu Ala Arg Lys Thr Leu Leu Leu Val Gly Glu Thr Thr Glu
275 280 285

Glu Leu Arg Val Phe Leu Gly Ala Asn Gln Asn Arg Leu Ile Ala Thr
290 295 300

Leu Asp Ser Ile Lys Thr Thr Ser Asp Arg Leu Gln Thr Thr Leu Ala
305 310 315 320

Ala Leu Asp Pro Ile Leu Thr Gln Val Gln Lys Ser Gln Ile Ile Asp
325 330 335

Asn Leu Asn Thr Ile Ser Ala Asn Ala Val Lys Leu Ser Glu Asn Leu
340 345 350

Gly Asn Phe Thr Ala Tyr Leu Ser Asp Pro Ala Thr Val Val Thr Leu
355 360 365

Gln Gln Leu Leu Asp Ser Ser Arg Ala Ala Phe Ala Asn Leu Gln Lys
370 375 380

Ile Thr Ser Asp Val Asp Glu Ile Thr Gly Asn Pro Gln Leu Arg Gln
385 390 395 400

Glu Ile Ile Arg Leu Ile Gln Gly Leu Ser Arg Leu Val Ser Ser Ser
405 410 415

Glu Gln Leu Gln Gln Glu Phe Ala Gln Gly Gln Ala Met Thr Arg Met
420 425 430

Ala Ala Gln Ile Ala Thr Ile Ala Pro Asn Pro Ala Pro Asn Thr Pro
435 440 445

Glu Lys Asp Pro Lys Lys Pro Glu Ser Glu
450 455

<210> SEQ ID NO 125
<211> LENGTH: 399
<212> TYPE: PRT
<213> ORGANISM: Acaryochloris marina

<400> SEQUENCE: 125

Met Arg Thr Arg Ala Val Arg Glu Gly Thr Val Gly Leu Leu Val Ile
1 5 10 15

Phe Gly Leu Gly Leu Val Thr Ser Leu Ile Phe Trp Val Arg Gly Phe
20 25 30

Asn Phe Gly Gly Arg Ala Tyr Thr Leu Gln Val Glu Leu Ala Asp Ala
35 40 45

Leu Gly Leu Ser Ile Gly Ser Pro Ala Lys Phe Arg Gly Val Lys Val
50 55 60

-continued

```
Gly His Ile Thr Gln Met Arg Pro Gln Ala Asn Arg Val Val Val Glu
65                  70                  75                  80

Val Glu Ile Thr Ser Ser Thr Val Leu Ile Pro Arg Gln Thr Lys Val
                85                  90                  95

Glu Thr Ser Gln Ser Gly Phe Val Gly Gln Ala Ala Leu Glu Phe Arg
            100                 105                 110

Pro Thr Glu Val Glu Phe Ser Asp Ala Ser Val Glu Asp Leu Ser Pro
        115                 120                 125

Phe Glu Pro Asp Cys Asp Pro Arg Met Ile Leu Cys Gln Gly Asp Arg
    130                 135                 140

Leu Glu Gly Asp Ser Gly Asn Asn Leu Glu Glu Leu Ile Arg Ala Thr
145                 150                 155                 160

Met Gln Ile Ala Thr Gln Leu Gly Gly Thr Asp Leu Lys Ala Thr Leu
                165                 170                 175

Asn Asn Leu Ser Gln Ala Ser Lys Asp Ile Ser Lys Leu Ser Lys Asp
            180                 185                 190

Thr Lys Val Ala Leu Lys Asp Val Ser Arg Ala Ala Arg Ser Val Thr
        195                 200                 205

Gln Leu Ser Leu Asp Thr Arg Lys Gln Leu Arg Gln Phe Gly Val Ala
    210                 215                 220

Ala Glu Ser Val Thr Ala Ala Ala Gln Gln Phe Asp Gln Leu Gly Gly
225                 230                 235                 240

Glu Val Asn Thr Leu Val Lys Gly Asn Lys Gly Thr Leu Val Thr Ser
                245                 250                 255

Leu Gln Asn Leu Gln Glu Thr Ser Gln Glu Leu Lys Val Val Val Thr
            260                 265                 270

Arg Leu Ser Pro Leu Leu Ser Arg Val Glu Gln Gly Lys Leu Leu Asp
        275                 280                 285

Asn Leu Glu Thr Leu Ala Ala Asn Gly Ala Gln Ala Ser Glu Thr Leu
    290                 295                 300

Lys Leu Leu Thr Thr Asp Val Asn Asn Pro Ala Thr Ala Ser Glu Leu
305                 310                 315                 320

Arg Gln Thr Leu Lys Ser Ala Arg Glu Thr Leu Asp Asn Ala Ser Gln
                325                 330                 335

Ile Thr Ser Asp Leu Lys Asp Ile Thr Gly Asn Glu Glu Val Arg Gln
            340                 345                 350

Asn Leu Ile Arg Leu Ile Asn Gly Leu Gly Lys Leu Leu Ser Ser Ser
        355                 360                 365

Gln Asp Leu Glu Gln Gln Met Gln Gly Val Gln Lys Ala Pro Leu Thr
    370                 375                 380

Ser Ala Phe Ser Gln Ser Asp Ala Pro Ser Thr Pro Ser Gln Asn
385                 390                 395
```

<210> SEQ ID NO 126
<211> LENGTH: 397
<212> TYPE: PRT
<213> ORGANISM: Thermosynechococcus elongatus

<400> SEQUENCE: 126

```
Met Met Gln Ser Arg Arg Val Gln Glu Ser Leu Val Gly Leu Val Ile
1               5                   10                  15

Leu Ala Gly Leu Ala Thr Leu Gly Val Gly Leu Leu Trp Leu Arg Gly
            20                  25                  30

Asn Leu Ala Gly Ala Asn Ser Tyr Thr Leu Glu Val Glu Leu Asp Thr
        35                  40                  45
```

```
Ala Pro Gly Leu Ala Val Gly Thr Gln Val Arg Tyr Arg Gly Val Gln
    50                  55                  60

Val Gly Arg Val Thr Ala Ile Gly Phe Asp Ala Asn Gly Val Gln Val
65                  70                  75                  80

Ser Val Arg Ile Asn Asn Val Leu Ile Pro Arg Arg Ala Val Pro Glu
                85                  90                  95

Ile Arg Gln Ser Gly Phe Ile Gly Gln Ala Phe Leu Asp Phe Thr Pro
            100                 105                 110

Lys Glu Arg Val Pro Glu Ile Pro Glu Gly Val Thr Ala Phe Ala Pro
        115                 120                 125

Lys Cys Gln Pro Glu Leu Val Tyr Cys Asn Gly Asp Arg Val Thr Gly
    130                 135                 140

Val Arg Thr Ala Ser Leu Glu Asp Leu Val Arg Ala Ala Thr Arg Phe
145                 150                 155                 160

Thr Thr Ala Leu Glu Glu Ser Gly Leu Ile Asn Asn Ala Asn Thr Leu
                165                 170                 175

Ile Leu Gly Ala Thr Arg Ile Val Asn Arg Ala Asp Gln Ser Leu Thr
            180                 185                 190

Lys Val Thr Thr Ala Leu Asp Ser Phe Asn Ala Leu Ser Asn Gln Ala
        195                 200                 205

Arg Ala Glu Leu Arg Asn Phe Gly Ile Ala Ala Gln Ala Val Thr Arg
    210                 215                 220

Ala Ala Asn Gln Ile Ser Glu Ile Val Glu Val Asn Arg Asn Thr Ile
225                 230                 235                 240

Asn Ser Ser Leu Arg Asn Ile Asp Ser Ala Ala Arg Glu Leu Arg Thr
                245                 250                 255

Thr Leu Lys Ala Leu His Pro Leu Thr Asn Gln Leu Glu Gln Gly Glu
            260                 265                 270

Leu Leu Ala Asn Leu Asp Ala Leu Ile Lys Asn Gly Ala Glu Ala Ala
        275                 280                 285

Ala Asn Leu Asn Lys Val Ser Gly Ala Leu Ser Ser Pro Leu Ile Met
    290                 295                 300

Leu Ser Ile Ala Gln Thr Leu Asp Ala Ala Arg Ala Thr Phe Ile Asn
305                 310                 315                 320

Ala Gln Lys Leu Thr Asn Asp Leu Leu Lys Leu Thr Ser Asp Pro Ser
                325                 330                 335

Phe Gln Ser Asp Leu Arg Arg Leu Ile Gln Ile Leu Arg Arg Leu Leu
            340                 345                 350

Ala Ser Ser Gln Asp Leu Glu Gln Gln Phe Leu Ala Leu His Ala Thr
        355                 360                 365

Ser Leu Gly Glu Ala His Glu Pro Met Pro Ala Ile Ser Ala Pro Thr
    370                 375                 380

Ala Ala Ala Lys Pro Thr Lys Glu Glu Glu Pro Glu Pro
385                 390                 395
```

<210> SEQ ID NO 127
<211> LENGTH: 265
<212> TYPE: PRT
<213> ORGANISM: Pseudomonas putida

<400> SEQUENCE: 127

```
Met Arg Arg Lys Ser Leu Leu Glu Arg Val Arg Leu Leu Gly Arg Ser
1               5                   10                  15

Ala Ile Asp Val Leu Ala Val Leu Gly Arg Ser Cys Leu Phe Leu Phe
            20                  25                  30
```

```
His Ala Leu Ile Gly Arg Gly Gly Ile Gly Gly Gly Phe Gln Leu Leu
        35                  40                  45

Thr Lys Gln Leu Tyr Ser Val Gly Val Leu Ser Leu Ala Ile Ile Val
    50                  55                  60

Val Ser Gly Val Phe Ile Gly Met Val Leu Ala Leu Gln Gly Phe Ser
65                  70                  75                  80

Ile Leu Thr Lys Tyr Gly Ser Glu Gln Ala Val Gly Gln Met Val Ala
                85                  90                  95

Leu Thr Leu Leu Arg Glu Leu Gly Pro Val Val Thr Ala Leu Leu Phe
            100                 105                 110

Ala Gly Arg Ala Gly Ser Ala Leu Thr Ala Glu Ile Gly Asn Met Lys
        115                 120                 125

Ser Thr Glu Gln Leu Ser Ser Leu Glu Met Ile Gly Val Asp Pro Leu
    130                 135                 140

Lys Tyr Ile Val Ala Pro Arg Leu Trp Ala Gly Phe Ile Ser Leu Pro
145                 150                 155                 160

Leu Leu Ala Leu Ile Phe Ser Val Val Gly Ile Trp Gly Gly Ser Trp
                165                 170                 175

Val Ala Val Asp Trp Leu Gly Val Tyr Glu Gly Ser Phe Trp Ala Asn
            180                 185                 190

Met Gln Asn Ser Val Ser Phe Thr Asp Asp Val Leu Asn Gly Leu Ile
        195                 200                 205

Lys Ser Leu Val Phe Ala Phe Val Thr Thr Trp Ile Ala Val Phe Gln
    210                 215                 220

Gly Tyr Asp Cys Glu Pro Thr Ser Glu Gly Ile Ser Arg Ala Thr Thr
225                 230                 235                 240

Lys Thr Val Val Tyr Ala Ser Leu Ala Val Leu Gly Leu Asp Phe Ile
                245                 250                 255

Leu Thr Ala Leu Met Phe Gly Asp Phe
            260                 265
```

<210> SEQ ID NO 128
<211> LENGTH: 161
<212> TYPE: PRT
<213> ORGANISM: Pseudomonas putida

<400> SEQUENCE: 128

```
Met Gln Asn Arg Thr Leu Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala Ser Pro Ser Ser Asp Thr Tyr Lys Val Tyr Ala Tyr Phe Asp Asn
        35                  40                  45

Ile Ala Gly Leu Thr Val Arg Ala Lys Val Thr Met Ala Gly Val Thr
    50                  55                  60

Ile Gly Lys Val Thr Ala Ile Asp Leu Asp Arg Asp Ser Tyr Thr Gly
65                  70                  75                  80

Arg Val Thr Leu Gln Leu Asp Lys Ser Val Asp Asn Leu Pro Thr Asp
                85                  90                  95

Ser Thr Ala Ser Ile Leu Thr Ala Gly Leu Leu Gly Glu Lys Tyr Ile
            100                 105                 110

Gly Ile Ser Val Gly Gly Glu Asp Gln Val Leu Lys Asp Gly Gly Thr
        115                 120                 125

Ile His Asp Thr Gln Ser Ala Leu Val Leu Glu Asp Leu Ile Gly Lys
    130                 135                 140
```

-continued

```
Phe Leu Leu Asn Ser Val Gly Lys Glu Pro Lys Glu Ala Gln Pro Ala
145                 150                 155                 160

Asn


<210> SEQ ID NO 129
<211> LENGTH: 87799
<212> TYPE: DNA
<213> ORGANISM: Arabidopsis thaliana

<400> SEQUENCE: 129

gatcaaaatt aaacaaaaga cttaaacttt atcattttct attcataaac tagttccttg     60

catgacttgt agaagaaaaa aaagtagata cagagaggaa gagggaagaa gaggcagagt    120

taagtacctg atggtgatat tcaagcttcc atgaaagtgt tttctcaaag agcttgaaat    180

aaaatgtttg aagagagaag agacccagag aaaaagagag atagagaaat taaaactaaa    240

ccctttgaaa agtttgcttc aaggggcttc gtcgagtcac caagtcaaga ctaatcttaa    300

cacttttttg tttctcggca attattgtaa ggttttagtc tttaatttaa tacacaaaat    360

tttatttaaa gagtttttcg atatcgcatt tttaacaaca ttacaatatt cagcatcacg    420

acggattcgc acacgaagag gtcgtcgtct ccttataatg actaaactac ccctcagcat    480

gttctttaac ggtggtggtg aagcaagccc tttttggtca ttcaagcttt ggctccaaat    540

tggtgactag gtttgccacg tgttgacact tctagttgaa agagatacgt tcacgtggca    600

ttgtctctgt tgcctgttac tacgccacca ccaaaacaca ctttaagttt tttgtttttg    660

tttcttcttc tttttggatt aagaaattct aattgtttgt tttaagaacc tgaacactgt    720

tcaacagttt tatagttata gttcttagga tttttgttaa ataggaaagt gtggaaaaga    780

aataaaaaga ctttggccaa aaacaatgaa agtgatagaa gaataagact tttctatcac    840

catcatgatc atgatcatgg atttagtttc ccatcaacaa gacaacattg gattctttca    900

tatgtgctaa atccaaacga caacaatgaa aatggtccct taatagtgaa tctatgacca    960

aaccaagtgt gttcttggaa ttggactctt attgccaaga gaatgaatga aagcaaatgg   1020

aacaacacac acaatttctt ctttgatttg tctgcaaaag aaaaatcccc aaaccggatc   1080

ttaaagatcg tataaaaagg gaacagttga tgctacagta tttgaaatca ttgtgtgttc   1140

atcactttat tatatcaaca agggaaaaga attggagatg ggtgtctttg aagcttccca   1200

gctgaaaagt tgagcttttt catcttttct tcacaccata gaagttgctc tttactgatt   1260

ttcgacatcc tcaaaacccg tgttgcgagt ttgatgtcaa tggctgcaaa caagagttga   1320

acaccttccc atgtttgagg ccatgatttc tttctcagcc cttttgtctt ctttgaaagc   1380

tcctttgctt tcaccctttt ctgcaaaagt tcctctctta tgagacacca aagaagcata   1440

cgatagtaat aacatttgag tacagagaaa tcgtacctta tcaatggatg actgaaccag   1500

tagtaaagga gttgtagaat tcacatggtt gttgttgtgg ttcccaaaca agtgaatacc   1560

cccatttggt ttcttcttat ccattttcaa gaagacgttg aaagtaagga tcgagctctc   1620

tatgactttg atgagatcat cagcgaggac catgaagcct gtatctttct ccatctcctt   1680

tttatctgac cctgatatgt tttgaacata accaacttca agtgttacta ctacacataa   1740

ggttttaagt cgcgcaatgt atgagagctg agaaatcacc ttgaatctta ggagcttgaa   1800

gtagcttagg cattgcattt ctagcacgag cataaagttc cgatcttgag ccttgctcaa   1860

acggttcatt ctctatatac ctctgcaaca agactaggaa ttgctgaaac agttgggcag   1920

tatggttgta gcaagtcggg gtttcgggtt ggcatgagat taagtggctc agctgcgtgt   1980

attgacagtg aagtgcctcc caagtgaggc agagttgagc aacataggcc gtctctagat   2040
```

-continued

```
cttgataagg gtcgtcaact tctgtcggct gcaaatgctc gatatcttcc tccggaacat   2100
caaacttttt gagagaaaga catcggaaag gcgatgacag cttcttagat gcagatcttg   2160
gcgatggagt tgaaggactt ggagcaattc caatgcctaa gagattgaaa agtaaccaac   2220
aaatccatga tcagtccaat ctatcacaat gaaaaacagt tcaaagcaag aagcttttac   2280
cagtttcctt gagctgctga gagcttaaac gatcaaagaa gagcatacgc tcgcaatact   2340
tttcatagac agcatcaaaa cctccccacc attgaagtcc ttcagcaacc acatctctcc   2400
actcacttga acacttgtct tctccgtcat catcatcttc atctagatac gattcctctt   2460
cttcttcttc ttcttcctca ggtatcaaca ccatgaaact gtttctcctc aactccttga   2520
gccttctctt aacctcattg gtaatgaaat catcatcgtc atcttcgatc tcatctcctt   2580
tccccgaatc tatcacacca gcttcagtgt tctcactcct tgcctgttct tgctgagcca   2640
atatcttgtc ttctttctcc ttttcaaggt ttggcttccg agactttcga aatttctaa    2700
ctttcaagaa atccattgcc tcctcaaaca cacttaggag agtgagtgtt ttttgttaaa   2760
tcataagatc taaactgaga ctagtctctt tgcatgagta aaagcgtttc tcttctgcca   2820
caacgaactt aatcaaagaa tcaaccaaac cagagaatga ggaaaatgca tgaatctagt   2880
aagatctcag agaatcatga gcaaacccta gagaattagg aacaccgaca gaagattaag   2940
aatgcataag tagatcagta gcaacaacag catttgtctg aaactttaga ttcgattcac   3000
taatctctag ctgataagaa cactagcatt ccctgataaa tcaacactcc actgaaacta   3060
ctactacact gagcaaagag tgtgagaaaa aaaacaaaaa gaaagaaaaa gattcaaaat   3120
ttaagaaaga aagagaaacc caaataaaag caaaacaaaa tcgaaagaca aagacaggag   3180
gaggaggaga ttaaagaagg agaaatgttt ctaaccactt gcaagagaga gagagagaaa   3240
gcaaagtata ataatgtctc aattcaagtt ttttcagtaa atggacagag agagcacaat   3300
ataaatgtga gagaggaaag gagagcaagt attattgatt cttaaacaga tgtcattaaa   3360
ttcaataatt aaactttgtg atttcaaatt ccaaaaaaaa actagaaatt ttcttccttt   3420
cttaaaaccc tttcctcaaa aatttccatt tgcagtcaaa accctcacaa agaggtttct   3480
gagtcaattt gactttttgt ttatttccta atgggtcgaa attgtctttt actgtttggt   3540
ttcttacttt actttttctg atacttcatt ttctattggt taatttttgg ttttgttttg   3600
gtgtttgatt agagaaggag agagatgtat gaatgaatga aaaggagaag aagcagtaac   3660
aagtaacaac tggtaggtag gtcagtgggg ggagagatag aaagaaaagc atcgtacaga   3720
gaatattgtc agaaaagccg cgctatctgt tctccttcca tttgctcact tctctctttt   3780
aaaattacat ctttaccctc ctccgtctca tacatctacg ggtcttatct ttgtttctga   3840
tgacaatttg ggcttctctt aaaatgggct ttttctttac caaatttatg tatactgcta   3900
tgaaacgacg tcgtctttta ctttggttat attggtatgg tttttgaatt tactttggtt   3960
acgattccgg tctagtggat tggatgaaac cgaattggag agcttgaggt tatgatccat   4020
ggcttcattt ggcatgtctc tcacaccagt tcttcttctc agggattact tactacctct   4080
tgtaagttct cattcgattc tatttttgct tgaattctgt ttcagctgat gaaacgcttg   4140
ttatcatctt agccgtttcg ttttctactc tttctagtta taaaattttg acttcttcaa   4200
gagaattttt tttgggttcc aatcaatcag attgctatga tcctctgaat agaatttttct  4260
tgttgatata gggacttgtg ttgttgagtt tgagcctata gtgatcaaat gggattctca   4320
tatgaatttt actcaaattt tgttactttt ttaatcttat aactgtagac aaaagcttat   4380
ccttttattg gttacaaatc gtatgaacat ttgattctat gctttttgct ttgccattaa   4440
```

```
gcaattgatt tttttagtt tgcttgtttc cggattatgg gaatgaagct tcactgggat   4500
taagaatctg taagtaatat gtttttgttt aataagcttt aggcttatag atatgttttt   4560
ttaaagttct aagttagtgt tgtgtttgtt actcttaaac atacttaaaa agctactaaa   4620
tgagtgctat tcaataatgt tctgtttgat ttcgatggaa taatttagtg tgactgatgt   4680
tgcttttatg tcgcttatgt attattggtg atctatgtgt aaaacatgtg ttgcaggata   4740
gtaatgaacc gaagtaaaga agagaacgtt gctccgacaa tgaaagatga tagtccattt   4800
ggaaagctta cagaggatct cttgatagag atatttatca gaattccaat aacaaattgg   4860
gaacaagtat cgtgtgttag aaagcagtgg gctaatttat tccgcggaga atgcttatgg   4920
ctggctgctc ttaatcgggc gtatccactt gctagcaaaa ctaagagctg gattggacca   4980
attcgtcaag gattaagcaa acggtgactg gaaacacact tgatttctat gaaaaaagct   5040
agcttaataa tgtcttagtt agattcaagg aacttaacag ccttttagct gcaggagata   5100
tgtggcttta tacatcagca gaaacatatt aggtgtggat gatacagaca tagatgagat   5160
gcttggacat atttacgtgt tcttgaatga tcagcttcaa ctttccacta tgcctgcttc   5220
aggcattttg catggaaccc ttatcggtaa gctagtttgg tatatgcatt tgactctgct   5280
taatgaatca ttgctaatga cggcattcat cttatattct ggtggcagac caattgattg   5340
tttgtggcca atcgaaagaa gaagctggtg agcttgcaac aaagatttgg ctggctcttc   5400
ttgacaattt agaggacaca aaacatacat ttaccgtgct gaaatcaatc gcacaagaat   5460
atgatgtaag aaaggataac agtgtccata aagttttcaa attcttttct agtagaaact   5520
aactatctaa gagatgcagg gctttcttcc atatccatat tcaagaccaa tcaaagtgca   5580
gtggaaggtg ttcgagaaac tgtttgtaga tttccgtgac ttgcttgatc attcagagta   5640
ctgcgactta ataggaattg ccaaaaataa gtttcaaacc ataccttatg tttggttagg   5700
ctactaaact tagcctgctt cttccagttt ccacagccct gtaaagtaat ttgaggtcca   5760
attctacaac atacttgtac ataagacatt caaagtctgc atcttgtaag aaagaaagac   5820
gtgtaaaatg cagattcttg gccatgtata attcgtggtt cgttttaaag caaaagtcaa   5880
acattttgtt gactatttta acttcttcgt tacttgctaa gttcagttat ccatccactt   5940
tattcttctt cttggaaatg gctctcatga aagtaatgac gattctggtt ctcttcgtct   6000
cggtgtcatc gaccttggcg caatccaaca atggcggtca catttcgata atcgtctcgg   6060
aaacaggtct tgaatttgct aaagattacc tcatcaagaa agtgatcact acgacgcttc   6120
cacttcagct accagacatt gagaataagg ttaagatccc tctaatcggg aaagttcgaa   6180
tgggtctatc gaatattcag attgatgcag ttcatgtcca gtcttcgaag atggagactc   6240
gaaaagatgg aatcattttg agtgttttag gtgctacagc aaatttgagt atggactggt   6300
cttatactta cagagcttcc ttctttgaga tttctgatca tggagatgct tctgttgagg   6360
taaaactctg aaattatcga aaaccaaatt gggtcttttt agtttgttg tttgtgttca   6420
gaacattgtt tcatcatcag aagaaaaagc ttaacaggtg aatgattatg acgatgaagg   6480
ttaaaggaat gaatgtgaga atcactgcca ctttggttaa tgataatgga agtctaaaga   6540
ttgcctcacg ggaaaatgat tgtacagtaa agaacattga tattcatatc aatggtggtg   6600
cttcttggct atatcaaggg tattattaaa tgttccataa gttttcgtat ctctaaaatc   6660
tcttattcca agattataat atttgttttc ctttttgcag ggtggttgat gcatttcaaa   6720
aaatgattat atctactgtt gaaaaaactg tctctactaa aattgtagaa aaaatgaaga   6780
agcttgattc tttcttgcaa tcacttccaa aacagagaaa gattgatgac tctgctgcag   6840
```

```
tgaatctcac ttttacaggc aaccctgtct tagggaattc gtcggttgaa gttgacatca   6900
atggtttatt catgccaaag ggtgatgata ttaaagttgc agggtctcgt tcttcttcct   6960
tctttggtgg ggttaataag agaatggtga caatttcagt agaagaagga gttttcaact   7020
ctgcaacact tgtctacttc aacgtaagtt ctcaaatctt gattagagta tggtggaaca   7080
aaacaatttg taagcttatt ggattggttt tgattcaggc taaggtgatg catttagtta   7140
tggaggaaac aaagaacggg tccattctaa gcacatctga ctggaaactc atccttccag   7200
agctgtacaa acattatcca gataataaaa tggtgcttaa catgtcagta acatctcctc   7260
ctgctgttaa aatcacagag aatggaattg atgcgacgat tcagctagat atagcgttcg   7320
atgttcaaga ctctggagaa aatctatctg tagcacgcct atcaacagta agactaatag   7380
taatccacca aacaatctaa cttaagaagc atcttttgat cactaaagtt agaatcttgt   7440
tcttgtttgc agattctgag tgttgcgtgt tctacagaaa tcgtaaagaa taatctaatc   7500
ggtagcctca gattaaatga tttcaatgca acaatgaagt ggagtaaaat tggagagttt   7560
caaacaaact atgttcaggt aagtcaagtt aattatcttg agtttaagat ttatcttgat   7620
tagcatcaaa ctggtggata tgtgttcttg ttgttaggct gctacgtcta ggattcttga   7680
agccttgttt ttgccgtacg taaacacacg tctcaagaga ggattccctt tgccgattcc   7740
cggcgatttc acgatcaaaa acataaagat tgtttatgtt aatagtggca ttttggtatg   7800
taccgatatc ggcactagca caaaccagta agcaagtatt atatagcttc ttagattgca   7860
tgtacgtaag cctgaagaaa tataatgaca accataattg tgatttgaac cgtttggaac   7920
ttcccctcta agaagcgttt tgacgagatc tctttatttc tttggctact tgcattatat   7980
ctggaacttc ccccctaag accaatgcat ctttctgaga ggttaaggaa aacttccatt   8040
aggcaattgc aagacacggc ccaatgattt atattacagg cctgttaaat atgggcccaa   8100
cttcgtaaac aatcaaaata ttattcatat gtacgcaaaa caacaataga aaaggataaa   8160
attgttattc tattatatct ctctaggaca aaaaaaagta aagtcaaaag atcctctctc   8220
atcgatctct ctctaacatc tccgtcttct gcttcgtgta atttgggtat tgttggctcc   8280
ctactctgat tcctcaaatt ccttattttt attaacccgc gaaaataaat tataaagagg   8340
gctttcaaaa ttttgaacct ttctctaaca atggagatct ccctccttcc ctttttcttc   8400
tttcgcgttt aaggtttctc ctcgtctctt ctcttttcaa tggatatagc gaccagtaat   8460
gctccaatga atcttgaatc cgtcgcaatg gttgatggca acggagcaga accggtgtct   8520
ccgcctgcga aaaagccacg ttttgacgag gagatgaata gagtggcgga gattgttctg   8580
gttctatcgg cgttagggag gatgcgtggt ggggaaactc cgacggcgtt ggaactcgag   8640
ctgatgtttg aagctaggtc caaattagct gggatgtgtc tggaatttga ccctaaggat   8700
attattcgta aggatgatgt taaatctgtg attgaggatt tgggtttcaa tggtaagctt   8760
aaagaccaga gattaggttt tcgagctcct acggtgacta tctctgagaa gctttctctt   8820
ggtaaacgaa aggtaatgcc ttttgtttct cagatcacaa ttgtgttttc tctttgatat   8880
tgctcacttc aattgggtat agttttgtca gcattttgag agatgcaatt ttctctgtgg   8940
cgttttcatc attgttttga ttttgtccag atggaagaag cagaaaagta tcctaccact   9000
tcgacagtat ccactggata tacattgtca cagccaaacg gtagtcttgc atctcctggt   9060
ggtcttggta aggctacaca ttttgacaaa ccatcaaagc tttatcttca ggcttcctga   9120
cagtttcttc acccttttgt ttctgcagcg aataaagctt ctgtggctca tcagtggcct   9180
agtagtgaag ttgctactgc taacactagt ggaagccatt tcaaattgga cagacctcag   9240
```

-continued

```
atggtactta acggtgcttc tcaagggact cgtaagtcct catatccccc tttgttttgt    9300
atagatgcag ttgtagtgat aagattcttt tagtctttga tttggaaatt acaacacttt    9360
tagtatgggt agggtattct ggttggtttg ctgttttgct ttatacgata ggacttgtaa    9420
attttagtga aggtaatcat aacagccaaa tacagataat tggctaatca ctaggcttgt    9480
agctgagtaa ctagccctca tgcttagaat aagtatacct tttgtgaata ctatcgtttt    9540
cttttgcaaa tcttactggt catggtagcc tttctttttg gttaggtttc tatcctgagt    9600
tgctaaattt atatgttatg tttctagttc tttaatagct ttttcatagt tgattttgag    9660
tttgtttcat atattacttg tttcagcagt ttcttccgcg aattattatg ctgaaccctg    9720
gtctgcccaa cttccatcca ccatatcttt cagtactgca ccagataaga aggttccaat    9780
tcaaagttct gtcaggacag cagatccaag ctttaggcca ttcaggcacg gtacattcac    9840
tggcacaaat cagccaatgc attacagtca aacttcttcg ttcggaggca accatactga    9900
aattgctaag ataatccata aatttctgca accacgggtt aaacaatatc ctttgtggaa    9960
tccaccttca agagagtata tgagcagggc aatggcatgc cagatatgtg aagttaccat   10020
caatgaaatg gacactctac tgatttgtga tgcctgtgaa aaagcatacc acttgaaatg   10080
tctgcaagga aacaatatga aaggggttcc aaaatctgaa tggcattgct caagatgtgt   10140
gcaagcattc aatgggaagc catttcctcc tacatatggg cgtgcgactc gtgccgtagc   10200
gacgactaca gcaaaaatgc cttttagggc agccggagtt ctatcatcct cagcaaagaa   10260
gattggaccg atggatataa aggctaatca acaaaaacca attgtatcta cgttttcaag   10320
attgcaaaat actggcttgg tttctggagc agcaactaca tctcagtttg agtctgctag   10380
tgtaaatgca aagacaactg caagcgcagc aaagactact aacattggat cacagggctc   10440
taaggaaaat gttgcctgtg gtgctaattc tccagcaccg gtatcgctta ccgagactcc   10500
aaatcgtaca ggaatcgcaa gtacaatttc tgtgataaac aatggcctca tttcaaaacc   10560
tttaacacca gttggtacta tgagcagcac ttctccattg cctgttgtta accaacttcc   10620
cgtgaatgca acctcaaacg caagtccgag tacaccaata actgctagcc ttgtagcaca   10680
agccccgaca gttacccaaa atggagatgg cagctcaacg gcctctggga ctgctgacca   10740
ttctatattg aatgctgaca ttaccactca agttcataca ttgactgtta cttccagtag   10800
taattctcaa caggcagtgt cacattctga ggttgcaaaa gcaactgaag atgcagctcc   10860
tttggaaaat gtttccgagt gtgagaaacc atcagaatct acatctcacc cagactctct   10920
gaatgataaa acaatatcag agaacgttca agaatcaagt aaggatgcta aagttgattc   10980
tgaagcttgc cagaaccacc caacagcatc cccagccact gttgtaccag atcaagactc   11040
gacgatcact gctgcaccat ccgtgacaca agaggattca gctttcaata cagagaaaac   11100
accacctcag ccactttcgg tgtcatctaa ctatgattca caaaccgaga aggaaacacc   11160
aaatgtccaa gattctgtac ataatgttcc gggagattca gagaagggta aagggttaaa   11220
tggtttagat gatagacatc aggaacagcc ttctgagccg gagttctata agtcagattc   11280
ggtaaaggaa gaaaatgctg cctaaaattt ttgagtaatc acctgggatt acttcaccag   11340
caattatcgt cttctctccc ctttggctct caaaggttta tatatctcag ttgttaacag   11400
aaaccaggaa tattcaaaac attgaagctg tggatgaact tgtcaaagca attagaataa   11460
tgtgagttga gacgctgacg gtttgatata acatgggttt aaggcatctt tgatctaact   11520
ctgtgatagc cgaagggaac tgtaatagaa tcttgattca ggttttgcaa cttatgaaat   11580
ataatgattt ttctcattga gtttaaactg ttttggatcc tacaaaatga ttcaatgaaa   11640
```

```
cgattgaaat gttacatagc acttgaatca ttttgttcct tttccttata acaaatccta  11700
tagatcggag attaattcaa gggttatacc caacaccata aaccaaacaa gcaaagaaat  11760
attaatttga tgcttacaat tatagaaaca gattattata tcgaaaagtt atcatgttag  11820
acttgatatt aacagtaata cttttggttt gtgatataag ccaattatca agtcagcact  11880
ctttatgttt gtctctattg tctacaaggc ttgtaagata caaatatgca ttaacgctca  11940
caagtcacaa gggctaggcc aaaagtgaat gtatagtttt ggattataca gcaaccgcag  12000
aagataagag ggatagaaat attaatcata agggtttttg aaatttttca agagctctgg  12060
gatgtcatac cccaacatat catcaacagt ctgcaacatt ttcggcttta gcttctcaaa  12120
cttgtcgatg ttgtaaccac ttagcacctc cctgaaatga tccacatttg ggaaatctcc  12180
tttaggtaag tgatgctctc tttgtacctg ttttcatgtc ccccacaaca ttgaaacaca  12240
tattagcatg aaatatgatc ggaatcagaa ccggcgtatt gaaaagatcc gcagaatcaa  12300
accaattacc aacctttcca aactcgtctt ccaagttatc tatcagtttc tgttgagctt  12360
tggctttccc cattatcgct ggcatctcct tcttcaaatg gctgatgatg tacgcatgta  12420
tctttgctgc tcttgcccgt ttcacaaact catttatcta ttagacagaa aacaaatatg  12480
gttaaatcca atgagaggag ggagtgaaag aagaaatgtg cacactcact cgacgatcac  12540
aagctttctt aggaatgtct ttcaaatcag caagaaggtc atcttgctcc ttttcaaaca  12600
actctctccc aattggacca gttgcagctt cgtttatggg tttatcactg aaggaactgt  12660
tcaaagcaag taaacaagga catcaaaaca tacattttag tttcaaaccg cttttatata  12720
agcaaaacac tgtcactagt tgaagaaaca ggtatgttta cccaatgtag acacgagaga  12780
cctcaggagt attgagaact ttcccaagtg accacatgag agctccatat accctcatta  12840
gctatacaag ataaggagaa agacggtgta aaaatgtata agaacatgta aaacaatgaa  12900
agaagtgtga aagaaggaac gaaataagaa tcgataaccg atcagggcgt caatggtcaa  12960
cctgctgagt gtccacttgg tcagccttat tcagaacaac gcggatcttg tcatcatgac  13020
cgcgtaaaga tgaaattaca cgcttgaact catcacttac atccagcttg tgtgggtcaa  13080
ataggaggag gataagatca cacttagagg caaaccatga tgtaacacca gtgaaatcat  13140
atgctcgctg tgttctttgt ttttccccctg ataaaactcc aggggtgtcg acaaatgtta  13200
catgctccag cagcttaaac aaagatgaat ggatcaacaa ttatcagcaa atcaatacag  13260
gcaaaagtaa tgaacgatct cctgtcagaa gcatgaggtt gttaaacata cagggtgagg  13320
catctgagag cattcaaact ttgacaaaaa ggcagtccca aaagttgtaa gaccactgaa  13380
tggcatatct gcttgaactg ctactgtgtt ccccggaatg cttctttcat caggtccaga  13440
ctgtgaaaca cattgaacat atagaagtca ccttcaagag aggtgcaaat gaagtaatct  13500
agctaccatt gtcaactaaa taattgacac ttaaaatatg tattccatta tccaacaaaa  13560
caagcaaatg aatagcagta catgatggat caacgttttg aaggactaat gcattctcac  13620
aaaaatgaaa ccttagaaaa ttacaaacta acataccatg acaacaacaa atctgtcagt  13680
agtcggctct ggtccaatat gagctcctga aaaaatatga caattgaagt tatataaagc  13740
tgttttacgg ttaatcattg acctgttccc atacttttta aaatatcgaa actagttagg  13800
tcacagaagg agaagaagat aggataagat ggataacttg cctggataag tagatttaag  13860
caaatgctta atgaatgttg tttttcctgt ggagtattga cccagaagca ttaccatagg  13920
ttttgcatcg aaatcactgt tagtctaaga aaaaaaacaa gtaactagtt caatggtcaa  13980
atatagttta gaattcaata gtatttggaa cttaaataac gccataggag caccaataag  14040
```

-continued

```
caatgcccaa ctcaccaaca aaggggatac aaaatcgtta aaccgatatg ctacttcaag  14100
tggcttcagc ttctgaatgt acaacctctt caggccatcc actatagatg ttacggagga  14160
cagagaaatc tgagaacaag agtcttagtt ttcagaaacg atagatgtaa actagctata  14220
tcttagcagc tgagaaaatc ttgacagaaa caatgccaat gaactttgtg gatacataat  14280
agagatattg gtaagaacga ccaaaaagga atctttactt aaaatgacaa tatatggttg  14340
gtggttaaat agactgcttg aggcaaaaca aacctttttt gaagattttg aagagaacca  14400
gtgagctgta agtgaggtgt ctgcggcagg gctacctgaa taattgaatc aaatgagata  14460
tataattaaa aaggtaaacc attggctcta gagtatgaag agattctttg taccattcat  14520
attaggatca ctcgactttg atgaatgctt ctttttctgt gataaatgaa cagttgtaag  14580
taatatttct ttgaactcga aagatataaa tcaaaattac aggcccaata ctaaccgcca  14640
ttaatacacc cagaccttcc atggtaggag gattgatatt tttgaaatca actgcagtca  14700
gccataaatg ttgcagaaag aagaacaata cattaacagg tattatttat acagtgggca  14760
tattaagatg aagacagccc ttaagcaaaa gatggaagac taaaagaaca cggattcaag  14820
atttattcac cataccatcg ctaataagaa cttcatgcga tatttcatgt ccagtttgag  14880
ccaacgaaac aagctataat gttggaaaat aacaacacat tagattcaca gcgagacatg  14940
gacatataaa tgtgagatat aaactggatc taaacctgca tggcaacaat aaactctttg  15000
aaaccaagat acccttgtct ctttgaatct gcaatagccc agatctatca acaaaccaga  15060
agagaaacag cataagcttc tcacagttag cacctcttag acaacttaaa tgaatcaaca  15120
aaaggcttca aatgctttgc caagtgagca attaagcatg atcgcaaggg cttgttattt  15180
gtaactccat taaacctaga actcaaaacc attcaagcat tcacctatgt gtttcctctt  15240
aactcattaa tacaactcca tccccaaatg aacttggtca atcattataa tggccattaa  15300
taaaggttcc acaagtaagc aacgtaataa atttcaacac aaaatcctta cctgcttcaa  15360
ttccggacga ggcaaattcg acatagtgaa gaacttgatc gcatcgttac cagtaatacg  15420
gccatcgccg tctgctcatt tacaccaaac agagaataag cttttagcgc atatagtgaa  15480
gacgagaatc gaagactgaa gaacacaaga caacaaaatg aacatgaaac gagacctgaa  15540
tcggagaatt cgaaccattc cttgtagatc atttgattct ccttggaaca agaaccagct  15600
gcgacggatt cgatctccat ctccgattgc aaaaatctag agatgtaccg attaacaaac  15660
ttctcaggtg tgaatccaga tttgtggatt cgcagatatt gaacttatac ggagaagaac  15720
aaaaggtaag ctaaacaaca acaattacaa aaaaaaaaaa aaaaaaaaaa aaagttggtt  15780
gatgtatacg tgagattacg gtttcagaga aagcgggttc ttcgtctcga cggcaaggga  15840
gaggaaaaag aattaccaat gcaagaaatt gccctttatt ttcaaaatct tacacatatg  15900
ccccagaact gttgagttgt tgaagtaacc cctattaaaa atctatgtga tagattttgc  15960
tgcgtcgtct caattattgg tagaagattt tgatagctac ttgtcaagga gcattaaaga  16020
ggtttgaata acagattggt ttcttggata agtgatgaac ttattttttg tgaaatttgg  16080
taaatgtact tttatgtctc aacatggtaa aaaaattttt tgtcaacaag gtaaaagact  16140
ttagatttta ataactttag attttaataa tttgattgat agattctaca ttaaaatgaa  16200
atctgttgac aaaaaaaggt tagactaatt aagtaaggct atggacaaaa aagggaaaaa  16260
aaaacagatg aatggcaaaa agcaaattat aactagtatg gacgattgtt tttagtaata  16320
tgtttttttt tttttgtat cttgactggg atgtcctagg aatagcggta agtgtaacgg  16380
aaaaacattc atcccttata ttggactttg ggaaccatat ttaaatagaa tagcttttgc  16440
```

aagtttgaac tgtcggctgc caaaagttac aaaccagagt tatcatgaat ttctgttggg 16500
gaaaattcaa ctataacaac tgcaaaatca caacacaaag atggaacaag agtggaaatc 16560
tcaaagacag taggagattt tacaaggcca atctaattta ctgtaagatc atttgttgaa 16620
cacatgaatt ctattacaaa tcgacatgtt aaagaaaaaa taagatgatt tacagtgata 16680
aaaaaacgag aaaacgttat tttacataga gcctctgtgt atacatacat gcatatacca 16740
acatcatcca acaagggagc caaaactttg agaactttaa tgatccaaag aatgattcaa 16800
gaaattccaa tggtcttacc aagtaaccag agaacaagcg acatttcgat accgaagatt 16860
gtatggagag tgcttctatc aagtgtaaac ccaaacaccg tgattcctga tctattgttc 16920
tcaaagtaat tcactacaaa acaaaaaatg tgaagatgaa taaacataac taaagatgtg 16980
aaggtatgag atttagtgtg gatgcagagg aatatatttt acatacctag agcttgccgt 17040
ttttggaatg atatggtgct ataagcataa gcaggaatga gattgttgtt atcgaaatca 17100
tcttcttcgt ctccataatc ttcactatct gattctccat tatcatcatc tgttggatag 17160
tatccgtgtc cgcttgctct atcaactaac cttggagtct ctccatccac agtctcaaag 17220
gattctatcg tcgcacatac atgccacttg gctgcaagac aagtcaccgc ctgagccttg 17280
tgtgtgatct ttgatgcact tcgtagtaaa atgagcagtg cagtgaccag cgtcattgaa 17340
catagctgag ataatcacaa gaaaaaaacaa agactaagca aaatatttca tcaagaacca 17400
atagtatgta gaaacagaac ttactgctag ttctccagct ctgtagatat tcaattcagc 17460
gtaggcctta gtggtaataa gcagagagta aaactgactt ccagtgacta atatcaagga 17520
caacaatata aaggttcggt atcggtggct gatgattctc agatgacgtc tgatacggag 17580
atgttcagac aagatagaac caacatctga atccatctgg aaaacctggg caaagtcttg 17640
cagcctaaga atctggagat ggcagatgag acggaagagg acacaaacca gaaagatcac 17700
ggtagtacgg tacaaccacg agcagagctc catcaaacaa gcaactgtat cactcaagat 17760
aacattacca aggaaaggaa tctgagaagc tcctgaagca taccaccata tcttataaga 17820
gctcatcgct aagaaacaag gagacacgaa gtaggagaga atcttaagcg atctctgcat 17880
aacaaaaagt tgtgatttca aatcattgtt atgcttgtgt agcaagtaag aagacgattg 17940
tcaagattat aagtacttca tcgttaacac caccacctaa tatttatgta aaccctaaga 18000
tttttcttgc ttctggattg agattcaatg gtgggctttt aagttcttaa gtttcatatt 18060
gttaatttga tctactcata atgcgacaag atctggaatg atccaaaatt tcgacagaac 18120
acgacagatt caaatactgt attgtcggaa aaagccaaag tcatttcaat caaaggccct 18180
caaaatcccc aaaatctaag gattccaccg aaaaatcgag aacccaaaat tcatattgga 18240
aacgacaaac gaagcaagag taaaccaaat taagaatgcg aaattcgaaa cggaattagg 18300
aaaagaaaaa caaaaactca cattgagctg attggtgtag cctagacgaa cggtctcgct 18360
ctcatcccaa agcttatcaa agaataggaa ccgtcggaga ccatacttgc taacgaatct 18420
ggagagacaa agaaacgaaa gagcagcgaa actgctaaga gaaagctgaa caacggaatc 18480
gtacggccta gagtgatggc tatcgcagtc agagcaagcg agcatgaagt gagacgtggc 18540
aggaacaacg agcgtgaaaa caacgaacat agaccatgat agaaccgccg tccaaggact 18600
cgactgatct acgcacatcc atcggagata tttccggaaa ctgtggagct cgtcttgtgc 18660
gtgagatacg ctacgtgtga acttgttttc tcggtttatt agacgttctc gtgtgcctcc 18720
tcttccttcg tttcctcctg ttgttgctgc ggttccgatg tcgatgtccg ccatggacga 18780
tcgctcggga aaatgagaaa ttaccggaga ggctctggct ttttttttt ttgttgtcta 18840 aatataaatt gatgacgcgg ttggaagaag gagaagacag aatcaggaat ggctaaaatt 18900
gtcttatggt tatttataaa ggatcgatgt ttaggtggat ttgacaaccg tatttaaatt 18960
gtaatttagt atcgtaaaac aaattactac aatatttcgt attaagatgt acatgttttg 19020
tatcttattg gctctgtttt attcgaatat ttacattttc aataatacta gtgacttggg 19080
gtttttctgc tctatgattc atgaggggat atttgaacaa acagtttaga atttggggat 19140
taagtagaga cgaaattgtg cacttccatt gtaagaaaga tttttctga ttcacgataa 19200
aaacgaaaaa ggaaagtaga ttttgtgttc atgcgacaac catgatttca caatcacggg 19260
gtctatctac ttgctaataa agtattatca tcattagatc atagattttt atttctgttt 19320
atataccta gtactgtaac atgtaaatta gtgtatctcg gatgaatttt ttttttagt 19380
ttgaaattca tggaatttat ctattaaaaa ggttttacta agtatattac agattaaata 19440
cactaaatac taattattct tttctttaaa aaaacaaaat ttgcatattg atatatttcc 19500
atatttcggc ggaaataggt ttacgtggca gtgacaaaat attatactgt aaacactgaa 19560
agaggcaaaa ataaaaacaa atgaaaagat gctggtgaag tgaacacagg ctgtagaatg 19620
ggtcccacgt tgacatgtga tgtgtaaaat ttaggccgta gattacgcat atctccgtac 19680
ttacggcgcc acgtatgttg ctaatataat tataagtacc attattttga ttttgatgtc 19740
ttcttataaa aaaacaaaaa cataagatat tatttagatc agctaaacta gtaaaggatt 19800
acttagaatt ttaaataccc ggcggcatgt cttgagttta ttggaaggat gagtatataa 19860
agtttaaagg ttttgaagat taatcgaatt atcaaaatga ggaatatcat atactttata 19920
gtataaagta tattaattgt caattattcg aatgaatcat gggtttggtt ttattacttg 19980
tgatcttatg agtggctgtc tatgcattcg tttttatatg ccctcatgac tttgagaata 20040
tttcattatt ccaattacta tacgataaat gttgttacat ctcttaatca aatgttgagt 20100
cgtttgatta ttttttatt ttattttatt ttttgtttgt ttgtttgttg aagaatcgaa 20160
accgcagacc aaaaatattt tctgttgttt gctgtattta aatttacacg caactatact 20220
tttgatttaa accttctttc ttgtgattta atactccttc ttttagtttt ttgaagattt 20280
tcaatctcta tgttatacaa atacgtgaaa aatatgcatt ttacccttag aaagttagaa 20340
gtagaaacga acatctcaca atgcttgatt ttctttgcta aagagtatag accacataag 20400
ataaagaaaa aaaaatatca tttaaagagc aacattatgt ttaatcgtgt taaaagtttc 20460
atagtaaaat ggtattcagg attcatcata gttgatagta gtaattggtt tgcaacattt 20520
gattgatttt gcttatttct aatgtatgta gcctttgaat ttagtagtag tacataaaaa 20580
gtgattcacg tctttacacg tttaagtatc agcaacgtgt attcacccag tttgaaattc 20640
aagattttga tcattcttta ttagcccca catatataaa gagtttcaag aactatagaa 20700
ccacagcttt cctgatttgg tcaaacctgg aaatatattc tttcgttatc tttcttttc 20760
ttaacttttt atttaaatcc catatgtaaa atgtaaatta gattgctata attaacttga 20820
tggatcagaa attttgaaaa gctgtgataa aataatagag aatgtataat gagataacaa 20880
atcaaaaact ttaacgatta catttcaaat aatctctaaa aataaacaat atagtaaatt 20940
ttagaataaa ttcactcggc gtacgtgtct ccaaatctca aaacgtttat agacacacaa 21000
gattcataac ttatactcta taaagaaaaa caaaatgcaa agtgaggggt ttggttgaag 21060
tggttgtctt gtgaatattg aattgttgta ttaaattcgt agaaaattag taaccagtac 21120
aagcttttgt gggctgataa agataaacac gttgagttag taatacgcaa accggtaatc 21180
tacttctaat caattaattt aaatgagttt tccaggcgtc tattataact tcaaagtctc 21240
gttttccgac aattaatata ttgtgtgatt aagatgaaaa taagacaact acgacgacaa 21300
gctagccaaa ctcttttgga agcgaataaa acaagactag ctatttgtga acttattatt 21360
ttcttcttag actgatgatt ttacaattgt aacaatgcac tcctatttag accagtgatt 21420
ggctgatggc caggttattt tgtataatac tctctaacct ttctccattt gtctagttaa 21480
cctttagcca tttgccttgt taattgctca tacacttctt tttctcctta gttcaagtgt 21540
aatgtccaag ccattcatta tccattgtct tgttaatgaa tccatttgtc tcaacagttt 21600
tttatattaa ttttctcctt aattctagaa ttatcttcaa taactaaaga ttagaccaag 21660
ttgttctcat ttaatagcaa tgtagaatca tttggagaga aactatcatt tcaaagccga 21720
acaaccgaat tctcgaaagg ttgtaaaagt aaaaagtaac attgtggatt aatctcaact 21780
ccagaataat agaagattat taagagtacg aaccgaaaca ggaaaagcga cttgagatca 21840
gttgtcttaa atcgttacag tgaaaataac aagacattgc ttttgacttc cactttaagt 21900
taagaagaag cctaccccaa aacggtaaaa aaatactcgg tttttgcttc agacacaaag 21960
attcactgtc tgaatccgtg gcatagaagc aaagtagata ccaaaattgg gaaaactctc 22020
taccagcaaa ttcaaatcaa aaaggtcaaa cacacaacga attctgccac ctcaacccac 22080
agctcttaaa gatcaaaaca atcatctcag ccaccaaact ttaacctaaa gatttggcct 22140
gtgctcattg agctttatcg atcacaacaa aaccactcac cgcccattga ccatgccctt 22200
aatctctatg ttcttcacca tccaaaatat tcattgggta cacaaaaggg aaagcctttc 22260
ttgtctcctc gctgatgaat gaaaacttga ggcttaacaa tgacaatgag tattctaact 22320
tcctcttcga atcacccaat tagatagcaa aggagcttca ccgtctttct tcctttcatc 22380
tttttattgc ttccatctca gagaaccact aagctttact tgttgaatag aagaaaccct 22440
gaattgatca agatcaagcc aagagacaaa acacaaacaa atacttgtgc cctgtgtggt 22500
tctgttacat actatgtaaa tgcagcttcc tacttacatc aggggacact ctatgaataa 22560
gtagaaatct aaagataatg gatttgaatc attcagaaat catcaccagc ttcagaatgt 22620
tatatatatg taacaaaggg ttgttggatc ttttataaga agaaacagat aaaaatgaaa 22680
cccagatctg gttcttacag taacagatct taacacaatc tctctctctt tttaatcgtc 22740
atcatcttcg ttgatgataa aatcatcacg ctcaatcttt ttttttgtt cttcctttt 22800
ttctctttca atatgatatc aaaggaaaat ggaaaaacaa aagagcataa agttatcatt 22860
ttgtaaaatt tgagaatttt ttttgtgtgt aatcaacgga ttttttttgt aaagcagcaa 22920
atcagagacg tagatcggta cagtggagat catctatccc gccagcgaat aagtcaacgc 22980
catccaacgg cgggaaatta agatcaaact gaaacggcgt tttccggcgg gaagacgaag 23040
atgcgatatc atctccgtcg tcaataacag acgacgaaga atcgcagtcg ctatgacaat 23100
cctccggagc taccggtgga gttctcggat atctcttaat cgcatgtaac ggtttcgcca 23160
ccgacgaaga cgccgccgcg gcttccatcg gtctcggtcc gctacaagat ttaacggtgc 23220
tgctcatgct gctactcgcc ggccgactaa taatctgctg ctgctgctgc tcctggaaat 23280
tacctccgcc gtataaccga tggtccataa acggatcgat ctggttctga atcaccggag 23340
gagaacagag gttttgattg tggaggtagg tgagaggttg gagaggagaa gaaggagaac 23400
aatcgatcgg gaaattggtc ttggcctttg gaccacggag gttacgtgcg gcggtatcgt 23460
aagcgcgtgc agcatctacg gcggaatcga aagtaccgag ccagacacga gattttttta 23520
atggatcacg gatctcagct gcgaatcgac cccaaggtct cttcctaacg cctctatacc 23580
tcggctcctt cacagatcca ccggcggtta ctggaagggc gggtccaacg acggaagagc 23640
ctctcccttt cctcatggag aagaaaaaag atgtaaagcc agaagtaatg tgatgaagaa 23700
gagatctgtg tgtgtttgtg tgaagaagag aagaaaatgt tgaagagaga agaaagatga 23760
ggaagaagat gaaggaacaa agggtagaga ttggaaatta ttattataat tctctttttt 23820
tttttctaaa taatttactc aaagaatttt catttaataa attaattaaa ataataattt 23880
atggttggaa tagcttttc ttttcttttt ttttttggtt gttaatttcg attttttctc 23940
taccttcacg cccgacccac aagaccgacc aattcgtttc tttaaaaatt taattatgga 24000
gtaacatttt tcctaacttg gattcttttt ttcttttgct ttaaactttt tattcgatat 24060
attgtgtgga gaaaaaaaaa caaaaaatta aaaaagagtt cacaagagat gtctcgaaat 24120
gcgaagaaag taaaagaggg taagcacttg cactctctgt cctgaccctg accacaatct 24180
atataataaa atcttatgtc ttactgtttg tttgttatca aattgatgca cctagagacc 24240
aaatagtcca cttgtaatga ccaaaaacac cctccagatt ttattttatt ttatttaata 24300
atacacccct cttcgaaatt attattagtt tcttctcctt cctttgggac cctacaagag 24360
acgagacgcg cttatcggca tcgtcgtcgt ctcccgtgtt aaaagtaaat gccgtgttga 24420
ggatacgcat taatgtggag aaacaaacat ttttgttctt ataaaaactg aattatgtct 24480
ctccattaaa ccccaatctc agaacacaaa acgaaaacaa aaataactct aaagaagaaa 24540
caacacattt ttcgaatttt taaaacttgc ttaccataaa attctggatt ttatttatcc 24600
agtctaaaat ctacaggctg atcatagtag cctgcttagg gatttgatga gtagtttaag 24660
gttttttctt gtggcttcat ctcctgtgaa tcccagaata tctgagctta tactctacaa 24720
tcaagaaaat caaaaaccaa gtctttgtta acattgtttc ttccaacttg tcaaagctgg 24780
tattgataga ataagaagaa aaaaaagttt acctcgacgt tcttcaaagt ataaaccaga 24840
gtgtagattg acttctgtat gagttctgta ttctcaggag tcataattga cgaattaacc 24900
tttctgcaat gtaaccaaaa tgaaaattat atttttgctg tctactgcaa gaatataggt 24960
tctcataatc acagttatca ctcagttgat catacgtatg taagtaaacg agcttttgca 25020
tatatgtggt ccaggaacat acattaagtg acagaaacag taggctagca gaagataagt 25080
agaggcaaca caagataaat tattgaaatt ttaagacaat agaggaaaga ttgaaaagca 25140
ctgatgagca aagcagttaa tttaacatgg aacccataag ataagacaca tttatgcata 25200
gatatgtatg tgttttaact ttttaaccat catctcttgt tcagaaactt aatccacaaa 25260
tagagtgttg aagccacata cgagaaattg aagctagtgt gcttatatct atcgtaaggt 25320
ctgctttcat catgatgcag aaagagtttt gcatttgcac tatggaattc aaaatattca 25380
taatgatata cagtcgatat gccaagattg ttccactaag agctattacc tcaaatcgtc 25440
agaagcttgg gtaaggcttc gagtaagaca ctcaacttcc ttgagcaagc cgctatcacg 25500
aaactcagag agcaaaggtt gagcatcttc agccatggct tgaatctgtg acatcactac 25560
atcaaaaccc aacgcataag caggagaata cattttttc caatcttgaa attcacctat 25620
cgattctttt tgaatactgt aaacaagatc taaacaaaga ccaccaaaat tactcatatc 25680
acctttttga gcaatggcct tgcttcctca ataaccgaag cagctctctc agcaagcgaa 25740
tacgtattgg caacaccaat ggcctcaact tcgcgtccaa tacgagtgaa aattccaact 25800
aattcatcta aactaactcc ttgcactcct tttattgtct gcctatcaca aacgatcaga 25860
ccttccttac cacattcagg atgcagaggt cctactgaag gttctggtat cggattccta 25920
ggcataatgt cgatcatagt ttccattaga agaccagact gattcacctc aaccaatgaa 25980
ttcctcggga taataatctt atcatcttct atctgcaaaa cataacacac gaccctcatt 26040

-continued

```
tcaaaaacaa atgtactatc aaaaccagat tcaaagtacc agatcatacc tcagcaacag  26100
cttcaatatt cttcaaggaa ggattaacac ggataatcgt accaacagta accccacgga  26160
tcctaaccgg tgttcccgtg caaataccag aagcatgact aagctcaaac acagtctgat  26220
atttcctaaa cttcgaccgc atttgaaaac ctcgcaacca agcccagcta agagcaagaa  26280
gagtagctcc agagacaata aacaaaccaa caccaccttc ccaaatactt ctcttaccaa  26340
acccaaaatc actcaaaggt tttaaagtct gtctccatat attcctgggc acatccaaaa  26400
caacggtgag aggattcttc cccccatcag acgatggttg accatgagca gcatcggaat  26460
tggatgcagc tctgaccact aaatgcctag ttctaggttt tggtggaaga taaggaaccc  26520
cattgggtga aactcgagga caagcaatca tggaggatga tggcattagt gatgatggaa  26580
cttgaattac tggattccca atcatccttc caaattcaat aaaaaaacta aactttatgc  26640
agcaagttcc aattttgttt tccgagctgt agttagaaag aagatagaga acatgtgaat  26700
tgcgtgaagc ttctacttta tcgatcgaat tataagtcga gattagggtt tttgagcgaa  26760
agagagaata cctgggctcg aagcttgtga cgaactggtg tcgtgaatct gagaatagct  26820
tctccaaagg ctttgttgtt gggatttaga cggtaaagag aaaagacgga aaatcccatg  26880
tgattatcat taatcataat taattaagta atttattaat cacctaattt cgaaaatgta  26940
aaggcttaat cagttaatct taagccaatt tggaaggaag caagggcatt tccgtgataa  27000
tcagaaaaat atacagcgaa agtgaacttt tctctgttca ctgtaatgtt tcgtcctttg  27060
gagaagtggt aggccaaact gtgaaaaata gctcaaatca atttattcat taagttcaac  27120
aactcttcct catatcagtc ttttaaccaa caaaccaaca gatccttctt ttaattaaca  27180
tcaagatcac agcttttgtg cttaacactc aaaaatcact aaagcttcgg attttattat  27240
tgcagattcc ttgagctcat ggtaggcttg agaatcagtc cattaaagga tttaacttaa  27300
cgaccatgaa ctatccaatc accaaccgac aagcagtagc tttagaagag ccattctaat  27360
gaacaaaccg ttctttgctt gtctgaagta ggcagctctt ggatcagcat caacatctgc  27420
ggtgatctac acaataagaa atacaaagag tgaggattgt gtcacggtac atatatgaaa  27480
aatagaggtt ttcttaactt acttcatcca atctcggtaa aggatgcatg ataatagctt  27540
ttttctgcat cactcctaac agatccttgt ctacgatata cttcccacga gctgcttcgt  27600
aaaggtccag cctttctcca aacctctctc tttggattcg tgtttgataa actacatcac  27660
acttggatgc tacttccatt aaatctgaac tttcttccca ttcaaccccg cttgatgtca  27720
aatagtcttt tatatcatcc taccattaaa agaacacact gaaaatggta aggaacatac  27780
acaatgatgt tctcgagtaa accaaaccat cttcttcagg ttctctcatg gagggtggca  27840
agtttagtgc tactaacctt cattttcaca atttcagggg aaacaaagta gatcttcacg  27900
tctttgaact tggcaagcaa gtatgcaaga gaccgcacag tccttccgtt ggcaaggtct  27960
ccaactaagg ctacactgat gccatctaat tttccaattt cactttggat ggtatagacg  28020
tccaatagag ccttcacaac agtaacagaa ccagaaataa gaaacaagga tgtaaagtaa  28080
tgtttgttta agacaattga aaaaaactaa aggttaagaa cacaacatac ctgagtagga  28140
tgctctccag gaccatcacc tgcattaatg acaggtatat tggcagtagc tgcagctttt  28200
cttgcagcac cgctttcaaa atgtcgcatc acaattatat ctgaataacc ctccactgtt  28260
cttattgtgt ctgaaaaatg ccccaaaaat ttccgtaaat aatctaacac tcaacatgtt  28320
tcacagcaat aatgagatac tagctaagat ggtaccttca agtgtttccc ctttcgcggc  28380
agacgaaaac tctctagcgt tctcagtagt taagacttca cctccaaggc gtttcatagc  28440
```

-continued

```
agattcaaat gaaagcctgg tacgggtaga aggctcataa aagagggtag ccattaaata  28500
acccttgagg atttcacttt gtgaagagct cttttctatc ttttccattt cgcgtgcaac  28560
atcgaatata gcgcttagca tctctctatc aaactgtttc ccttcaatca catcactaag  28620
ttcaaatttc ttcaactccc tcgtcccagc ttgcatagca tgacacctga ctggaccaac  28680
atttcgagtc agattcaaag tagcattttt cttgagatcc ctagaggcag gaaacgaagt  28740
caaacaaatc tttgaacttt caaaagggct gggaagattg atagggaact cagagctgca  28800
ggctaatgct ttaggaaaaa ctgaggcgcc gcaaagtgtg gctgaagtaa gtgatgatgc  28860
aatagacatt cttgcgcagg atgctaattc gttgaagggg agatactgag tcacaacttc  28920
cagaatctgc taaaataaca gacaacaata tatgatgccg ttagtttaag aataatcgaa  28980
agcaactaag ttttcgagac tatgagaaaa aaactgcaaa ttttataaac tctaaagatg  29040
attacaagta tccacactcc atcaagctag tgccaacgat acttgttgcg gattatattg  29100
gtaacctctc ttacatatcc acttgctttc atataagaat ctaaacatta cttgaatcct  29160
gaattcaatt gtcttagatg gatagaggga gaatcaaaac cttgggtact ctatggaaat  29220
gatccttaat ctcaattata ataaaattat gagaaagtag ttaccataat ccgaaactat  29280
aacaaatttc aatttcaatc aatcgtaaat caaaaatcga aaaagaaaaa aattcagaat  29340
ctgatccgca gaatttcaaa acctacacag acctaaaaga gcgattgaat cagtaaagca  29400
gtcaaatggg gaagagtctg gctggtcgat gtaacgccgg tagagaatcc gacagcaatg  29460
agcacaaaaa gaaggaatta gactcaatcc tggttaaatc ggagaccggc ggcgggaacg  29520
gccggggaga aatcaaaggc gggcggagaa atgtagggtt ttactaagga aaggaaacta  29580
gtaatgatga attcaagacg ttttggaata ttaggggagg gaaaaaacga aacgcattgg  29640
gatgataatt aataaatcat atttaatgtc ttgtttcttt ttcgttggac gagtaaagtg  29700
aatttgggct tctaaagccc ataatatgtc ttcttttcct cccgcgaagc ccaaacagaa  29760
acagaaagct ccggcggata gtcaaagaga gagaggatca acaacggaga agagaggttt  29820
catgtcatga caagtttcag ctaaatcaag taagtcctgg tattaacaac aagctttttg  29880
attctgcttt tatgcttttt tatttacatt ctaacaaaca aaaacagaag cgtcatgtgt  29940
ccaaaccaaa atttacatca aaactcttac cctaacacat atcaagaaag tgaagaaacc  30000
ctaagcatat acaaacatgg ccatctctga aaacaaaact cagttaactt ctggtatgct  30060
ctgtagaacc ggtctccata accgttgttg attggcttct tcgtacccgc gattgttcag  30120
gattggacat gagaaggttt gttgctggaa ggtcaagtca tggacgttga ctttactcag  30180
taaatcatgg agttgcttct tcgtgagcct gatcttgatc tcatgagatg gaacagagga  30240
tttactgtca cgtgttacaa ttactggttt gccatctctt gtggttttag agctataatg  30300
atgatcttct tcatcttctg tgatgaattc atcccagtct tcaccagccc aatgcatttc  30360
tgattcatgc cttaaacaat tccccatttt ttgtttctat ttttctttgg aggtaacccg  30420
taaaagagct tatatatata taacgtaggt agaagctggt gagatattat aatcataaaa  30480
ggagataaag atcaggagca gtgaatatat taaaaaaaaa ttaggatcaa tgataagaac  30540
atatacaata tgccacgtca gatttcagag tactttagtc ctacgtggac atgtgtttgt  30600
tgaactcacc gtcaccagct tttgtccttt tcaatttcca acgttccacg tgtccttatt  30660
ggctcgtcag ctcggcttgg atatttttgc tgattataat attttttatc tttgttttcc  30720
ggtggaaata aaatgcccat gaaataagag aaaaaaaaag aagaagaagt ataataattg  30780
cctaacgtga cgtctaacga aaacagaact cagcacgaaa gattctagtt catatgtggc  30840
```

```
taaaggaaaa catgtgaaat atgaataatg agaaggaagt ctcaaaggtc caatactctg  30900
atgctatgtt ttgttgtaga caaataaaac gtataacgtt gaggtacgta aacgtatacc  30960
aaaaaagaag tcatttatct tgtgcgtgta ataatacctt tgataatgag atgtcccatt  31020
ttttcttctt ctttttcttt taagaaatac acatttatta gctagactat ctaccactga  31080
aaattaatat atatttacca atttttaaag tgttatacaa caaatgttta acgtgtaaat  31140
ctacgaaatg gtcattgaca acaaattatg atcaatttca agatatatcg atcataacct  31200
taacagtaaa aaaatatatt ttctcagctt atgtaagtaa ataaaacgta aagtagaaca  31260
attagaaatg tatataacca aaaaaaaaaa gtgtggatgg agccgagcta ggcagaagaa  31320
gccgagtgaa gtgaagtagt gtgaacacgg cattggggaa gggatcttca aagtgtgaac  31380
gcaaccaaag ggaacagaat ctctgaacca aagatgccct acccaatttt caattactcg  31440
tttaggccat ctcatgttac acacactcac gtctcccacc tttccataat tttccattgc  31500
catcaccttt tttttttttt ttttttttaaa gttttaaata tttctaaggt ttttgttttc  31560
ctgttaaaaa tagttacaag gttttgggta tttggaattt aagtaaatat tttgaatttg  31620
ttagttatta taccattaaa aatcactatt caaactcatg ttctacatta atcacttttt  31680
ttttatctgt ccatttgccg ttgtttgcat agtttgttct actatcatca tctgatctta  31740
ttaacatcaa ttacccaatt tactctacaa atgctttata tgatatattc aaatgcaatt  31800
caacaaccaa tataccatta ttattcatat aagtcaaaag cctgaggttg gtgttacatc  31860
gaattattcc actactagta tatagcattt ttatttaagt agtatcgatc acttgaccca  31920
catacccoga actttatttt tataaatgaa actgatctgt ataacattgg ttgatctatc  31980
gatctctctc acctattgct ctcattattt gttaattcga accgattagt aaataagtaa  32040
aagttataga atcttggtgt tcataccact gtagagacga aaaatctaat catctcatca  32100
taattaagtt aaatatgctt tatataccta tctctttatt catttttttat agttgaatat  32160
tatacattaa cgaatcaata caatgggtcg atcaataaaa tgtgtctatt atcaactttt  32220
tgtgttacat gttacacaaa catatattaa ttattaatta ttttcggctg ctatgtgata  32280
caacactcac cattttgtac aatttttttt ttgttttttt ttctcttttt tttttcattt  32340
tgtacaattg ttcaatcatt atattgaaac gaaattaaac tgagattctt ttgttattaa  32400
tgagctctat tgagtttgtg tttaagtacc acccgaagac tttttgttaa attgcgtagg  32460
ttaagacttt agaccgtcaa gaagttttgc ctaataaaaa tgacagtcaa agaataaaaa  32520
agaccacttc ctggttcctg ctactcgata tgcgtagcgt aaatataata atttaaagta  32580
atcaacaaca tttgttttttg tttttttgaca tttaatcaac aagtttttga agttccacgc  32640
ataaacacag acgcataact ataagaaaca ttaaaggaaa aaaaaagcag agctaagaag  32700
atgcaaaaaa aaaagatcta aagaagatgc cattgagaca cctatatata gtgattattt  32760
caaagacaaa gagttaacgc aatcaagatc aggtgtttaa aacacaaatg atacaaaatt  32820
atatactcgt atattggaaa ccatgatctt tgagctttcc atccaatttt cttctgtaat  32880
taaacaaacc agaaagacat taaataaaaa aaaataaaca tgcatagcat atagtacaca  32940
tttagatagt aagatcgtat tgtatacatc tttttttttta ttcactgaga agtgagatca  33000
ttatcacaat aacaagaaac aaactaacga atcaaataaa atatgatgta acagtttcta  33060
tgtaataaaa tataaaatga gaaaaaagac aaagaatgca gaatccatgt gaagggaatg  33120
ggagtggaag aagcccatct atattaaaac ttactaaaag tactaatgat cgactacaat  33180
ctcataatta aggttttgac cacctctaat ctagccctta aataatttat ccttgtatgt  33240
```

-continued

```
atatgggctt tatttgtata tttgttgttg ggcttcgatg atacttaaag aatctgaagc  33300
acccaaaaag aaaaaaagag atttggtgaa actaatcaaa ttagtcagag acaccccagt  33360
acctccttca tcatcactct ctctctttcg ttacagttcc ctaatcaagc aagttgcata  33420
tcacgagctc tctcaactct caatccaatc catctctctc tcacgcattt tcgtttgttt  33480
cttcgttttc ctcttttcag attcttctct tcgattcttc acattgataa aacttgtcta  33540
tggtggttgt tacgtcgatt gagtagatga agttcaccgg aaaatcaaat ttgacggcta  33600
cattacccgc aactgtccca aatatcaggg atattcatag aaggagagcg cgaaaaccga  33660
gcttcactcg tcaacgaaga tctggcgtgt ctgtcaggag gctaagcagg ccggagactc  33720
ctcaattgaa atcgaaggtg gaggatcaaa acattgagcg atgcggcggg gttgaagatg  33780
gtgataacga ggatgatgat tgtaataaga tgcgttgtca ggaacggagt aggagtgtac  33840
ggcctgatac tgttaggaaa cttgctgccg gagtgtggcg attgcgagtc ccggatgcgg  33900
tttctagcgg cggagataag aggagcaagg atcggttacg gtttcaggta cagctttgct  33960
tttgaaaaaa tgagacattt ataggatccg cattgtgatg aagtgaattg tatgaaagca  34020
atcaaaagat tataggattg ctgattttgc cttagctttg aatctaaagt atgagagcac  34080
tggattgatt ttagctggtt gttttaatag taatgtcaaa gtaatctgaa atagaaatga  34140
ctgttgattc caggatcttc acactagttc ataactgttt gctcatgtct ctggaatctg  34200
tacactctgt ttcttgtgtg atggatctga attagttggc tttagctact atctcagagg  34260
agttcatatg tcaaataaat ttctctttat tttctttggt gtttttctcc aggaaactgc  34320
tggtcctgct ggaaacttgg gtcctctgtt ttattatcac caccatgatg acaaacattc  34380
tggctttcaa agcaacaatt caagaaacaa gcatagtaga ttcttgtgta aggtttgttg  34440
ataatctcaa acttctaggt gaagattata ttatgtcaat tcaattagat gtggatatgc  34500
ttcaaaaagt cttatacatg ttacttgagg tgctttatta agaaccataa ctaaatgttg  34560
tggttgagat gaaggttcta tgagtttaga gttgttactt gagctagtaa atctgacctc  34620
ggtcggttta accgtctggt cggagtatga aaatactgcc ttagcttcac tatagttgtt  34680
aacttgaaca ctttaagaca ttgacacgct gcacatttct tggttggcta ttcctttgtc  34740
tgagtcctct taaggttctt tatttatgtg acagtttccg ttaatcatta ctttttttctt  34800
tttcttttgc tgttagcatg agccttcagt tccatttccc cactgcgcga tggagggagc  34860
aacaaaatgg gatcccatct gcttggatac aagggatgat gtacaccaaa tctataccaa  34920
cgtgaagtgg aataatcaac aagtgaatga tgtttcatta gcttcttcta ttgaattgaa  34980
acttcaggaa gctcgtgctt gcattaagga tcttgagagt gagaagcgat ctcagaaaaa  35040
gaagcttgag cagttcctga agaaagttag cgaggagagg gcagcttggc ggagcagaga  35100
gcatgagaag gtccgagcaa ttattgatga catgaaagct gacatgaacc aggaaaagaa  35160
gactcgtcag agattagaaa tcgtcaattc aaaaattagtc aatgagcttg cagattcaaa  35220
gttagcagta aagcgttaca tgcatgatta ccaacaggaa aggaaggcaa gagaattgat  35280
cgaagaagtt tgtgatgaac tggcaaagga aatagaagaa gataaagctg agattgaagc  35340
attgaagagc gaatccatga atctcagaga ggaagtagac gatgaaagaa gaatgctgca  35400
gatggctgag gtttggcgtg aggaacgtgt ccagatgaag cttattgatg ccaaagtaac  35460
actcgaggaa aagtattcac aaatgaacaa actcgtagga gatatggaag ccttcctcag  35520
ttcaagaaat actacaggtg tgaaagaggt gagagttgcg gaattgttaa gagaaactgc  35580
tgcatcagtt gataatatcc aagaaatcaa ggaatttacg tatgaacccg caaagccgga  35640
```

cgatatcctc atgttgtttg aacaaatgaa catgggtgaa aaccaggata gagaaagcga 35700
gcaatatgtt gcctacagtc cggtcagcca cgcttcaaaa gctcacacgg taagtccaga 35760
tgtcaatttg attaacaaag ggagacactc gaatgctttc actgatcaga atggtgaatt 35820
tgaagaagat gacagtggct gggaaactgt gagccattct gaagaacacg gatccagtta 35880
ctctccagat gagagcatcc ctaatattag caacactcat caccgtaaca gcaatgtatc 35940
gatgaatgga acagagtatg aaaagactct attgagagaa ataaaagaag tgtgctcggt 36000
tccaagacga caatccaaaa agttaccgtc aatggcaaag ctctggagtt cattagaagg 36060
tatgaatgga agggtttcaa acgcgagaaa atcaaccgtg gagatggttt caccagaaac 36120
aggctcaaac aaaggcggat tcaacacatt ggacctggtt ggtcaatgga gctcatcacc 36180
agactcggct aatgctaatt taaatcgagg agggaggaaa gggtgcatag agtggccaag 36240
aggggcacat aagaacagct tgaagacaaa gctcatagaa gcacaaatcg agagccaaaa 36300
ggttcagctg aagcatgtcc ttgagcataa gatctaggcc acaacatatt ccaaaactac 36360
cagtcctagg ccattctact aatctttgtg gctgagcagc agaactggat ttttgatccc 36420
gttctcctgc tattgccatt gtcgcatgat ctagcgctgg tcaaaccaat caacgtggta 36480
tattttcgtt agctaaaagc aaaatgatct ttgtgattga ttactgtcat agcttggctg 36540
ggctagcttc agccacgtcc cagcaacccc ttggaacaga ggcacaatgg tgtttttctt 36600
tactgaattt tgttcctctt cagtccaact tgtgatgcta ggtcattaat atcttctttt 36660
attacattgt gtatatactt cgaaactgta ggatgcattc ttctatatgt aagttaaaga 36720
tatgataaac agaagaattt aaatgatata tccatttatt ttagaccaag tgggagaaag 36780
aaataaggtt ttccattcga aagaacgaac acttgaaaca caaagcataa gaaacatgat 36840
attaagttaa agcacaaaag ataagactat ataacacata tattatagat gccacggttt 36900
aagcttctaa acaagtctat ttgggaaggt aatttgtaga agaaatttcc tccatagcga 36960
cttgaacaac caacatatca ttcacaagaa aaccctttga tgaatttctc agatcagaaa 37020
gaggcatgaa gtcagcgtat ccccacccga ttgtttgggg actgaaccag ttatcaactg 37080
ccagaaaaga aaagaaaaaa cacatattag tcatcgtagt gattgaagat gttatgaatt 37140
tcacattaaa taacagtcat aatcacatat ctagtatcca cttacgtggc ctttccaaaa 37200
cgagattgga ttgggatccg aattggttag gaacacgaag cttggctcgt acgtaaacct 37260
tgtcataagg ttttgctttt agtagctctt gtggcccaag gttaagataa agcgacaaat 37320
ttttgccttc aaaagcgcca aaaccatttt taaagattcg taaattcctg attcagcatt 37380
tgaaaaactt gttaaacact taatagtagt atactactac gtacccacca cacttgcact 37440
acaactaatt atattgagaa actcaccagc tttttcctcc gatgatgaac tcctctgata 37500
ggtaatcagt aggcagtgtc gagtatcctt gaatatacca ggtgaatctc gggctcggaa 37560
aactcttggt gacagagaaa acttccgatt tttcgtagaa tggtggaatg ataacgtcaa 37620
cgccaaactc acaatggtca acgtcataaa ggtatccatt ttttaggttg ttaaacgtaa 37680
tcagaggaag aaccttagaa aatccccaca ttcttttgat tgcactgaat cgccatacat 37740
cagtatctgg taacaccgca tagacataat aatagacaga tagatgttac tataaatata 37800
gaaacaatga catatttatt tgagtattac cgcataaagt tacttatata ttaaccttgg 37860
atcgtaaagt acttcgtctc tttcttgttg aatacgtaaa atctgagatc tacatgaacc 37920
tcttcacttt gagaggtgag agttgagttg tctaagacga cgtatagcga aatgtgccct 37980
gtaccgttat cgttcttgtt tcccttcgga tacacaacaa gcgtcctgtt tcaatttgtt 38040
caacacgatt cagcaaacaa ctatagtaca taatgaagtg gcttgaacaa agataggcca 38100
aggtcctcca ttaggaatat agggattgat caacgttttg tagtccagtc acaaacaata 38160
gtttttatca tggagctaga tagattttgg gacaaaggtt cctaatcttt tagctaataa 38220
aatagaagaa aaaacaaaga tggtacgtaa cgtaccagtt gtatctaccg accctaaaag 38280
gacgagattc gtatctctca gtgtaaacag acttcatgag tgtgttgaaa gactccatct 38340
tgagagagta agacgatgga ggacgttctc tcagaccctt caccgtgctc gatagagaaa 38400
ccttactatc acgtgatgat atctgagtgg ggaaaatttt ctgagatcca ttttcctggt 38460
ttggaactgg tcctgcaaaa gaagaggtga tgaagagaca agacaagaga gaaattacaa 38520
tgcataaggt gtttatgtag tgatagctca tcatttcaaa gatctatgaa tgaagtttag 38580
agagtcactg tgagacttgt taacgataat ggcatgtgtg tgtgtatata tatagaaggg 38640
gagattggtt aactagatgc ttactggggc taaaaatagt gagattttgg catgataatg 38700
tttttcttct gcctagtgta ccagttggtt cattaatatt tgaaatacca atctcgtttg 38760
ataatgcgtt tacttttacc attgacttag gttatatatt atatttcctc catatttgga 38820
ttggatcagt cttttcgaat cggggatctt tttttaaata attgcaaatt catagaaata 38880
caccattcgt tcacaattgt agtagtattg aactcgaatc tgataactaa aacaatgcct 38940
ctctaactag ctagctacta tctaatttaa ttaatgccca taaactcgca aaatcaatta 39000
tctatgtaaa cgttgaattg ttttaacatt atagagtgta gactaaactt caaagcgaaa 39060 ctttttttctt tgtctccttg ttcaacgaaa cgaaacctta taaatagcat acgtactttt 39120
gaaatcggag aactaaaaac taaagtgatg caaaatgaaa ggacataata tttgtctata 39180
acctaaactt tcttaattta tttctacttt aggggtttcg agttaaaatc agatttccta 39240
gttcctacta tatgcctctg cctcaagtcc aagatgccga caaaaaatag tcacaaagat 39300
tagataattg cagtgccaga tcaaaactca ctcacgtgtt ctcatctccc tccgcaacta 39360
gcgtcgatat cagtggtagg ttcacgtgga ccaaacaaac cttctcatct tccctattaa 39420
tttggtccat ctttagagac gtatgctatg acggagccac gaatttcatt tataagagtc 39480
acaaaacatt tatttttcta aacctaaaat aaaactaaat atttatttt cttatatata 39540 tacattttaa cctaaaatgt ttcatatttc atctttcaaa ataaacatac tctcaactta 39600 tctttttta gttgtatcat caaattccct ttctcatcaa cactcttttt gttaatatat 39660
tgtggagatt gagtagttgt tgtgtttatc ttgattcatg atttttagaa tatatatttt 39720 agatttttttt tttgaaaaga atgtagaaac taaaactgga tatctaaaaa gaagaaaaaa 39780
gtattgattt gttaatgaat attacagggt ttttaataag atattatagt ttttataatt 39840
agccaaacaa aaatgcaaaa aggcattaag attaaatgac aaaatgaata tgcatggggt 39900
caaagacaag cataaatcac ataacatgag gtcattgtga gtactttaac ccaaaacata 39960
taattatctt agaagatata ccctatattt tttttttaaa ctataaattt tatgggggtc 40020
gactgagccc ccttcttgta tgttgcctcc ggcacacgta tgattggatt ttatcatctc 40080
catgatactt cagagttctg acaatctcga atataatgcc actttgtttt tttgctttgt 40140
aatggacatc atcgatgctt caatcttcga aaactgaaaa taacgtccgt ctgttttctt 40200
ccaaggtcgt gtggtagaca tgacatcttt tcggattatg aacatgagaa cagcccttat 40260
caattgtttg aaaacaaatc gaagatactc atatttcgga tgatgtctat tgatcgtcca 40320
gaatagattc taaacctctg cttccaatac gacgagaagg atctccgatc gaatatggaa 40380
acgtactacc aacgatgatc ccgaataatt catgttgcac cacaaagcat gaaacatctt 40440

```
ctttatttaa ttcgtacgac aacattctat tagtgacaga aaacaacaat taactttgta  40500
gctgttaaaa atactggtaa aagataaaaa aaagattgag ccgagtttat ctgttgtata  40560
tactattctt tttgatagat acatacaccc aagatatttt atcttgacat gtgatgaaga  40620
gatacggatt atcctctgaa caataatttt ctaaaaaaaa agaagcaaat ttttgataac  40680
ttaacttata aatccacctt tttccctaat tagaagatgg attctggctg attttcttgg  40740
attagtgtta gacagggata ctactatttc ttaacaatga gatgaggcaa tctatcaagg  40800
aaagtaaaaa aaaaacgaaa cttaaccctc tttttttctt ttttttttta tgttagacca  40860
atcacttctt gaaaagattc cgtaactaga cgatttttat atatattttt ttattttta  40920
atttttaata tttccacttc aaatataaaa agaaagtata tttatttgtt atagaattat  40980
gattagaata tgaatacaaa tgtaaaaaaa aaatgatata gaattctata gaaaaaagaa  41040
aaaaccttat aagctagtca taccatttca tttcattata ttgacaatta aaaaaaactg  41100
atcatactat gatcatagta tgatggcggt tgagcaagta tgcccccatc gtctagtggt  41160
tcaggacatc tctctttcaa ggaggcagca gggattcgac ttcccctggg ggtagggtac  41220
tacgaaagga agttgatcat ggattatcca taaagttaga atagattctt cctgggtcga  41280
tgcccgagcg gttaatgggg acggactgta aattcgttgg caatatgtct acgctggttc  41340
aaatccagct cggcccaata attagctgtc tacataacca ttttttttt ttgcataaat  41400
gacagagaag gggtaagaaa aaaaggtcaa atttcagggt atagggtata gttcgacttt  41460
acttttttt ttatttctta tgtttagtta cttttttttc cataaaaaat tccgatcttg  41520
atcttgctaa ggattccgat atggatcctt taaagagaaa ctttaatgaa cagagtcgat  41580
aaaataatct atttgcttct gttcaatata taatgactga agctaacttt ggttggttaa  41640
tccgatcagt tcatcgatgg tcgtatagtt tagttattta ggcaataaaa ggtaggggtt  41700
agaaattcag atgatggtac aaaaattaaa aatagatgcc aatacgtata tttttcttat  41760
taaaaatatt atatcaaata ataattaaaa aaaaatatat atatatatat ataaatatac  41820
atagcacgca aataagaaaa tgcattattg aatattgaag aaactatgat tactctttga  41880
caacaaagag aaactataat caattaaaaa ctttaattag aataaacttg aaagaaaata  41940
tgagtaatac gttttcttag cagaaaaatt cgttttggaa gagttgagtg tgaatatgag  42000
gttttttttg ggtgtattta ctatttacag taattgttag aagtcatgct tatcttttga  42060
gaatttgtat atacataatt cattcataaa cgttaaaaaa aatgtgttta tatgatagct  42120
tttaatcaat tgatgtacaa tgaggtaatg aaactcagat gagtcaccaa ctaagttgag  42180
aacttgagat ggattcaata gtcaatgatg ctaggtgaaa taacgtaatc aaccaaaaat  42240
attattcaat ttttaattcg cattcgcaaa cacgaggcac ataaaataat attatcagtc  42300
tcaataaaat cttgattctt gatcttgagc atcccaaagc attattaact aagcatgtat  42360
ctcccactaa ggcacaaatt actaaccata taagtctcag tactctctgt tctgcaaact  42420
tcatacacaa aaccaacatt aagagatggc gagccactac agaaacacaa gcgctattgc  42480
ttatctattg ctttgtctct tcattacatc tgccactgca cattccttca tacgacaaat  42540
cactgatgac ctcaaaacaa atctgcagcg tatgccaatt ttctatgttc ttttagttgt  42600
tataaatgga aaacagatcc tttgttttta tttctcaaat gctctgtttt tgtctggaaa  42660
cagaggaggt aggagcagaa ccaatccaaa acctggacgt aggacattac ttacaagaaa  42720
ataaggagat ctcatcacgt gattataaag tatcagcttc aaacgcagtg aaaggtttga  42780
gagatcgtcc tccatcgtct tactctctca agatggagtc tttcaacacg ctccttaagt  42840
```

-continued

```
caacttacac ggagaaatat gtatctcgtc ccttttcagt tggtggatac aactggtatg  42900
ttggtcatct gatctttatt tgcttgaatc tataatctta cataccaaat atattttgat  42960
gaatctcaat atatacagga cacttgttgt gttcccaaat ggtaacaaga aggatagtgg  43020
ttcagggtac ctttctcttt acgtagccat agacaactca actctcggac agcaagagat  43080
ttacgcagat ctaaggtttt acatctttaa caagaatgag aggaagtact tcactatcca  43140
aggttcttat aattttcaat caagaaatgt agtgttttag caagaaagat actttgtgca  43200
tgatagtaat atgtatctat atatcgactg gtctttgtta tataatctgt agataccgat  43260
gtgtggaagt ttagtgtctt caaaacgatg tggggattct ctcaggtcct ccccattgat  43320
acattcaaag atccgacaaa aggatatctc tacgatggag atcactgcga gtttggtgtt  43380
gatgtaacca tgccttctct ctacgaaaaa tcggaacttt tctctgtcac agagaatttt  43440
ctaaatccga gattcacctg gaccattcgg ggattctcta cgctgctaaa aaacagttac  43500
ctatcagaag tgttctccat cggaggaaga agttggtgag tcaacattat ttcaaaataa  43560
aaactctggt ggagtagtaa aatggtggta agtagtaaca agtattttat atgttgatta  43620
ggaatataca aatcaatcca agtggtcttg gtacgggaga gggaaaagct ttgtcgatgt  43680
atcttggcct taatgtgaat gagatattca gaccatatga gaagatttat gttcgagcca  43740
agcttcgagc tcttaaccaa ctcaatctca gtaacatcga aagggaacgt aagtaaatga  43800
tatgtgttca ttgatgggta tacataacat ctcatcgcaa tgactaatga gatttacttc  43860
ttttttttgg gcagtcgata tttggtacaa tggtccggga tatggagaat atagctgggg  43920
tttccctgag tttatctatt tcccttatct cacagattca tcaaagggtt tcgttaagaa  43980
cgatgtgttg atggttcaag ttgaaatgga ggccatttct tcaaccaagt acttcccgag  44040
ttagattttc tctaagcaaa gaacttgtac ctacctccat gtgtttgatt tgttatcaaa  44100
tactaataag aatttgatta tgcatttcaa atacaattgt ttctttttct tcagcatatc  44160
attatcaaat tatcatatat cttcttgaaa gatcaaatag tcttcaccca aaaaaaaatc  44220
cgccaatcca acattcggct cagttttgtt tgttttgata cctaagaatt aaagaattaa  44280
tggataattt atgatggagg ttagagtcta ctgctaaatt actatcacta atgtattgcc  44340
ataaacaata aaataatata attgctaatc ttaaatctca acttgactat aaagataaag  44400
actaaatcga tcaaaaacca atacactaga tgaagcctgg cttttggtgg gggattttaa  44460
tgaaattcaa tgtgaaaatt taataagaac ttttgtgaaa agaaaattgg aaaatataag  44520
taaaagaaaa aggttaaata aaactatcta acatcataaa aagttaaaga atagagcaat  44580
tggatctagt gtattggttt ttgatcgatt tagtctttat ctttataatc aagtggagat  44640
ttaagattag caattataat attgtttatt gtttatggca atacattaat gatagtactt  44700
tagcagtaga ctccaacctc catagaaaaa aatccattga ttcttttatt cataggtatc  44760
aaaacttaca atgcatttga acctatttta taatttaatt caaactactg tattcagttc  44820
caatcatatg tttttgaatg ttttttttaag aaaattgaag ttcatatagg atttataaaa  44880
atttattcat ctgatgtaga attattttat ggtcaagtta atgaaaactt caagtgaggg  44940
cactcccaaa cttgagatgg attcaaaagt caacgatgct aaatgaaacc atcgaatcat  45000
gttttgtttt tgaaacaaca ttattacgta agaatctaac taatattcga agactccatc  45060
ctaaagcatt tctctatctc tttaatatat aagttccact aacctctctt ctcttcactt  45120
cattcacata agtcataacc ttgaaagatg acgagtctct acagaaacac atcctctttt  45180
gtttatctcc tgttttgtct cttcatcaca tcttcgtctg cgggttcctt tatacgacaa  45240
```

ttcagtgatg acttcaacac aattcaacag cgtataaaat ctctttcact cttagattca 45300
tctatgtaac ttagattttg tgtgtggaca taatcctctg ttttttttc tttttcaaa 45360
tgctctgtat ttttgtctga aacagagaag ggaaaagatg gaccaacacc aaacctggaa 45420
aaaggaaatt acttgcataa acataatgag atctcatcat cacttgatta taaagtatca 45480
gcttcaaaca tagtgaaagg tctaacagaa gttcctccct cgtcttactc tttcaagata 45540
gagtcttata actcgttcct taaaatcccc tacttgggat tcgaatctcg tccctttgca 45600
gctggtggat acaactggta tgttggtatt ctgatcttca ttttcatgaa tcgaatctta 45660
tgtaccaaaa atcttttgat gggtcttaaa agacatgata tataatacag ggtacttaag 45720
gtacacccta acgggctcac gtgggatggt acttcaggat acgtttcgct ttacgtactc 45780
ttacacgaat cgaccccat cactgcagat caagtcgttt acgcggatct aaggttttac 45840
atcttcaata acaacgagaa gaagtacttt accgtccaag gtttttgcta aattttttca 45900
atatgtataa caagcaagaa taattatcta tgcgtgcatg atatatagta acatttttgt 45960
tataatctat agataccaac gtatggaaat ttactgcacc caaaaggctt ttgggattcc 46020
ctaaggtcat gtctgcagat caattcgaag acctgcgaaa cggatacatc tacgataatc 46080
actgtgagtt tggtgttgat gtgaccgttg cttctcacta ccaaaaatct gaatctttat 46140
ttgtcactga gaaattcgat aacccaatat tcacttatgc actcctgaga ttctcgacgc 46200
tgctcaaaga aagttaccaa tccgatgtgt tctccattgg aggaagaagc atgtgagtac 46260
cacatcatta cagaagtaaa aactttgcgc tataagagta tagtggtagt aattaacaat 46320
tattgtttta tatgatgatc aggtatttac aagtgtttcc gaatggtcgt aatctttcaa 46380
agggaaaagc catgtcgctg tatcttaaca ttaacgataa attcaaaccc tttgagatga 46440
tttatgttcg agccaagctt cgagttctta accaacgcaa actcaataac gtcgaaatac 46500
aaggtacgta agaaaatgga tatataacat ctcatcgcca ttgactaatg ggattttact 46560
ttcttttttc gcagttagta attggtacac ttcttggttt tattactcgg gcgactttca 46620
gattatccct ctagctgatc tcagagattc atcaaagggt tttgttgtga atgatatgtt 46680
gaaggttgaa gttcaactcg agggcatttc ctcaaccaag tggtacccta gttagatttc 46740
tcaaactata ggaacttgaa gctccatgtt tttcctttgt taccaaacca cctaataata 46800
ataaagggta atttgtgttt gcattttttt ttacatatat tttctttctc tagcaatatt 46860
aaattatcat tcctcttcta acgaccatat taagttatta actcttgtct cttcaagcat 46920
aatggttttc actcaaataa aataatgtat acaatcaata catatacgtc aacagcaaat 46980
gagggtggac aagacactaa ataacttatt cttgattaga ggcttttgat ttgtaaccaa 47040
cctaatggtt gataatccgc aacatttttc gtagtgcagc aaaatgaaaa gtaggttaaa 47100
tatgggttaa gccccaaaaa ccattgtttc tcttatttgt tttgacatct tccggaccaa 47160
aatacccttc gtagagattg atttgagtgt tctagagtgt tgcaatacat tcaatctcga 47220
tcttggcgtt tagaggcaaa gctgcaactt gatacgtcga tcgtgctgga gaaggagctg 47280
ggaagtctgc aacagagaca aatgtttcat gcccttaacg actccactaa taattatgca 47340
tctcaaacaa agtaggaaca caaacaatct tgttaaagaa ctcacatttg gcatatatct 47400
cgttcactgt cttgaagtca gccaaatcag ccaacctttg agagaaaacc agaagagatt 47460
gtttttcttt ctatttagat tcagaattca aatggacaat ggtactgttg aaaaaaacaa 47520
gatcccttac atgattgttg tcttcaccac cgaggaataa tcagcaccac tagctttcaa 47580
tatctccccc atgtttttga gtacctttga tattccataa gataatagaa gcaagtagat 47640

-continued

```
aaaatcagga aggaaaaaca gagcaactca accttgctac aactacactg gaacaagtta  47700
atttgaagac taataccaac caaatcaaga attttaaagc aaaacccaaa agtttcaaag  47760
gcttagtttt gtatcatgaa agtttatatc ccaataaact cagctagaat aaggcacatt  47820
aagttgtcat ccctcactac attttcacca acaaacaaca tcatgacgac ctagaggcta  47880
gacctccttt tctgtggata atcatccacc aaaacagaga agcaagtgga aagtactcta  47940
aacaaaacca atttttatag agactacggt gacagtttga aagctaacct gctcagtctg  48000
atcttcgacg ctctccgaaa caaactttcc agtctatata cacaaaacaa aaagagcaaa  48060
tcttgtaatc ttagaacaca gaaaagagaa acaacatggt gattacacag tttcatatct  48120
tatatatacg gacctcaggt ataagtccaa gaacacctga aagaaaaacc agattattgg  48180
ctttaatggc ctgagagtaa ggtcccaaag cagctggtgc tttctcagta gacacaactt  48240
ccttcttcac tgcacaccac acacaacatc acatttcttt agtaaaaacc ctattctcaa  48300
acccttgatc attcaatacg gaagatgaaa gaaactaaaa cccaatacta acaaacatat  48360
gcattgatga taactgaaat caatttcaac tttttgacac tgacattcat aaaaatcgca  48420
tctttagaaa gtactaatat cggtccaaat tggagaaaat tgagtaaaat cgtcaccaga  48480
agaagcagag acagagaggg aagcgaaagg aggagatcta gaagacattc tgaagagaga  48540
aacaccagcg aatgttgcgc agccgacacc agcagcgacc aatggggtac gagtggagcg  48600
aagtgcggtg gagaggtcga gtgttggagt atttatggat ctgaaaaccg accaagtcat  48660
ctcactctct ccggcgccga caagaagtat agaatagcga atggaccacg agagagagag  48720
agaaaggtag gtgaagaaga agaagaagac tgagtcgatg cgattggatt ttaagcagat  48780
gattctcgtg cttcttcttt tgtcttcttc cttctcttcg aaatgttttt ttgtatttcc  48840
cactttaccc ttagttaggt acatatatta ctgagaattt aatttttatt tttgtgtagt  48900
ttagttggat tgcaaatttt aaaaatttgg acccgttggg tcatgtcggt ccatagcttt  48960
gtgaagttta tccacaacat attgttatgt agaagttgtg ttatgtgaaa gatggtctct  49020
acaaatgggg caagtttctt gtctaagcaa ccactcatct atgcaattca tatgaaatgt  49080
gtggccacat cttgctagct ttcttcctac ttccccttct tcccaatcct acacacccca  49140
aaaatgaaca ttagaaatat atatgattta agtcattatt atcatatatt aaaatctgat  49200
tcctagatga ttctaattaa ttacattttt atcacctgta agcaaatcga gcaactcgat  49260
tttgtttgat gttctgaacg gttgtagaac atcgggatgt tctgaataga gctcttcgat  49320
agtccctttt tttcatgatt gaaatcgtat aagtttgaac tctccatgta acttgtatcc  49380
aatgctatta tctgcatttt gtattataat attaccggag ttaaaatttt gtaaaatata  49440
cttagtttaa cgctttttgt tatggttctg attttacgtt agaaaatatc gtgttcttgt  49500
caaataaaaa gacgtagttg aaaaaaagtc agaagaacaa aaagaatgga gagtacttac  49560
ttgccattga tatgctttga gaacaaaagg tctaaccaat cccataatgg ctttcccatt  49620
cactactctc ctgagtaaag ccacctgcca ctcttttcat atttttgtca ccaaactatt  49680
gttaccataa catcatcttt tattcagata actagttact agaataccat tcatttttag  49740
ctagctttct taattacagg accactccca ctatttaact agaaacatat ggttgtttag  49800
tgatttattt tttagattct agggttatat gtagagtcac aatcacctta gacaaaggtt  49860
gatcactatg tagcaccggt ccaaagagtt ggaccgcagt gataactcca gccaccactc  49920
caagcacact accttgaaga aatccgatgt cagtggtgtg accttcgatg gctcctacaa  49980
tggcggctac cacaacacta gctacattca aaattaatga catttcgtga tcttataaaa  50040
```

ttgtttaaca tggaatgtgg aatgaaaaca atgcaatgtg atatgttaaa atgatacata 50100
ccaaaaagaa agtatatttt tctaagaatt tggatgaaga tattgttgac aaaaagatat 50160
acttttctta aagaatgaga atttaagggt agagaatcca tacataagat aagttattaa 50220
attcaattaa ggaatgcata gacaacaagt aattcaggtt aaaggaaaaa actaagaaaa 50280
tggaaaagaa gatcccacat cagactctta tggtaagtag aagttgcttg acacatcgca 50340
tccattcaag aattttctct ttatcttttt gttaatatgt tttagttctt ttatcaaaca 50400
ctcatgtcaa gttgtcaact atatatagta tacatatgtg tggattcata tatgagaggt 50460
aagtacatgt caatgaagta catatatcca aaaccaatga gatggcgtct caagtttcat 50520
ctttaaaagt acgttagttt agcaagcatc tatagaattc aaaaaaaaaa aggggaacaa 50580
acagcattaa atgataagaa aatgaagata acttgtaaat ttaccggaag caagaatgaa 50640
gatgaatgag cccaacaaag ctcgttttat cgttcttgac attttgaaga tcacgcaagt 50700
aatccagaaa gaaacaacat atgtgaattt cagaagaatc atcttagaaa tgcccatgaa 50760
gaaaagatgg aagactaatt gatttttttt ctttctctta taagatattt tgaatttgtc 50820
tatttatggg gtgagagctt gaattggaga gtggtgtgga gtgtgagaaa agagcaattt 50880
ataaaggaaa aaagagagaa aggaggagga gttgcattta agaagctgaa ctacccatac 50940
ctctaatcta cattgcattg gcgactctat tggcgcatgc atgaacttgc gcccacagaa 51000
gaatctaaat gttttataaa ataaaataaa agcaagaaaa ttgaatggag aaattaatgc 51060
agttttgaaa tatgaaaatg ggaagggatg ggataagctt gagattgaaa tatatccaat 51120
ttacattcca ctacgatctg aatgagttgt ttattgccat ttacattcta gtcattatag 51180
tggtagcagt aaacttccaa tcttggattc ttaatctagc aaaaagaagc tcttcattaa 51240
ccaatgttta tcaatgagtt tggatagact aatttttacc gcatttgttt gttagctcaa 51300
ctagatttat gtttcatata ggctatgaca cagacttgta tagtaagaag actagcatac 51360
attagaaatg gagatctggg ttacaactaa gattgagccc aacatgttgt cgtggggcag 51420
caaggtcttc ttatcagtgg atatgacacc actcactggc aacgatttta tgttttcgtt 51480
tatggctaca agtttcttca ttgatgaaga gaagaaaatc gctgtggttt ttaatcaaag 51540
caaagacagg aagcacaaca cagctttcat cattggacag gatggatcct tgaaagaagt 51600
ggatcttgga gaagttcgaa acagagatct caaaccactt gtgtcctctt atgttccaag 51660
ttcaatgcaa cttgaatagt gcattttaca aaacccataa tctatttctt gcacttttac 51720
ttgtttcttt ttctctttg tcatcttctt ctttgaacaa tatatagaaa tttaattcgt 51780
ctctcatact tctttttgtt tgccatattt gacttcgttt tgttgccttt agttgtttaa 51840
tttacttctt ctgttgtagt agactcattg ctaaatctct gtttctcttc taacatttgt 51900
tatgtttgtg ttcttgcaaa taggcagctc tgctgttgta atttatgtag aacagacaac 51960
agagtaagct gcgtttaact ttgaaatttg caagtacgca tgcttagatt tgagtttccc 52020
attttaactt ttgtccttgt cagttttaca aagtgcaagt ggctgctagg ctgacacgta 52080
gaagattgaa tgatttctcg gagttaagtt ttgtcctttg atactccctg gtcttaaagc 52140
atacttacag agtaaccgta gctgaatatc aacctcaagc aagtcatgga accatacacc 52200
ttccttcaat ccaccagttt tggctggtt agcgctctcc tagatttatg tttcatataa 52260
gctaaccatt aaaagtttaa gagaagcttg tgtagtaaga agacaagcta aatgagttct 52320
cagtagcctt aattcttctt cttttttga ctaaatatga gcacttatag atgaagacta 52380
gtaatgcatt gattatgaga atactaaaaa gttaagatga ataatcaaaa aaattatttg 52440
gttagtatta aaatcttcaa atgaaactta gtcttaagat ttgttgagat ctttcatact 52500
atcgaagtca tgtagagtgg aggtacgtag ccaggcctag gagaagagaa gagaagagaa 52560
ggagaagcaa gctaagaaac tgaaagccta aaaacttttg aatgttgatg attaaaaaag 52620
aatagataca tgctaacagc ttatgcattt ttgaaatagt ttttgttaac tgtcgtgtag 52680
cttgtgtgta aatatgtcga cgacaagtca atgatgtcac acacactaca caaaacaaaa 52740
cactgcttca aactaccttc aacttcgagt ccattactat aagcaaaagt cccaaatcaa 52800
aacatcaatt ttcttgttct tgtcagctac tcaaacctca acatgttaca tatatttttt 52860
cagataaaac aaatcattct catcgttctt atctgaccag gaataattca atggaagtat 52920
gagtttgact cggtttcctt ttgatattag tcgtactttt caacatttta cctagataga 52980
gccgtcctct tataattatt catcatttca tgcttctcat gttacatttc tgcaattttt 53040
caactctttg attttatata atcatttgtt tcctttctta atcaaatcca tctggctaac 53100
attatttagc ttgatgcaat taaggtatat tatctaatga ggtgatgctt ccacgtcttt 53160
atattattat aatccctcaa caattttaaa aaaagatcct gactttcaat tttctctctt 53220
gtttcttctt ttgatcatct tcaacaaaaa aaagttacga tctttctctc cgggtcatcg 53280
gaatttgagc tagcttagct aaagttccga tctttcctct ctgggtcgtc ggaatttgag 53340
ctttttaaaa tcatgggaaa ttgttttgcc aagaaccatg gattgatgaa gccacagcaa 53400
aatggtaata ccactagatc agttgaagta ggagtaacca accaagatcc accgtcgtat 53460
actccacaag cgagaaccac tcagcagccg gagaaaccag gttccgtgaa tagtcaacca 53520
ccaccgtgga gggcggcggc tgcagcacca ggactaagtc ccaagaccac cactaagagc 53580
aattcaatac tagagaacgc tttcgaagac gtgaagctct tttacacatt gggtaaagag 53640
ctaggtcgtg gtcaatttgg ggtaacgtat ctgtgcacag agaattccac ggggaagaag 53700
tacgcttgca aatcgatctc gaagaagaag ctggtgacta aagctgataa ggatgatatg 53760
aggagagaga ttcagataat gcagcatttg agtgggcagc ctaatattgt ggagtttaaa 53820
ggagcttatg aggatgagaa agctgtgaat ttggtgatgg agctttgtgc tggtggtgaa 53880
ttgtttgata gaatcattgc taagggacat tacactgaga gagctgctgc ttctgtttgt 53940
agacagattg tgaatgttgt caagatttgt catttcatgg gtgtgttgca tagagacttg 54000
aagcctgaga atttcttgct ctctagcaaa gatgagaagg ctttgatcaa ggctactgat 54060
ttcggattgt ctgtctttat tgaagagggt aaaataatca gacttttctt tagggtttag 54120
tacattttga tgaagttggt tgtctctagg acatagatag gatacgtatc aaggttctgg 54180
ttatattggt atcttgtgtc tcttggttcc gtgaattgca tgaagaagtt cagacctttc 54240
ttgatatacg gactaggcta gagaccgctg tttttgttct ctgatagagt ttgatgtttc 54300
ttactcttca tcatttggtg tttcttcttc ttgtctttgc aggaaaagta tatagagata 54360
ttgttgggag tgcatactat gttgctccag aagtcttacg tcgcagatat gggaaagaag 54420
ttgatatctg gagtgctgga atcatcttat acattctact cagcggtgtg cccccgtttt 54480
gggctggtaa cgcgatattc tctcttcttt gttcctttcc cttttgagat ttatatgttg 54540
tgaataaaaa gctgaaaaca gaacattgga tatgcagaga ctgagaaagg aatatttgat 54600
gctatattgg aaggccatat cgactttgag agccaaccat ggccgtcaat ctccagcagt 54660
gccaaagatt tggtacgtag aatgttgact gcggatccaa aaaggcggat ttctgctgct 54720
gatgttcttc gtaagtacct tttgaagaca ttttacggag ccacaacaca atgcaaagtt 54780
ctggaagatt ccattatcgg ttccttcttg attctgagat ttgctctact gttttgtgca 54840

```
gagcatccat ggcttagaga aggtggagaa gcatcagaca agccaattga cagtgctgtt  54900
ctctcaagga tgaaacaatt tagagcaatg aataagctaa agaaacttgc tttaaaggtg  54960
aagtcaagat ttttcacata tgcaatgtga ttctgtggtt gtggtcctct ttttcgttat  55020
actcatgatg agattctaac aggtcatagc ggagaatatt gacacggaag aaatccaagg  55080
attgaaggca atgtttgcta acatagacac tgacaacagt ggcacaatca cttatgaaga  55140
actgaaagaa ggattagcca aattgggatc taaactcaca gaggcagaag tgaaacagct  55200
catggatgct gtaagttggt caaaaactat attttccccc attccgttcc tttactttaa  55260
gaactcagat tctcgggttt gtgattaggc tgatgttgat gggaacgggt ccatcgacta  55320
catagagttt attacagcaa caatgcatag gcacaggctt gaaagtaatg agaatcttta  55380
caaagctttc cagcattttg acaaagacag cagcgggtaa gtgacctgtt tcttctcgat  55440
gttattcatt cttaaccggt atatatataa gcaagatggt gagccttttc ttgggatcaa  55500
aatgtgtaca cagatacatt acaatagacg aactggaatc tgcattgaag gaatatggaa  55560
tgggagatga tgcaacaatc aaagaggttt tgtcagatgt cgactccgat aacgtaagtt  55620
aaaataattc atctcctctc tttatcttct tcttcttctt cttataagga aactgaactc  55680
tgtccataac ggtttgcctc tcttgcagga tggtagaatc aactatgaag agttctgcgc  55740
aatgatgaga agtggaaatc cacaacaaca acaacctcgg ctgttctagt ggacattgtt  55800
gctggattaa aagtcttttt gtttgtatct aatccagaaa aatcaggagc tgaattaatg  55860
tttgttcaga caaaaaccac gtaaagagga agatactcaa aactctgatt gcttgtgttt  55920
tgtattttgt tcttcacttc ttctgttttg tcctttgtgt tctgtactca ggctgttgtg  55980
atatgagaga aagagaggtt tcatttttac cgttaagatt ttgatcctga ctgtgttaac  56040
attttacctc agttcctcca cttttaatgt gattctccat tccatcaaat gtcaaatcaa  56100
cgaaacaact gctaaagcag agctttccta tattttaaca tattccggag gcgcaagtat  56160
ctttggcaaa tggcttggtt cgcctacaaa ttctccgtag tgggggtaca agagactaat  56220
taaccccagg ctagtaggtt caaagaaaaa cataaaattc gaaagtgatt cattagaggg  56280
tgtttttggt tcaagggtaa atacaatttt taattttaca aatgatacaa gaccattaga  56340
gataatgaga ttttctcaag gctctaatca tgtgatacgc cgaggagctt tctgctttct  56400
ttatcttgga ctgttcatct cccttcatat ataatgtttt ttcttctgtt atcttaatct  56460
tagcagagca aacaaatctc tttccctgta ccgagcttct atcttcctca acgctgaaaa  56520
aatgtgaaaa acaataacaa aatgttttta aacaatggct tatcaaatgt gttctgcttc  56580
ttgagattat aagactttag actactcaag tatgtgaatg cttccaagat gtaggagtag  56640
gatatacctg tagataggct taggccactt tttctttaag caaatctcgt tcaacttcgt  56700
tttagcatgt gtaagttgaa tctctacact atcttcatca ataaccattt caacgggaaa  56760
aacttctgac aacttccgta acgcttcttt agcagcgatc agccttgcga tatctttatt  56820
ctcagctcgg cctgaagcca aaagctcatc atcaagatat ataacagcaa tactgacatt  56880
accatctttc caattcttga tgtcgattcg cttcttatgt ttatgacata atttaaaaag  56940
catagacaca ggttgaggtt gcttctgcaa atcgtccaat gtaactatcg gttccaaaag  57000
acccctaaag atctgcaaaa tcgacaataa gaaagaagcc cttaactttc agtaacaaag  57060
acaaaacaca caagagtaga tctaaagaag aagtagacac agaccaccca tagtctttgt  57120
agatcaaagt tgacatcaac atacacagct ccagctaaag actcaaaaag atcagctaga  57180
actttagggg ctttgactaa tccaccatat gacactgaca aatcatcttc tttccccacc  57240
```

gcctctgaga actctttaac ctatcaaacg acatcaacac acacaacttg gtggtgaaga 57300
tatcacaaga atcactctgt ttcacataaa gaatcactct gtttccaggg ttcttcaatg 57360
caaagacaag ttttatggat taccttttca tctaaagaag gagcattgcg tcgaagaaat 57420
gaatagagac catgattaag agagacacga gcgagtttct cagtactaac attagctgct 57480
ctcaacagag acaagtcgtg tggctcaagg ctagggtacg ttaggtatag gtaatttgag 57540
attgctaaac caatagcact atcgcctatg aactctagcc gctcgtaaga aggaaagtct 57600
gtacacgagg tgtgtgtaat cgcttccttg agaagactct tgttactgaa tttgtagttg 57660
agtatcttct ctactgcttc catagactcc atctccgacg aaaccggaac gcttggtgct 57720
gatggggaaa gagaattgta gaagcggtgg atatcggccg aagacggcag tggtgatggt 57780
ggacggtgag gaagtgaatt ggataaacta cagcgagtga tggccgggaa attgtactcc 57840
ggtgagatag agtgatccat ggtagagaga atctaaagag acgccaagtc ttctctgttt 57900
caattttcct tttaattctt tttgttttcc taattctatt agttttgact ttttcattga 57960
ctatagtcct caggacaaat aaggaaagta tatatatata atttattata ttggggcaaa 58020
atataattaa aaactttttat ataaaggaaa tggattaagc ttttttctta aagggcaaaa 58080
attgcctaaa ccctaaagct gagatttttc ttgctcagta ttgggtcgat gacgatgaag 58140
tgtgtgtttt gttgataatc tcgagtgtgg gtgatcgaag agcaaaggaa gtcccaaggt 58200
tagcttctta ttttgtttat ttcgcgattc taattgatct actttgtatt gagcaatttt 58260
ttgagagatt catgtttttg aaatcgtgtt attggatgtt cttgtgagat tatcgttgta 58320
aatgtaaatg gtttcgaagt ttttgtttga atggattggg atttttgtgc gagtgttgtt 58380
ttgttatgtg ttacattttg aagttgtgtt tggtttttgg ttgggatttt aggtttttga 58440
tctcatggag ggagaagaga gtttgttgga tgctataaat gaagaagacg gatttgaaaa 58500
cttggaggat gttgaaatgg ttgatgttga agaaggggag attgttgtgg atcatgattt 58560
agattctgga gagaggcaaa atgatgatgg tgatggagtc aaagataaag aggcgatttt 58620
gggtgagaag aatggactgc aacagacaaa caagaacaag aggaagaaga agaagaaaaa 58680
gagaaaaggc cctgtgatgg acaaacccat gagtgtagac tggtaagtgt tctttttcta 58740
tatgctaata ttgttgtgta aattcttggt atagctgcct gatcttggct atggttgaaa 58800
cgttgctcat tgtttgatgt tttgttatgg caggtttgtt agggatactt gtagacgcct 58860
taaggagaag aagtcttaca tgatatacac agctgttggg tgtctcggaa ttgctgcctt 58920
aagtgatctt gtcaatgagg tatacactac ttcaagatgt tttctgtgtt attccagtta 58980
aaaccttgtt tgatctgtgt gtgaccagca gtggcaatct tgtttagctg tattgtttca 59040
cctgcagttc aagatattcc tagtggagcc ttttttgctg cttgtgcctt ttgctgagat 59100
gtagatggta aaacttcata ttttaggttg attttttttt cccttctctt gtgcacatct 59160
gtcttttctc tgtttttatt gatctagaca atttgtatga aaccataagt ggatagatga 59220
agtttttatg atcaacagtg tcaaccatat tttcatgatc gagaccataa gtggtttgag 59280
tgagaccaac agtgtcaacc ttattttcat gatcgagaaa tgactgtcca catattcact 59340
actgctttgt ggattgatcc ttctgttact cccactgtat gcttttaagt tggttaagaa 59400
tatttctatt ccacttcgca agattcttgc caaagatatg attgatgatg gcaagaaata 59460
ttttttctta ggtggtagca attgagacct gtggaggtca ggtgactgct gatggcacta 59520
ggaaacggac aagtggtggt gtattgtgga acatcatcaa agcgagacag cctgaagctt 59580
atagagagat aatgaaaaag accaaggagt ttgaggtttg tacttgccta tcatatcaca 59640

-continued acattcgtaa atatatcctg ctttcttagc ttaaatgtga aatagcagtc atgaagatgt 59700
tatatcactg ttttctatct tacacctctt tctctcttgc tctttgtctt acgctttcaa 59760
actttgcaga aacaatttag gcaaccaaac acgagaccaa aatcagggcc taaaagagat 59820
cagggtagct cctccgaagg acttgcctct ggaaatgtat ctgctgatga agctctggtg 59880
agcgagatgt gtgttatgcc ggtagctgag caaactgaat ccaaaccgga aaaggaaagg 59940
aaatctgttc atgagaggat cagggtacct gtttcatatg atgacctttt cagagatgca 60000
cctttggatg attcactagc acatcatcct tctgcttaag ctcatttata caccgtttac 60060
cttggacttt ttttaactag gtaaacaata tatctaagct actggatgac ttctcttgtg 60120
gaaagcaatt gttttgtcga gaaatggaaa gcattgattt tgtcgagaaa tgcattaaca 60180
aaactatata taccaactac caaagatttc ttaaatacac aaacttgagc acctcctaga 60240
aatttactac ataacatcag tcggcctaca ccattaagag gttcatgtgt taacttctcg 60300
ttacatgatg cagctgattt gatacaaaac atttgtttgc ttgaactaca ccacgagatg 60360
aattggtctt cctgggattc tctttatgaa ctgcttgttc ttttattgca cctctgtgaa 60420
ggcgtgattg ataatcttct taactgccat catcgcttgg acgagccatg ttaatattac 60480
atcacctctt gtagtgacct tgggttcata cctagcctct cagacaaaca tgcttggtgt 60540
ttgtatgtgg catacaaaga gagaggatca tattcggagg atccgggtca acttgtaaac 60600
ctgagaatat aaaaatggag tttgaatcaa catatgacag gttgaatgca tctatgaatc 60660
aattctcatg gcagtagata gcatagagag agagcaaaag aaggagagag agagagagag 60720
ctgacttggg cagtccggct aggcaaaaac acctctaagc aatttctttg accatcaatt 60780
ctgcacaaat gtggattcgg ttcaaaatga tgaacagata acatccttat atctttgcta 60840
agtaggatac tataacatta aactaaaatt acaaacctct tgctaattga ccgttgaaga 60900
tagtggtctt ctgttacaat cccttgaccc ccatacttta cttcatcgga gttcagtatc 60960
atctgcaaaa tccaggtaat attctcaggt gaaacgcatt gaacaacctt atagtggagt 61020
tcattgttct atcaacgagt aaaaacgcgg tagcaactgt gtttcatgga gagcaaagca 61080
gtggtttcat tgacagacac ttattaaaga tgatagatga tgggtgcaat atctaaacag 61140
agaatggaaa aaacttacgg tatattcacc agcttcctct acaccgacat catacttttc 61200
atatgaattt gatgggtgga agttaaagat aaataggaaa ggacccccttg agaaagaaat 61260
cacctgtaga gaacaattag ttgactagta agcaggctca ttgtacaaac tctttcattt 61320
ctgatgctta ctttaggtag tctcattttg ctcaggttta cactgttatt ttataattct 61380
ataaatgtat ttggagaatt cccaaatgtt gcaggaagac agttggttta tttattttcc 61440
gcattagctg aataatatcg tatataaagg catatacaaa cactagcatg ccaaagaatg 61500
ccaggaactc atttttcaga ccctgaaccc aatcaatttt cagtggaaaa taaaagagaa 61560
aaaggattca attaccatat ttgcatcatt cacatggtgg atgctgggca gacctcttga 61620
aaggataccc ttgcttttat ccaagtccat tagctcctac aaataaagaa cgagatcagt 61680
agctaaaaag catctcttct gatacaagag gatatatgct tggaacattt tctagtcctt 61740
acattttaaa gatatacaat taaaacttca ataagaaatc aagcatttag tttcttctga 61800
tatgatatcg gcagtaaagt tttttaagtt cgagttctga caactttctc ggcttgataa 61860
catttatttg ccgccttcat agactaatac agtattaaat tgctaggaaa tttaaggaag 61920
aaaattttca gagatgctaa caaaatcatg gatatggaag ctgcactttt gtaaacaggt 61980
ggtaatggta agactgatac cttgtcaaag gaaaacaagt gatgatgcac tccactttcc 62040
agcaggtccc agcggcggtt agcaagtgaa aacgagaagt tattgctctg cgttggaaac 62100
tcaaccctct gacacaagga tgaaacgtca gaatcagaaa catgaagatg atgtctttag 62160
aacagtggga gtttgtagat ttacctcagg atgtccaaat tcatttccca tgaaattgag 62220
gtatgcacgg ccaccacttg taaaagtaat cagtctaatc atctggtcgt ccaagcaatg 62280
acaagaaacg ttagctttca gaatataagt gaaacaatat agataaaaga caacagaggg 62340
caataattag acaatcttcc agatttcata ttttcacttt tcaatgcaaa aatcaaaata 62400
atatcaaatc ttattctaca gttgtgttct catcaggata gaggtatgct aagttcggga 62460
agtagtgcgt aaaggactaa gaaagggata ccttatgtag tgaaattccc ctgtctagca 62520
attcttttcc tccaggagaa ccattatcga ctccaccgaa taagatttca gcaaatgaac 62580
gccctcctga tatggactgg tggaaaggaa aagtagaata aacaacaatg tcaatgcaac 62640
ataaaagttt agttgtgtag tagaaatgaa aaactaaagt tacaacgtag atacttggtt 62700
gtgattttcg gcatagctga gcatcttgtc tgcatactct ttgttagcca ccaatgtact 62760
gacaatctgt agcactggct gaacatcaga caacaggaca aaagtcttgt tctgccatat 62820
ataacaatgg aaacgtaaaa gctataacct tgctcatgct ccattcatta tccggtacat 62880
tgtcgaggag agaaacccac atttctgacg cagaaagatt cacataataa tcaaatccaa 62940
gtccaccttg agaaactggc tcacacaacc cagggtaata tgttgcctaa aagcaaaagg 63000
aaaccttgtt aagttctata agtgggtaga tagtgaaacc caacgagcaa cgattcagat 63060
catcgacaga aaaattaatg caatttttct gtcaataaga atcttaaact ttttacccac 63120
tgatatacat ctaacattcg taaaagataa ttcgtcaaga acttcttttc ctgcgtatgg 63180
ccagtttaaa ttggcttaca caagccagtc gacactatgg ttaccgtcat gtgttgtaca 63240
tgagaaagca tatatataca tgttacatgt tactctctta cacaactttt tatctacata 63300
tagcatattt ggaaaaagca tgaaaagttt tcactaactg gcagtaacag tactaattct 63360
actaaccaac acttgcaaga ctaaaaacta gagataattt agaagcaatt atgcccagaa 63420
atatacttca gagacttagt gatattctat gatgaaagca gtgtcagtag ctagtccccc 63480
tcaatactat caattaagac aaagcaattc aataaggatg aatatttaat agctttaaac 63540
aaaagcatga ccaaaaaaaa gtgatgtgta gcttacatcc tcagcaattg ttattatatt 63600
tggatgttga acgtgcagga tttcattggc caaaatgagg tacatcagag catctcggtc 63660
aacatactga ttgcaatagc tgccaacagg aaagacgtca acagtttgac caactgtaat 63720
caaaattata caaagaggtg tgtagtctca tagatgcctt actcatccaa atcgttgtta 63780
aatgaagcaa acccattgtg cgtgtaaatc atcgaggcaa gcgagtgaaa ttggtaacca 63840
tcaacttgat actctgtaat ccacctgcaa aagccaaatg caacagcatc agattcctat 63900
aaccaaaaag tgtgcaacac tttcctacta taccaaaaga gtgagtacaa ccaatacatt 63960
attaacaaac cacttaataa tgtagctgcc tttaccagtt caaatttgat attagaaaat 64020
gaagaacatc caaatcaccg tatttgaaca tccgggtgcc ccagtgtttg tgatgccccc 64080
ttttacctat ttccacgatg aagaaaatgg aacattgtgt ttttagacag gcccatattc 64140
aactatgtca gacatgtttg acgtcatctt tggacgtaca caagattatg aacaacattg 64200
gttgtaacac gaaaattatg gtgcatactt tctagttaca taccaatgac ttggacatca 64260
acacgttaga ataaaggcat gcaagaagtc ttttattcat gcaagaactc atgaaataaa 64320
taaaaagtga actactatta tggaaattac cataatgaaa atagcaatca tttgaaccat 64380
cgaagagaga aagcccaacc atctgatcag ctgctgcata agaatgcacg atgtccaaaa 64440
agacaagaag tcctaggcct gtatatcatg tgcttcgtca ctacatggtt atacaacatc 64500
aagaaaacaa gaaagacgag aaataattac catgtgcctc atcaaccaac cgtttgaaat 64560
catctggcgt gccatatcgg ctactggcag caaagaagtt cgtaacctga aatggtgatg 64620
gataccaatt atgacaaatg aggtaaaaaa taattttcat aaatccattc attcggttta 64680
aagataagtg acagtagttt ccttaataat ttgtaaaatc tgccatatta tgtactagga 64740
attctggtta ttagcttgag tgtagttcca tagctgttat ttttttcaaa tgtaactagt 64800
aaaaggacct gatcaggact aaatgacata tgcaatgccc actaatcaaa attgtttctt 64860
tccactttat ttctatcaag ttgttctctt cttgttccat atttttcatc aattctctct 64920
attctacact attgtctatt ttttactaat cattcggcaa agaccttcag aacctttcat 64980
gcacagtgga cagcaaagcc aaagacgata taatcataag aactggaggt aacataagac 65040
tatgaataac agctatgctg accctataac cagactaaga agtagtaaaa aagaaagttt 65100
aagtgctaga agtttagctt gctgacccta taaccaacag taaaataatc cttgtgctca 65160
gggacaccaa tcaactggat tgcattgtat ccagctcttt tcacatgagg aaggacctga 65220
tgtttgatag gccacagaaa aactgagatg tgtgcataat aagattgcaa gtaagaatac 65280
aatgaataca ttaggaggta ccttcttagt aaattcttcg aaagttgaaa cttttggctc 65340
ggacccactg attccaacat gacattcgta tatgcgcaag gactctggaa cttttggctt 65400
ggaatatttc cacttgtatg cagcttcagg agaaggttcc caatgaattg cgtaagcttg 65460
ctttccttca tcctctattt tagagaaaaa tgaatacatt aataataaac aagatacatt 65520
atcgtggaaa tattaacatg acacatacaa aaacgttatt ttaaaagcat ctctgcatag 65580
aaacatcaag cagtagcgta tagaaacaag aaaggtttta cagcttctct gaaaaatgtt 65640
gttcagtaag actgttaatt tagtgcttac aaagttctag taactctgga catgaaaagc 65700
agagagtaaa aaaaatggaa aaaaactcct tccgtttgtt caattcgtgc aaatacttct 65760
aagcatgtgt catcagatga aagaaaaact gaatgcttgc ttccatatat ttatgaatgt 65820
tatgaaattt gttaaatttc atgtgctact cctaaccata gaaataccaa acgctgtcat 65880
acctggttgc acatatgtag cccaagcagg cactcgttca agcggtccat caggagtatt 65940
gaaatacaat ctatacttgc ttccatgtgg aacagctgga atatattttt gcaaccatgc 66000
ctttcttcct ttacgtgtct ctaaccaata tggaatcgga ggttctttct cataaaattt 66060
ctttgtccat tctggagatg tcacgacatt aaaaatatca tatggctttc cttgaccttt 66120
atcaatgatg tcgcatggag gtagattact tggcgggtca tctttatgct cctctttcca 66180
ctgtttatat ctcgtttctg catctggtat atctccaagc tcttctaacg tttgtggact 66240
gttcgggcca aacatctgct cgtatagttt ggcaggaact tcaaagcggt ttttaataaa 66300
ccgatcctca ccaggttccc aatactcatc attagctttc tggaagattt cttcagctga 66360
tacaccacta tcacccttat catagtcatc gacatagtta tactgctgaa agtatagttc 66420
atctggttct tcaccctctc ttaacttatc ttcaagaata atgaaccaat acccataatc 66480
atcatggcca aataggccct ctctagctgc attttctgta ggcgaccatc cattgaaatc 66540
tccgattata gccccataac gagaacctga atttaggatt ggttagtatt ctcaaacttc 66600
ccaacataca tatcaagttt ctgaacatca ttcattctgt ttcagaacca aatgtaagta 66660
atgaactgac taatgaaatt ttaagattag agcaagagac agaacctgga ccccagtcca 66720
taaagtcaac ccggtgttcc atatgtcgat gcatccccaa taactcaaat ctacaatgaa 66780
aagaaggcta ttcattagac aaagcatttt ggatacacat cagtcactaa tccaggatca 66840

```
aaatcttctc ttgaaagaaa ctgggaccaa gaggatacat accctgaagc aaaatctctg  66900
aaatcgaaat ggcgtttgaa aatctcatct ttaaggtctt tcaaagcttt atgcctacag  66960
aaaaacgaac aggcttatta tacacagctg taatcaaaat tgatcctttt ttgttgccca  67020
ttttttcaaa atcaaagttg atacattttt ataccttttcc cggagaaatt gagcaaagat  67080
tctgtcagca attccgagtc tggtgagaaa cccaacaggg tcaactccag cctcagcgtc  67140
gctagtgctc tggctctgac tcttcttttt ctgtttctcc tggcgtggtc tctcggcggc  67200
gaagcaagtg attttcaact tgatcttcct gggaaaattg actcctgaga ttcccaggcg  67260
ccgtttctcg gaaacgacaa gattgtttgg gtggaaagag aatctggttt gattagagag  67320
ggacaccatt tttgttggtg ctacgaagaa gatttgttca tactctcact cacactcagg  67380
gttttagtct ttttttaaga taagagaggt ttttgagtcg actcgttata aagaacgacg  67440
acgagttcac tcggtattcg gatatttttc tcaatttgaa atttgaacca aaccgagcgt  67500
aatttaaacc ggttcaatcc cgaaccgatt gataagaact acatggattt gtgatcttga  67560
aagtgagatt tctcgttttt tatttacttt taattaaatt caacacgagt atggttttct  67620
tttgataaat ttttaacatt cacatatttt tacagattta attgaatttt ggatgccaat  67680
ttttggttta agcaccggtt ttgcccttct ttacagcaat ctccaagttt cttcttgtga  67740
tttgaagctc tcttgtgtag taatgcattc tatctataac catggccaag aacaagacag  67800
tccctttca cacacataaa aataaaaata aattaagaat tagatccaaa aaaaacacat  67860
aaaaatggtg tgtgaaataa aatggtgttt taatgtcact atttacccat gaggaaagct  67920
tcgaggaggc gattggcaaa catgacttga tcggtcgagt tagctacacc accagattca  67980
gagacccttg tgtggatttg aatagtgctg aacataaccg agccaaacaa cacaagcata  68040
gtggctgcga ccgttttcgc aaccagtggt gctcgacctt gctttgatag gtctagcagt  68100
ttcaccacca ctcttctcgc tggagtcccg aacccgagtg ttaatatcag gacggcttcg  68160
attgtcacga ttgtgaatag aagttgaaac atctctacga acattttta ttagtacatg  68220
gagaagttta gagtggatca atccaaaaat gggttcaagt tgttataaaa agtgttgatg  68280
agtagaaaga ataagaagtt tgcttggtgc gatggtaact gataatatat aactaaggat  68340
ttggaatgga atactagctc atatgctttg tgtgctctca tgattcaagg aacggatgat  68400
tttactctct cttttttttt tttgtagttt aattatttcg agatttagtt tgttttatta  68460
aaagaagtat taattttgtg aagaaaaaaa atataacaag gaaataacaa tcggaacaaa  68520
atatgcaaaa ctctttatac attatttgaa actctttaac aaaaaagtat gcaaaactct  68580
tgaatttgag atcactgaat tcaaaatcct tgtcaaaatt ttgtgttatt catatagtat  68640
tttaaaatgt tagttaaaat tcattttta tccaacatat tgttttttaa tgttcaagta  68700
tattcaaatt aaacatacaa agactcaaat acaaaaaaaa actttattat tctaaataaa  68760
ctttattatt tctaagtaaa attcattttt aatcaacata ttgttcttca ctatgttgca  68820
tgaaaacgga aacggaaacg cggaaacgaa acgtttcaaa actgaaaaac gattttttc  68880
taaaattagg gtatggaaac gttttgaaaa cgtatacaca cacatattgt atatatatat  68940
atatatactt taaataacaa aaatctaaaa cataaatatc aaatagttta actaaaattc  69000
taaaaagtaa agattaaaaa gcttaatctc aaatatttag accatcatct tcattagttc  69060
catcaaaaat catatgaagc atatgaaatt tgattcgtcg ggagaaaaat cttaaaactc  69120
gcgtctccca aaattaatta aatcttgata ttttcaaact ttttaattat taagttttca  69180
aagtaaaaag acaagatttt tcgacgtgag tttccattga gtttccgaga gttttcgttt  69240
```

-continued ccgaaacatt tcagaaacga gaaacgcatt gtggagagag tttccatgca acatagtgtc 69300
caagtatatt caaattaaaa atacaaagat aaactttatt attctaaata catttttaat 69360
aaaaatcgaa atcgacaaga tcgattttga aatcagtgaa ttctacgaca ctaagatttg 69420
aaatctatgt agatttttta aattaaaata gaaaaactat taaaccttct ttacttttgt 69480
tttttctcca tatatactac aaactaataa tataaacaaa aatactagct gtgaaattga 69540
atgtttctgg tgtgtcatga gtttctcatt caacgatcac ttgatcaaag aatacaaaat 69600
tttgttaatg ccaatgattt gcgtaatcta tatattaaat tctatttgaa cattcaaaca 69660
atcgctgtat atagattcca ttgataagat gcaaacatat atgacattga cattttatct 69720
gtctgtgatg ttgatccggt catcttcatg ctgttcaggg atcttatgac acatatgtat 69780
gtacatgaac atcgatctga tttagcatat taatatatat aattacaaaa tactaaaatt 69840
atgaaatcat caaatactca attaacaaaa aatatatttt tcaacaaaat caactagttg 69900
tgattataac tttattttat gtttataaaa agactataag cagatatata tataaaaaaa 69960
aaaatgataa atcacactat atatgaattt actgcggata tatcaatcca cctaagaatt 70020
aatgaattat gatctccaaa actttgttag aaaaaaatat attatggaaa aggaacgtgc 70080
accatcttta tcagttacaa atcaaattcc aaattttagc taaaaataat tgattttctt 70140
ttaatattcc attcgtatta tgtggaaacg taatgtgtct atatggactc catgtctagc 70200
atgattaaat gaaatgaact tttgccattt taagtcgtgt ctcccaaatt gtctttcttt 70260
gtttgctttt ttatatgcat cgttcttcca caaatcctac gcaaaagttt gattgaatgc 70320
aattctaaca aattcagttg tttgttacaa ataaatgaaa taagaacaat caatatttgt 70380
tgacaaatat tgattgttta ctgaaagtat tcaagtaaat caaataaaca gtaaattata 70440
aaaacacgtt attcatgtgg gttcactttt ttttttaat cttttttaag tttggtcaac 70500
taggggtgtt accgtgttat ttatatgttt ttcagtggga tatcccacac taaaatttat 70560
tgtcattttt ataagtttc aacagctata gaaatttggc aatagcaaaa aatgaaaggg 70620
attattgttt gaaatgcatt ttttgggaaa caagcttacc aaaataccat tttgaatagt 70680
ttatggattt tttcattttt atacatttaa caatatactt atttacaatt tttccctgca 70740
aaaacatgta ctttatatca aatactaatt tttaaaaatt aaaaaaaaaa acgaataaac 70800
tcaaaaataa cgagtaaaaa tgtatgttaa attataattt tttttgcctg ataaatgata 70860
aaattcacaa aatagtttaa gaaggggcaa atttaacgaa tgtcactcta caaagaggca 70920
tacccgcaaa agtcgatcat tggtcaatac tcaaacataa aaaattacaa ctagatgttg 70980
acagcaagaa aattactcac tagcttaacg tcatcgaagt agtttttcca taccactgac 71040
tcaaatgtga accggtttct taactggtgt atatatatct agaatttttc tttcttattt 71100
ttcgaccgaa aattgtaagt gctatgtttt tatgtaacat atattggctt tcacttgccg 71160
atttttttat ttatctttta cttctgtaaa acctagttta cgtttcttgc ttaaatcttt 71220
tatttatttt aaacatattt ctcatttaaa tcactggaat tgatgcgtca aaaatcacta 71280
taattaattg aaatcacata atcgcttagt caaacttgag tatcattcaa aagccttata 71340
ttatatttag ctttatatac aatttgttcc aggctcttgt cacccatgta aaaagcttca 71400
tatacaactg tatgtatata tatatatata cacatataac aaaatgtata tattatatag 71460
tatatgtctc ttcgttcaca tgtacgatat tgttttttag aaataatgta aggttaacgt 71520
atatataaaa aatggaatca agtgatgagg caccagttaa gaaaatacgg taaaaaacca 71580
attgacgatt tttatcatga actgtttgaa aaaaacaata caaaaaccta gcctaaaata 71640

```
attccaaatt gtttgctcca acagtccaac tgtttgaaat taattaatta cacacagtta  71700
gactactgtc taaaataatt tattactaat caatcttgta aaataaattt aaatatttcc  71760
ctaggcattc taaacctgac aaattggctg tagaaaatac cataaataag aatggttcaa  71820
atgaaaaagt attaaatgtt taaacaaaca aaaaaatctt ttttgttgag acttgcacgt  71880
catactctgt tgtttcttaa tctttatccc acatataatg gaattagccc cacgaaactt  71940
agtctatctc attaatcttt ctttccttca atctgtctgt tgctctctct ctctctcaca  72000
cacactgatc agccatggga gacgaaccac ttcttcagaa agtcaagatt caagaagaca  72060
ttgaatccgt accacttctt cagaaagtca agattcaaga agacattgaa tccgttaaag  72120
gaattcgtgt aaataatgac ggcgaagagg acggtcccgt tactttaatt ctactcttca  72180
caaccttcac tgctctctgc ggcaccttct cctatggcac tgccgtaatt ttcttcatct  72240
tctcttcttt ttttcttttc tctatgtttt ttctagggta aacacagaat ctaatcccat  72300
aattaattag ttaccataag atttaaccaa aattgtaagt tatagctaat tcgttatcta  72360
tttgaaaaag ggtccaaatc aaagagaatg atgtatcaac aaggattatg ccgtcgcaga  72420
aaaagcaaca tttttcaaat gattgataac gacatgaata ttataggttt atgttatttt  72480
tgtgtaggcc ggctttacat caccagctca aaccgggatt atggcaggac tgaacctttc  72540
tttggctgag gtcagtgctg agttgttaat tttatttcca ttttttattg attagtttta  72600
ttaatttgtt aatcgttgtc ttaaaaatat atagatggat tgtcacaaaa aaaaaaagta  72660
tatatgagat agaagtatat ataaaaagta tatattagtg acttagtgtg gtagaaaaaa  72720
aaaatgcaaa gaatcattta tctaaaaagt aattagtctt caaaatccaa tatttgcata  72780
taaaaattgt ctatttatta gagttcaaat tttctactta aaagtatatg attgtttttg  72840
gtaatggcgt aagagtgtgc gctagtgtca ttgttaaaca cttttgcaga ttttgatcat  72900
cttttaattt aaatattagt tataaccact ttaatgtgta ttactgtatt agaagaaaag  72960
gtactcaagt cattgttcgt tcatggatgt agttctcatt ctttggggct gtcttaacaa  73020
ttggtggact tgtgggagcc gcgatgtcgg gaaaacttgc tgatgtcttt ggtcgaagag  73080
gcgtaagctc tctttttat atttttaat ctctttttat catcatgact aaaattacaa  73140
ttccattaag gagtttcttt acacatatat tccaaacaaa agatatatag cggtttcatg  73200
aatgactata cgcaggcttt gggggtttca aactcgtttt gcatggccgg ctggcttatg  73260
attgccttct ctcaggtttc taacgatcat tttatatatc tcaatactta tttaaatagt  73320
gtttgtttgt cacgtatgac ataagcttaa gcgtttgaat gtttcaagtt ttaccaaaga  73380
aaaactctgg tttagagttc cctcgactat tattctagac aaaaaaagat ctttcaaaat  73440
caaaagttta tacgaatagt taattgtttg ctgtttctta agtattgttt atcatatata  73500
ggcgacttgg tcccttgata tcggaagact tttctcggg gtcgcagctg gcgtagcttc  73560
ttatgtggta cgtagttaaa taggtcgcct ggtaattact gtttattgac ttttactcca  73620
agcaaccaat ttaagtattt tttgtcatta actccacgca tctaatctca ggtaccagtc  73680
tatattgttg aaatcgctcc caaaaaagtt cgtggcacat tctctgcgat taactcggta  73740
atacactgga aaaaaaaatt taagagaaat tttaatttta ttagtttgaa atcattcatt  73800
ttttttttt ttggttgata gcttgtgatg tgtgctagcg tcgccgtcac atacctcctt  73860
ggatcagtca tttcatggca aaaattagct ctcataagta aatactggac tctgcctatg  73920
aactaattat aatatttaaa ttaattttta actatgttaa attaatcaag ttgacaaaat  73980
atttacttgg tgttgtttgg agttgtgcag gtacggttcc ttgtgttttt gaattcgtcg  74040
```

gtttattctt cataccggag tctcctaggt ggctggtaat tagttaatta gtcttgttac 74100
tttttagtaa ctaacatata caaataaaac atattaaaaa ttgttactac aagtaaatca 74160
aaccattatt aacagtttgg tatctttgta atttatagtc tagaaacggt agggtgaaag 74220
aatcggaagt ttcactccaa cgcctacgag gaaacaacac tgatatcact aaagaggctg 74280
cagaaatcaa agtaaaacaa aaaaagagtt cgaaaaagtg acactatacg taaatttgac 74340
aaaaacttat tttgattgtt cttttttttt cttcagaaat atatggataa tcttcaagaa 74400
ttcaaagaag atggtttttt cgatctcttc aacccacgat attctcgtgt cgttactgta 74460
agaattttat taattgaaat ttgaatgtct ttttgagtaa aaatgcgtta atactcttgt 74520
aaattttgta ggttggaatt ggattgctag tactacaaca actgggaggt ctcagtggct 74580
atacatttta ccttagctcg atattcaaaa aatcgggtaa attaaaactc aaatgactta 74640
ctgaaagaga attattttgt ctaatataat gaccaaaact atactattta atatgcaatt 74700
taattatttt gtagggtttc ctaacaacgt aggagtaatg atggcgagcg tggtgcagtc 74760
tgtgacaagc gttttaggaa tagtaatcgt ggataaatat ggaagacgat ccccttttaac 74820
ggttataatt tgttttatat ccttttaatc agtgaaactg tataatatat agtgggtaac 74880
cagaagttaa ttaacgttgt ttctttgttc tttctgtgaa ttacttattt acaggttgcg 74940
acgatcatga tgtgtttggg ctcattaatt acaggactat cgtttttgtt tcaggttttt 75000
tttttcctga aataaaatta cttattagtt aaataaaaag ttatatgatt tatgtacatt 75060
ctactctctt tttttagttt gtttttcttg aaatgagttt tattactatt tttttctttt 75120
tcaatataac taatacaatc aaaactaata tgcagagcta tggtttactt gaacattaca 75180
ccccaatttc aacatttatg ggagtgttgg tacgtactac tacataatga tttcattctg 75240
tcctcctttt ttcttttata aataaaatca tgtcctcctt cttatataaa cataatgata 75300
tatgaatatt tcgttcctcc ttttttatat gattacatag acataatcat ataaaatcat 75360
gtcctcctcc tttttttttt tcttttagac aaaaaagata aaaattaata tttcttaaga 75420
taaattttac cgactcttgt tacaggtttt tctaacttcg attacaatcg gaataggagg 75480
tattccatgg gttatgatat ctgaggtaat catttgtctt cagtttgatc gtaaccagat 75540
gaatagttca acaatatatt tatgttcgac aaaaatattt tgtatatagt caaattcaaa 75600
agcatatata aagattatga atatctatga ccaggttaga tgaataatga aacaatctga 75660
tacacagaaa aaagaagtag atctgatcat ctgataagaa aatgttagaa taaattattt 75720
ttcgtataat ttaaaaatag acccttttgg tatgataaca taatacaatt tattattttt 75780
aaaataaagt ataacataat gacttataaa ccataataac ttgataaatg aagtggttat 75840
aaattgtttt aaaacgtggc tacatttaaa aaacaagaac tcgattttat ttttatgtca 75900
ataaaaaatg ttccttattg gtctgagcca gtgaaaaata ttactaagtg ttctgcttct 75960
gtatgcagca tgcaaatagt tattacactt gagaatatta gttgggtgct aacattaatt 76020
taagataaca ttaatttagg atataatcta gataaaaact aactagtagt tttcaatata 76080
tctaattatt atatttgtgg gataattaga tgacaccgat caatataaaa ggatcagcag 76140
ggacgctatg caatttaact agctggtcca gcaattggtt cgtctcttac acattcaact 76200
tcctcttcca gtggagctct tctggtaatt tacttcattt tacaattgtc tctaagtaaa 76260
taatgcattt actaactttt gatcaaattt taatcatttg ttgatattta aatcataggt 76320
gtgtttttca tatatacaat gatatcgggt gtgggcatcc tgtttgtgat gaagatggta 76380
cccgagactc gaggtcgttc gctcgaagaa attcaagctg ccattacccg ataactttgt 76440

-continued

```
aaaatatcat ttacttggtg tcaaaattca tataattgta tacatggcct ccctcactta  76500
tcaatgaatt cagaattgtt tgtcccagtt tttaaatgct tgattttgac atcattcacc  76560
aaacaattgg ctcttttatt ttttaaggtt ggttggttca tgttttgaga tacatttcca  76620
tacaagatat aaatttaaag cttgaacaaa tatgtactat ttgagtttaa atttttggat  76680
ggtaacatat caacatcact aacacgaaat cattaccgct ttttgccatg atcagtaata  76740
atttcaatga aacaaaagtt aatttaccaa gtatatatat acagtttaga gtacgaacat  76800
tggaccatcg gagttattgc tatatatcca accatggcca gttaataaat agtccagata  76860
tatgtggtat tctatgttat tataaaaata ttttttacca ctgtcaaata atgttgttgt  76920
tccttttggt tacgatccga aaaattaaac agatctaaaa tcctaagaaa aatcgttcac  76980
gtcagtgaaa tagtcaaata taaagcccta tttagatgtt caatgttctt tttttctctc  77040
atatttagag aattagaggt attaatttct tgttcatttt tagtttatat ttgggttgta  77100
cggtattaat acctcattaa gaaagttgca tttagagttt gattccattc aatgtagacg  77160
gtacgtttca aattcatcta agaatccacc taaaatttat tgatttcaaa ttatataaat  77220
ttacttggag gatgcatctt tatatttctg catgcttttg gaaatagggc tttatttacg  77280
tgtttatggt tataaattaa atggtcaagt atttctcttc gtgtttacgt tgagtaacag  77340
tcaaatcgaa ttgaacatgt caaagaaaca ctgaagaaga tatagactgg ccgggtcacc  77400
aagtagagct cgattatttt ttctaattca ttcatttatt tcctcaaagg ccgataataa  77460
cacaaaatca tggaccgaat cactttagat gaataatata ttaatctttt ttcataagac  77520
tttggtacgt aaaacccatt gccatgcatt ccattccatg gtttaacgtc aagatcttat  77580
agcttctcat caatgatgtc caccaccgaa accacctccg gcaccggctc ccccaccgaa  77640
accaccacca ataccgcttc cgcctcctcc tccaaaccca ccaccgccac cagctccacc  77700
tcctcctccg agtccacccc cagcaccagc tcctcctcca aaccctccac ctgaaccacc  77760
accagcccca ccgccaaatc ctccaccagc accaccaccc ccaccaagac caccaccgct  77820
cccagctcct ccaccaaatc ctcctccagc tccaccacca gctcctcctc ctaaaccgcc  77880
accgcctcca gctcctccgc caagaccgcc tcctccacca aagccgcctc ctccaccaag  77940
accactgcct ccaccaatac cgcctcctcc accgagacct ccgcctggat ggtggaagaa  78000
tgtcttttgg tcctcgagac cactcttcag cttcctgtta gcgacactgg caaatgaagt  78060
gaaagcaaaa gagccgacaa gtaaggcaac aagaaagagt gacttggaag ccatgtcgat  78120
ttttgtgttt tgcgtatgtg atgatgagga actctatcag ccaataaggt gtttatatag  78180
accatttggc atgagctgaa gaatcaaaca attgaataaa aagagggaga gagtaaagtt  78240
ttagagtgag taattatcat taattcatct gcccatctaa ttcatgttgg caaatttaat  78300
gcaatcccta actaccagtg ttgacaaaca tgttactcat ccacatgtag tagacccctt  78360
ctttattctt tgtgttagta ctacttaata gtactcattt tcttgccttt cacatttaaa  78420
tttggctgca gtatttgatg aatctgagat tttagattat tcttatgtcc ggagaccgga  78480
gttatttaat gtttttgtta atgtgttttt tagtacattt tggtgtccac cattattaaa  78540
gaaaacaaca acaaggtatc tatattttca tgtttacgat aaataaactt tacacattac  78600
attggaagag aataataagt atgaaataat ttgttttcac tacatttctt gacttggaca  78660
aggttaattt aaattcggga tctgcctcgc actggcccat ggtataaaca atctcgttgt  78720
ttaatgcatt tacgcgagta aaatattcat catggtgact gtttgtgatt tttataggaa  78780
agagaataat tatgcaacaa gccgatatgt tttcaaaact tggttctctt cttggattga  78840
```

atgctctctt cttaattacg ttctcatcca taatttgaac atctaattaa taataaaatt 78900
gtcaaagttc cgtggtccca gtagactatt ggcaataagt taatatatga aaataactta 78960
aaaccaactt taagtcaaaa tttgatctta atacgattta attagatgtc tgaaaaaagt 79020
ttgcgtaatc aatagattgt aaatctagct atgattagaa ttgttaacac attgttctat 79080
aactcaaatt actaatataa agtaatcgaa tgttacctat tacttaagat aaaattttac 79140
ggggttaaaa gtctgaaaag ttatcattta aatgtggcta atagttatac atgaagacat 79200
gatacatggt acaatactac aattacaatg accttggatc tatataccat agtttgtctc 79260
ttgaaaccaa aattatggag atttttattg gtgatctcat gtgttttact aatcatcctt 79320
ttttcttaca caaatcaatt atccgaatat ttacttacga tataaaaaaa gtcacgattt 79380
caaataagtt ttagttagga tatttaatat ctatggatgt tttaaattat cgaataacaa 79440
agaaattatt taataatgat tgattttcca tattgtatat atatatatat atatatatat 79500
atatatatat caatattggt tatgtatgat atatacataa ttttattaac gacttcattt 79560
tatacagata tttatgcatt ttttccttta ggacatactc cacatgtaaa ttttatattt 79620
cacaattatt tgaaatttag tgaatttacc aatcgaatga atatattctg taaaattggt 79680
tgctgatgga aattcgaaga aaacaaggcc gttcaaaatt gattgaaagt gttaattaaa 79740
ggatgtttca tattggtcac aaatgattgt acaatcaaat tattagtctt catgatataa 79800
tagaaattct ataaattaat atttttaaaa ttaataattt ttgtcggtcc caaatcagaa 79860
caatgtaaaa attaaccaaa atcgataaga taataaaata ataatttttt ttcaaatctc 79920
tatataaaat tatggtctaa ataatatcat aaatattaaa catacattct aagacaattt 79980
aatataatat aaatctagtg ttgtttgtct ccgcttaagt gtttacggta atgtcgtaga 80040
tataaagaca taatatcttg caaaaagaaa gttaataaag taaaaaataa aaatttagta 80100
ttgtgtcttc cataaatatt tttaaaatta atattttata ggataatata actataaatt 80160
aataaatttt atgatcgaac attattaatt tatagagctt ccactatata aatatattcg 80220
atgaaaagaa aataaataaa tagaaattct aatttctgca atcggacggt gagaaaacgt 80280
ggaaatttaa ttcgacggtg acaacgtttg ttcgataatt agtttttttt tttttgtcga 80340
ttgtttttct ttttcttaaa cgcgatattt aacttatcta tataaaaaac aaattcccat 80400
caaattcgga gactttggat tctctgtttc gcgcgcttcg cagttcatct tccccaacga 80460
ctctgctcct tccccttctc tccatctctc tctcgttcta atcttcgaca atggaggaaa 80520
tggaagacac tgaaaccgaa ccacaggtat cttcgattac atattctctc taaattcgct 80580
ttctcttctg attttgccgt tcgtcgtcac tagagagaga gcgattttat gccgattgtg 80640
atcgatgtgt aaaaatttga tatctagtta gggattattg aataaaaacc tcggatctat 80700
tgttgaatcg atctcaatag tacagacatt gataaaccct agctgtttcc ccttttcaac 80760
ctcaaatttg attaatcgga agtagttgtt ccgccgattt gatcccagaa acactaatat 80820
ctgaggcact gtgcattaac acagaaccaa tcctactttt actctcttgc ttcgtatgtg 80880
aaattgtgaa tgtaccaatc tgttttcaat gcaatgcagg tttacatggc ttgtattcag 80940
cacggtcgga ggttagcaat tgaattcaac ttctgtgcac aatttttgag aaactttaac 81000
aatttctcaa ttacaagtgg acaagaaaga gcatatgagt gaatgcttat gctcatattc 81060
ttctctttat gttgttttag taaggatcag tgtctcactt aaacattctc ttctcagagt 81120
tggagtttct tactacgact gtagtgtacg ccagcttcat gtgctagaat tttgggaaga 81180
agattgctca gattttacat tgatcaatat gggtataact tttcaacttc aaacagaatt 81240
gatatcattg catgtcgagt cttgccattc cttactatct gtaccctact ctaaatgaag 81300
tttggtgaag caatttcttg attaacatct actttgcagc acttttgttc tgctacactg 81360
tccctataac atttgttttt tgatcgcttc atttgtcttg gttatatatc ttcagtaaaa 81420
tatcaagcga agccatcgat catttacgca agcacgaaaa gtgaagaatc ctttgtagct 81480
gctttgcagc agaatggtat ggtgctatct attttgttga aatatgagtc cttaagttta 81540
tggtcttgca taattacatt gtttctgcag acggaactga cgagactacc atggtaaagc 81600
tggtaaagag ctcaacattc agctacgagc aagcgtggca caggtacaga aagtttaatc 81660
aactccattt ttcaccttat ttatgtggtt ctggttagtc ctattacatg atgaattccc 81720
catgaaaaat ggtctagtag gaaactggtt cctgcagttt cagtttcttg actcaaatgt 81780
aatagcttac ttggcttatg atatttttat gatacctgct gttttacact gattgttatc 81840
ccaatattgt gtagactggt atatcttcga gtaactggaa tggatgatgg attgaacatc 81900
aaagaaagga tttgttatgt aagtttcagc gagggaaatg ttaatccctt tttactaagg 81960
attttgatca tttggttatt gtattctcca gttggaatct caatcataat gttgaattaa 82020
ttgatatttt cgatgtcaca atgaaataat ttgacattgt agctaactag ttttatggtc 82080
cttatctatc tacaattgta tgaagtttct tcattttgct tgtaaatttc agctgagttc 82140
catgatggat gtgggcagtg aagtccaagt tcgtgttagt ggtggtcttc ttgctatatt 82200
agaaagcgaa cgaattgtag aaaccctgga acaaaacgaa tctgggagtg catcaatcgc 82260
aattgattca gtcatggaag taccattgta tcctttactt tttctgttct gtttcttatg 82320
tcttgatgat ctatactttc ctgaattatt gggatgataa tgctgcatgc aaatccttta 82380
caaaatttat aacaggaaca agtttcttaa acttgatgct gctgctcacg aggctctgca 82440
gatatttcag acagataaac atccaagcca tatgggcatt ggccgggcca aagaagggta 82500
aatgactaaa tgccttagtt aatctgtgga atcttatatc tccttttcct actttgactt 82560
gtaatcttca ctgaaacttt gaaatgaagg ttctcggtat ttggaatgat gaataaggtt 82620
tgctttcctt gcattggttc attctgggtt atgctgcttg catatatgat ttaacttacc 82680
ttggcctatt tcagtgtgcc acgccaatgg gtagacgcct tttaaggtaa taaatgaaaa 82740
ttatagatat atgcaaactg ttctgaagct gatgtagtct tacgacattg gtttccttct 82800
ctctatttca gaagctggtt tatgagacca attttagatc ttgaagtgtt agatcgccgt 82860
ctcaatgctg tatcctttga tctcttgtga aggagtttgc cttatgtcaa gcagaatagg 82920
agttaacaat caacatcaaa taagagaaac caatagatta aactttatgt ctgctttctg 82980
tagccttatc agcatagttt taaccgatcg tcatttgttc tgaacgaaaa aaaaaattgt 83040
tcgaccacta attgacaggg gtgcctttca ctgatgttct gagaggtttc ttttgactgt 83100
actagatttc ctttttcatt tcttcagtag agctgatggc atcattgcgg gagacactga 83160
aatcagtgaa ggacatttca catctactca aggtatgtag gtaccattat tctatataat 83220
atagttttag catgcctatc tcttttagcc ataagagcct gtgaaggaga attaaaatta 83280
ctaactaatg gtacagagaa aactttccac aaagtttgcg gtgaatatgt taattgttaa 83340
tctgttggta gaaatagtgt tatatgagca tattctgccc agacagagga cgtggatata 83400
ttgcatgcca aatatcttct tgtatgccaa ttctgtagat tccattttag ttttgataac 83460
acttttttttt tttttttctg gcattcttat gttaaaacaa gaaattcaac tctccgacgt 83520
ccctctgtac cagtaacgac tggacagctt tcttgaaggt aaattccatt ttcttgacta 83580
tcatctttca tttagtctat aaaactagtc ttccaagccc caatataatg ctatcttatt 83640
gtgtgcatta gagcataagt gcgctcctgc acgtgaataa gatatttgaa gttggagttt 83700
cagaaagtct cagagagcat atgagacgct tcaacttgga cattattgag aaggttactt 83760
atgttttatc aattgttatt ctcccactct tcaatccact ttcgtggttg ttgctaagtt 83820
ctcttttcat gttgcaggcc ggcttatgta tcagcacaga gctagattat gtctatgaac 83880
tggtcagttg attttacgtt ctgtttcttc aattccatta taatccatac tctccttttc 83940
aaaagaacag atcttgaatt cttgatgctt tcaaaattgg ggtcttaaca tctctctata 84000
ccttttcctc ctttgataca tttcttattc ctatatcatc cttagaaatt ttaaacctta 84060
atggagttat attgttaaaa aaacgggaaa gtcacaattt tttgagtggc taaagaaagg 84120
tcagctaaga tttattctga aaaagtcaca attttaaggc tattcagaag ttggataccc 84180
caagatttga gaaactgggt taaacaaatt cagcaggcct tagtgagaga taattatgac 84240
tacagttagt aacaacagac aataactcca caggtcattg gagtcattga tgttactaga 84300
agcaaagaga ggggatatca aactttggtt aaagaaggat tctgtgctga ggttatcata 84360
gaagttcatt ttgttcaggt tgtcatacca ctaatctttt gtttttgca agtaactcat 84420
ttcttatttt accagttgga tgagctcagg caaatatatg aggagttgcc agaatttctg 84480
caggaggttt gttctatgtg ataagttcct ttaattgata aatgaaggta aactggaatc 84540
tctcctaaat gattctaatt actgacaggt ttcagcgatg gagttagaac actttcctca 84600
tttgcataag gaaaagcttc ctccttgtat cgtctatatt caacaaattg gtgggtctga 84660
agtttcacgt tttaagtttg acataagttc tatacagtgt tatatcctca aaggtttatc 84720
tgcgctgatt ttttaacata attacctttt agaatttcac ctcatcccta agaaaggtga 84780
aatctagctg cacgaattca ttttttggaa ccaccatgtc ctggaattat cagctcaact 84840
atggtgtcta tgcttcttga ttgctcaata gcctttcact ttatgatgcg tctttaacaa 84900
atcgcgacca catgtatttc ttcacacatt gaaaacagtt atttcgtttc tgtaaatgaa 84960
tatatagttt atctgttctg cagggtacct catgtgtatc tttggagaaa agcttgatga 85020
aactgctctt aataggctta ctgaatttga atttgcggta cagtttgttt gtgttcaaaa 85080
tcttaatccc atactttggg cactatgcat atatgtcatt atgaaacaga agttttaatc 85140
atatctatct tgtgattagt tttctgatat ggatggagag actcagcgat tcttttacca 85200
tacctcgaag acacgagagt tagacaacct tcttggagat atctaccaca aaattttagg 85260
tatgttcttc ttgctggttt atattttcca tggcgtattc ttcttgagta caatgacgtt 85320
gtttcttgtt ttacaaaatt ttgctgacag atatggaaag ggcaattatt agggacttgc 85380
tgtcacacac acttttgttc tcggctcacc tgctgaaggc agttaacttt gttgcagaac 85440
ttgattggta atcaatattc aagagctacg gatatcccat atcatttcta gtctctcctc 85500
ttgaagaaaa gcaacacatt ttcacgtacc tattatctaa ttagctactt atgagaaatg 85560
actaatgact tatccattat tcttggcttt tctagcattt tatcgttggc ttgtgtagcc 85620
catcagaata actacgtaag gcctgtcctg acagtagaat cattgcttga tattcgaaat 85680
ggaaggtgaa gttgactcta tcagctgcac ttatgtcttg ttgttgcatt tatacataaa 85740
ctccttacga aaaattatat ctgaatatca atactggtgg gcaggcatgt tttgcaggaa 85800
atggctgtag atacttttat cccaaacgac actgaaatca atgataatgg tgagctgaat 85860
gttgataaag ttgttttgac tatttaggca tgcattacaa cttaaacttg tgaactagtt 85920
tttgtccatc acctgattgc aagcttgtct gtcgcaggac gaattcatat aattaccggg 85980
cctaattact caggaaagag catatatgta aagcaggtcg gctttacttt tctaagtctt 86040
atttctcttc gttcaaccaa agtgtactgc atcatcatga attgacaact caagttctga 86100
cttgctattt gtaggtggcg ttaattgttt tcctatccca tattggaagc tttgtaccag 86160
cagatgcagc aactgttggt ttaactgaca ggtctaacgt catacattct ttttgatctt 86220
tttacaatcg ctttttatgt atattttcgt tactaagatt agtcgtacta caacaggatc 86280
ttttgtgcaa tgggaagcaa gttcatgacc gcggagcaat ctacattcat gatagatctg 86340
catcaagtag gaatgatgct caggtattcc aaactgcttc tatttttaac ttgatttcaa 86400
ttagctccac tactgatagg ccttgtgagc cggtctcagt ctcttcagtc agttagtgac 86460
ttctagttca cgaggtccat tatttaagtt catggggacc caagaatgaa gatatcaatc 86520
aaaattcaac tgtgcattgc tcatgactta tgatcgtgtt cctaatcatt gtgaccgatc 86580
caaattctcc aggcaggcaa cttcaagatc tctgtgtctc ttagacgagt ttggtaaagg 86640
cactcttaca gaaggtatgg atttctccgc cctctgcatt ggcataaaag gcatgtgttt 86700
gtgaaaactt ctgccttacc cacactcttt tttaagtaca gatggtattg gcttgcttgg 86760
tgggacaatt agtcactttg ctacatgtgc tgagccacca agggtaccgt atagcgttct 86820
cttgtctgtc tctaagcttg tagattcttt tagaacccta acatgacatt gcctattgct 86880
gcatgctttc aggttgtagt atgtacgcac ttgactgagc tacttaacga gagctgcttg 86940
cctgttgtat gtactccgac tcaatttcag atagataact cagcagattt tgaagtggtt 87000
ccttgcttat agtgagagtc tatctttttt tactttttca tttcagtctg agaagattaa 87060
gttctacaca atgagcgttc ttaggccaga cacagaatct gcaaacatgg aagagattgt 87120
ttttctttat aggtatggag tctcattgac tagcattcta cctaaactgc ctacattctt 87180
aagacttcca tgttttgacc aatgattttg ccggcaggtt aattccggga caaactttgc 87240
tgagctatgg tgagcatttt tgtcctttgc gttattgtct acatgatctt cttgtgtata 87300
caccgagctt catcaaacct atttatgtaa tgcaggcctt cactgtgcgc tactcgctgg 87360
tacatttagg aagattacta atatctttaa tgaattgaat acaattttttg atggatctat 87420 ttacgactgt ggattataga gtaacaaaag gaaattttca ctattgttga tgcaaggtgt 87480
cccggaggaa gtcgtgaaga gagcagccat cgtgttggac gcctttgaga gtaacaacaa 87540
cgtcgataaa ctaagccttg acaaaatatc gtctcaagat caagcattca aggtcttttt 87600
gctctctctc acttacacaa gcttttaccc cctttatctt cttctgtcct ctcaggcctt 87660
accaaacttt tactgatttc gaatgaaatt tgcaggatgc tgttgacaag tttgcggagc 87720
ttgacatcag taaaggtgac atccatgcct tctttcaaga tatcttcact tcctaaaccc 87780
ttacttaaaa gtcaagatc 87799

<210> SEQ ID NO 130
<211> LENGTH: 286
<212> TYPE: PRT
<213> ORGANISM: Arabidopsis thaliana

<400> SEQUENCE: 130

Met Asn Arg Met Arg Trp Val Gly Glu Gly Asp Ile Trp Asp Leu Asp
1 5 10 15

Met Ser Thr Pro Val Thr Leu Glu Gly Thr Ala Arg Ala Val Pro Asp
20 25 30

Asp Pro Leu Pro Leu Gly Leu Ser Arg Gly Thr Arg Leu Ser Arg Pro
35 40 45

Lys Gln Val Glu Phe Phe His Arg Phe Met Ala Ser Pro Leu Ile Pro
50 55 60

Ser Phe Ser Pro Ile Arg Pro Asn Thr Gly Asp Gly Gly Gly Gly Gly
65 70 75 80

Phe Ser Leu Gln Arg Val Leu Thr Leu Pro Phe Ser Asn Asn Trp Leu
85 90 95

Val Ser Leu Leu Gly Gln Phe Asp Val Gln Arg Phe Val Thr Glu Ile
100 105 110

Asp Lys Thr Lys Ala Phe Gly Arg Gly Ser Ser Ser Thr Val Ala Ser
115 120 125

Arg Leu Asn Thr Ile Gly Lys His Leu Lys Asp Lys Ser Leu Tyr Ala
130 135 140

Leu Gly Phe Cys Ser Glu Phe Leu Leu Ser Pro Asp Asp Thr Leu Leu
145 150 155 160

Leu Ser Tyr Asp Ala Tyr Lys Gly Asp Leu Asp Lys Asn Pro Arg Ala
165 170 175

Lys Ala Ile Phe Asn His Glu Phe Pro Leu His Asn Leu Thr Ala Glu
180 185 190

Ala Val Trp Pro Gly Leu Phe Val Asp Lys His Gly Glu Tyr Trp Asp
195 200 205

Val Pro Leu Ser Met Ala Ile Asp Leu Ala Ser Leu Pro Ala Glu Ser
210 215 220

Gly Pro Ser Tyr His Leu Cys Leu His His Asn Ser Gly Ser Pro Lys
225 230 235 240

Lys Leu His Ser Asp Thr Met Glu Val Pro Pro Pro Ser Leu Leu Pro
245 250 255

Gly Leu Ser Leu Lys Ser Ala Val Ser Tyr Arg Thr Asn Met Asp Leu
260 265 270

Trp Arg Gly Thr Thr Pro Lys Leu Glu Thr Cys Lys Pro Tyr
275 280 285

<210> SEQ ID NO 131
<211> LENGTH: 171
<212> TYPE: PRT
<213> ORGANISM: Arabidopsis thaliana

<400> SEQUENCE: 131

Phe Gly Glu Asn Ser Ile Arg Ser Lys Phe Glu Asn Asp Ser Glu Gly
1 5 10 15

Val Gly Gly Phe Ser Leu His Phe Pro Ser Val Asn Ser Gly Phe Met
20 25 30

Ala Asp Ala Leu Gly Arg Ala Ser Leu Thr Ala Gln Tyr Gly Asn Phe
35 40 45

Gln Lys Phe Phe Phe Asp Leu Thr Arg Phe His Ala Arg Leu Asp Phe
50 55 60

Pro His Gly Leu Arg Phe Leu Thr Gly Ala Thr Ser Val Ala Gln Asp
65 70 75 80

Leu Leu Asn Ser Arg Gln Pro Ser Leu Glu Ala Phe Gln Lys Ile Cys
85 90 95

Pro Glu Val Leu Val Ser Leu Gln Gln Gln Ile Val Gly Pro Phe Ser
100 105 110

Phe Lys Val Glu Ser Gly Ile Glu Ile Asp Leu Arg Asn Gly Ala Asn
115 120 125

Pro Val Thr Val Asp Lys Thr Val Phe Ala Ile Glu Tyr Ala Leu Gln
130 135 140

Val Leu Leu Ser Ala Lys Ala Val Val Ser Tyr Ser Pro Lys Gln Asn
145 150 155 160

```
Glu Phe Met Val Glu Leu Arg Phe Phe Glu Thr
                165                 170


<210> SEQ ID NO 132
<211> LENGTH: 479
<212> TYPE: PRT
<213> ORGANISM: Arabidopsis thaliana

<400> SEQUENCE: 132

Met Asn Arg Met Arg Trp Val Gly Glu Gly Asp Ile Trp Asp Leu Asp
1               5                   10                  15

Met Ser Thr Pro Val Thr Leu Glu Gly Thr Ala Arg Ala Val Pro Asp
            20                  25                  30

Asp Pro Leu Pro Leu Gly Leu Ser Arg Gly Thr Arg Leu Ser Arg Pro
        35                  40                  45

Lys Gln Val Glu Phe Phe His Arg Phe Met Ala Ser Pro Leu Ile Pro
    50                  55                  60

Ser Phe Ser Pro Ile Arg Pro Asn Thr Gly Asp Gly Gly Gly Gly Gly
65                  70                  75                  80

Phe Ser Leu Gln Arg Val Leu Thr Leu Pro Phe Ser Asn Asn Trp Leu
                85                  90                  95

Val Ser Leu Leu Gly Gln Phe Asp Val Gln Arg Phe Val Thr Glu Ile
            100                 105                 110

Asp Lys Thr Lys Ala Phe Gly Arg Gly Ser Ser Ser Thr Val Ala Ser
        115                 120                 125

Arg Leu Asn Thr Ile Gly Lys His Leu Lys Asp Lys Ser Leu Tyr Ala
    130                 135                 140

Leu Gly Phe Cys Ser Glu Phe Leu Leu Ser Pro Asp Asp Thr Leu Leu
145                 150                 155                 160

Leu Ser Tyr Asp Ala Tyr Lys Gly Asp Leu Asp Lys Asn Pro Arg Ala
                165                 170                 175

Lys Ala Ile Phe Asn His Glu Phe Pro Leu His Asn Leu Thr Ala Glu
            180                 185                 190

Ala Val Trp Pro Gly Leu Phe Val Asp Lys His Gly Glu Tyr Trp Asp
        195                 200                 205

Val Pro Leu Ser Met Ala Ile Asp Leu Ala Ser Leu Pro Ala Glu Ser
    210                 215                 220

Gly Pro Ser Tyr His Leu Cys Leu His His Asn Ser Gly Ser Pro Lys
225                 230                 235                 240

Lys Leu His Ser Asp Thr Met Glu Val Pro Pro Pro Ser Leu Leu Pro
                245                 250                 255

Gly Leu Ser Leu Lys Ser Ala Val Ser Tyr Arg Thr Asn Met Asp Leu
            260                 265                 270

Trp Arg Gly Thr Thr Pro Lys Leu Glu Thr Cys Lys Pro Tyr Asp Val
        275                 280                 285

Phe Leu Ser Ser Pro His Val Ala Val Ser Gly Ile Ile Gly Ser Val
    290                 295                 300

Met Thr Ala Ala Phe Gly Glu Asn Ser Ile Arg Ser Lys Phe Glu Asn
305                 310                 315                 320

Asp Ser Glu Gly Val Gly Gly Phe Ser Leu His Phe Pro Ser Val Asn
                325                 330                 335

Ser Gly Phe Met Ala Asp Ala Leu Gly Arg Ala Ser Leu Thr Ala Gln
            340                 345                 350

Tyr Gly Asn Phe Gln Lys Phe Phe Phe Asp Leu Thr Arg Phe His Ala
        355                 360                 365
```

```
Arg Leu Asp Phe Pro His Gly Leu Arg Phe Leu Thr Gly Ala Thr Ser
    370                 375                 380

Val Ala Gln Asp Leu Leu Asn Ser Arg Gln Pro Ser Leu Glu Ala Phe
385                 390                 395                 400

Gln Lys Ile Cys Pro Glu Val Leu Val Ser Leu Gln Gln Gln Ile Val
                405                 410                 415

Gly Pro Phe Ser Phe Lys Val Glu Ser Gly Ile Glu Ile Asp Leu Arg
            420                 425                 430

Asn Gly Ala Asn Pro Val Thr Val Asp Lys Thr Val Phe Ala Ile Glu
        435                 440                 445

Tyr Ala Leu Gln Val Leu Leu Ser Ala Lys Ala Val Val Ser Tyr Ser
    450                 455                 460

Pro Lys Gln Asn Glu Phe Met Val Glu Leu Arg Phe Phe Glu Thr
465                 470                 475


<210> SEQ ID NO 133
<211> LENGTH: 456
<212> TYPE: PRT
<213> ORGANISM: Arabidopsis thaliana

<400> SEQUENCE: 133

Met Asn Arg Met Arg Trp Val Gly Glu Gly Asp Ile Trp Asp Leu Asp
1               5                   10                  15

Met Ser Thr Pro Val Thr Leu Glu Gly Thr Ala Arg Ala Val Pro Asp
            20                  25                  30

Asp Pro Leu Pro Leu Gly Leu Ser Arg Gly Thr Arg Leu Ser Arg Pro
        35                  40                  45

Lys Gln Val Glu Phe Phe His Arg Phe Met Ala Ser Pro Leu Ile Pro
    50                  55                  60

Ser Phe Ser Pro Ile Arg Pro Asn Thr Gly Asp Gly Gly Gly Gly Gly
65                  70                  75                  80

Phe Ser Leu Gln Arg Val Leu Thr Leu Pro Phe Ser Asn Asn Trp Leu
                85                  90                  95

Val Ser Leu Leu Gly Gln Phe Asp Val Gln Arg Phe Val Thr Glu Ile
            100                 105                 110

Asp Lys Thr Lys Ala Phe Gly Arg Gly Ser Ser Ser Thr Val Ala Ser
        115                 120                 125

Arg Leu Asn Thr Ile Gly Lys His Leu Lys Asp Lys Ser Leu Tyr Ala
    130                 135                 140

Leu Gly Phe Cys Ser Glu Phe Leu Leu Ser Pro Asp Asp Thr Leu Leu
145                 150                 155                 160

Leu Ser Tyr Asp Ala Tyr Lys Gly Asp Leu Asp Lys Asn Pro Arg Ala
                165                 170                 175

Lys Ala Ile Phe Asn His Glu Phe Pro Leu His Asn Leu Thr Ala Glu
            180                 185                 190

Ala Val Trp Pro Gly Leu Phe Val Asp Lys His Gly Glu Tyr Trp Asp
        195                 200                 205

Val Pro Leu Ser Met Ala Ile Asp Leu Ala Ser Leu Pro Ala Glu Ser
    210                 215                 220

Gly Pro Ser Tyr His Leu Cys Leu His His Asn Ser Gly Ser Pro Lys
225                 230                 235                 240

Lys Leu His Ser Asp Thr Met Glu Val Pro Pro Pro Ser Leu Leu Pro
                245                 250                 255

Gly Leu Ser Leu Lys Ser Ala Val Ser Tyr Arg Thr Asn Met Asp Leu
            260                 265                 270
```

```
Trp Arg Gly Thr Thr Pro Lys Leu Glu Thr Cys Lys Pro Tyr Gly Glu
        275                 280                 285

Asn Ser Ile Arg Ser Lys Phe Glu Asn Asp Ser Glu Gly Val Gly Gly
    290                 295                 300

Phe Ser Leu His Phe Pro Ser Val Asn Ser Gly Phe Met Ala Asp Ala
305                 310                 315                 320

Leu Gly Arg Ala Ser Leu Thr Ala Gln Tyr Gly Asn Phe Gln Lys Phe
                325                 330                 335

Phe Phe Asp Leu Thr Arg Phe His Ala Arg Leu Asp Phe Pro His Gly
            340                 345                 350

Leu Arg Phe Leu Thr Gly Ala Thr Ser Val Ala Gln Asp Leu Leu Asn
        355                 360                 365

Ser Arg Gln Pro Ser Leu Glu Ala Phe Gln Lys Ile Cys Pro Glu Val
    370                 375                 380

Leu Val Ser Leu Gln Gln Gln Ile Val Gly Pro Phe Ser Phe Lys Val
385                 390                 395                 400

Glu Ser Gly Ile Glu Ile Asp Leu Arg Asn Gly Ala Asn Pro Val Thr
                405                 410                 415

Val Asp Lys Thr Val Phe Ala Ile Glu Tyr Ala Leu Gln Val Leu Leu
            420                 425                 430

Ser Ala Lys Ala Val Val Ser Tyr Ser Pro Lys Gln Asn Glu Phe Met
        435                 440                 445

Val Glu Leu Arg Phe Phe Glu Thr
    450                 455
```

<210> SEQ ID NO 134
<211> LENGTH: 858
<212> TYPE: DNA
<213> ORGANISM: Arabidopsis thaliana

<400> SEQUENCE: 134

```
atgaacagaa tgagatgggt cggagaggga gacatctggg acctcgatat gtcaactccg     60

gtgacgctcg agggcaccgc acgagctgtt cctgacgatc ctcttcctct aggtctctct    120

agaggcactc gtctatctcg ccctaagcaa gttgagttct tccaccgctt catggcctca    180

cctctcatcc cttccttctc ccctatccgt cccaacaccg gagatggagg cggtggtgga    240

ttctctcttc aaagagtcct cactcttcct ttctccaaca actggcttgt gtctcttctg    300

ggccaattcg atgttcagag attcgtaacg gagatagata agactaaagc ttttggtcga    360

gggtcttcgt ctacagtagc ttctcgttta aacacaattg gcaagcattt gaaggataaa    420

tctttgtacg cattgggttt ttgttctgag tttttgttat caccagatga tactttgctt    480

cttagctatg atgcttacaa aggtgatctc gataagaatc ctagagctaa ggctatcttc    540

aatcacgagt ttccgcttca caatctgaca gcagaagcgg tttggcctgg actttttgtg    600

gataaacatg gtgaatattg ggatgtgcca ctctcaatgg ctattgatct agcatctctt    660

cctgctgaat ctggtccaag ttaccattta tgtttacacc ataacagcgg atcacccaag    720

aagttacatt ctgatactat ggaagtgcct ccaccgtcac tgcttcctgg tttgtctctg    780

aaatctgcag tctcttatag gacaaacatg gatctctgga ggggtaccac tccaaagctc    840

gaaacttgca agccctat                                                  858
```

<210> SEQ ID NO 135
<211> LENGTH: 514
<212> TYPE: DNA
<213> ORGANISM: Arabidopsis thaliana

<400> SEQUENCE: 135
tttggtgaaa attcaatcag atcaaaattt gaaaatgatt ctgagggtgt tggagggttc 60
tctcttcatt ttccatctgt aaattccgga ttcatggctg atgccttagg gcgggcatca 120
ctcacagctc aatatggaaa cttccagaaa ttcttctttg atctcacccg tttccatgct 180
agattagact ttccgcatgg tttgaggttt cttaccggtg ccactagcgt cgcacaagat 240
cttttaaatt ctcggcagcc tagtttagaa gcatttcaga aaatctgccc tgaagtatta 300
gtttctctac agcaacagat tgttggaccg tttagtttca aagtggagtc tggaattgag 360
atcgatctga ggaacggagc taaccctgtg actgtagata agacagtatt tgctattgaa 420
tatgctcttc aagtgcttct ttctgccaag gctgttgttt cgtactcccc aaaacagaat 480
gagttcatgg ttgagcttcg tttctttgag acat 514

<210> SEQ ID NO 136
<211> LENGTH: 1654
<212> TYPE: DNA
<213> ORGANISM: Artificial Sequence
<220> FEATURE:
<223> OTHER INFORMATION: Synthetic

<400> SEQUENCE: 136
agctgggtgt agaaatcgag cgacggcggc ggagacgacg gagatgaaca gaatgagatg 60
ggtcggagag ggagacatct gggacctcga tatgtcaact ccggtgacgc tcgagggcac 120
cgcacgagct gttcctgacg atcctcttcc tctaggtctc tctagaggca ctcgtctatc 180
tcgccctaag caagttgagt tcttccaccg cttcatggcc tcacctctca tcccttcctt 240
ctcccctatc cgtcccaaca ccggagatgg aggcggtggt ggattctctc ttcaaagagt 300
cctcactctt cctttctcca acaactggct tgtgtctctt ctgggccaat tcgatgttca 360
gagattcgta acggagatag ataagactaa agcttttggt cgagggtctt cgtctacagt 420
agcttctcgt ttaaacacaa ttggcaagca tttgaaggat aaatctttgt acgcattggg 480
tttttgttct gagtttttgt tatcaccaga tgatactttg cttcttagct atgatgctta 540
caaaggtgat ctcgataaga atcctagagc taaggctatc ttcaatcacg agtttccgct 600
tcacaatctg acagcagaag cggtttggcc tggacttttt gtggataaac atggtgaata 660
ttgggatgtg ccactctcaa tggctattga tctagcatct cttcctgctg aatctggtcc 720
aagttaccat ttatgtttac accataacag cggatcaccc aagaagttac attctgatac 780
tatggaagtg cctccaccgt cactgcttcc tggtttgtct ctgaaatctg cagtctctta 840
taggacaaac atggatctct ggaggggtac cactccaaag ctcgaaactt gcaagcccta 900
tgatgtcttc ctcagtagtc ctcatgtcgc agtatctggg attatcggct ctgtgatgac 960
cgcagcattt ggtgaaaatt caatcagatc aaaatttgaa aatgattctg agggtgttgg 1020
agggttctct cttcattttc catctgtaaa ttccggattc atggctgatg ccttagggcg 1080
ggcatcactc acagctcaat atggaaactt ccagaaattc ttctttgatc tcacccgttt 1140
ccatgctaga ttagactttc cgcatggttt gaggtttctt accggtgcca ctagcgtcgc 1200
acaagatctt ttaaattctc ggcagcctag tttagaagca tttcagaaaa tctgccctga 1260
agtattagtt tctctacagc aacagattgt tggaccgttt agtttcaaag tggagtctgg 1320
aattgagatc gatctgagga acggagctaa ccctgtgact gtagataaga cagtatttgc 1380
tattgaatat gctcttcaag tgcttctttc tgccaaggct gttgtttcgt actccccaaa 1440
acagaatgag ttcatggttg agcttcgttt ctttgagaca tagtatcagg attttccact 1500
caaaatgtca agcttgatcc tgtgaagatt gtagtcttgc agagaagtaa atactaaata 1560
gacaatgttc taattgttca gtttcttatg tcaaacagaa gaatgtttca atagaaggga 1620
agtttacatt ttgttatagt gtgatgtcta ccag 1654

<210> SEQ ID NO 137
<211> LENGTH: 4070
<212> TYPE: DNA
<213> ORGANISM: Artificial Sequence
<220> FEATURE:
<223> OTHER INFORMATION: Synthetic

<400> SEQUENCE: 137
cggtaaagct catcagcgtg gtcgtgaagc gattcacaga tgtctgcctg ttcatccgcg 60
tccagctcgt tgagtttctc cagaagcgtt aatgtctggc ttctgataaa gcgggccatg 120
ttaagggcgg tttttcctg tttggtcact gatgcctccg tgtaaggggg atttctgttc 180
atgggggtaa tgataccgat gaaacgagag aggatgctca cgatacgggt tactgatgat 240
gaacatgccc ggttactgga acgttgtgag ggtaaacaac tggcggtatg gatgcggcgg 300
gaccagagaa aaatcactca gggtcaatgc cagcgcttcg ttaatacaga tgtaggtgtt 360
ccacagggta gccagcagca tcctgcgatg cagatccgga acataatggt gcagggcgct 420
gacttccgcg tttccagact ttacgaaaca cggaaaccga agaccattca tgttgttgct 480
caggtcgcag acgttttgca gcagcagtcg cttcacgttc gctcgcgtat cggtgattca 540
ttctgctaac cagtaaggca accccgccag cctagccggg tcctcaacga caggagcacg 600
atcatgcgca cccgtggcca ggacccaacg ctgcccgaga tctcgatccc gcgaaattaa 660
tacgactcac tatagggaga ccacaacggt ttccctctag aaataatttt gtttaacttt 720
aagaaggaga tataccatgg acaacaccga ggacgtcatc aaggagttca tgcagttcaa 780
ggtgcgcatg gagggctccg tgaacggcca ctacttcgag atcgagggcg agggcgaggg 840
caagccctac gagggcaccc agaccgccaa gctgcaggtg accaagggcg gccccctgcc 900
cttcgcctgg gacatcctgt ccccccagtt ccagtacggc tccaaggcct acgtgaagca 960
ccccgccgac atccccgact acatgaagct gtccttcccc gagggcttca cctgggagcg 1020
ctccatgaac ttcgaggacg gcggcgtggt ggaggtgcag caggactcct ccctgcagga 1080
cggcaccttc atctacaagg tgaagttcaa gggcgtgaac ttccccgccg acggccccgt 1140
aatgcagaag aagactgccg gctgggagcc ctccaccgag aagctgtacc cccaggacgg 1200
cgtgctgaag ggcgagatct cccacgccct gaagctgaag gacggcggcc actacacctg 1260
cgacttcaag accgtgtaca aggccaagaa gcccgtgcag ctgcccggca accactacgt 1320
ggactccaag ctggacatca ccaaccacaa cgaggactac accgtggtgg agcagtacga 1380
gcacgccgag gcccgccact ccggctccca gggatccgaa ttcgagctcc gtcgacaagc 1440
ttgcggccgc actcgagcac caccaccacc accactgaga tccggctgct aacaaagccc 1500
gaaaggaagc tgagttggct gctgccaccg ctgagcaata actagcataa ccccttgggg 1560
cctctaaacg ggtcttgagg ggttttttgc tgaaaggagg aactatatcc ggattggcga 1620
atgggacgcg ccctgtagcg gcgcattaag cgcggcgggt gtggtggtta cgcgcagcgt 1680
gaccgctaca cttgccagcg ccctagcgcc cgctcctttc gctttcttcc cttcctttct 1740
cgccacgttc gccggctttc cccgtcaagc tctaaatcgg gggctccctt tagggttccg 1800
atttagtgct ttacggcacc tcgaccccaa aaaacttgat tagggtgatg gttcacgtag 1860
tgggccatcg ccctgataga cggtttttcg ccctttgacg ttggagtcca cgttctttaa 1920
tagtggactc ttgttccaaa ctggaacaac actcaaccct atctcggtct attcttttga 1980
tttataaggg attttgccga tttcggccta ttggttaaaa aatgagctga tttaacaaaa 2040
atttaacgcg aattttaaca aaatattaac gcttacaatt taggtggcac ttttcgggga 2100
aatgtgcgcg gaacccctat ttgtttattt ttctaaatac attcaaatat gtatccgctc 2160
atgagacaat aaccctgata aatgcttcaa taatattgaa aaaggaagag tatgagtatt 2220
caacatttcc gtgtcgccct tattcccttt tttgcggcat tttgccttcc tgtttttgct 2280
cacccagaaa cgctggtgaa agtaaaagat gctgaagatc agttgggtgc acgagtgggt 2340
tacatcgaac tggatctcaa cagcggtaag atccttgaga gttttcgccc cgaagaacgt 2400
tttccaatga tgagcacttt taaagttctg ctatgtggcg cggtattatc ccgtattgac 2460
gccgggcaag agcaactcgg tcgccgcata cactattctc agaatgactt ggttgagtac 2520
tcaccagtca cagaaaagca tcttacggat ggcatgacag taagagaatt atgcagtgct 2580
gccataacca tgagtgataa cactgcggcc aacttacttc tgacaacgat cggaggaccg 2640
aaggagctaa ccgctttttt gcacaacatg ggggatcatg taactcgcct tgatcgttgg 2700
gaaccggagc tgaatgaagc cataccaaac gacgagcgtg acaccacgat gcctgtagca 2760
atggcaacaa cgttgcgcaa actattaact ggcgaactac ttactctagc ttcccggcaa 2820
caattaatag actggatgga ggcggataaa gttgcaggac cacttctgcg ctcggccctt 2880
ccggctggct ggtttattgc tgataaatct ggagccggtg agcgtgggtc tcgcggtatc 2940
attgcagcac tggggccaga tggtaagccc tcccgtatcg tagttatcta cacgacgggg 3000
agtcaggcaa ctatggatga acgaaataga cagatcgctg agataggtgc ctcactgatt 3060
aagcattggt aactgtcaga ccaagtttac tcatatatac tttagattga tttaaaactt 3120
catttttaat ttaaaaggat ctaggtgaag atcctttttg ataatctcat gaccaaaatc 3180
ccttaacgtg agttttcgtt ccactgagcg tcagaccccg tagaaaagat caaaggatct 3240
tcttgagatc ctttttttct gcgcgtaatc tgctgcttgc aaacaaaaaa accaccgcta 3300
ccagcggtgg tttgtttgcc ggatcaagag ctaccaactc tttttccgaa ggtaactggc 3360
ttcagcagag cgcagatacc aaatactgtc cttctagtgt agccgtagtt aggccaccac 3420
ttcaagaact ctgtagcacc gcctacatac ctcgctctgc taatcctgtt accagtggct 3480
gctgccagtg gcgataagtc gtgtcttacc gggttggact caagacgata gttaccggat 3540
aaggcgcagc ggtcgggctg aacggggggt tcgtgcacac agcccagctt ggagcgaacg 3600
acctacaccg aactgagata cctacagcgt gagctatgag aaagcgccac gcttcccgaa 3660
gggagaaagg cggacaggta tccggtaagc ggcagggtcg gaacaggaga gcgcacgagg 3720
gagcttccag ggggaaacgc ctggtatctt tatagtcctg tcgggtttcg ccacctctga 3780
cttgagcgtc gatttttgtg atgctcgtca ggggggcgga gcctatggaa aaacgccagc 3840
aacgcggcct ttttacggtt cctggccttt tgctggcctt ttgctcacat gttctttcct 3900
gcgttatccc ctgattctgt ggataaccgt attaccgcct ttgagtgagc tgataccgct 3960
cgccgcagcc gaacgaccga gcgcagcgag tcagtgagcg aggaagcgga agagcgccca 4020
atacgcaaac cgcctctccc cgcgcgttgg ccgattcatt aatgcagctg 4070

<210> SEQ ID NO 138
<211> LENGTH: 1372
<212> TYPE: DNA
<213> ORGANISM: Artificial Sequence
<220> FEATURE:
<223> OTHER INFORMATION: Synthetic

<400> SEQUENCE: 138
atgaacagaa tgagatgggt cggagaggga gacatctggg acctcgatat gtcaactccg 60
gtgacgctcg agggcaccgc acgagctgtt cctgacgatc ctcttcctct aggtctctct 120
agaggcactc gtctatctcg ccctaagcaa gttgagttct tccaccgctt catggcctca 180
cctctcatcc cttccttctc ccctatccgt cccaacaccg gagatggagg cggtggtgga 240
ttctctcttc aaagagtcct cactcttcct ttctccaaca actggcttgt gtctcttctg 300
ggccaattcg atgttcagag attcgtaacg gagatagata agactaaagc ttttggtcga 360
gggtcttcgt ctacagtagc ttctcgttta aacacaattg gcaagcattt gaaggataaa 420
tctttgtacg cattgggttt ttgttctgag tttttgttat caccagatga tactttgctt 480
cttagctatg atgcttacaa aggtgatctc gataagaatc ctagagctaa ggctatcttc 540
aatcacgagt ttccgcttca caatctgaca gcagaagcgg tttggcctgg actttttgtg 600
gataaacatg gtgaatattg ggatgtgcca ctctcaatgg ctattgatct agcatctctt 660
cctgctgaat ctggtccaag ttaccattta tgtttacacc ataacagcgg atcacccaag 720
aagttacatt ctgatactat ggaagtgcct ccaccgtcac tgcttcctgg tttgtctctg 780
aaatctgcag tctcttatag gacaaacatg gatctctgga ggggtaccac tccaaagctc 840
gaaacttgca agccctattt tggtgaaaat tcaatcagat caaaatttga aaatgattct 900
gagggtgttg gagggttctc tcttcatttt ccatctgtaa attccggatt catggctgat 960
gccttagggc gggcatcact cacagctcaa tatggaaact tccagaaatt cttctttgat 1020
ctcacccgtt tccatgctag attagacttt ccgcatggtt tgaggtttct taccggtgcc 1080
actagcgtcg cacaagatct tttaaattct cggcagccta gtttagaagc atttcagaaa 1140
atctgccctg aagtattagt ttctctacag caacagattg ttggaccgtt tagtttcaaa 1200
gtggagtctg gaattgagat cgatctgagg aacggagcta accctgtgac tgtagataag 1260
acagtatttg ctattgaata tgctcttcaa gtgcttcttt ctgccaaggc tgttgtttcg 1320
tactccccaa aacagaatga gttcatggtt gagcttcgtt tctttgagac at 1372

<210> SEQ ID NO 139
<211> LENGTH: 27
<212> TYPE: DNA
<213> ORGANISM: Artificial Sequence
<220> FEATURE:
<223> OTHER INFORMATION: Synthetic

<400> SEQUENCE: 139
cgagctcatg aacagaatga gatggtc 27

<210> SEQ ID NO 140
<211> LENGTH: 37
<212> TYPE: DNA
<213> ORGANISM: Artificial Sequence
<220> FEATURE:
<223> OTHER INFORMATION: Synthetic

<400> SEQUENCE: 140
atagtttagc ggccgctgtc tcaaagaaac gaagctc 37

<210> SEQ ID NO 141
<211> LENGTH: 27
<212> TYPE: DNA
<213> ORGANISM: Artificial Sequence
<220> FEATURE:
<223> OTHER INFORMATION: Synthetic -continued

<400> SEQUENCE: 141
cgagctcatg aacagaatga gatggtc 27

<210> SEQ ID NO 142
<211> LENGTH: 37
<212> TYPE: DNA
<213> ORGANISM: Artificial Sequence
<220> FEATURE:
<223> OTHER INFORMATION: Synthetic

<400> SEQUENCE: 142
atagtttagc ggccgctgtc tcaaagaaac gaagctc 37

<210> SEQ ID NO 143
<211> LENGTH: 33
<212> TYPE: DNA
<213> ORGANISM: Artificial Sequence
<220> FEATURE:
<223> OTHER INFORMATION: Synthetic

<400> SEQUENCE: 143
catgccatgg atatgaacag aatgagatgg gtc 33

<210> SEQ ID NO 144
<211> LENGTH: 30
<212> TYPE: DNA
<213> ORGANISM: Artificial Sequence
<220> FEATURE:
<223> OTHER INFORMATION: Synthetic

<400> SEQUENCE: 144
catgccatgg tatagggctt gcaagtttcg 30

<210> SEQ ID NO 145
<211> LENGTH: 30
<212> TYPE: DNA
<213> ORGANISM: Artificial Sequence
<220> FEATURE:
<223> OTHER INFORMATION: Synthetic

<400> SEQUENCE: 145
cgagctcggt gaaaattcaa tcagatcaaa 30

<210> SEQ ID NO 146
<211> LENGTH: 37
<212> TYPE: DNA
<213> ORGANISM: Artificial Sequence
<220> FEATURE:
<223> OTHER INFORMATION: Synthetic

<400> SEQUENCE: 146
atagtttagc ggccgctgtc tcaaagaaac gaagctc 37